US010858339B2

(12) United States Patent
deLong et al.

(10) Patent No.: US 10,858,339 B2
(45) Date of Patent: Dec. 8, 2020

(54) ARYL CYCLOPROPYL-AMINO-ISOQUINOLINYL AMIDE COMPOUNDS

(71) Applicant: Aerie Pharmaceuticals, Inc., Irvine, CA (US)

(72) Inventors: Mitchell A. deLong, Chapel Hill, NC (US); Jill M. Sturdivant, Chapel Hill, NC (US); Cynthia L. Lichorowic, Raleigh, NC (US); Andriy Kornilov, Ypsilanti, MI (US)

(73) Assignee: Aerie Pharmaceuticals, Inc., Bedminster, NJ (US)

( * ) Notice: Subject to any disclaimer, the term of this patent is extended or adjusted under 35 U.S.C. 154(b) by 16 days.

(21) Appl. No.: 15/941,993

(22) Filed: Mar. 30, 2018

(65) Prior Publication Data
US 2018/0327381 A1    Nov. 15, 2018

Related U.S. Application Data

(60) Provisional application No. 62/643,131, filed on Mar. 14, 2018, provisional application No. 62/480,239, filed on Mar. 31, 2017.

(51) Int. Cl.
*C07D 401/12* (2006.01)
*C07D 217/02* (2006.01)
(Continued)

(52) U.S. Cl.
CPC ............ *C07D 401/12* (2013.01); *A61P 27/06* (2018.01); *C07C 69/76* (2013.01); *C07D 217/02* (2013.01);
(Continued)

(58) Field of Classification Search
CPC .................................................. C07D 401/12
See application file for complete search history.

(56) References Cited

U.S. PATENT DOCUMENTS

| 4,146,637 A | 3/1979 | Metz et al. |
| 4,337,256 A | 6/1982 | Yasushi et al. |

(Continued)

FOREIGN PATENT DOCUMENTS

| EP | 0109023 | 5/1984 |
| EP | 0232569 | 8/1987 |

(Continued)

OTHER PUBLICATIONS

International Search Report and Written Opinion for International Application No. PCT/US2017/025609 dated Jul. 3, 2017 (8 pages).

(Continued)

*Primary Examiner* — John S Kenyon
(74) *Attorney, Agent, or Firm* — K&L Gates LLP; Louis C. Cullman; Benjamin D. Heuberger

(57) ABSTRACT

Provided herein are arylcyclopropyl amino-isoquinoline amide compounds. In particular, the disclosure provides compounds that affect the function of kinases in a cell and that are useful as therapeutic agents or with therapeutic agents. The compounds of the disclosure are useful in the treatment of a variety of diseases and conditions including eye diseases such as glaucoma, cardiovascular diseases, diseases characterized by abnormal growth, such as cancers, and inflammatory diseases. The disclosure further provides compositions containing isoquinoline amide compounds.

3 Claims, 1 Drawing Sheet

Specification includes a Sequence Listing.

(51) Int. Cl.
*C07D 405/12* (2006.01)
*C07D 417/12* (2006.01)
*C07D 217/24* (2006.01)
*C07D 217/22* (2006.01)
*C07D 401/04* (2006.01)
*C07D 405/14* (2006.01)
*C07C 69/76* (2006.01)
*A61P 27/06* (2006.01)
*C07D 401/14* (2006.01)
*C07D 409/12* (2006.01)

(52) U.S. Cl.
CPC ......... *C07D 217/22* (2013.01); *C07D 217/24* (2013.01); *C07D 401/04* (2013.01); *C07D 401/14* (2013.01); *C07D 405/12* (2013.01); *C07D 405/14* (2013.01); *C07D 409/12* (2013.01); *C07D 417/12* (2013.01); *C07C 2601/02* (2017.05)

(56) References Cited

U.S. PATENT DOCUMENTS

| | | | |
|---|---|---|---|
| 4,456,757 | A | 6/1984 | Hidaka et al. |
| 4,709,032 | A | 11/1987 | Hidaka et al. |
| 4,911,928 | A | 3/1990 | Wallach |
| 4,954,512 | A | 9/1990 | Oguro et al. |
| 5,508,288 | A | 4/1996 | Forbes et al. |
| 5,519,036 | A | 5/1996 | Himmelsbach et al. |
| 5,770,759 | A | 1/1998 | Ueno et al. |
| 5,798,380 | A | 8/1998 | Kaufman et al. |
| 5,889,052 | A | 3/1999 | Klimko et al. |
| 5,891,646 | A | 4/1999 | Barak et al. |
| 5,977,173 | A | 11/1999 | Wos et al. |
| 5,994,397 | A | 11/1999 | Selliah et al. |
| 6,025,392 | A | 2/2000 | Selliah et al. |
| 6,030,999 | A | 2/2000 | Stjernschantz et al. |
| 6,037,364 | A | 3/2000 | Burk |
| 6,037,368 | A | 3/2000 | Selliah et al. |
| 6,048,895 | A | 4/2000 | Wos et al. |
| 6,110,693 | A | 8/2000 | Barak et al. |
| 6,110,912 | A | 8/2000 | Kaufman et al. |
| 6,362,177 | B1 | 3/2002 | Shiota et al. |
| 6,586,425 | B2 | 7/2003 | Kaufman et al. |
| 6,699,891 | B1 | 3/2004 | Kawaanishi et al. |
| 6,787,534 | B2 | 9/2004 | Haneda |
| 7,268,143 | B2 | 9/2007 | Jagtap et al. |
| 7,329,684 | B2 | 2/2008 | Mjalli et al. |
| 7,345,158 | B2 | 3/2008 | Egashira et al. |
| 7,361,678 | B2 | 4/2008 | Mjalli et al. |
| 7,374,891 | B2 | 5/2008 | Shahbaz |
| 7,378,498 | B2 | 5/2008 | Worley et al. |
| 7,470,787 | B2 | 12/2008 | deLong et al. |
| 7,671,205 | B2 * | 3/2010 | deLong ............... C07D 217/02 546/146 |
| 8,034,943 | B2 | 10/2011 | deLong et al. |
| 8,129,411 | B2 | 3/2012 | Ehara et al. |
| 8,357,699 | B2 | 1/2013 | deLong et al. |
| 8,394,826 | B2 | 3/2013 | deLong et al. |
| 8,450,344 | B2 | 5/2013 | deLong et al. |
| 8,455,513 | B2 | 6/2013 | deLong et al. |
| 8,455,514 | B2 | 6/2013 | deLong et al. |
| 8,455,647 | B2 | 6/2013 | deLong et al. |
| 8,716,310 | B2 | 5/2014 | deLong et al. |
| 8,759,388 | B2 | 6/2014 | deLong et al. |
| 8,809,326 | B2 | 8/2014 | Bosanac et al. |
| 8,871,757 | B2 | 10/2014 | deLong et al. |
| 8,921,392 | B2 | 12/2014 | deLong et al. |
| 9,096,569 | B2 | 8/2015 | deLong et al. |
| 9,255,101 | B2 | 2/2016 | Berrebi-Bertrand et al. |
| 9,415,043 | B2 | 8/2016 | Kopczynski |
| 9,643,927 | B1 | 5/2017 | Sturdivant et al. |
| 9,884,840 | B2 | 2/2018 | deLong et al. |
| 10,112,920 | B2 | 10/2018 | deLong et al. |
| 10,174,017 | B2 | 1/2019 | deLong et al. |
| 2004/0091946 | A1 | 5/2004 | Oakley et al. |
| 2004/0157859 | A1 | 8/2004 | Wu et al. |
| 2004/0176462 | A1 | 9/2004 | Kawanishi et al. |
| 2005/0032125 | A1 | 2/2005 | Oakley et al. |
| 2005/0176712 | A1 | 8/2005 | Wakabayashi et al. |
| 2005/0245509 | A1 | 11/2005 | Nakajima et al. |
| 2005/0282805 | A1 | 12/2005 | Hangeland et al. |
| 2006/0270670 | A1 | 11/2006 | Chew et al. |
| 2007/0111983 | A1 | 5/2007 | Fong |
| 2007/0123561 | A1 | 5/2007 | Lee et al. |
| 2007/0129404 | A1 | 6/2007 | Hagihara et al. |
| 2007/0135499 | A1 | 6/2007 | deLong et al. |
| 2007/0149473 | A1 | 6/2007 | Chatterton et al. |
| 2007/0149548 | A1 | 6/2007 | Hellberg et al. |
| 2007/0167444 | A1 | 7/2007 | Kuramochi et al. |
| 2007/0238741 | A1 | 10/2007 | Nagarathnam et al. |
| 2008/0021026 | A1 | 1/2008 | Kahraman et al. |
| 2008/0021217 | A1 | 1/2008 | Borchardt |
| 2008/0058384 | A1 | 3/2008 | Lee et al. |
| 2008/0096238 | A1 | 4/2008 | Sharif et al. |
| 2008/0125427 | A1 | 5/2008 | Sehon et al. |
| 2008/0139595 | A1 | 6/2008 | Schirok et al. |
| 2008/0153799 | A1 | 6/2008 | Laurent et al. |
| 2008/0153813 | A1 | 6/2008 | Chen et al. |
| 2008/0161297 | A1 | 7/2008 | Bosanac et al. |
| 2008/0194584 | A1 | 8/2008 | Birault et al. |
| 2008/0275029 | A1 | 11/2008 | Berdini et al. |
| 2008/0287516 | A1 | 11/2008 | Wu et al. |
| 2009/0005321 | A1 | 1/2009 | Zimmer et al. |
| 2009/0069371 | A1 | 3/2009 | deLong et al. |
| 2009/0143381 | A1 | 6/2009 | Ruah et al. |
| 2009/0186917 | A1 | 7/2009 | deLong et al. |
| 2010/0004239 | A1 | 1/2010 | Tang et al. |
| 2010/0063025 | A1 | 3/2010 | Plettenburg et al. |
| 2010/0093790 | A1 | 4/2010 | deLong et al. |
| 2010/0105650 | A1 | 4/2010 | Plettenburg et al. |
| 2010/0144713 | A1 | 6/2010 | deLong et al. |
| 2011/0015204 | A1 | 1/2011 | Bencsik et al. |
| 2011/0039893 | A1 | 2/2011 | Kori et al. |
| 2012/0135984 | A1 | 5/2012 | deLong et al. |
| 2012/0196916 | A1 | 8/2012 | deLong et al. |
| 2013/0137721 | A1 | 5/2013 | deLong et al. |
| 2013/0296363 | A1 | 11/2013 | Faraoni et al. |
| 2013/0318457 | A1 | 11/2013 | Bjorklund |
| 2014/0187617 | A1 | 7/2014 | deLong et al. |
| 2014/0275160 | A1 | 9/2014 | Kopczynski |
| 2014/0275161 | A1 | 9/2014 | Kopczynski |
| 2014/0288086 | A1 | 9/2014 | Cui et al. |
| 2014/0357652 | A1 | 12/2014 | Bosanac et al. |
| 2015/0119419 | A1 | 4/2015 | deLong et al. |
| 2015/0175534 | A1 | 6/2015 | Harvey et al. |
| 2015/0175549 | A1 | 6/2015 | deLong et al. |
| 2015/0297581 | A1 | 10/2015 | Bosanac et al. |
| 2015/0299159 | A1 | 10/2015 | deLong et al. |
| 2016/0016951 | A1 | 1/2016 | Schiemann et al. |
| 2016/0243102 | A1 | 8/2016 | Bosanac et al. |
| 2016/0243105 | A1 | 8/2016 | Kopczynski et al. |
| 2016/0272589 | A1 | 9/2016 | deLong et al. |
| 2016/0280656 | A1 | 9/2016 | deLong et al. |
| 2016/0346269 | A1 | 12/2016 | Kopczynski et al. |
| 2017/0000819 | A1 | 1/2017 | Capriotti et al. |
| 2017/0233381 | A1 | 8/2017 | deLong et al. |
| 2017/0281613 | A1 | 10/2017 | Kopczynski et al. |
| 2018/0050990 | A1 | 2/2018 | Sturdivant et al. |
| 2018/0055833 | A1 | 3/2018 | Lin et al. |
| 2018/0186746 | A1 * | 7/2018 | deLong ............... C07D 217/02 |
| 2018/0244666 | A1 | 8/2018 | deLong et al. |
| 2018/0333405 | A1 | 11/2018 | Kopczynski et al. |
| 2018/0344724 | A1 | 12/2018 | Kopczynski et al. |
| 2019/0127346 | A1 | 5/2019 | deLong et al. |
| 2019/0322625 | A1 | 10/2019 | deLong et al. |

FOREIGN PATENT DOCUMENTS

| | | |
|---|---|---|
| EP | 0389995 | 10/1990 |
| EP | 0482939 | 4/1992 |
| EP | 1541151 | 6/2005 |
| EP | 1550660 | 7/2005 |
| JP | 2005227441 | 8/2005 |

(56) References Cited

FOREIGN PATENT DOCUMENTS

| | | |
|---|---|---|
| JP | 2007236388 | 9/2007 |
| JP | 2007246466 | 9/2007 |
| WO | 1993/018028 | 9/1993 |
| WO | 1995/019964 | 7/1995 |
| WO | 1996/010407 | 4/1996 |
| WO | 1997/023223 | 7/1997 |
| WO | 1998/012175 | 3/1998 |
| WO | 1998/020880 | 5/1998 |
| WO | 1998/020881 | 5/1998 |
| WO | 1998/021180 | 5/1998 |
| WO | 1998/021181 | 5/1998 |
| WO | 1998/021182 | 5/1998 |
| WO | 1998/039293 | 9/1998 |
| WO | 1988/050024 | 11/1998 |
| WO | 1998/057930 | 12/1998 |
| WO | 1998/057942 | 12/1998 |
| WO | 1999/002165 | 1/1999 |
| WO | 1999/012895 | 3/1999 |
| WO | 1999/012896 | 3/1999 |
| WO | 1999/012898 | 3/1999 |
| WO | 1999/025358 | 5/1999 |
| WO | 1999/026629 | 6/1999 |
| WO | 1999/032441 | 7/1999 |
| WO | 2000/003736 | 1/2000 |
| WO | 2000/003980 | 1/2000 |
| WO | 2000/071508 | 11/2000 |
| WO | 2000/076970 | 12/2000 |
| WO | 2001/037826 | 5/2001 |
| WO | 2001/047891 | 7/2001 |
| WO | 2001/053268 | 7/2001 |
| WO | 2001/053274 | 7/2001 |
| WO | 2001/056607 | 8/2001 |
| WO | 2002/022576 | 3/2002 |
| WO | 2002/032864 | 4/2002 |
| WO | 2002/085857 | 10/2002 |
| WO | 2002/085859 | 10/2002 |
| WO | 2003/064397 | 8/2003 |
| WO | 2003/068749 | 8/2003 |
| WO | 2003/073999 | 9/2003 |
| WO | 2003/080578 | 10/2003 |
| WO | 2004/029045 | 4/2004 |
| WO | 2004/078747 | 9/2004 |
| WO | 2005/020921 | 3/2005 |
| WO | 2005/035503 | 4/2005 |
| WO | 2005/037257 | 4/2005 |
| WO | 2006/041119 | 4/2006 |
| WO | 2006/051290 | 5/2006 |
| WO | 2006/062982 | 6/2006 |
| WO | 2006/076706 | 7/2006 |
| WO | 2007/008926 | 1/2007 |
| WO | 2007/008942 | 1/2007 |
| WO | 2007/060028 | 5/2007 |
| WO | 2007/065916 | 6/2007 |
| WO | 2007/076360 | 7/2007 |
| WO | 2007/076367 | 7/2007 |
| WO | 2007/100880 | 9/2007 |
| WO | 2007/0142323 | 12/2007 |
| WO | 2008/011557 | 1/2008 |
| WO | 2008/011560 | 1/2008 |
| WO | 2008/016016 | 2/2008 |
| WO | 2008/036459 | 3/2008 |
| WO | 2008/036540 | 3/2008 |
| WO | 2008/049000 | 4/2008 |
| WO | 2008/049919 | 5/2008 |
| WO | 2008/054999 | 5/2008 |
| WO | 2008/077057 | 6/2008 |
| WO | 2008/077550 | 7/2008 |
| WO | 2008/077551 | 7/2008 |
| WO | 2008/077552 | 7/2008 |
| WO | 2008/077553 | 7/2008 |
| WO | 2008/077554 | 7/2008 |
| WO | 2008/077555 | 7/2008 |
| WO | 2008/077556 | 7/2008 |
| WO | 2008/079880 | 7/2008 |
| WO | 2008/079945 | 7/2008 |
| WO | 2008/086269 | 7/2008 |
| WO | 2008/124665 | 10/2008 |
| WO | 2009/091898 | 7/2009 |
| WO | 2010/011853 | 1/2010 |
| WO | 2010/019903 | 2/2010 |
| WO | 2010/126626 | 11/2010 |
| WO | 2010/127329 | 11/2010 |
| WO | 2010/127330 | 11/2010 |
| WO | 2010/146881 | 12/2010 |
| WO | 2011/085351 A2 | 7/2011 |
| WO | 2012/063237 | 5/2012 |
| WO | 2012/105674 | 8/2012 |
| WO | 2014/144781 | 9/2014 |
| WO | 2016/123627 | 8/2016 |
| WO | 2018/034702 | 2/2018 |
| WO | 2018/045091 | 3/2018 |
| WO | 2018/183911 A1 | 10/2018 |
| WO | 2019/191654 A1 | 10/2019 |
| WO | WO 2020/056345 A1 * | 3/2020 |

OTHER PUBLICATIONS

International Search Report and Written Opinion for International Application No. PCT/US2017/065631 dated Feb. 13, 2018 (6 pages).

Ito, N. et al., "A medium-term rat liver bioassay for rapid in vivo detection of carcinogenic potential of chemicals," Cancer Science, Jan. 2003, vol. 94, No. 1, pp. 3-8.

Jacobs, M. et al., "The structure of dimeric ROCK I reveals the mechanism for ligand selectivity," J. Bio. Chem., 2006, pp. 260-268, published on Jan. 6, 2006.

Japanese Patent Office Action for Application No. 2009-545622 dated Mar. 1, 2013 (8 pages—including English Translation).

Japanese Patent Office Action for Application No. 2009-545622 dated Oct. 21, 2013 (8 pages—Including English Translation).

Japanese Patent Office Action for Application No. 2010-543237 dated Aug. 8, 2013 (10 pages—Including English Translation).

Japanese Patent Office Action for Application No. 2010-543237 dated Jan. 8, 2014 (2 pages—Including English Translation).

Japanese Patent Office Action for Application No. 2011-520203 dated Jan. 28, 2014 (8 pages, English translation included).

Japanese Patent Office Action for Application No. 2012-508492 dated Apr. 2, 2015 ( 4 pages, English translation included).

Japanese Patent Office Action for Application No. 2012-508492 dated Apr. 7, 2014 (5 pages, English translation only).

Japanese Patent Office Action for Application No. 2014-131231 dated Jan. 14, 2015 (8 pages, English translation attached).

Japanese Patent Office Action for Application No. 2014-131231 dated Jan. 27, 2016 (3 pages, English translation only).

Japanese Patent Office Action for Application No. 2015-216395 dated Nov. 14, 2016 (7 pages including translation).

Karaman, M.W. et al., "A quantitative analysis of kinase inhibitor selectivity," Nature Biotech. (2008) 26(1):127-132.

Katritzky, A.R. et al., "Benzotriazole mediated amino-, amide-, alkoxy- and alkylthio-alkylation," Tetrahedron (2005) 61:2555-2581.

Kumar et al., Catalyst-free water mediated reduction of nitroarenes using glucose as a hydrogen source. RSC Advances, 3:4894-4898 (2013).

Lala, P.K. et al., "Role of nitric oxide in tumor progression: lessons from experimental tumors," Cancer and Metastasis Reviews (1998) 17:91-106.

Liljebris, C. et al., "Derivatives of 17-Pheny 1-18,19 ,20-trinorprostaglandin F2a Isopropyl Ester: Antiglaucoma Agents," J. Med. Chem. (1995) 38(2)289-304.

Loge et al., Synthesis and pharmacological study of rho-kinase inhibitors: Pharmacomodulations on the lead compound Fasudil. J. of Enzy Inhib & Med Chem, 2003, 18(2),127-128.

Matsui et al., "Novel 5-HT3 antagonists. Isoquinolinones and 3-aryl-2-pyridones." J. Med. Chem. (1992) 35:3307-3319.

McCutcheon's, "Emulsifiers & Detergents", North American Edition (1994) vol. 1:236-239.

Meanwell, "Synopsis of some recent tactocal application of bioisosteres in drug design," J. Med. Chem., 2011, vol. 54, pp. 2529-2591.

(56) References Cited

OTHER PUBLICATIONS

Makanishi et al., Effects of protein kinase inhibitors and protein phosphatase inhibitors on cyclic AMP-dependent down-regulation of vesicular monoamine transport in pheochromocytoma PC12 cells. FEBS Letters 368, (1995) 411-414.
Oakley et al., "The Cellular Distribution of Fluorescently Labeled Arrestins Provides a Robust, Sensitive and Universal Assay for Screening G Protein-Coupled Receptors." Assay and Drug Development Technologies vol. 1, No. 1-1:21-30 (2002).
Olson, "Application for ROCK kinase inhibition," Current Opinion in Cell Biology, 2008, vol. 20, pp. 242-248.
Parang et al., "Design strategies for protein kinase inhibitors." Curr. Opin. In Drug Disc. & Dev. (2004) 7(5):617-629.
Pardridge, "The Blood-Brain Barrier: Bottleneck in Brain Drug development," J. Am. Soc. Exper. NeuroTherapeutics, 2005, vol. 2, p. 3-14.
Partial International Search Report and Invitation to pay Additional Fees for Application No. PCT/US2009/031117 dated Apr. 16, 2009 (4 pages).
Penmetsa et al., Development of Reversed-Phase Chiral HPLC Methods Using Mass Spectrometry Compatible Mobile Phases. J. Liquid Chroma. & Rel. Tech. 23(6):831-839 (2000).
Penn et al., "Pharmacological Inhibition of Protein Kinases in Intact Cells: Antagonism of Beta Adrenergic Receptor Ligand Binding by H-89 Reveals Limitations of Usefulness." J. Pharm. Exp. Ther. 288(2):428-437 (1999).
Pharmasolve (N-Methyl-2-Pyrrolidone) product spcification, International Specialty Products, 2000, 10 pages.
Poradowska et al., The Preparation of 6-Aminoisoquinoline. Synthesis 11:733, 1975.
PubChem, AC1 NQAJU (compound sumary for CID 5172372) '372' date created: Sep. 26, 2005 date access: Jan. 5, 2016, 10 pages.
Rashid et al., "Development of Rho-kinase inhibitors for cardiovascular medicine," Trends in Pharmacological Science, 2007, vol. 28, pp. 296-302.
Shankar et al., "Protein-kinase-specific inhibitors block Langerhans' cell migration by inhibiting interleukin-1alpha release." Immunology (1999) 96:230-235.
Sharma et al., Highly Chemo- and Regioselective Reduction of Aromatic Nitro Compounds Catalyzed by Recyclable Copper(II) as well as Cobalt(II) Phthalocyanines. Advanced Synthesis and Catalysis, 352:1834-1840 (2010).
Sharma et al., Zinc phthalocyanine with PEG-400 as a recyclable catalytic system for selective reduction of aromatic nitro compounds. Green Chem., 14:2289-2293 (2012).
Sharma et al., Phosphane-Free Green Protocol for Selective Nitro Reduction with an Iron-Based Catalyst. Chem. Eur. J., 17:5903-5907 (2011).
Stirewalt et al., "The Role of FLT3 in Haematopoietic Malignancies." Nature Reviews Cancer (2003) 3:650-665.
STN Registry Database entry for CAS RN 309930-43-6, Published in database Dec. 20, 2000.
Sturdivant et al., Discovery of the ROCK inhibitor netarsudil for the treatment of open-angle glaucoma. Bioorganic & Medicinal Chemistry Letters, 26:2475-2480 (2016).
Sturdivant et al., Identification of intermediates in the stepwise reduction of 1,3-dichloro-6nitroisoquinoline to 6-aminoisiquinoline. 248th National Meeting of the American Chemical Society, Aug. 2014, MEDI 153.
Tamura, M., et al., "Development of specific Rho-kinase inhibitors and their clinical application," Biochimica et Biophysica Acta, 2005, vol. 1754, pp. 245-252.
Torres, G.E. et al. (2003). "Plasma membrane monoamine transporters: structure, regulation and function". Nat. Rev. Neurosci. 4 (1): 13-25.
United States Office Action for U.S. Appl. No. 11/485,182 dated Apr. 16, 2009 (13 pages).
United States Office Action for U.S. Appl. No. 11/621,892 dated Aug. 8, 2008 (9 pages).
United States Office Action for U.S. Appl. No. 11/621,892 dated Mar. 9, 2009 (6 pages).
United States Office Action for U.S. Appl. No. 12/274,887 dated Jun. 16, 2009 (11 pages).
United States Patent Office Action for U.S. Appl. No. 11/621,887 dated May 18, 2010 (8 pages).
United States Patent Office Notice of Allowance for U.S. Appl. No. 13/442,263 dated Apr. 15, 2014 (8 pages).
United States Patent Office Action for U.S. Appl. No. 13/442,263 dated Dec. 19, 2012 (13 pages).
U.S. Appl. No. 15/941,783, filed Mar. 30, 2018.
United States Patent Office Action for U.S. Appl. No. 13/442,263 dated Jun. 12, 2013 (17 pages).
United States Patent Office Notice of Allowance for U.S. Appl. No. 13/723,811 dated Aug. 19, 2014 (11 pages).
United States Patent Office Notice of Allowance for U.S. Appl. No. 13/768,594 dated Oct. 29, 2013 (7 pages).
United States Patent Office Notice of Allowance for U.S. Appl. No. 14/213,961 dated Jun. 20, 2016 (8 pages).
United States Patent Office Notice of Allowance for U.S. Appl. No. 14/273,895 dated Apr. 1, 2015 (8 pages).
United States Patent Office Notice of Allowance for U.S. Appl. No. 14/583,439 dated Feb. 12, 2016 (8 pages).
United States Patent Office Notice of Allowance for U.S. Appl. No. 14/790,376 dated Aug. 2, 2016 and supplemental Notice of Allowability dated Aug. 19, 2016 (10 pages).
U.S. Appl. No. 15/844,399, filed Dec. 15, 2017.
U.S. Appl. No. 15/901,361, filed Feb. 21, 2018.
U.S. Appl. No. 15/858,981, filed Dec. 29, 2017.
U.S. Appl. No. 15/924,089, filed Mar. 16, 2018.
Van Muijl Wijk-Koezen et al., "A novel class of adenosine A3 receptor-ligands. 2. Structure affinity profile of a series of isoquinoline and quinazoline compounds." J. Med. Chem. (1998) 41:3994-4000.
Vippagunta et al., "Cystalline solids." Advanced Drug Delivery Reviews, 48:3-26 (2001).
Wallach and Philippot, "New Type of Lipid Vesicle: Novasome®", Liposome Technology, vol. 1, pp. 141-156 (1993).
Webster, F.X. et al., "Following the Course of Resolution of Carboxylic Acids by 13C NMR Spectrometry of Amine Salts" J. Org. Chem. (1982) 47(26):5225-5226.
West, A.R., "Solid state chemistry and its applications," Wiley, New York (1988) pp. 358 and 365.
Westaway et al., "N-tetrahydroquinolinyl, N-quinolinyl and N-isoquinolinyl biaryl carboxamides as antagonists of TRPV1." Biorg. Med. Chem. Lett. (2006) 16:4533-4536.
Westra et al., "p38 Mitogen-Activated Protein Kinase (MAPK) in Rheumatoid Arthritis." Mini-Reviews in Medicinal Chemistry (2006) 6(8):867-874.
Yamashita et al., "The therapeutic effects of Rho-Rock inhibitors on CNS disorder," Therapeutics and Clinical Risk Management, 2008, vol. 4, pp. 605-615.
U.S. Appl. No. 15/970,635, filed May 3, 2018.
United States Patent Notice of Allowability for U.S. Appl. No. 11/621,887 dated Oct. 29, 2010 (14 pages).
United States Patent Office Action for U.S. Appl. No. 11/856,740 dated Aug. 16, 2013 (14 pages).
United States Patent Office Action for U.S. Appl. No. 11/856,740 dated Dec. 6, 2010 (12 pages).
United States Patent Office Action for U.S. Appl. No. 11/856,740 dated Jun. 29, 2010 (10 pages).
United States Notice of Allowance for U.S. Appl. No. 12/009,326 dated Feb. 3, 2011 (8 pages).
United States Patent Office Action for U.S. Appl. No. 12/180,259 dated Jul. 5, 2011 (11 pages).
United States Patent Office Action for U.S. Appl. No. 12/639,670 dated Jan. 31, 2011 (8 pages).
United States Patent Office Action for U.S. Appl. No. 12/639,670 dated Jul. 27, 2011 (5 pages).
United States Patent Office Action for U.S. Appl. No. 12/694,965 dated May 17, 2012 (13 pages).
United States Patent Office Action for U.S. Appl. No. 12/701,963 dated May 10, 2011 (3 pages).

(56) References Cited

OTHER PUBLICATIONS

United States Patent Office Action for U.S. Appl. No. 12/704,822 dated Apr. 30, 2012 (34 pages).
United States Patent Office Action for U.S. Appl. No. 12/704,822 dated May 8, 2014 (13 pages).
United States Patent Office Action for U.S. Appl. No. 121704,822 dated Oct. 10, 2013 (11 pages).
United States Patent Office Action for U.S. Appl. No. 13/017,708 dated Apr. 3, 2012 (11 pages).
United States Patent Office Action for U.S. Appl. No. 13/230,105 dated Mar. 5, 2012 (8 pages).
United States Patent Office Action for U.S. Appl. No. 13/318,457 dated Jun. 6, 2013 (12 pages).
United States Patent Office Action for U.S. Appl. No. 13/723,811 dated Jan. 27, 2014 (8 pages).
United States Patent Office Action for U.S. Appl. No. 13/723,811 dated Jun. 17, 2014 (6 pages).
United States Patent Office Action for U.S. Appl. No. 13/768,594 dated Jul. 10, 2013 (14 pages).
United States Patent Office Action for U.S. Appl. No. 14/138,592 dated Dec. 9, 2014 (14 pages).
United States Patent Office Action for U.S. Appl. No. 14/138,592 dated Jul. 28, 2014 (17 pages).
United States Patent Office Action for U.S. Appl. No. 14/213,940 dated Oct. 29, 2015 (33 pages).
United States Patent Office Action for U.S. Appl. No. 14/213,961 dated Oct. 30, 2015 (37 pages).
United States Patent Office Action for U.S. Appl. No. 14/273,895 dated Aug. 20, 2014 (8 pages).
United States Patent Office Action for U.S. Appl. No. 14/273,895 dated Dec. 24, 2014 (7 pages).
United States Patent Office Action for U.S. Appl. No. 14/461,597 dated Jan. 30, 2015 (19 pages).
United States Patent Office Action for U.S. Appl. No. 14/583,439 dated Jun. 23, 2015 (6 pages).
United States Patent Office Action for U.S. Appl. No. 14/583,439 dated Oct. 30, 2015 (7 pages).
United States Patent Office Action for U.S. Appl. No. 14/641,962 dated Sep. 22, 2015 (16 pages).
United States Patent Office Action for U.S. Appl. No. 14/754,787 dated Oct. 30, 2015 (20 pages).
United States Patent Office Action for U.S. Appl. No. 14/790,376 dated Jan. 22, 2016 (14 pages).
United States Patent Office Action for U.S. Appl. No. 15/076,216 dated Sep. 1, 2016 (6 pages).
United States Patent Office Advisory Action for U.S. Appl. No. 11/856,740 dated Feb. 10, 2011 (3 pages).
United States Patent Office Final Rejection for U.S. Appl. No. 12/704,822 dated Jan. 16, 2013 (16 pages).
United States Patent Office Final Rejection for U.S. Appl. No. 13/230,105 dated Jul. 9, 2012 (11 pages).
United States Patent Office Final Rejection for U.S. Appl. No. 13/318,457 dated Nov. 27, 2013 (13 pages).
United States Patent Office Final Rejection for U.S. Appl. No. 13/442,263 dated Dec. 6, 2013 (8 pages).
United States Patent Office Notice of Allowability for U.S. Appl. No. 13/017,708 dated Dec. 12, 2012 (5 pages).
United States Patent Office Notice of Allowance for U.S. Appl. No. 11/621,887 dated Feb. 27, 2013 (8 pages).
United States Patent Office Notice of Allowance for U.S. Appl. No. 11/856,740 dated Apr. 1, 2014 (8 pages).
United States Patent Office Notice of Allowance for U.S. Appl. No. 12/009,326 dated Feb. 25, 2013 (8 pages).
United States Patent Office Notice of Allowance for U.S. Appl. No. 12/009,326 dated Jan. 6, 2012 (5 pages).
United States Patent Office Notice of Allowance for U.S. Appl. No. 12/180,259 dated Dec. 19, 2011 (6 pages).
United States Patent Office Notice of Allowance for U.S. Appl. No. 12/180,259 dated Feb. 25, 2013 (8 pages).
United States Patent Office Notice of Allowance for U.S. Appl. No. 12/694,965 dated Nov. 19, 2012 (4 pages).
United States Patent Office Notice of Allowance for U.S. Appl. No. 12/694,965 dated Nov. 2, 2012 (8 pages).
United States Patent Office Notice of Allowance for U.S. Appl. No. 12/704,822 dated Sep. 9, 2014 (11 pages).
United States Patent Office Notice of Allowance for U.S. Appl. No. 13/017,708 dated Oct. 23, 2012 (7 pages).
United States Patent Office Notice of Allowance for U.S. Appl. No. 13/017,708 dated Sep. 17, 2012 (8 pages).
United States Patent Office Notice of Allowance for U.S. Appl. No. 13/230,105 dated Mar. 19, 2013 (5 pages).
Chinese Patent Office Action for Application No. 201480027763.3 dated Nov. 1, 2016 (18 pages including translation).
Dancey, J. et al., "Issues and Progress with Protein Kinase Inhibitors for Cancer Treatment", Nature Reviews Drug Discovery (2003) 2:296-313.
DeLong et al., "Discovery and SAR of a Class of Oculary-active Compounds Displaying a Dual Mechanism of Activity for the Treatment of Glaucoma" (May 6-10, 2012) Retrieved from the Internet:URL:http://www.aeriepharma.com.
Dorwald, F.Z., Side Reactions in Organic Synthesis. A Guide to Successful Synthesis Design, Wiley-VCH, Weinheim (2005) IX of Preface and 1-15.
Dowton et al., "Influence of Liposomal Composition on Topical Delivery of Encapsulated Cyclosporin A", S.T.P. Pharma Sciences, vol. 3, pp. 404-407 (1993).
Ehara et al., Structure-based design of substituted piperidines as a new class of highly efficacious oral direct renin inhibitors. ACS Medicinal Chemistry Letters, 5(7):787-792 (2014).
Ehara, abstract only, CA 161:93707 (2014).
European Patent Office Action for Application No. 08713603.2 dated Aug. 14, 2012 (3 pages).
European Patent Office Action for Application No. 08713603.2 dated Nov. 21, 2013 (4 pages).
European Patent Office Action for Application No. 09702189.3 dated Feb. 1, 2011 (5 pages).
European Patent Office Action for Application No. 09702189.3 dated Dec. 28, 2011 (5 pages).
European Patent Office Action for Application No. 09790775.2 dated Oct. 24, 2011 (5 pages).
European Patent Office Search Report for Application No. 15002893.4 dated Jun. 27, 2016 (5 pages).
Extended European Search Report for European Patent Application No. 12007093.3 dated Nov. 23, 2012 (5 pages).
European Patent Office Action for Application No. 12007093.3 dated Mar. 26, 2014 (4 pages).
European Patent Office Action for Application No. 12007093.3 dated Aug. 23, 2013 (5 pages).
European Patent Office Action for Application No. 12007092.5 dated Nov. 23, 2012 (5 pages).
Extended European Search Report for European Patent Application No. 12007089.1 dated Nov. 23, 2012 (5 pages).
European Search Report for European Application No. 18160338.2 dated May 25, 2018 (6 pages).
Examination Report from the Australian Patent Office for Application No. 2008205047 dated Nov. 26, 2012 (6 pages).
Examination Report from the Australian Patent Office for Application No. 2009273932 dated Mar. 13, 2013 (3 pages).
Examination Report from the Australian Patent Office for Application No. 2009273932 dated Jun. 6, 2014 (2 pages).
Fox et al., 19F and 13C GIAO-NMR chemical shifts for the identification of perfluoro-quinoline and -isoquinoline derivatives. Journal of Fluorine Chemistry, 155, pp. 62-71 (2013).
Foye, Foye's Principles of Medicinal Chemistry, 5th Edition (2002) Lippencott, Williams, Wilkins, p. 59-61.
Gingras et al., "In Synthesis and evaluation of 4-(1-aminoalkyl)-N-(4-pyridyl)-cyclohexanecarboxamides as Rho-kinase inhibitors and neurite outgrowth promoters," Bioorganic & Medicinal Chemistry Letters, 2004, vol. 14, pp. 4931-4934.
Golub, T.R. et al., "Molecular classification of cancer: class discovery and class prediction by gene expression monitoring," Science (1999) 286:531-537.

(56) References Cited

OTHER PUBLICATIONS

Guha et al., Solid supported rhodium(0) nanoparticles: an efficient catalyst for chemo- and regio-selective transfer hydrogenation of nitroarenes to anilines under microwave irradiation. Tetradedron Letters, 55:2912-2916 (2014).
Hackam, A.S. et al., "The Wnt Signaling Pathway in Retinal Degenerations", IUBMB Life (2005) 57(6):381-388.
Hazeldine, S.T. et al., "II. Synthesis and biological evaluation of some bioisosteres and cogeners of the anti tumour agent, 2{4[7-chloro-2-quinoxalinyl)oxy ]phenoxy }propionic acid (XK469)," J. Med. Chem. (2002) 45:3130-3137.
He et al., "Further structure-activity relationship studies of piperidine-based monoamine transporter inhibitors: effects of piperidine ring stereochemistry on potency. Identification of norepinephrine transporter selective ligands and broad-spectrum transporter inhibitors". J. Med. Chem. 48 (25): 7970-9 (2005).
Helal, C.J. et al., "Discovery and SAR of 2-aminothiazole inhibitors of cyclin-dependent kinase 5/p25 as a potential treatment for Alzheimer's disease," Bioorg. Med. Chem. (2004) 14(22):5521-5525.
Helzner, "Bright New Ideas in Glaucoma Treatment" (2013) Retrieved from the Internet: URL:http://mydigimag.rrd.com.
Hu, E. et al., "Rho kinase as potential therapeutic target for cardiovascular diseases: opportunities and challenges," Exp. Opin. Ther. Targets (2005) 9:715-736.
Inouye, Y. et al., "The Absolute Configurations of TRANS-1,2 Cyclopropanedicarboxylic Acid and TRANS-2-Phenylcyclopropanecarboxylic Acid", Int'l. J. Org. Chem. (1964) 20(5)1695-1699.
International Search Report and Written Opinion for Application No. PCT/US2015/61177 dated Feb. 2, 2016 (16 pages).
International Preliminary Examination Report for Application No. PCT/US2006/026947 dated Jan. 24, 2008 (10 pages).
International Preliminary Report on Patentability for Application No. PCT/US08/50374 dated Jul. 14, 2009 (12 pages).
International Search Report and Written Opinion for Application No. PCT/US2006/026976 dated Feb. 15, 2007 (14 pages).
International Search Report and Written Opinion for Application No. PCT/US2007/078343 dated Apr. 15, 2008 (12 pages).
International Search Report and Written Opinion for Application No. PCT/US2009/031117 dated Sep. 24, 2009 (13 pages).
International Search Report and Written Opinion for Application No. PCT/US2009/051569 dated May 20, 2010 (11 pages).
International Search Report and Written Opinion for Application No. PCT/US2010/022246 dated Nov. 10, 2010 (7 pages).
International Search Report and Written Opinion for Application No. PCT/US2010/33316 dated Jul. 14, 2010 (10 pages).
International Search Report and Written Opinion for Application No. PCT/US2010/33317 dated Aug. 17, 2010 (10 pages).
International Search Report and Written Opinion for Application No. PCT/US2014/029335, dated Jul. 2, 2014 (11 pages).
International Search Report for Application No. PCT/US08/50374 dated Oct. 28, 2008 (7 pages).
International Search Report for Application No. PCT/US2006/026947 dated Nov. 17, 2006 (4 pages).
Invitation to Pay Additional Fees and Partial International Search Report for International Application No. PCT/US2009/051569 dated Oct. 15, 2009 (4 pages).
International Search Report and Written Opinion for International Application No. PCT/US2017/049473 dated Nov. 30, 2017 (15 pages).
"Cancer", MedlinePlus (retrieved Jul. 6, 2007) 10 pages, http://www.nlm.nih.gov/medlineplus/cancer.html.
Anonymous, "Aerie Pharmaceuticals, Inc. Gets Good News on Glaucoma Treatment" (Feb. 11, 2012) Retrieved from the Internet: URL:http://www.biospace.com.
Australian Patent Examination Report No. 1 for Application No. 2009206075 dated Jan. 29, 2013 (3 pages).
Australian Patent Examination Report for Application No. 2016201754 dated Oct. 19, 2016 (4 pages).
Australian Patent Examination Report No. 1 for Application No. 2010241996 dated Apr. 1, 2015 (4 pages).
Australian Patent Office Action for Application No. 2010241996 dated Mar. 21, 2016 (3 pages).
Banker, G.S. et al., Modern Pharmaceutics, Marcel Dekker, Inc., New York, (1979) Chapters 9 and 10.
Basu et al., Ultrasound-promoted highly efficient reduction of aromatic nitro compounds to the aromatic amines by samarium/ammonium chloride. Tetrahedron Letters, 41:5603-5606 (2000).
Berge et al, 1977, "Pharmaceutically Acceptable Salts." J. Pharm. Sci. vol. 66, pp. 1-19.
Bird, G.J. et al., "N-methyl as a bioisostere for the oxygen link between the aromatic rings of aryloxyphenoxypropionate herbicides," Bioorg. Med. Chem. Lett. (1997) 7:1489-1492.
Blough BE, Keverline KI, Nie Z, Navarro H, Kuhar MJ, Carroll FI (2002). "Synthesis and transporter binding properties of 3beta-[4'-(phenylalkyl, phenylalkenyl, and phenylalkynyl) phenyltropane]-2beta-carboxylic acid methyl esters: evidence of a remote phenyl binding domain on the dopamine transporter". J. Med. Chem. 45 (18):4029-37.
C.T.F.A. Cosmetic Ingredient Handbook, "Surfactants—Emulsifying Agents", Second Edition, The Cosmetic, Toiletry, and Fragrance Association, New York, Wenninger, J.A. et al., eds. (1992) 587-592.
Calmes et al., Asymmetric Synthesis of (S)-beta^2-Homoarylglycines. Eur. J. Org. Chem. 2000, 2459-2466.
Canadian Patent Office Action for Application No. 2,731,869 dated Jun. 9, 2015 (3 pages).
Canadian Patent Office Action for Application No. 2,731,869 dated Feb. 18, 2016 (4 pages).
Canadian Patent Office Action for Application No. 2,760,562 dated Feb. 2, 2015 (4 pages).
Canadian Patent Office Action for Application No. 2,760,562 dated Jul. 3, 2015 (3 pages).
Canadian Patent Office Action for Application No. 2,712,443 dated Dec. 27, 2013 (3 pages).
Capdeville, R. et al., "Glivec (STI571, IMATINIB), A Rationally Developed, Targeted Anticancer Drug", Nature Reviews Drug Discovery (2002) 1:493-502.
Chen, P. et al., "Identification of novel and potent isoquinoline aminooxazole-based IMPDH inhibitors," Bioorg. Med. Chem. Lett. (2003) 13(7)1345-1348.
Cheung et al., N-methylamino acids in peptide synthesis. V. The syntesis of N-tert-butyloxycarbonyl, N-methylamino acids by N-methylation. Can. J. Chem. 1977, 55,906-910.
European Search Report for European Patent Application No. 18206195.2 dated Feb. 11, 2019 (10 pages).
International Search Report and Written Opinion dated Aug. 23, 2018 for International Application No. PCT/US2018/025494 filed on Mar. 30, 2018.
U.S. Appl. No. 16/138,837, filed Sep. 21, 2018.
Al-Rashida et al., Diarylsulfonamides and their bioisosteres as dual inhibitors of alkaline phosphatase and carbonic anhydrase: Structure activity/relationship and molecular modelling studies. Bioorganic & Medicinial Chemistry, vol. 23, Issue 10, pp. 2435-2444 (2015).
International Search Report and Written Opinion dated Nov. 15, 2019, for International Patent Application Serial No. PCT/US2019/051136 filed on Sep. 13, 2019.
International Search Report and Written Opinion dated Jul. 25, 2019, for International Patent Application Serial No. PCT/US2019/024954 filed on Mar. 29, 2019.
International Patent Application Serial No. PCT/US2019/051136 filed on Sep. 13, 2019.
Donegan et al., Discovery of molecular therapeutics for glaucoma: Challenges, successes, and promising directions. Journal of Medicinal Chemistry, vol. 59, Issue 3, pp. 788-809 (2016).
U.S. Appl. No. 16/435,254, filed Jun. 7, 2019.
U.S. Appl. No. 16/570,849, filed Sep. 13, 2019.
U.S. Appl. No. 16/680,359, filed Nov. 11, 2019.
U.S. Appl. No. 16/712,186, filed Dec. 12, 2019.

* cited by examiner

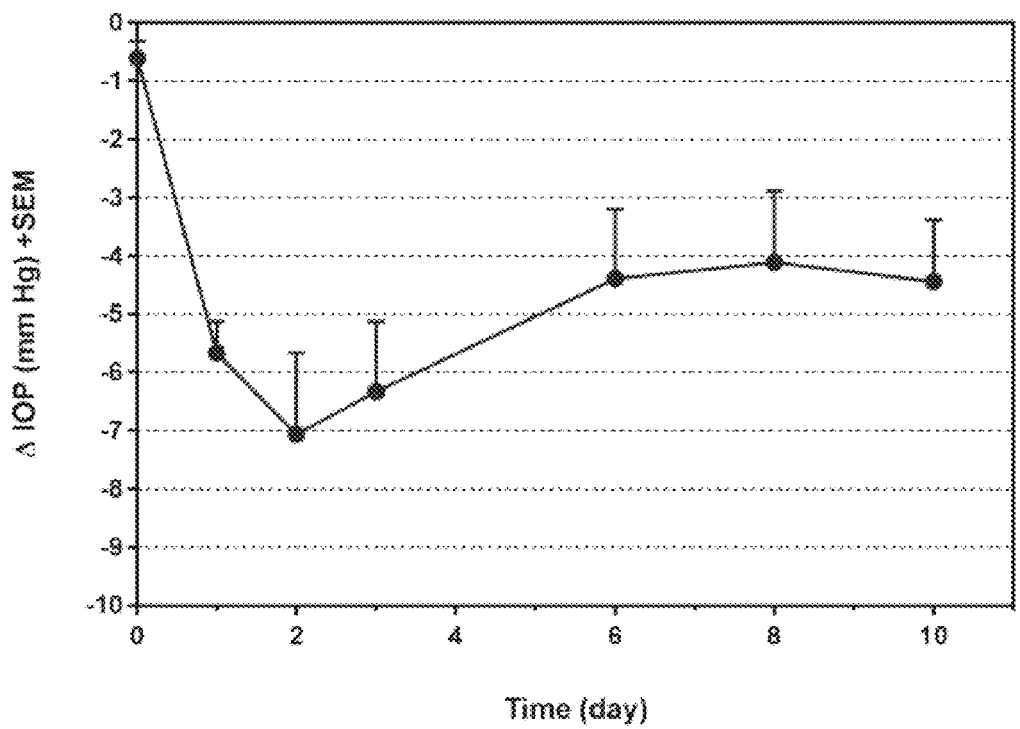

ARYL CYCLOPROPYL-AMINO-ISOQUINOLINYL AMIDE COMPOUNDS

RELATED APPLICATIONS

This application claims priority to U.S. Provisional Patent Application No. 62/643,131, filed on Mar. 14, 2018, and U.S. Provisional Patent Application No. 62/480,239, filed on Mar. 31, 2017, the entire contents of each of the U.S. applications, and each of the U.S. patents and each of the U.S. publications issued therefrom, are herein incorporated by reference.

SEQUENCE LISTING

This application contains a sequence listing having the filename 1959002-00112_ST25.txt, which is 706 bytes in size, and was created on Mar. 29, 2018. The entire content of this sequence listing is herein incorporated by reference.

FIELD OF THE INVENTION

The present disclosure relates to amino isoquinolinyl amide compounds that affect the function of kinases and other proteins in a cell and that are useful as therapeutic agents or with therapeutic agents. In particular, these compounds are useful in the treatment of eye diseases such as glaucoma and retinal diseases, as anti-inflammatory agents, for the treatment of cardiovascular diseases, and for diseases characterized by abnormal growth, such as cancers.

BACKGROUND

A variety of hormones, neurotransmitters and biologically active substances control, regulate or adjust the functions of living bodies via specific receptors located in cell membranes. Many of these receptors mediate the transmission of intracellular signals by activating guanine nucleotide-binding proteins (G proteins) to which the receptor is coupled. Such receptors are generically referred to as G-protein coupled receptors (GPCRs) and include, among others, α-adrenergic receptors, β-adrenergic receptors, opioid receptors, cannabinoid receptors and prostaglandin receptors. The biological effects of activating or inhibiting these receptors is not direct, but is mediated by a host of intracellular proteins. The importance of these secondary proteins has been recognized and modulation of this class is now being investigated as intervention points in disease states. One of the most important classes of these downstream effectors is the "kinase" class.

The various kinases play important roles in the regulation of various physiological functions. For example, kinases have been implicated in a number of disease states, including, but not limited to: cardiac indications such as angina pectoris, essential hypertension, myocardial infarction, supraventricular and ventricular arrhythmias, congestive heart failure, atherosclerosis, renal failure, diabetes, respiratory indications such as asthma, chronic bronchitis, bronchospasm, emphysema, airway obstruction, upper respiratory indications such as rhinitis, seasonal allergies, inflammatory disease, inflammation in response to injury, rheumatoid arthritis. The importance of p38 MAPK inhibitors in particular as new drugs for rheumatoid arthritis is reflected by the large number of compounds that has been developed over the last years (J. Westra and P. C. Limburg Mini-Reviews in Medicinal Chemistry Volume 6, Number 8, August 2006). Other conditions include chronic inflammatory bowel disease, glaucoma, hypergastrinemia, gastrointestinal indications such as acid/peptic disorder, erosive esophagitis, gastrointestinal hypersecretion, mastocytosis, gastrointestinal reflux, peptic ulcer, Zollinger-Ellison syndrome, pain, obesity, bulimia nervosa, depression, obsessive-compulsive disorder, organ malformations (e.g., cardiac malformations), neurodegenerative diseases such as Parkinson's Disease and Alzheimer's Disease, multiple sclerosis, Epstein-Barr infection and cancer (*Nature Reviews Drug Discovery* 2002, 1: 493-502). In other disease states, the role of kinases is only now becoming clear. The retina is a complex tissue composed of multiple interconnected cell layers, highly specialized for transforming light and color into electrical signals that are perceived by the brain. Damage or death of the primary light-sensing cells, the photoreceptors, results in devastating effects on vision. Despite the identification of numerous mutations that cause inherited retinal degenerations, the cellular and molecular mechanisms leading from the primary mutations to photoreceptor apoptosis are not well understood, but may involve the wnt pathway (A S Hackam "The Wnt Signaling Pathway in Retinal Degeneration" *IUBMB Life* Volume 57, Number 6/June 2005).

The success of the tyrosine-kinase inhibitor STI571 (Gleevec) in the treatment of chronic myelogenous leukemia (*Nature Reviews Drug Discovery* 2003, 2: 296-313) has spurred considerable efforts to develop other kinase inhibitors for the treatment of a wide range of other cancers (*Nature Reviews Cancer* 2003, 3: 650-665). The balance between the initiation and the inactivation of intracellular signals determines the intensity and duration of the response of the receptors to stimuli such as agonists. When desensitization occurs, the mediation or regulation of the physiological function mediated or regulated by the G proteins to which the receptors are coupled is reduced or prevented. For example, when agonists are administered to treat a disease or condition by activation of certain receptors, the receptors relatively quickly become desensitized from the action of the GRKs such that agonist administration may no longer result in therapeutic activation of the appropriate receptors. At that point, administration of the agonist no longer enables sufficient or effective control of or influence on the disease or condition intended to be treated.

Janus Kinases (or JAK) are a family of cytoplasmic protein tyrosine kinases. The JAK family plays a role in the cytokine-dependent regulation of proliferation and function of cells involved in immune response. Currently, there are four JAK family members are known JAK1, JAK2, JAK3, and TYK2. The JAKs usually associate with cytokine receptors in pairs as homodimers or heterodimers. Specific cytokines are associated with specific JAK pairings. Each of the four members of the JAK family is implicated in the signaling of at least one of the cytokines associated with inflammation. Binding of cytokine to a JAK-dependent cytokine receptor induces receptor dimerization which results in phosphorylation of tyrosine residues on the JAK kinase, effecting JAK activation. Phosphorylated JAKs, in turn, bind and phosphorylate various STAT proteins which dimerize, internalize in the cell nucleus and directly modulate gene transcription, leading, among other effects, to the downstream effects associated with inflammatory disease.

In view of the role that kinases play in many disease states, there is an urgent and continuing need for small molecule ligands which inhibit or modulate the activity of kinases. Without wishing to be bound by theory, it is thought that modulation of the activity of kinases, in particular ROCK and JAK kinases, by the compounds of the present disclosure is, at least in part, responsible for their beneficial effects.

BRIEF DESCRIPTION OF THE FIGURES

FIG. 1 shows changes (reductions) in rabbit IOP achieved via intracameral injection of a formulation of a (1R,2R)—N-(fluoroisoquinolin-6-yl)-2-(4-(pyridinylmethyl) phenyl) cyclopropane-1-carboxamide.

SUMMARY

In an aspect, the present disclosure provides a compound according to Formula (I):

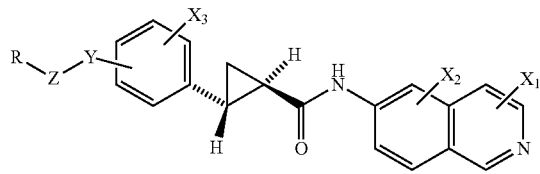

(I)

or tautomers, stereoisomers and pharmaceutically acceptable salts thereof,
wherein:
$X_1$, $X_2$ and $X_3$ are independently H, halogen, nitrile, hydroxyl, or $C_{1-6}$ alkyl;
Y is —$NR^{N1}S(O)_2$—, —$NR^{N1}C(O)$—, —$O(CR^1_2)_n$—, —$NR^{N1}(CR^1_2)_m$—, —C(O)O—, —OC(O)—, —$S(O)_2$—, —C(O)—, —$NR^{N1}C(O)O(CR^1_2)_n$—, —(R)O— $C_{1-6}$ alkylene, aryl, or heteroaryl;
Z is a direct bond or $C_{1-6}$ alkylene;
R is H, halogen, cyano, $OR^3$, $C_{1-6}$ alkyl, amino, cycloalkyl, heterocyclyl, aryl, or heteroaryl, carbonyl, or R may form a ring of 5 to 7 member atoms with $R^{N1}$ or $R^1$, wherein the ring may contain up to 2 heteroatoms selected from N, O, and S, the ring being either saturated or unsaturated;
$R^{N1}$ is H or $C_{1-6}$ alkyl, $NH_2$, $SO_2$-aryl, $SO_2$-heteroaryl, morpholine or piperidine, or forms a ring with R;
$R^1$ is H, F, or Me or forms a ring with R;
$R^3$ is H or $C_{1-6}$ alkyl;
n is an integer from 0 to 6; and
m is an integer from 1 to 6.

In an aspect, the present disclosure provides a compound according to Formula (Ia):

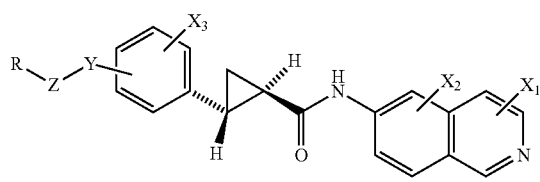

(Ia)

or tautomers, stereoisomers and pharmaceutically acceptable salts thereof,
wherein:
$X_1$, $X_2$ and $X_3$ are independently H, halogen, nitrile, hydroxyl, or $C_{1-6}$ alkyl;
Y is —$NR^{N1}S(O)_2$—, —$NR^{N1}C(O)$—, —$NR^{N1}(CR^1_2)_m$—, —$S(O)_2$—, —C(O)—, —$NR^{N1}C(O)O(CR^1_2)_n$—, or $C_{1-6}$ alkylene;
Z is a direct bond or $C_{1-6}$ alkylene;
R is H, halogen, cyano, $OR^3$, $C_{1-6}$ alkyl, amino, cycloalkyl, heterocyclyl, aryl, or heteroaryl, carbonyl, or R may form a ring of 5 to 7 member atoms with $R^{N1}$ or $R^1$, wherein the ring may contain up to 2 heteroatoms selected from N, O, and S, the ring being either saturated or unsaturated;
$R^{N1}$ is H or $C_{1-6}$ alkyl, $NH_2$, $SO_2$-aryl, $SO_2$-heteroaryl, morpholine or piperidine, or forms a ring with R;
$R^1$ is H, F, or Me or forms a ring with R;
$R^3$ is H or $C_{1-6}$ alkyl;
n is an integer from 0 to 6; and
m is an integer from 1 to 6.

In an aspect, the present disclosure provides a compound according to Formula (Ib):

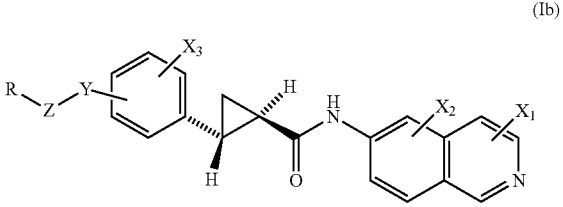

(Ib)

or tautomers, stereoisomers and pharmaceutically acceptable salts thereof,
wherein:
$X_1$, $X_2$ and $X_3$ are independently H, halogen, nitrile, hydroxyl, or $C_{1-6}$ alkyl;
Y is —$NR^{N1}S(O)_2$—, —$NR^{N1}C(O)$—, —$O(CR^1_2)_n$—, —$NR^{N1}(CR^1_2)_m$—, —C(O)O—, —OC(O)—, —$S(O)_2$—, —C(O)—, —$NR^{N1}C(O)O(CR^1_2)_n$—, —(R)O— $C_{1-6}$ alkylene, aryl, or heteroaryl
Z is a direct bond or $C_{1-6}$ alkylene;
R is halogen, cyano, $OR^3$, amino, cycloalkyl, heterocyclyl, aryl, or heteroaryl, or R may form a ring of 5 to 7 member atoms with $R^{N1}$ or $R^1$, wherein the ring may contain up to 2 heteroatoms selected from N, O, and S, the ring being either saturated or unsaturated;
$R^{N1}$ is H or $C_{1-6}$ alkyl, $NH_2$, $SO_2$-aryl, $SO_2$-heteroaryl, morpholine or piperidine, or forms a ring with R;
$R^1$ is H, F, or Me or forms a ring with R;
$R^3$ is H or $C_{1-6}$ alkyl;
n is an integer from 0 to 6; and
m is an integer from 1 to 6.

In an aspect, the present disclosure provides a compound according to Formula (Ic):

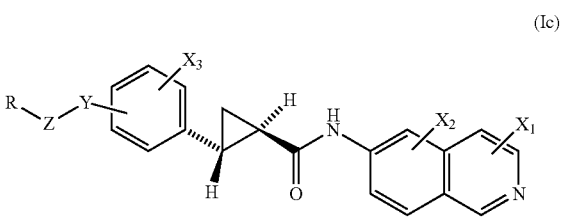

(Ic)

or tautomers, stereoisomers and pharmaceutically acceptable salts thereof, wherein:

$X_1$, $X_2$ and $X_3$ are independently H, halogen, nitrile, hydroxyl, or $C_{1-6}$ alkyl;

Y is —$NR^{N1}S(O)_2$—, —$NR^{N1}C(O)$—, —$O(CR^1_2)_n$—, —$NR^{N1}(CR^1_2)_m$—, —$C(O)O$—, —$OC(O)$—, —$S(O)_2$—, —$C(O)$—, —$NR^{N1}C(O)O(CR^1_2)_n$—, —(R)O— $C_{1-6}$ alkylene, aryl, or heteroaryl Z is a direct bond or $C_{1-6}$ alkylene;

R is H, halogen, cyano, $OR^3$, $C_{1-6}$ alkyl, amino, cycloalkyl, heterocyclyl, aryl, or heteroaryl, carbonyl, or R may form a ring of 5 to 7 member atoms with $R^{N1}$ or $R^1$, wherein the ring may contain up to 2 heteroatoms selected from N, O, and S, the ring being either saturated or unsaturated;

$R^{N1}$ is H or $C_{1-6}$ alkyl, $NH_2$, $SO_2$-aryl, $SO_2$-heteroaryl, morpholine or piperedine, or forms a ring with R;

$R^1$ is F, or Me or forms a ring with R;

$R^3$ is H or $C_{1-6}$ alkyl;

n is an integer from 0 to 6; and m is an integer from 1 to 6.

In an aspect, the present disclosure provides a compound according to Formula (Id):

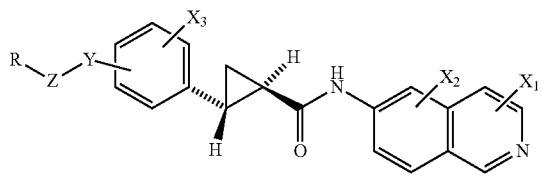

(Id)

or tautomers, stereoisomers and pharmaceutically acceptable salts thereof, wherein:

$X_1$, $X_2$ and $X_3$ are independently H, halogen, nitrile, hydroxyl, or $C_{1-6}$ alkyl;

Y is —$NR^{N1}S(O)_2$—, —$NR^{N1}C(O)$—, —$O(CR^1_2)_n$—, —$NR^{N1}(CR^1_2)_m$—, —$C(O)O$—, —$OC(O)$—, —$S(O)_2$—, —$C(O)$—, —$NR^{N1}C(O)O(CR^1_2)_n$—, —(R)O— $C_{1-6}$ alkylene, aryl, or heteroaryl Z is a direct bond or $C_{1-6}$ alkylene;

R is H, halogen, cyano, $OR^3$, $C_{1-6}$ alkyl, amino, cycloalkyl, heterocyclyl, aryl, or heteroaryl, carbonyl, or R may form a ring of 5 to 7 member atoms with $R^{N1}$ or $R^1$, wherein the ring may contain up to 2 heteroatoms selected from N, O, and S, the ring being either saturated or unsaturated;

$R^{N1}$ is H or $C_{1-6}$ alkyl, $NH_2$, $SO_2$-aryl, $SO_2$-heteroaryl, morpholine or piperidine, or forms a ring with R;

$R^1$ is H, F, or Me or forms a ring with R;

$R^3$ is H or $C_{1-6}$ alkyl;

n is 2, 3, 4, 5, or 6; and m is an integer from 1 to 6.

In an aspect, the present disclosure provides a compound is a compound of Formula (II):

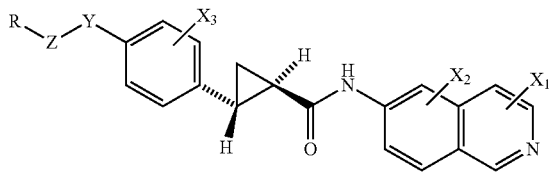

(II)

or tautomers, stereoisomers and pharmaceutically acceptable salts thereof, wherein:

$X_1$, $X_2$ and $X_3$ are independently H, halogen, nitrile, hydroxyl, or $C_{1-6}$ alkyl;

Y is —$NR^{N1}S(O)_2$—, —$NR^{N1}C(O)$—, —$O(CR^1_2)_n$—, —$NR^{N1}(CR^1_2)_m$—, —$C(O)O$—, —$OC(O)$—, —$S(O)_2$—, —$C(O)$—, —$NR^{N1}C(O)O(CR^1_2)_n$—, $C_{1-6}$ alkylene alkylene, aryl, or heteroaryl Z is a direct bond or $C_{1-6}$ alkylene;

R is H, halogen, cyano, $OR^3$, $C_{1-6}$ alkyl, amino, cycloalkyl, heterocyclyl, aryl, or heteroaryl, or R may form a ring of 5 to 7 member atoms with $R^{N1}$ or $R^1$, wherein the ring may contain up to 2 heteroatoms selected from N, O, and S, the ring being either saturated or unsaturated;

$R^{N1}$ is H or $C_{1-6}$ alkyl or forms a ring with R;

$R^1$ is H, F, or Me or forms a ring with R;

$R^3$ is H or $C_{1-6}$ alkyl;

n is an integer from 0 to 6; and m is an integer from 1 to 6.

In an aspect, the present disclosure provides a compound is a compound of Formula (III):

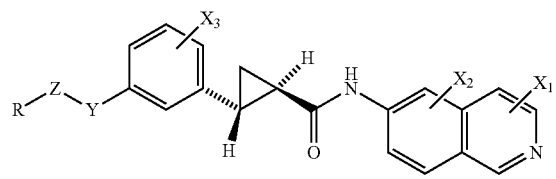

(III)

or tautomers, stereoisomers and pharmaceutically acceptable salts thereof, wherein:

$X_1$, $X_2$ and $X_3$ are independently H, halogen, nitrile, hydroxyl, or $C_{1-6}$ alkyl;

Y is —$NR^{N1}S(O)_2$—, —$NR^{N1}C(O)$—, —$O(CR^1_2)_n$—, —$NR^{N1}(CR^1_2)_m$—, —$C(O)O$—, —$OC(O)$—, —$S(O)_2$—, —$C(O)$—, —$NR^{N1}C(O)O(CR^1_2)_n$—, $C_{1-6}$ alkylene, aryl, or heteroaryl Z is a direct bond or $C_{1-6}$ alkylene;

R is H, halogen, cyano, $OR^3$, $C_{1-6}$ alkyl, amino, cycloalkyl, heterocyclyl, aryl, or heteroaryl, or R may form a ring of 5 to 7 member atoms with $R^{N1}$ or $R^1$, wherein the ring may contain up to 2 heteroatoms selected from N, O, and S, the ring being either saturated or unsaturated;

$R^{N1}$ is H or $C_{1-6}$ alkyl or forms a ring with R;

$R^1$ is H, F, or Me or forms a ring with R;

$R^3$ is H or $C_{1-6}$ alkyl;

n is an integer from 0 to 6; and m is an integer from 1 to 6.

In an aspect, the present disclosure provides a compound according to Formula (IV):

(IV)

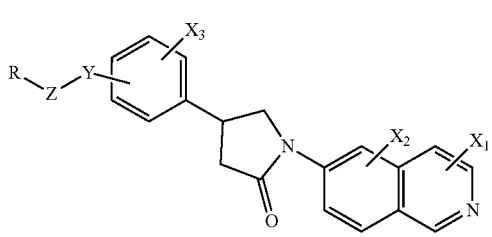

or tautomers, stereoisomers and pharmaceutically acceptable salts thereof,
wherein:
$X_1$, $X_2$ and $X_3$ are independently H, halogen, nitrile, hydroxyl, or $C_{1-6}$ alkyl;
Y is —$NR^{N1}S(O)_2$—, —$NR^{N1}C(O)$—, —$O(CR^1_2)_n$—, —$NR^{N1}(CR^1_2)_m$—, —$C(O)O$—, —$OC(O)$—, —$S(O)_2$—, —$C(O)$—, —$NR^{N1}C(O)O(CR^1_2)_n$—, $C_{1-6}$ alkylene, alkylene, aryl, or heteroaryl
Z is a direct bond or $C_{1-6}$ alkylene;
R is H, halogen, cyano, $OR^3$, $C_{1-6}$ alkyl, amino, cycloalkyl, heterocyclyl, aryl, or heteroaryl, or R may form a ring of 5 to 7 member atoms with $R^{N1}$ or $R^1$, wherein the ring may contain up to 2 heteroatoms selected from N, O, and S, the ring being either saturated or unsaturated;
$R^{N1}$ is H or $C_{1-6}$ alkyl or forms a ring with R;
$R^1$ is H, F, or Me or forms a ring with R;
$R^3$ is H or $C_{1-6}$ alkyl;
n is an integer from 0 to 6; and
m is an integer from 1 to 6.

In an aspect, the present disclosure provides a compound according to Formula (VII):

(VII)

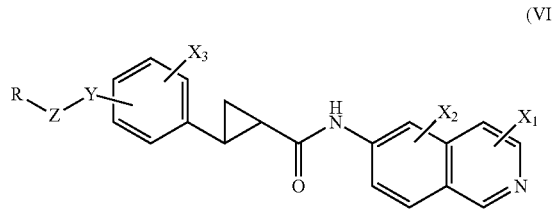

or tautomers, stereoisomers and pharmaceutically acceptable salts thereof,
wherein:
$X_1$, $X_2$ and $X_3$ are independently H, halogen, nitrile, hydroxyl, or $C_{1-6}$ alkyl;
Y is —$NR^{N1}S(O)_2$—;
Z is a direct bond or $C_{1-6}$ alkylene;
R is H, halogen, cyano, $OR^3$, $C_{1-6}$ alkyl, amino, cycloalkyl, heterocycylaryl, or heteroaryl, or R may form a ring of 5 to 7 member atoms with $R^{N1}$ or $R^1$, wherein the ring may contain up to 2 heteroatoms selected from N, O, and S, the ring being either saturated or unsaturated;
$R^{N1}$ is H or $C_{1-6}$ alkyl or forms a ring with R;
$R^1$ is H, F, or Me or forms a ring with R; $R^3$ is H or $C_{1-6}$ alkyl;
n is an integer from 0 to 6; and
m is an integer from 1 to 6.

In an aspect, the present disclosure provides a compound according to Formula (VIII):

(VIII)

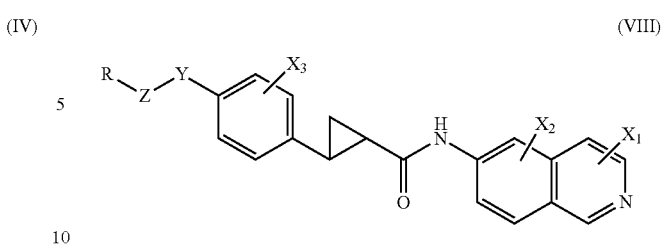

or tautomers, stereoisomers and pharmaceutically acceptable salts thereof,
wherein:
$X_1$, $X_2$ and $X_3$ are independently H, halogen, nitrile, hydroxyl, or $C_{1-6}$ alkyl;
Y is —$NR^{N1}S(O)_2$—;
Z is a direct bond or $C_{1-6}$ alkylene;
R is H, halogen, cyano, $OR^3$, $C_{1-6}$ alkyl, amino, cycloalkyl, heterocycyl, aryl, or heteroaryl, or R may form a ring of 5 to 7 member atoms with $R^{N1}$ or $R^1$, wherein the ring may contain up to 2 heteroatoms selected from N, O, and S, the ring being either saturated or unsaturated;
$R^{N1}$ is H or $C_{1-6}$ alkyl or forms a ring with R;
$R^1$ is H, F, or Me or forms a ring with R;
$R^3$ is H or $C_{1-6}$ alkyl;
n is an integer from 0 to 6; and
m is an integer from 1 to 6.

In an aspect, the present disclosure provides a compound according to Formula (IX):

(IX)

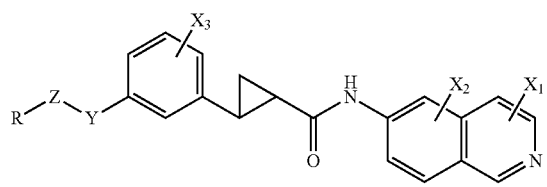

or tautomers, stereoisomers and pharmaceutically acceptable salts thereof,
wherein:
$X_1$, $X_2$ and $X_3$ are independently H, halogen, nitrile, hydroxyl, or $C_{1-6}$ alkyl;
Y is —$NR^{N1}S(O)_2$—;
Z is a direct bond or $C_{1-6}$ alkylene;
R is H, halogen, cyano, $OR^3$, $C_{1-6}$ alkyl, amino, cycloalkyl, heterocyclyl, aryl, or heteroaryl, or R may form a ring of 5 to 7 member atoms with $R^{N1}$ or $R^1$, wherein the ring may contain up to 2 heteroatoms selected from N, O, and S, the ring being either saturated or unsaturated;
$R^{N1}$ is H or $C_{1-6}$ alkyl or forms a ring with R;
$R^1$ is H, F, or Me or forms a ring with R;
$R^3$ is H or $C_{1-6}$ alkyl;
n is an integer from 0 to 6; and
m is an integer from 1 to 6.

In one aspect, provided herein are compounds of Formula (X):

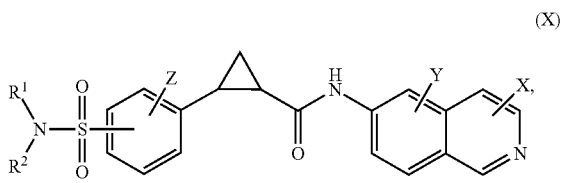

or a pharmaceutically acceptable salt thereof,
wherein, $R^1$ is H, —$C_{1-6}$ alkyl, —$C_{1-6}$ haloalkyl, aryl, heteroaryl, —($C_{1-6}$ alkyl)-pyridinyl, —($C_{1-6}$ alkyl)-N($R^3$)$R^4$, —($C_{1-6}$ alkyl)-heterocyclyl or heterocycloalkyl;

$R^2$ is H, —$C_{1-6}$ alkyl, —$C_{1-6}$ haloalkyl, aryl, heteroaryl, —($C_{1-6}$ alkyl)-pyridinyl, —($C_{1-6}$ alkyl)-N($R^3$)$R^4$, —($C_{1-6}$ alkyl)-heterocyclyl or heterocycloalkyl;

or $R^1$ and $R^2$, together with the nitrogen to which they are attached, form a heterocyclyl;

$R^3$ is H, $C_{1-6}$ alkyl or —$C_{1-6}$ haloalkyl;

$R^4$ is H, $C_{1-6}$ alkyl or —$C_{1-6}$ haloalkyl;

X is H, $C_{1-6}$ alkyl, —$C_{1-6}$ haloalkyl, halogen or hydroxyl;

Y is H, $C_{1-6}$ alkyl, —$C_{1-6}$ haloalkyl, halogen or hydroxyl; and

Z is H, $C_{1-6}$ alkyl, —$C_{1-6}$ haloalkyl, halogen or hydroxyl.

In an aspect, the present disclosure provides a pharmaceutical composition comprising a compound according to the present disclosure and a pharmaceutically acceptable excipient.

In an aspect, the present disclosure provides a method of treating an ocular disorder in a subject in need of treatment, comprising administering to the subject a compound or composition according to the present disclosure.

In an aspect, the present disclosure provides a method of reducing intraocular pressure in a subject in need thereof, comprising administering to an eye of the subject a compound or composition according to the present disclosure.

In an aspect, the present disclosure provides a kit comprising a compound or composition of according to the present disclosure and instructions for use.

DETAILED DESCRIPTION

Publications and patents are referred to throughout this disclosure. All U.S. Patents cited herein are hereby incorporated by reference. All percentages, ratios, and proportions used herein are percent by weight unless otherwise specified.

Arylcyclopropyl amino-isoquinolinyl amides are provided.

"Alkyl" refers to a saturated aliphatic hydrocarbon including straight chain and branched chain groups. "Alkyl" may be exemplified by groups such as methyl, ethyl, n-propyl, isopropyl, n-butyl and the like. Alkyl groups may be substituted or unsubstituted. More than one substituent may be present. Substituents may also be themselves substituted. When substituted, the substituent group is preferably but not limited to $C_1$-$C_4$ alkyl, aryl, heteroaryl, amino, thioalkyl, cyano, halogen, alkoxy or hydroxyl. "$C_1$-$C_4$ alkyl" refers to alkyl groups containing one to four carbon atoms.

"Alkenyl" refers to an unsaturated aliphatic hydrocarbon moiety including straight chain and branched chain groups. Alkenyl moieties must contain at least one alkene. "Alkenyl" may be exemplified by groups such as ethenyl, n-propenyl, isopropenyl, n-butenyl and the like. Alkenyl groups may be substituted or unsubstituted. More than one substituent may be present. When substituted, the substituent group is preferably alkyl, halogen or alkoxy. Substituents may also be themselves substituted. Substituents can be placed on the alkene itself and also on the adjacent member atoms or the alkynyl moiety. "$C_2$-$C_4$ alkenyl" refers to alkenyl groups containing two to four carbon atoms.

"Alkynyl" refers to an unsaturated aliphatic hydrocarbon moiety including straight chain and branched chain groups. Alkynyl moieties must contain at least one alkyne. "Alkynyl" may be exemplified by groups such as ethynyl, propynyl, n-butynyl and the like. Alkynyl groups may be substituted or unsubstituted. More than one substituent may be present. Substituents are not on the alkyne itself but on the adjacent member atoms of the alkynyl moiety. When substituted, the substituent group is preferably alkyl, amino, cyano, halogen, alkoxyl or hydroxyl. Substituents may also be themselves substituted. "$C_2$-$C_4$ alkynyl" refers to alkynyl groups containing two to four carbon atoms.

"Acyl" or "carbonyl" refers to the group —C(O)R wherein R is hydrogen, alkyl, alkenyl, alkynyl, aryl, heteroaryl, carbocyclic, heterocarbocyclic, $C_1$-$C_4$ alkyl aryl or $C_1$-$C_4$ alkyl heteroaryl. $C_1$-$C_4$ alkylcarbonyl refers to a group wherein the carbonyl moiety is preceded by an alkyl chain of 1-4 carbon atoms.

"Alkoxy" refers to the group —O—R wherein R is alkyl, alkenyl, acyl, alkyl alkenyl, alkyl alkynyl, aryl, carbocyclic, heterocarbocyclic, heteroaryl, $C_1$-$C_4$ alkyl aryl or $C_1$-$C_4$ alkyl heteroaryl.

"Amino" refers to the group —NR'R' wherein each R' is, independently, hydrogen, amino, hydroxyl, alkoxyl, alkyl, aryl, cycloalkyl, heterocycloalkyl, heteroaryl, $C_1$-$C_4$ alkyl aryl or $C_1$-$C_4$ alkyl heteroaryl. The two R' groups may themselves be linked to form a ring. The R' groups may themselves be further substituted, in which case the group also known as guanidinyl is specifically contemplated under the term 'amino".

"Aryl" refers to an aromatic carbocyclic group. "Aryl" may be exemplified by phenyl. The aryl group may be substituted or unsubstituted. More than one substituent may be present. Substituents may also be themselves substituted. When substituted, the substituent group is preferably but not limited to alkyl, alkenyl, heteroaryl, acyl, carboxyl, sulfonyl, sulfonylamino, thioalkyl, trifluoromethyl, carbonylamino, amino, cyano, halogen, or hydroxyl.

"Carboxyl" refers to the group —C(=O)O—$C_1$-$C_4$ alkyl.

"Carbonyl" refers to the group —C(O)R wherein each R is, independently, hydrogen, alkyl, aryl, cycloalkyl; heterocycloalkyl; heteroaryl, $C_1$-$C_4$ alkyl aryl or $C_1$-$C_4$ alkyl heteroaryl.

"Carbonylamino" refers to the group —C(O)NR'R' wherein each R' is, independently, hydrogen, alkyl, aryl, cycloalkyl; heterocycloalkyl; heteroaryl, $C_1$-$C_4$ alkyl aryl or $C_1$-$C_4$ alkyl heteroaryl. The two R' groups may themselves be linked to form a ring.

"$C_1$-$C_4$ alkyl aryl" refers to $C_1$-$C_4$ alkyl groups having an aryl substituent such that the aryl substituent is bonded through an alkyl group. "$C_1$-$C_4$ alkyl aryl" may be exemplified by benzyl.

"$C_1$-$C_4$ alkyl heteroaryl" refers to $C_1$-$C_4$ alkyl groups having a heteroaryl substituent such that the heteroaryl substituent is bonded through an alkyl group.

"Carbocyclic group" or "cycloalkyl" means a saturated or unsaturated hydrocarbon ring. Carbocyclic groups are monocyclic, or are fused, spiro, or bridged bicyclic ring systems. Monocyclic carbocyclic groups contain 3 to 10 carbon atoms, preferably 4 to 7 carbon atoms, and more preferably 5 to 6 carbon atoms in the ring. Bicyclic carbocyclic groups contain 8 to 12 carbon atoms, preferably 9 to 10 carbon atoms in the ring. Carbocyclic groups may be substituted or unsubstituted. More than one substituent may be present. Substituents may also be themselves substituted. Suitable substituents include halogen, cyano, alkoxyl, amino, trifluoromethyl, and trifluoromethoxyl. Preferred carbocyclic groups include cyclopropyl, cyclobutyl, cyclopentyl, cyclohexyl, cyclohexenyl, and cycloheptyl. The most preferred carbocyclic groups are cyclohexyl and cyclopentyl. Carbocyclic groups are not aromatic.

"Halogen" refers to fluoro, chloro, bromo or iodo moieties. Preferably, the halogen is fluoro, chloro, or bromo.

"Heteroaryl" or "heteroaromatic" refers to a monocyclic or bicyclic aromatic carbocyclic radical having one or more heteroatoms in the carbocyclic ring. Heteroaryl may be substituted or unsubstituted. More than one substituent may be present. When substituted, the substituents may themselves be substituted. Preferred but non limiting substituents are halogen, cyano, alkoxyl, amino, trifluoromethyl, trifluoromethoxyl, aryl, $C_1$-$C_4$ alkylaryl, hydroxyl, carboxyl, carbonylamino, or $C_1$-$C_4$ alkyl. Preferred heteroaromatic groups include benzo[b]thiophenyl, pyrrolidyl, benzofuranyl, isoquinolinyl, imidazolyl, quinolinyl, cinnolinyl, tetrazoyl, triazolyl, thienyl, thiazolyl, purinyl, pyrimidyl, pyridyl, and furanyl. More preferred heteroaromatic groups include isoquinolinyl, benzo[b]thiophenyl; thienyl, furanyl, tetrazoyl, triazolyl, and pyridyl.

"Heteroatom" means a polyvalent atom other than carbon in the ring of a heterocyclic group or a heteroaromatic group or the chain of a heterogeneous group. Preferably, heteroatoms are selected from the group consisting of nitrogen, sulfur, and oxygen atoms. Groups containing more than one heteroatom may contain different heteroatoms. Halogens are monovalent and thus are not considered heteroatoms in this sense, but have their own category.

"Heterocarbocyclic group" or "heterocycloalkyl" or "heterocyclic" means a saturated or unsaturated hydrocarbon ring containing at least one heteroatom. Heterocarbocyclic groups are monocyclic, or are fused, spiro, or bridged bicyclic ring systems. Monocyclic heterocarbocyclic groups contain 3 to 10 carbon atoms, preferably 4 to 7 carbon atoms, and more preferably 5 to 6 carbon atoms in the ring. Bicyclic heterocarbocyclic groups contain 8 to 12 carbon atoms, preferably 9 to 10 carbon atoms in the ring. Heterocarbocyclic groups may be substituted or unsubstituted. More than one substituent may be present. Substituents may also be themselves substituted. Suitable substituents include halogen, nitrile, hydroxyl, alkoxyl, amino, trifluoromethyl, and trifluoromethoxyl. Preferred heterocarbocyclic groups include epoxy, tetrahydrofuranyl, azacyclopentyl (or pyrrolidyl), azacyclohexyl, piperidyl, and homopiperidyl. More preferred heterocarbocyclic groups include pyrrolidyl, piperidyl, and homopiperidyl. The most preferred heterocarbocyclic group is piperidyl. Heterocarbocyclic groups are not aromatic.

"Hydroxy" or "hydroxyl" means a chemical entity that consists of —OH. Alcohols contain hydroxy groups. Hydroxy groups may be free or protected. An alternative name for hydroxy is hydroxyl.

"Linker" means a linear chain of n member atoms where n is an integer from 1 to 4.

"Member atom" means a carbon, nitrogen, oxygen or sulfur atom. Member atoms may be substituted up to their normal valence. If more than one stable valence is available for a member atom, e.g., sulfur, then all stable valences are contemplated. If substitution is not completely specified, the unspecified substituents required for valency are hydrogen.

"Ring" means a collection of member atoms that are cyclic. Rings may be carbocyclic, aromatic, or heterocyclic or heteroaromatic, and may be substituted or unsubstituted, and may be saturated or unsaturated. More than one substituent may be present. Ring junctions with the main chain may be fused or spirocyclic. Rings may be monocyclic or bicyclic. Rings contain at least 3 member atoms and at most 10 member atoms. Monocyclic rings may contain 3 to 7 member atoms and bicyclic rings may contain from 8 to 12 member atoms. Bicyclic rings themselves may be fused or spirocyclic.

"Thioalkyl" refers to the group —S-alkyl.

"Sulfonyl" refers to the —S(O)$_2$R' group wherein R' is alkoxy, alkyl, aryl, carbocyclic, heterocarbocyclic; heteroaryl, $C_1$-$C_4$ alkyl aryl or $C_1$-$C_4$ alkyl heteroaryl.

"Sulfonylamino" refers to the —S(O)$_2$NR'R' group wherein each R' is independently alkyl, aryl, heteroaryl, $C_1$-$C_4$ alkyl aryl or $C_1$-$C_4$ alkyl heteroaryl.

"Pharmaceutically acceptable carrier" means a carrier that is useful for the preparation of a pharmaceutical composition that is: generally compatible with the other ingredients of the composition, not deleterious to the recipient, and neither biologically nor otherwise undesirable.

"A pharmaceutically acceptable carrier" includes both one and more than one carrier. Embodiments include carriers for topical, ocular, parenteral, intravenous, intraperitoneal intramuscular, sublingual, nasal and oral administration. "Pharmaceutically acceptable carrier" also includes agents for preparation of aqueous dispersions and sterile powders for injection or dispersions.

"Excipient" as used herein includes physiologically compatible additives useful in preparation of a pharmaceutical composition. Examples of pharmaceutically acceptable carriers and excipients can for example be found in Remington Pharmaceutical Science, 16$^{th}$ Ed.

"Therapeutically effective amount" as used herein refers to a dosage of the compounds or compositions effective for influencing, reducing or inhibiting the activity of or preventing activation of a kinase. This term as used herein may also refer to an amount effective at bringing about a desired in vivo effect in an animal, preferably, a human, such as reduction in intraocular pressure.

"Administering" as used herein refers to administration of the compounds as needed to achieve the desired effect.

"Eye disease" as used herein includes, but is not limited to, glaucoma, allergy, cancers of the eye, neurodegenerative diseases of the eye, such as diabetic eye disease, macular degeneration (AMD), inflammation, and dry eye.

The term "disease or condition associated with kinase activity" is used to mean a disease or condition treatable, in whole or in part, by inhibition of one or more kinases.

The term "controlling the disease or condition" is used to mean changing the activity of one or more kinases to affect the disease or condition.

The term "contacting a cell" is used to mean contacting a cell in vitro or in vivo i.e. in a subject, such as a mammal, including humans, rabbits, cats and dogs.

Compounds

In an aspect, the compound according to Formula (I) is provided:

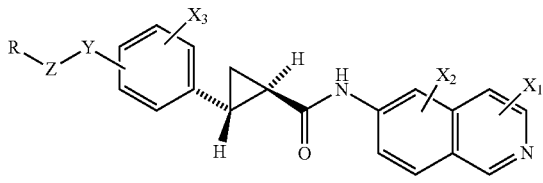

(I)

or tautomers, stereoisomers and pharmaceutically acceptable salts thereof,
wherein:
$X_1$, $X_2$ and $X_3$ are independently H, halogen, nitrile, hydroxyl, or $C_{1-6}$ alkyl;
Y is —$NR^{N1}S(O)_2$—, —$NR^{N1}C(O)$—, —$O(CR^1_2)_n$—, —$NR^{N1}(CR^1_2)_m$—, —$C(O)O$—, —$OC(O)$—, —$S(O)_2$—, —$C(O)$—, —$NR^{N1}C(O)O$—, $C_{1-6}$ alkylene, aryl, or heteroaryl;
Z is a direct bond or $C_{1-6}$ alkylene;
R is H, halogen, cyano, $OR^3$, $C_{1-6}$ alkyl, acyl, amino, cycloalkyl, heterocyclyl, aryl, or heteroaryl, or R may form a ring of 5 to 7 member atoms with $R^{N1}$ or $R^1$, wherein the ring may contain up to 2 heteroatoms selected from N, O, and S, the ring being either saturated or unsaturated;
$R^{N1}$ is H or $C_{1-6}$ alkyl or forms a ring with R;
$R^1$ is H, F, or Me or forms a ring with R;
$R^3$ is H or $C_{1-6}$ alkyl;
n is an integer from 0 to 6; and
m is an integer from 1 to 6.

In an aspect, the present disclosure provides a compound according to Formula (Ia):

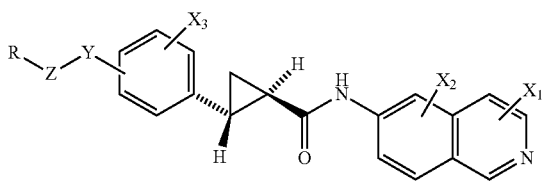

(Ia)

or tautomers, stereoisomers and pharmaceutically acceptable salts thereof,
wherein:
$X_1$, $X_2$ and $X_3$ are independently H, halogen, nitrile, hydroxyl, or $C_{1-6}$ alkyl;
Y is —$NR^{N1}S(O)_2$—, —$NR^{N1}C(O)$—, —$NR^{N1}(CR^1_2)_m$—, —$S(O)_2$—, —$C(O)$—, —$NR^{N1}C(O)O(CR^1_2)_n$—, or $C_{1-6}$ alkylene;
Z is a direct bond or $C_{1-6}$ alkylene;
R is H, halogen, cyano, $OR^3$, $C_{1-6}$ alkyl, amino, cycloalkyl, heterocyclyl, aryl, or heteroaryl, carbonyl, or R may form a ring of 5 to 7 member atoms with $R^{N1}$ or $R^1$, wherein the ring may contain up to 2 heteroatoms selected from N, O, and S, the ring being either saturated or unsaturated;
$R^{N1}$ is H or $C_{1-6}$ alkyl, $NH_2$, $SO_2$-aryl, $SO_2$-heteroaryl, morpholine or piperidine, or forms a ring with R;
$R^1$ is H, F, or Me or forms a ring with R;
$R^3$ is H or $C_{1-6}$ alkyl;
n is an integer from 0 to 6; and
m is an integer from 1 to 6.

In an aspect, the present disclosure provides a compound according to Formula (Ib):

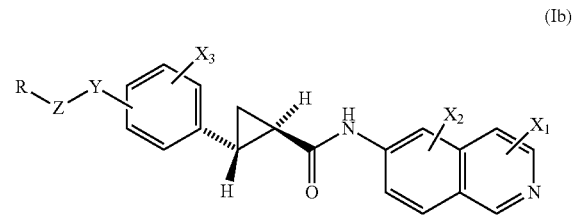

(Ib)

or tautomers, stereoisomers and pharmaceutically acceptable salts thereof,
wherein:
$X_1$, $X_2$ and $X_3$ are independently H, halogen, nitrile, hydroxyl, or $C_{1-6}$ alkyl;
Y is —$NR^{N1}S(O)_2$—, —$NR^{N1}C(O)$—, —$O(CR^1_2)_n$—, —$NR^{N1}(CR^1_2)_m$—, —$C(O)O$—, —$OC(O)$—, —$S(O)_2$—, —$C(O)$—, —$NR^{N1}C(O)O(CR^1_2)_n$—, —(R)O— $C_{1-6}$ alkylene, aryl, or heteroaryl
Z is a direct bond or $C_{1-6}$ alkylene;
R is halogen, cyano, $OR^3$, amino, cycloalkyl, heterocyclyl, aryl, or heteroaryl, or R may form a ring of 5 to 7 member atoms with $R^{N1}$ or $R^1$, wherein the ring may contain up to 2 heteroatoms selected from N, O, and S, the ring being either saturated or unsaturated;
$R^{N1}$ is H or $C_{1-6}$ alkyl, $NH_2$, $SO_2$-aryl, $SO_2$-heteroaryl, morpholine or piperidine, or forms a ring with R;
$R^1$ is H, F, or Me or forms a ring with R;
$R^3$ is H or $C_{1-6}$ alkyl;
n is an integer from 0 to 6; and
m is an integer from 1 to 6.

In an aspect, the present disclosure provides a compound according to Formula (Ic):

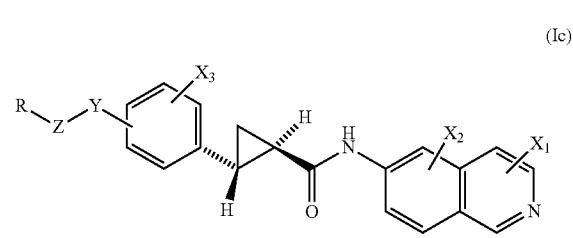

(Ic)

or tautomers, stereoisomers and pharmaceutically acceptable salts thereof,
wherein:
$X_1$, $X_2$ and $X_3$ are independently H, halogen, nitrile, hydroxyl, or $C_{1-6}$ alkyl;
Y is —$NR^{N1}S(O)_2$—, —$NR^N C(O)$—, —$O(CR^1_2)_n$—, —$NR^{N1}(CR^1_2)_m$—, —$C(O)O$—, —$OC(O)$—, —$S(O)_2$—, —$C(O)$—, —$NR^{N1}C(O)O(CR^1_2)_n$—, —(R)O— $C_{1-6}$ alkylene, aryl, or heteroaryl
Z is a direct bond or $C_{1-6}$ alkylene;
R is H, halogen, cyano, $OR^3$, $C_{1-6}$ alkyl, amino, cycloalkyl, heterocyclyl, aryl, or heteroaryl, carbonyl, or R may form a ring of 5 to 7 member atoms with $R^{N1}$ or $R^1$, wherein the ring may contain up to 2 heteroatoms selected from N, O, and S, the ring being either saturated or unsaturated;
$R^{N1}$ is H or $C_{1-6}$ alkyl, $NH_2$, $SO_2$-aryl, $SO_2$-heteroaryl, morpholine or piperedine, or forms a ring with R;
$R^1$ is F, or Me or forms a ring with R;

$R^3$ is H or $C_{1-6}$ alkyl;
n is an integer from 0 to 6; and
m is an integer from 1 to 6.

In an aspect, the present disclosure provides a compound according to Formula (Id):

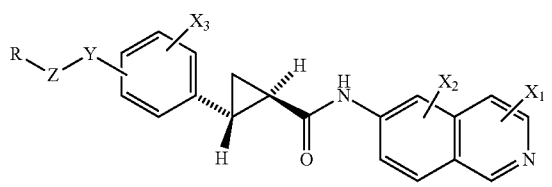

(Id)

or tautomers, stereoisomers and pharmaceutically acceptable salts thereof,
wherein:
$X_1$, $X_2$ and $X_3$ are independently H, halogen, nitrile, hydroxyl, or $C_{1-6}$ alkyl;
Y is —$NR^{N1}S(O)_2$—, —$NR^{N1}C(O)$—, —$O(CR^1_2)_n$—, —$NR^{N1}(CR^1_2)_m$—, —C(O)O—, —OC(O)—, —$S(O)_2$—, —C(O)—, —$NR^{N1}C(O)O(CR^1_2)_n$—, —(R)O— $C_{1-6}$ alkylene, aryl, or heteroaryl
Z is a direct bond or $C_{1-6}$ alkylene;
R is H, halogen, cyano, $OR^3$, $C_{1-6}$ alkyl, amino, cycloalkyl, heterocyclyl, aryl, or heteroaryl, carbonyl, or R may form a ring of 5 to 7 member atoms with $R^{N1}$ or $R^1$, wherein the ring may contain up to 2 heteroatoms selected from N, O, and S, the ring being either saturated or unsaturated;
$R^{N1}$ is H or $C_{1-6}$ alkyl, $NH_2$, $SO_2$-aryl, $SO_2$-heteroaryl, morpholine or piperidine, or forms a ring with R;
$R^1$ is H, F, or Me or forms a ring with R;
$R^3$ is H or $C_{1-6}$ alkyl;
n is 2, 3, 4, 5, or 6; and
m is an integer from 1 to 6.

In an aspect, the compound according to Formula (II) is provided:

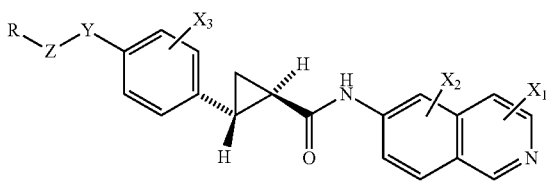

(II)

or tautomers, stereoisomers and pharmaceutically acceptable salts thereof,
wherein:
$X_1$, $X_2$ and $X_3$ are independently H, halogen, nitrile, hydroxyl, or $C_{1-6}$ alkyl;
Y is —$NR^{N1}S(O)_2$—, —$NR^{N1}C(O)$—, —$O(CR^1_2)_n$—, —$NR^{N1}(CR^1_2)_m$—, —C(O)O—, —OC(O)—, —$S(O)_2$—, —C(O)—, —$NR^{N1}C(O)O$—, $C_{1-6}$ alkylene, aryl, or heteroaryl;
Z is a direct bond or $C_{1-6}$ alkylene;
R is H, halogen, cyano, $OR^3$, $C_{1-6}$ alkyl, amino, cycloalkyl, heterocyclyl, aryl, or heteroaryl, or R may form a ring of 5 to 7 member atoms with $R^{N1}$ or $R^1$, wherein the ring may contain up to 2 heteroatoms selected from N, O, and S, the ring being either saturated or unsaturated;
$R^{N1}$ is H or $C_{1-6}$ alkyl or forms a ring with R;
$R^1$ is H, F, or Me or forms a ring with R;
$R^3$ is H or $C_{1-6}$ alkyl;
n is an integer from 0 to 6; and
m is an integer from 1 to 6.

In an aspect, the compound according to Formula (III) is provided:

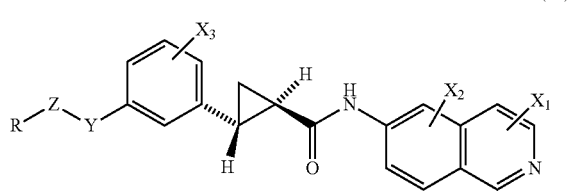

(III)

or tautomers, stereoisomers and pharmaceutically acceptable salts thereof,
wherein:
$X_1$, $X_2$ and $X_3$ are independently H, halogen, nitrile, hydroxyl, or $C_{1-6}$ alkyl;
Y is —$NR^{N1}S(O)_2$—, —$NR^{N1}C(O)$—, —$O(CR^1_2)_n$—, —$NR^{N1}(CR^1_2)_m$—, —C(O)O—, —OC(O)—, —$S(O)_2$—, —C(O)—, —$NR^{N1}C(O)O$—, $C_{1-6}$ alkylene, aryl, or heteroaryl,
Z is a direct bond or $C_{1-6}$ alkylene;
R is H, halogen, cyano, $OR^3$, $C_{1-6}$ alkyl, amino, cycloalkyl, heterocyclyl, aryl, or heteroaryl, or R may form a ring of 5 to 7 member atoms with $R^{N1}$ or $R^1$, wherein the ring may contain up to 2 heteroatoms selected from N, O, and S, the ring being either saturated or unsaturated;
$R^{N1}$ is H or $C_{1-6}$ alkyl or forms a ring with R;
$R^1$ is H, F, or Me or forms a ring with R;
$R^3$ is H or $C_{1-6}$ alkyl;
n is an integer from 0 to 6; and
m is an integer from 1 to 6.

In an aspect, the compound according to Formula (IV) is provided:

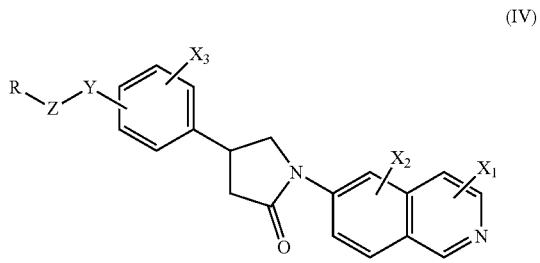

(IV)

or tautomers, stereoisomers and pharmaceutically acceptable salts thereof,
wherein:
$X_1$, $X_2$ and $X_3$ are independently H, halogen, nitrile, hydroxyl, or $C_{1-6}$ alkyl;
Y is —$NR^{N1}S(O)_2$—, —$NR^{N1}C(O)$—, —$O(CR^1_2)_n$—, —$NR^{N1}(CR^1_2)_m$—, —C(O)O—, —OC(O)—, —$S(O)_2$—, —C(O)—, —$NR^{N1}C(O)O$—, $C_{1-6}$ alkylene, aryl, or heteroaryl;

Z is a direct bond or $C_{1-6}$ alkylene;

R is H, halogen, cyano, $OR^3$, $C_{1-6}$ alkyl, amino, cycloalkyl, heterocyclyl, aryl, or heteroaryl, or R may form a ring of 5 to 7 member atoms with $R^{N1}$ or $R^1$, wherein the ring may contain up to 2 heteroatoms selected from N, O, and S, the ring being either saturated or unsaturated;

$R^{N1}$ is H or $C_{1-6}$ alkyl or forms a ring with R;

$R^1$ is H, F, or Me or forms a ring with R; $R^3$ is H or $C_{1-6}$ alkyl;

n is an integer from 0 to 6; and m is an integer from 1 to 6.

In an aspect, the compound according to Formula (V) is provided:

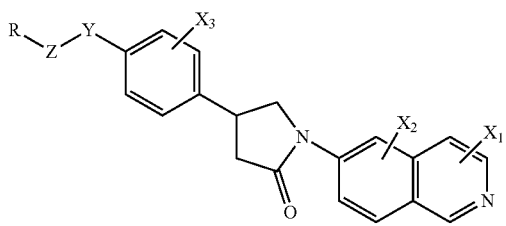

(V)

or tautomers, stereoisomers and pharmaceutically acceptable salts thereof, wherein:

$X_1$, $X_2$ and $X_3$ are independently H, halogen, nitrile, hydroxyl, or $C_{1-6}$ alkyl;

Y is —$NR^{N1}S(O)_2$—, —$NR^{N1}C(O)$—, —$O(CR^1_2)_n$—, —$NR^{N1}(CR^1_2)_m$—, —C(O)O—, —OC(O)—, —$S(O)_2$—, —C(O)—, —$NR^{N1}C(O)O$—, $C_{1-6}$ alkylene, aryl, or heteroaryl Z is a direct bond or $C_{1-6}$ alkylene;

R is H, halogen, cyano, $OR^3$, $C_{1-6}$ alkyl, amino, cycloalkyl, heterocyclyl, aryl, or heteroaryl, or R may form a ring of 5 to 7 member atoms with $R^{N1}$ or $R^1$, wherein the ring may contain up to 2 heteroatoms selected from N, O, and S, the ring being either saturated or unsaturated;

$R^{N1}$ is H or $C_{1-6}$ alkyl or forms a ring with R;

$R^1$ is H, F, or Me or forms a ring with R;

$R^3$ is H or $C_{1-6}$ alkyl;

n is an integer from 0 to 6; and m is an integer from 1 to 6.

In an aspect, the compound according to Formula (VI) is provided:

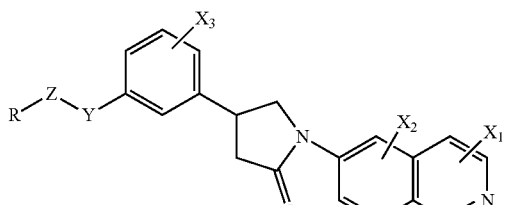

(VI)

or tautomers, stereoisomers and pharmaceutically acceptable salts thereof, wherein:

$X_1$, $X_2$ and $X_3$ are independently H, halogen, nitrile, hydroxyl, or $C_{1-6}$ alkyl;

Y is —$NR^{N1}S(O)_2$—, —$NR^{N1}C(O)$—, —$O(CR^1_2)_n$—, —$NR^{N1}(CR^1_2)_m$—, —C(O)O—, —OC(O)—, —$S(O)_2$—, —C(O)—, —$NR^{N1}C(O)O$—, $C_{1-6}$ alkylene, aryl, or heteroaryl Z is a direct bond or $C_{1-6}$ alkylene;

R is H, halogen, cyano, $OR^3$, $C_{1-6}$ alkyl, amino, cycloalkyl, heterocyclyl, aryl, or heteroaryl, or R may form a ring of 5 to 7 member atoms with $R^{N1}$ or $R^1$, wherein the ring may contain up to 2 heteroatoms selected from N, O, and S, the ring being either saturated or unsaturated;

$R^{N1}$ is H or $C_{1-6}$ alkyl or forms a ring with R;

$R^1$ is H, F, or Me or forms a ring with R;

$R^3$ is H or $C_{1-6}$ alkyl;

n is an integer from 0 to 6; and m is an integer from 1 to 6.

In an aspect, the compound according to Formula (VII) is provided:

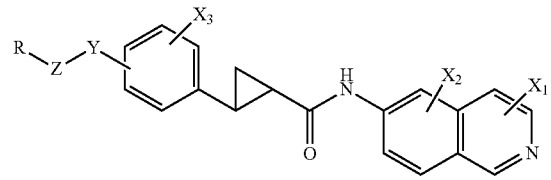

(VII)

or tautomers, stereoisomers and pharmaceutically acceptable salts thereof, wherein:

$X_1$, $X_2$ and $X_3$ are independently H, halogen, nitrile, hydroxyl, or $C_{1-6}$ alkyl;

Y is —$NR^{N1}S(O)_2$—, —$NR^{N1}C(O)$—, —$O(CR^1_2)_n$—, —$NR^{N1}(CR^1_2)_m$—, —C(O)O—, —OC(O)—, —$S(O)_2$—, —C(O)—, —$NR^{N1}C(O)O$—, $C_{1-6}$ alkylene, aryl, or heteroaryl Z is a direct bond or $C_{1-6}$ alkylene;

R is H, halogen, cyano, $OR^3$, $C_{1-6}$ alkyl, amino, cycloalkyl, heterocyclyl, aryl, or heteroaryl, or R may form a ring of 5 to 7 member atoms with $R^{N1}$ or $R^1$, wherein the ring may contain up to 2 heteroatoms selected from N, O, and S, the ring being either saturated or unsaturated;

$R^{N1}$ is H or $C_{1-6}$ alkyl or forms a ring with R;

$R^1$ is H, F, or Me or forms a ring with R;

$R^3$ is H or $C_{1-6}$ alkyl;

n is an integer from 0 to 6; and m is an integer from 1 to 6.

In an aspect, the compound according to Formula (VIII) is provided:

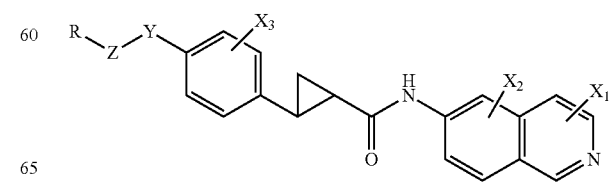

(VIII)

or tautomers, stereoisomers and pharmaceutically acceptable salts thereof, wherein:

$X_1$, $X_2$ and $X_3$ are independently H, halogen, nitrile, hydroxyl, or $C_{1-6}$ alkyl;

Y is $-NR^{N1}S(O)_2-$, $-NR^{N1}C(O)-$, $-O(CR^1_2)_n-$, $-NR^{N1}(CR^1_2)_m-$, $-C(O)O-$, $-OC(O)-$, $-S(O)_2-$, $-C(O)-$, $-NR^{N1}C(O)O-$, $C_{1-6}$ alkylene, aryl, or heteroaryl Z is a direct bond or $C_{1-6}$ alkylene;

R is H, halogen, cyano, $OR^3$, $C_{1-6}$ alkyl, amino, cycloalkyl, heterocyclyl, aryl, or heteroaryl, or R may form a ring of 5 to 7 member atoms with $R^{N1}$ or $R^1$, wherein the ring may contain up to 2 heteroatoms selected from N, O, and S, the ring being either saturated or unsaturated;

$R^{N1}$ is H or $C_{1-6}$ alkyl or forms a ring with R;

$R^1$ is H, F, or Me or forms a ring with R;

$R^3$ is H or $C_{1-6}$ alkyl;

n is an integer from 0 to 6; and m is an integer from 1 to 6.

In an aspect, the compound according to Formula (IX) is provided:

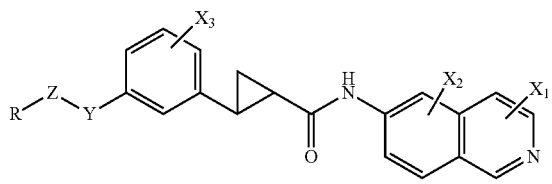

(IX)

or tautomers, stereoisomers and pharmaceutically acceptable salts thereof, wherein:

$X_1$, $X_2$ and $X_3$ are independently H, halogen, nitrile, hydroxyl, or $C_{1-6}$ alkyl;

Y is $-NR^{N1}S(O)_2-$, $-NR^{N1}C(O)-$, $-O(CR^1_2)_n-$, $-NR^{N1}(CR^1_2)_m-$, $-C(O)O-$, $-OC(O)-$, $-S(O)_2-$, $-C(O)-$, $-NR^{N1}C(O)O-$, $C_{1-6}$ alkylene, aryl, or heteroaryl;

Z is a direct bond or $C_{1-6}$ alkylene;

R is H, halogen, cyano, $OR^3$, $C_{1-6}$ alkyl, amino, cycloalkyl, heterocyclyl, aryl, or heteroaryl, or R may form a ring of 5 to 7 member atoms with $R^{N1}$ or $R^1$, wherein the ring may contain up to 2 heteroatoms selected from N, O, and S, the ring being either saturated or unsaturated;

$R^{N1}$ is H or $C_{1-6}$ alkyl or forms a ring with R;

$R^1$ is H, F, or Me or forms a ring with R;

$R^3$ is H or $C_{1-6}$ alkyl;

n is an integer from 0 to 6; and m is an integer from 1 to 6.

In embodiments for Formulas (I)-(IX), one or more of $X^1$, $X^2$, and $X^3$ are hydrogen. In embodiments for Formulas (I)-(IX), $X^1$ is OH, CN, F, Br, Cl or $CH_3$. In embodiments for Formulas (I)-(IX), $X^2$ is CN, F, Br, Cl or $CH_3$. In embodiments for Formulas (I)-(IX), $X^3$ is $-CF_3$, $-OCH_3$, CN, F, Br, Cl, $OCF_3$ or $CH_3$.

In embodiments for Formulas (I)-(IX), $R^{N1}$ is H. Alternatively, $R^{N1}$ is $C_{1-6}$ alkyl, which may be substituted.

In embodiments for Formulas (I)-(IX), R is amino. Alternatively, R is heteroaryl, heterocyclyl, or aryl, such as phenyl, pyridyl, piperidinyl, morpholino, thiophenyl, isoquinolinyl, quinolinyl or pyrrolidinyl. In embodiments for Formulas (I)-(IX), R is H, $C_{1-6}$ alkyl, cycloalkyl, or heterocyclyl, or R may form a ring of 5 to 7 member atoms with $R^{N1}$, wherein the ring may contain up to 2 heteroatoms selected from N, O, and S, which may be saturated or unsaturated.

In embodiment for Formulas (I)-(IX), Z is a direct bond. Alternatively, Z is $C_{1-6}$ alkylene, such as $-CH_2-$.

In embodiments for Formulas (I)-(IX), Y is $-NR^{N1}S(O)_2-$. In embodiments for Formulas (I)-(IX), Y is $-NR^{N1}S(O)_2-$ and $R^{N1}$ is H. In embodiments, Y is $-NR^{N1}S(O)_2-$ and R is alkyl, aryl, heteroaryl, carbocyclyl, or heterocyclyl.

In embodiments for Formulas (I)-(IX), Y is $-NR^{N1}C(O)-$. In embodiments for Formulas (I)-(IX), Y is $-NR^{N1}C(O)-$ and R is piperidinyl, morpholino, thiophenyl, isoquinolinyl, quinolinyl, thiofuranyl, benzothiophenyl, or pyrrolidinyl. In embodiments for Formulas (I)-(IX), Y is $-NR^{N1}C(O)-$ and R is H, $C_{1-6}$ alkyl, cycloalkyl, or heterocyclyl, or R may form a ring of 5 to 7 member atoms with $R^{N1}$, wherein the ring may contain up to 2 heteroatoms selected from N, O, and S, which may be saturated or unsaturated. In embodiments, Y is $-NR^{N1}C(O)-$, R is piperidinyl, $R^{N1}$ is H, Z is $-CH_2-$ and $X^1$, $X^2$, and $X^3$ are H. In embodiments, Y is $-NR^{N1}C(O)-$ R is isoquinolinyl, $R^{N1}$ is H, Z is a direct bond, and $X^1$, $X^2$, and $X^3$ are H.

In embodiments for Formulas (I)-(IX), Y is $-O(CR^1_2)_n-$. In embodiments, Y is $-O(CR^1_2)_n-$ and R is cycloalkyl, heterocyclyl, or heteroaryl, or R may form a ring of 5 to 7 member atoms with $R^1$, wherein the ring may contain up to 2 heteroatoms selected from N, O, and S, which may be saturated or unsaturated.

In embodiments for Formulas (I)-(IX), Y is $-NR^{N1}(CR^1_2)_m-$. In embodiments for Formulas (I)-(IX), Y is $-NR^{N1}(CR^1_2)_m-$ and R is H, $C_{1-6}$ alkyl, cycloalkyl, heterocyclyl, aryl, or heteroaryl, or R may form a ring of 5 to 7 member atoms with $R^{N1}$, wherein the ring may contain up to 2 heteroatoms selected from N, O, and S, which may be saturated or unsaturated.

In embodiments for Formulas (I)-(IX), Y is $-C(O)O-$ or $-OC(O)-$. In embodiments for Formulas (I)-(IX), Y is $-C(O)O-$ or $-OC(O)-$ and R is H, cycloalkyl, heterocyclyl, aryl, or heteroaryl and wherein Z is a direct bond.

In some embodiments of these aspects, Y is $-NR^{N1}S(O)_2-$, $-NR^{N1}C(O)-$, $-NR^{N1}(CR^1_2)_m-$, $-S(O)_2-$, $-C(O)-$, $-NR^{N1}C(O)O(CR^1_2)_n-$, or $C_{1-6}$ alkylene.

In some embodiments of these aspects, R is halogen, cyano, $OR^3$, amino, cycloalkyl, heterocyclyl, aryl, or heteroaryl, or R may form a ring of 5 to 7 member atoms with $R^{N1}$ or $R^1$, wherein the ring may contain up to 2 heteroatoms selected from N, O, and S, the ring being either saturated or unsaturated.

In some embodiments of these aspects, $R^1$ is F, or Me or forms a ring with R.

In some embodiments of these aspects, n is 2, 3, 4, 5, or 6.

Compounds according to the present disclosure include those shown in Table 1.

TABLE 1
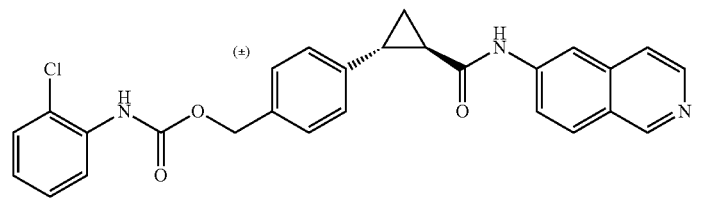 [SMILES: O=C(Nc1ccccc1Cl)OCc1ccc([C@@H]2C[C@H]2C(=O)Nc2ccc3cnccc3c2)cc1]
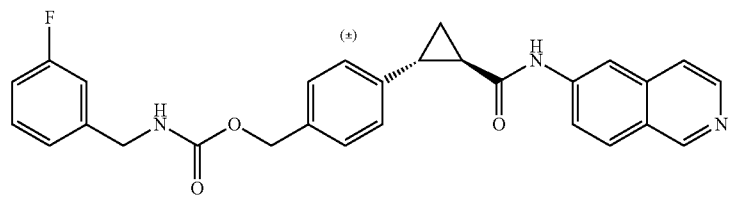 [SMILES: O=C(NCc1cccc(F)c1)OCc1ccc([C@@H]2C[C@H]2C(=O)Nc2ccc3cnccc3c2)cc1]
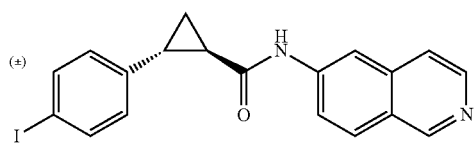 [SMILES: O=C(Nc1ccc2cnccc2c1)[C@@H]1C[C@H]1c1ccc(I)cc1]
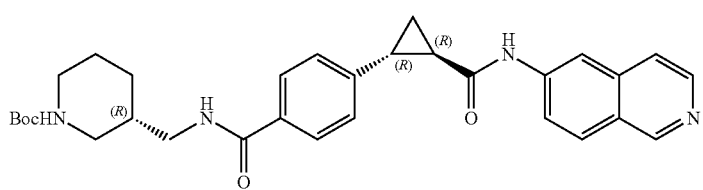
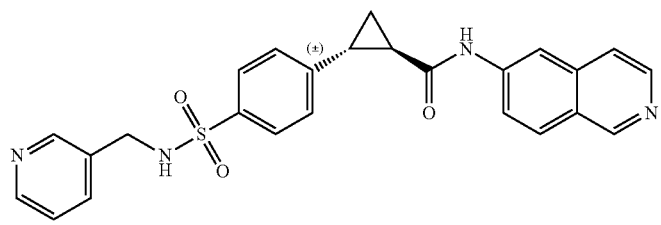 [SMILES: O=C(Nc1ccc2cnccc2c1)[C@@H]1C[C@H]1c1ccc(S(=O)(=O)NCc2cccnc2)cc1]
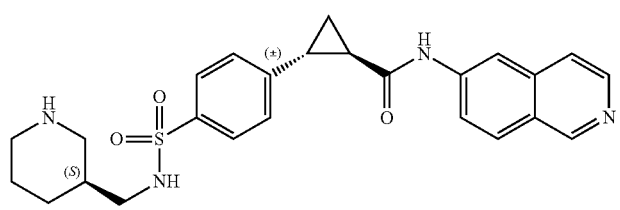
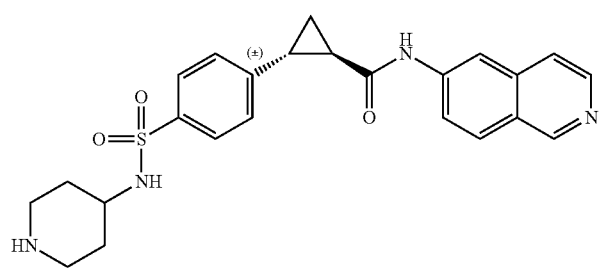 [SMILES: O=C(Nc1ccc2cnccc2c1)[C@@H]1C[C@H]1c1ccc(S(=O)(=O)NC2CCNCC2)cc1]

TABLE 1-continued
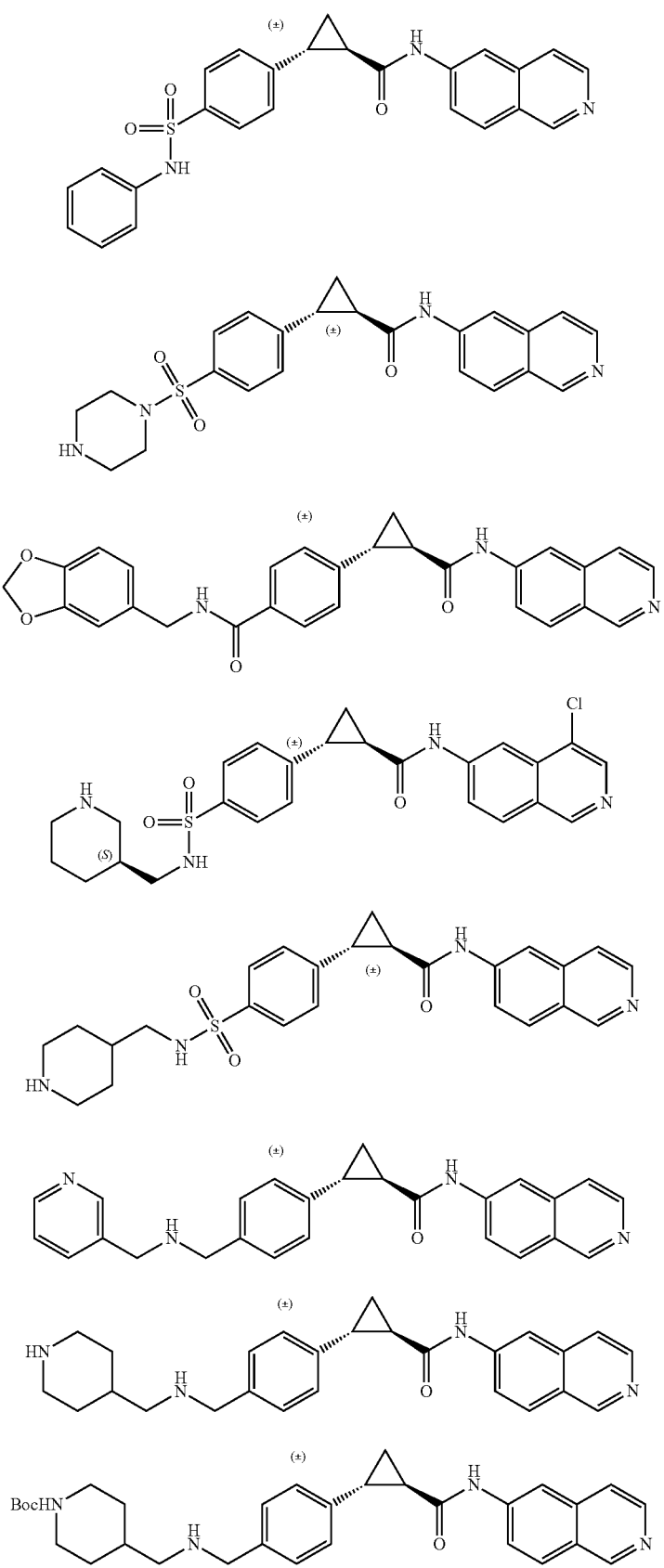

TABLE 1-continued
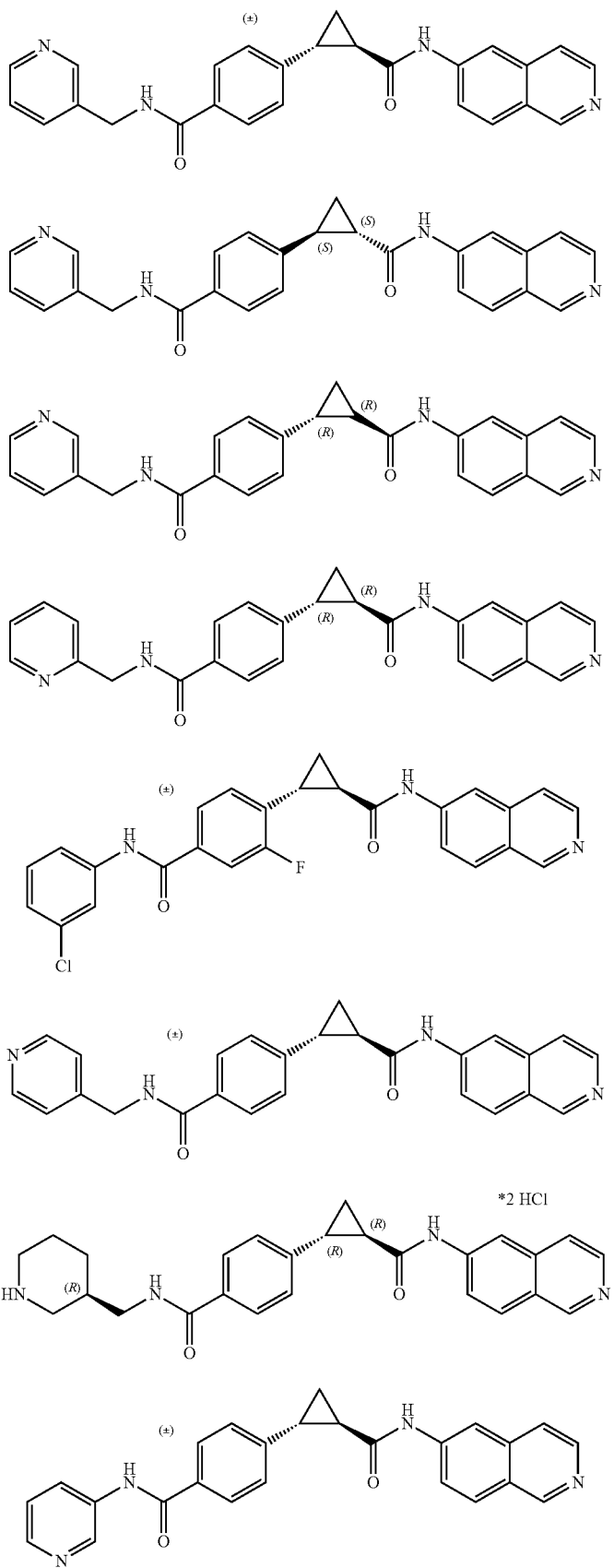

TABLE 1-continued
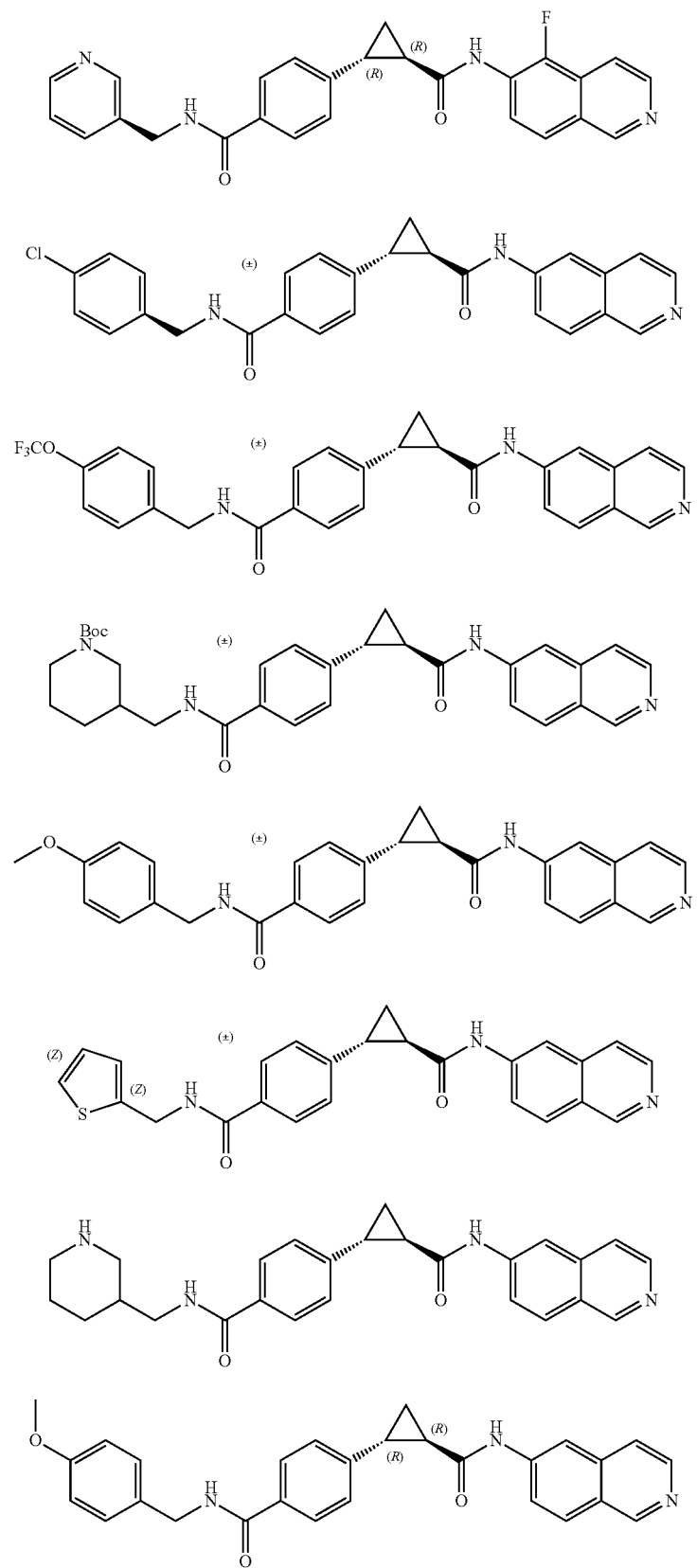

TABLE 1-continued
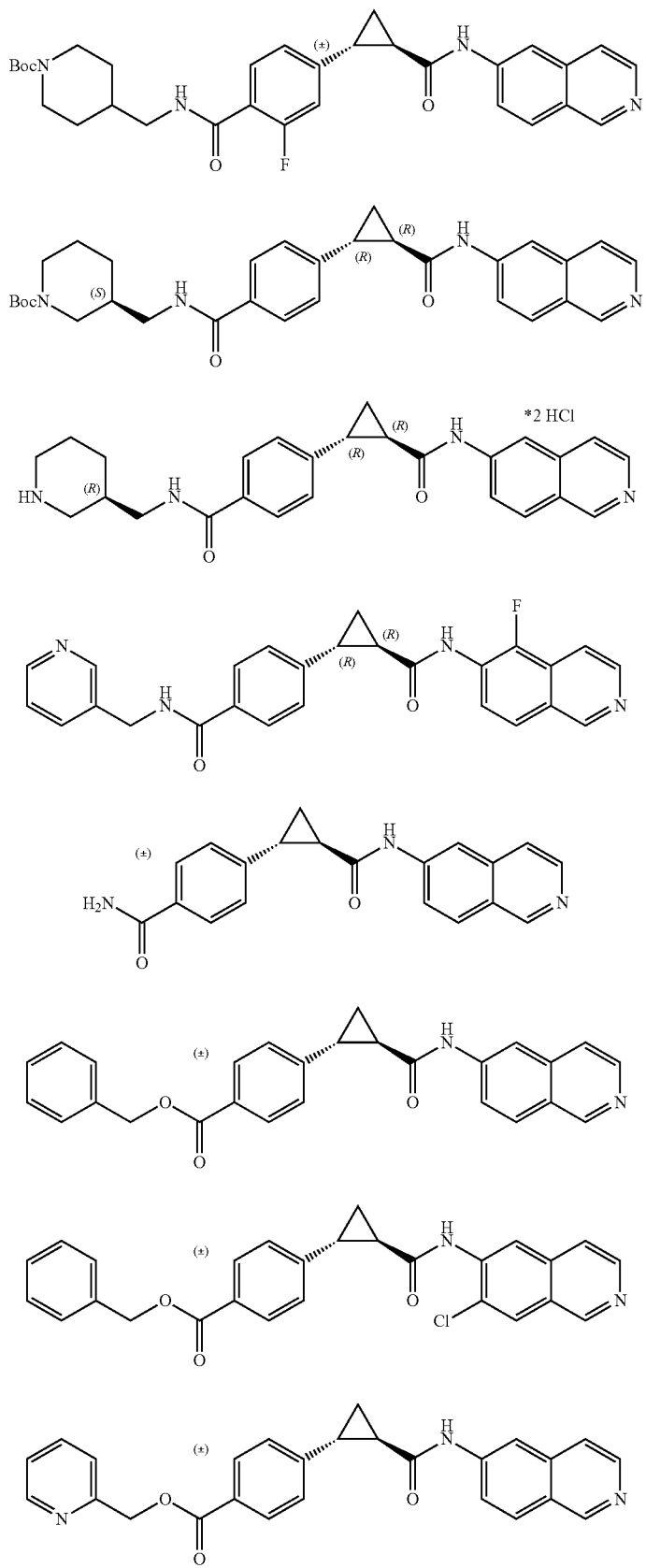

TABLE 1-continued
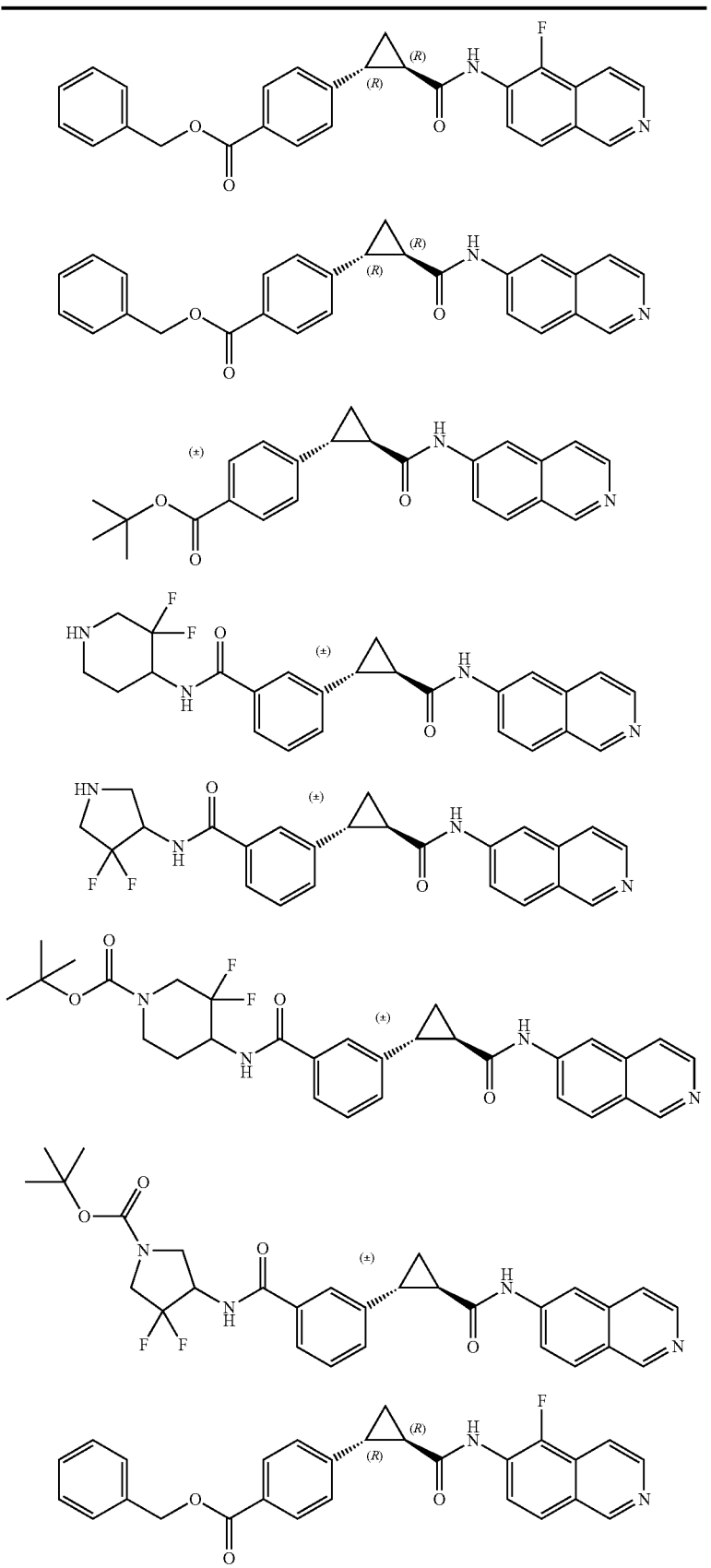

TABLE 1-continued
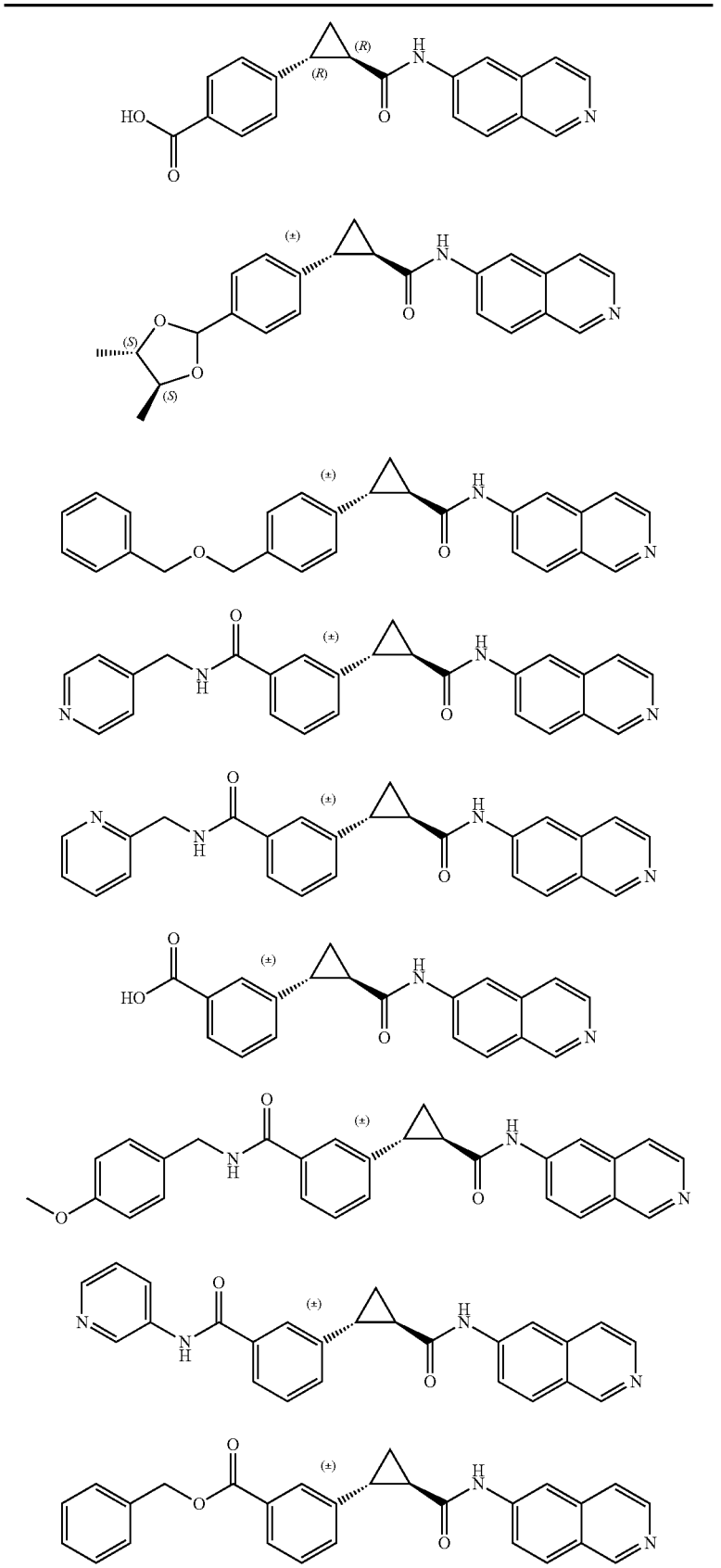

TABLE 1-continued
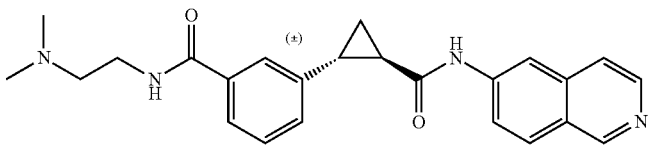 [SMILES: CN(C)CCNC(=O)c1cccc([C@@H]2C[C@H]2C(=O)Nc2ccc3cnccc3c2)c1]
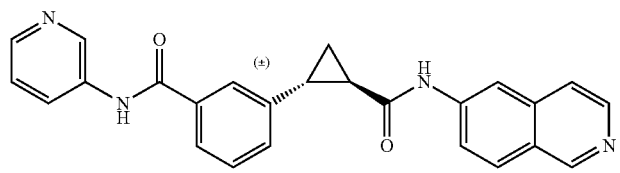 [SMILES: O=C(Nc1cccnc1)c1cccc([C@@H]2C[C@H]2C(=O)Nc2ccc3cnccc3c2)c1]
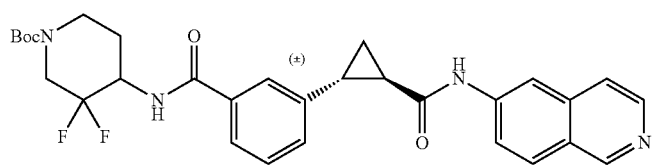 [SMILES: CC(C)(C)OC(=O)N1CCC(NC(=O)c2cccc([C@@H]3C[C@H]3C(=O)Nc3ccc4cnccc4c3)c2)C(F)(F)C1]
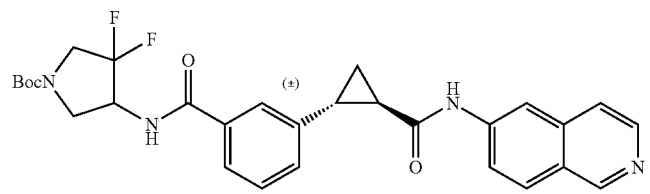 [SMILES: CC(C)(C)OC(=O)N1CC(NC(=O)c2cccc([C@@H]3C[C@H]3C(=O)Nc3ccc4cnccc4c3)c2)C(F)(F)C1]
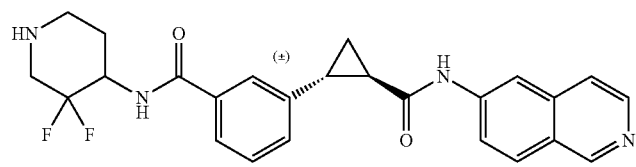 [SMILES: O=C(NC1CCNCC1(F)F)c1cccc([C@@H]2C[C@H]2C(=O)Nc2ccc3cnccc3c2)c1]
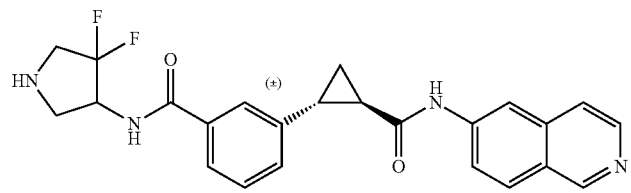 [SMILES: O=C(NC1CNCC1(F)F)c1cccc([C@@H]2C[C@H]2C(=O)Nc2ccc3cnccc3c2)c1]
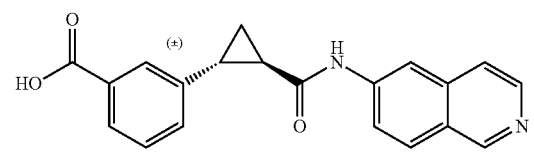 [SMILES: O=C(O)c1cccc([C@@H]2C[C@H]2C(=O)Nc2ccc3cnccc3c2)c1]
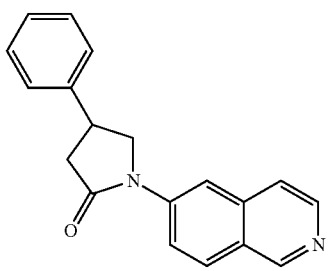 [SMILES: O=C1CC(c2ccccc2)CN1c1ccc2cnccc2c1]

TABLE 1-continued
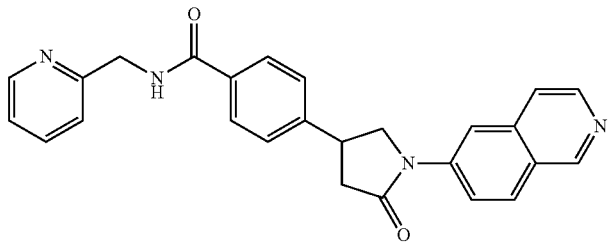 [SMILES: O=C(NCc1ccccn1)c1ccc(C2CC(=O)N(c3ccc4cnccc4c3)C2)cc1]
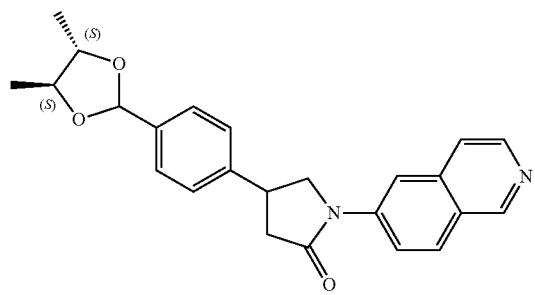
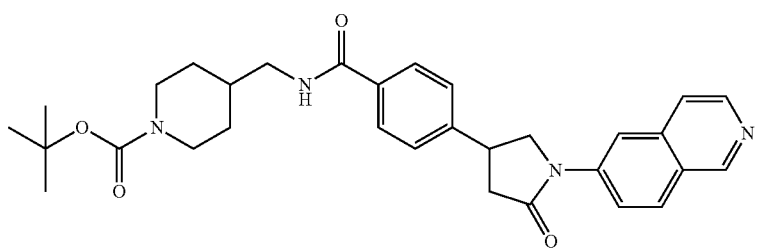 [SMILES: CC(C)(C)OC(=O)N1CCC(CNC(=O)c2ccc(C3CC(=O)N(c4ccc5cnccc5c4)C3)cc2)CC1]
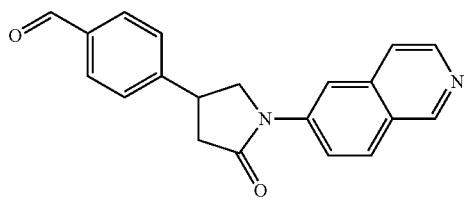 [SMILES: O=Cc1ccc(C2CC(=O)N(c3ccc4cnccc4c3)C2)cc1]
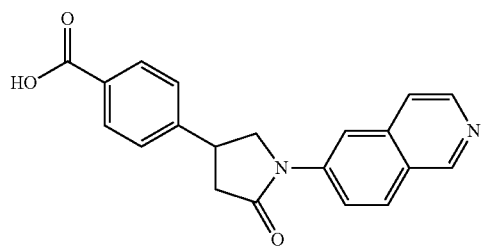 [SMILES: O=C(O)c1ccc(C2CC(=O)N(c3ccc4cnccc4c3)C2)cc1]
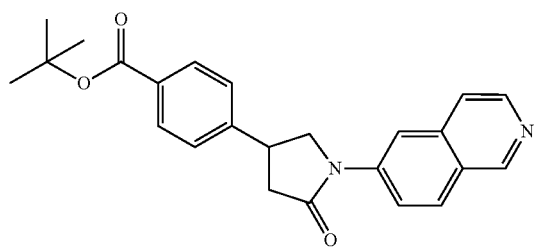 [SMILES: CC(C)(C)OC(=O)c1ccc(C2CC(=O)N(c3ccc4cnccc4c3)C2)cc1]

TABLE 1-continued
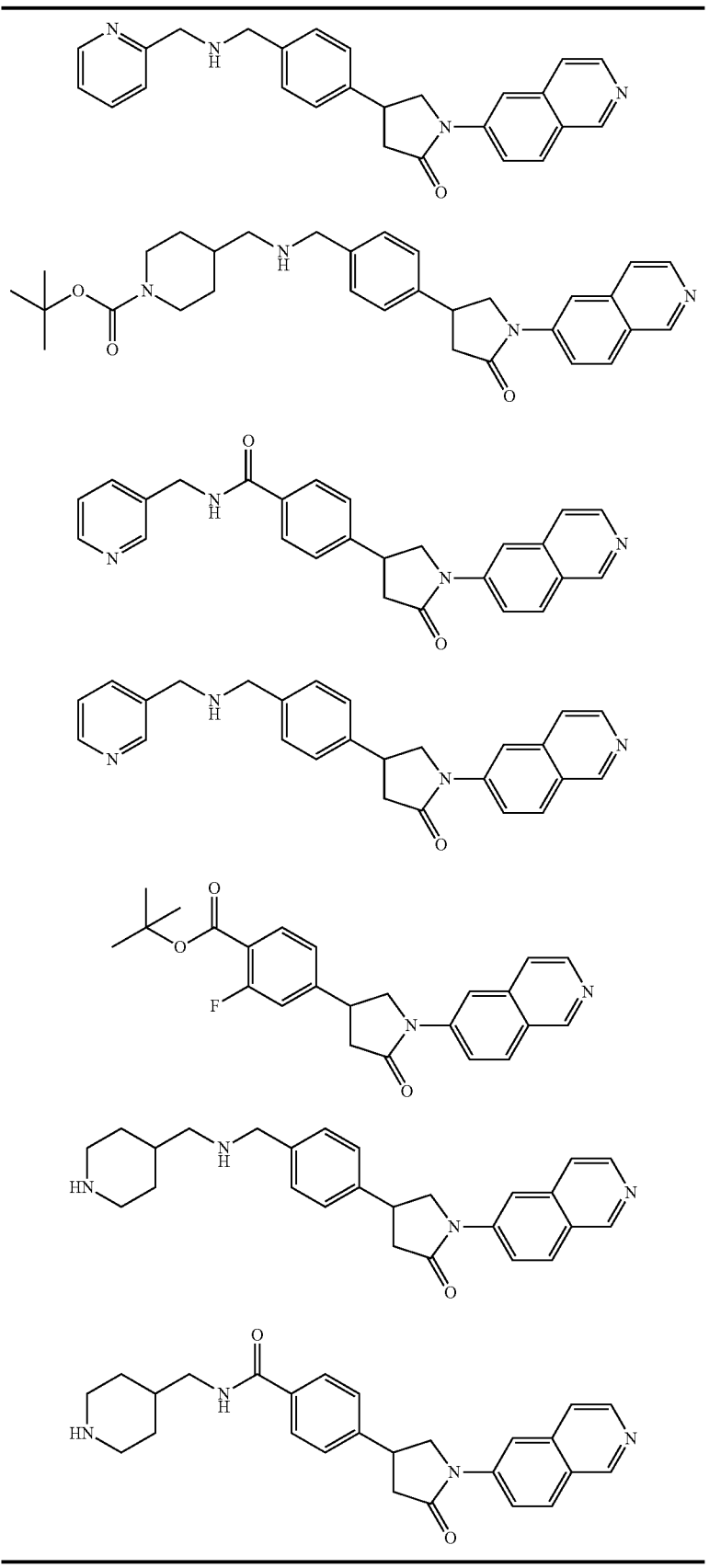

Compounds according to the disclosure also include:

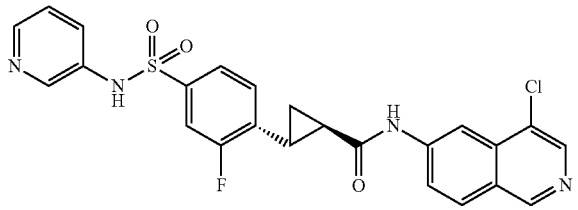

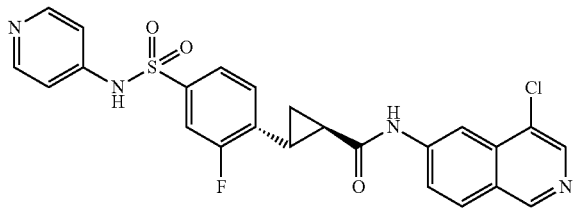

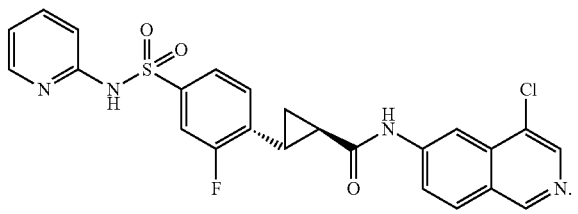

In another aspect, provided herein are compounds of Formula (Xa):

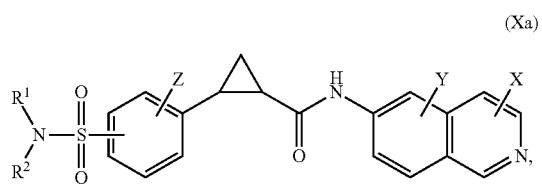

(Xa)

or a pharmaceutically acceptable salt thereof,
wherein,
R$^1$ is H, —C$_{1-6}$ alkyl, —C$_{1-6}$ haloalkyl, aryl, heteroaryl, —(C$_{1-6}$ alkyl)-pyridinyl, —(C$_{1-6}$ alkyl)-N(R$^3$)R$^4$, —(C$_{1-6}$ alkyl)-heterocyclyl or heterocycloalkyl;

R$^2$ is H, —C$_{1-6}$ alkyl, —C$_{1-6}$ haloalkyl, aryl, heteroaryl, —(C$_{1-6}$ alkyl)-pyridinyl, —(C$_{1-6}$ alkyl)-N(R$^3$)R$^4$, —(C$_{1-6}$ alkyl)-heterocyclyl or heterocycloalkyl;

or R$^1$ and R$^2$, together with the nitrogen to which they are attached, form a -heterocycle or a heterocycle substituted with —C$_{1-6}$ alkyl;

R$^3$ is H, C$_{1-6}$ alkyl or —C$_{1-6}$ haloalkyl;

R$^4$ is H, C$_{1-6}$ alkyl or —C$_{1-6}$ haloalkyl;

X is H, C$_{1-6}$ alkyl, —C$_{1-6}$ haloalkyl, halogen or hydroxyl;

Y is H, C$_{1-6}$ alkyl, —C$_{1-6}$ haloalkyl, halogen or hydroxyl; and

Z is H, C$_{1-6}$ alkyl, —C$_{1-6}$ haloalkyl, halogen or hydroxyl.

In an embodiment, the compound of Formula (Xa) is a compound of Formula (X):

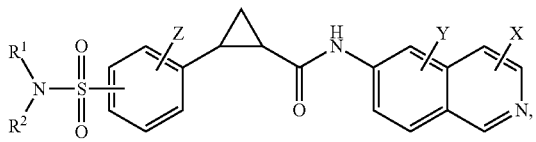

(X)

or a pharmaceutically acceptable salt thereof,
wherein,
R$^1$ is H, —C$_{1-6}$ alkyl, —C$_{1-6}$ haloalkyl, aryl, heteroaryl, —(C$_{1-6}$ alkyl)-pyridinyl, —(C$_{1-6}$ alkyl)-N(R$^3$)R$^4$, —(C$_{1-6}$ alkyl)-heterocyclyl or heterocycloalkyl;

R$^2$ is H, —C$_{1-6}$ alkyl, —C$_{1-6}$ haloalkyl, aryl, heteroaryl, —(C$_{1-6}$ alkyl)-pyridinyl, —(C$_{1-6}$ alkyl)-N(R$^3$)R$^4$, —(C$_{1-6}$ alkyl)-heterocyclyl or heterocycloalkyl;

or R$^1$ and R$^2$, together with the nitrogen to which they are attached, form a -heterocycle;

R$^3$ is H, C$_{1-6}$ alkyl or —C$_{1-6}$ haloalkyl;

R$^4$ is H, C$_{1-6}$ alkyl or —C$_{1-6}$ haloalkyl;

X is H, C$_{1-6}$ alkyl, —C$_{1-6}$ haloalkyl, halogen or hydroxyl;

Y is H, C$_{1-6}$ alkyl, —C$_{1-6}$ haloalkyl, halogen or hydroxyl; and

Z is H, C$_{1-6}$ alkyl, —C$_{1-6}$ haloalkyl, halogen or hydroxyl.

In an embodiment, the compound of Formula (X) is a compound of Formula (XI):

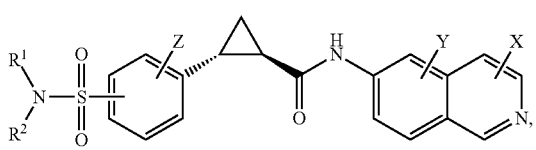

(XI)

or a pharmaceutically acceptable salt thereof.

In an embodiment, the compound of Formula (X) is a compound of Formula (XII):

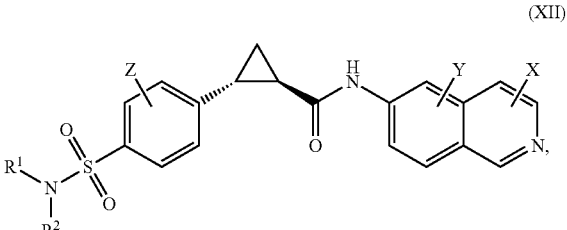

(XII)

or a pharmaceutically acceptable salt thereof.

In an embodiment, the compound of Formula (X) is a compound of Formula (XIII):

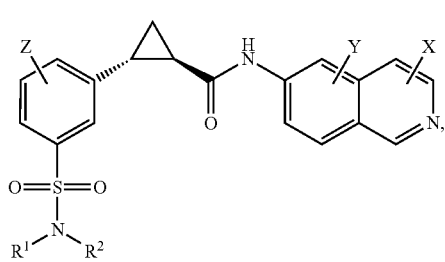

(XIII)

or a pharmaceutically acceptable salt thereof.

In an embodiment, the compound of Formula (X) is a compound of Formula (XIV):

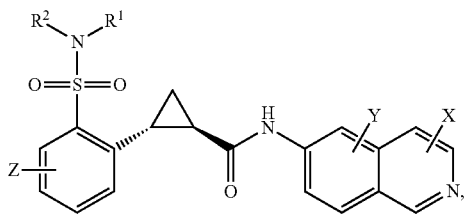

(XIV)

or a pharmaceutically acceptable salt thereof.

In an embodiment, the compound of Formula (X) is a compound of Formula (XV):

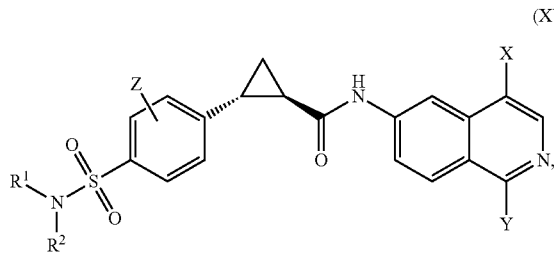

(XV)

or a pharmaceutically acceptable salt thereof.

In an embodiment, the compound of Formula (X) is a compound of Formula (XVI):

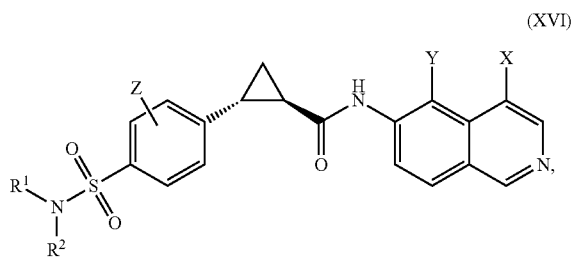

(XVI)

or a pharmaceutically acceptable salt thereof.

In an embodiment, the compound of Formula (X) is a compound of Formula (XVII):

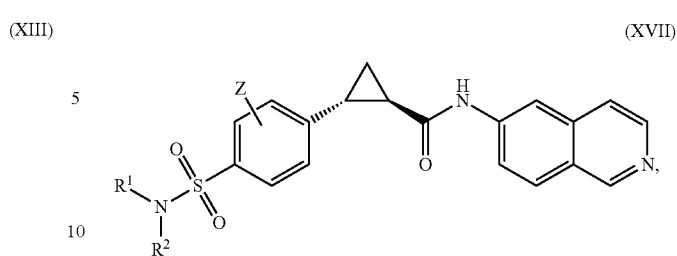

(XVII)

or a pharmaceutically acceptable salt thereof.

In an embodiment, the compound of Formula (X) is a compound of Formula (XVIII):

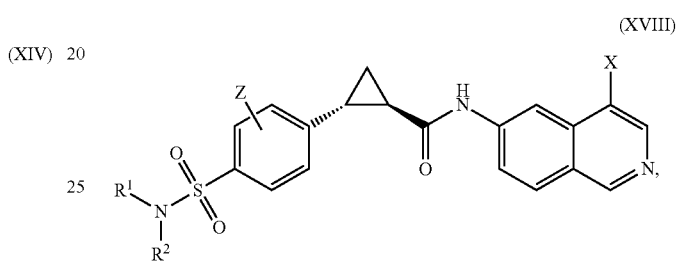

(XVIII)

or a pharmaceutically acceptable salt thereof.

In an embodiment, the compound of Formula (X) is a compound of Formula (XIV):

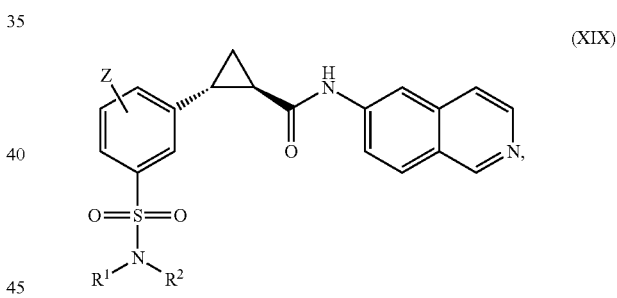

(XIX)

or a pharmaceutically acceptable salt thereof.

In an embodiment, the compound of Formula (X) is a compound of Formula (XX):

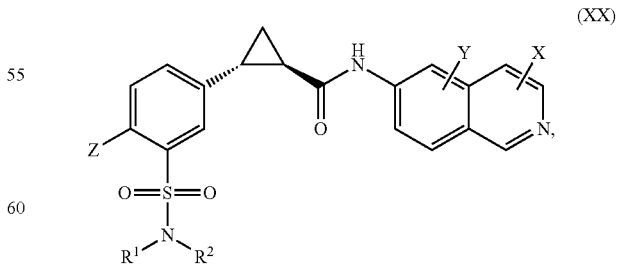

(XX)

or a pharmaceutically acceptable salt thereof.

In an embodiment, the compound of Formula (X) is a compound of Formula (XXI):

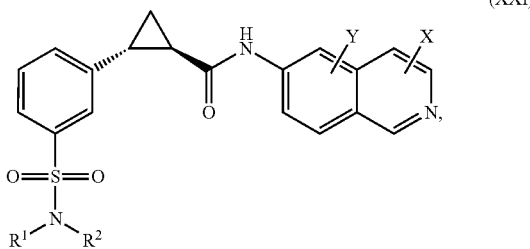

(XXI)

or a pharmaceutically acceptable salt thereof.

In an embodiment, the compound of Formula (X) is a compound of Formula (XXII):

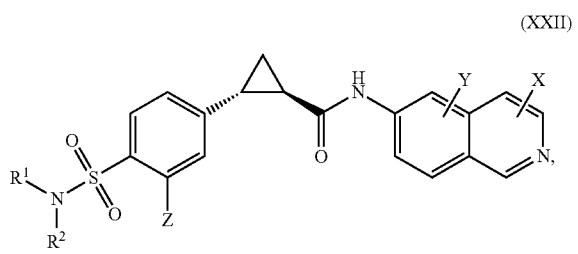

(XXII)

or a pharmaceutically acceptable salt thereof.

In an embodiment, the compound of Formula (X) is a compound of Formula (XXIII):

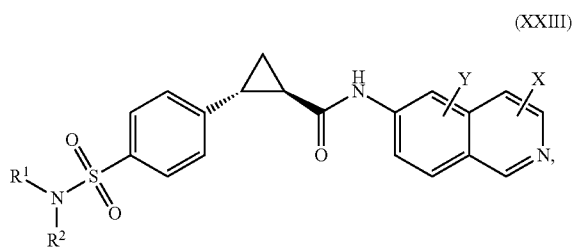

(XXIII)

or a pharmaceutically acceptable salt thereof.

In some embodiments of the Formulae provided herein, the compound is trans (±) with respect to the stereocenters of the cyclopropyl ring of the compound. In some embodiments of the Formulae provided herein, the compound is (R,R) with respect to the stereocenters of the cyclopropyl ring of the compound. In some embodiments of the Formulae provided herein, the compound is (S,S) with respect to the stereocenters of the cyclopropyl ring of the compound.

In some embodiments of the Formulae provided herein,
$R^1$ is H, —$C_{1-6}$ alkyl, aryl, heteroaryl, —($C_{1-6}$ alkyl)-pyridinyl, —($C_{1-6}$ alkyl)-N($R^3$)$R^4$, —($C_{1-6}$ alkyl)-heterocyclyl or heterocycloalkyl;
$R^2$ is H, —$C_{1-6}$ alkyl, aryl, heteroaryl, —($C_{1-6}$ alkyl)-pyridinyl, —($C_{1-6}$ alkyl)-N($R^3$)$R^4$, —($C_{1-6}$ alkyl)-heterocyclyl or heterocycloalkyl;
or $R^1$ and $R^2$, together with the nitrogen to which they are attached, form a heterocycle;
$R^3$ is H or $C_{1-6}$ alkyl;
$R^4$ is H or $C_{1-6}$ alkyl;
X is H, $C_{1-6}$ alkyl, halogen or hydroxyl;
Y is H, $C_{1-6}$ alkyl, halogen or hydroxyl; and
Z is H, $C_{1-6}$ alkyl, halogen or hydroxyl.

In some embodiments of the Formulae provided herein,
$R^1$ is H, —$C_{1-4}$ alkyl, aryl, heteroaryl, —($C_{1-4}$ alkyl)-pyridinyl, —($C_{1-4}$ alkyl)-N($R^3$)$R^4$, —($C_{1-4}$ alkyl)-heterocyclyl or heterocycloalkyl;
$R^2$ is H, —$C_{1-4}$ alkyl, aryl, heteroaryl, —($C_{1-4}$ alkyl)-pyridinyl, —($C_{1-4}$ alkyl)-N($R^3$)$R^4$, —($C_{1-4}$ alkyl)-heterocyclyl or heterocycloalkyl;
or $R^1$ and $R^2$, together with the nitrogen to which they are attached, form a heterocycle;
$R^3$ is H or $C_{1-4}$ alkyl;
$R^4$ is H or $C_{1-4}$ alkyl;
X is H, $C_{1-4}$ alkyl, halogen or hydroxyl;
Y is H, $C_{1-4}$ alkyl, halogen or hydroxyl; and
Z is H, $C_{1-4}$ alkyl, halogen or hydroxyl.

In some embodiments of the Formulae provided herein,
$R^1$ is H, phenyl, pyridinyl, —($C_{1-6}$ alkyl)-pyridinyl, —($C_{1-6}$ alkyl)-N($R^3$)$R^4$, —($C_{1-6}$ alkyl)-heterocyclyl or heterocycloalkyl; and
$R^2$ is H, phenyl, pyridinyl, —($C_{1-6}$ alkyl)-pyridinyl, —($C_{1-6}$ alkyl)-N($R^3$)$R^4$, —($C_{1-6}$ alkyl)-heterocyclyl or heterocycloalkyl.

In some embodiments of the Formulae provided herein,
$R^1$ is H; and
$R^2$ is H, phenyl, pyridinyl, —($C_{1-6}$ alkyl)-pyridinyl, —($C_{1-6}$ alkyl)-N($R^3$)$R^4$, —($C_{1-6}$ alkyl)-heterocyclyl or heterocycloalkyl.

In some embodiments of the Formulae provided herein, $R^1$ is H or —$C_{1-6}$ alkyl.

In some embodiments of the Formulae provided herein, $R^1$ is —$C_{1-6}$ alkyl.

In some embodiments of the Formulae provided herein, $R^1$ is H.

In some embodiments of the Formulae provided herein, $R^2$ is phenyl, pyridinyl, —($C_{1-6}$ alkyl)-pyridinyl, —($C_{1-6}$ alkyl)-N($R^3$)$R^4$, —($C_{1-6}$ alkyl)-heterocyclyl or heterocycloalkyl.

In some embodiments of the Formulae provided herein, pyridinyl is 2-pyridinyl.

In some embodiments of the Formulae provided herein, pyridinyl is 3-pyridinyl.

In some embodiments of the Formulae provided herein, pyridinyl is 4-pyridinyl.

In some embodiments of the Formulae provided herein, $R^2$ is phenyl, pyridinyl, —($C_{1-6}$ alkyl)-pyridinyl, —($C_{1-6}$ alkyl)-heterocyclyl or heterocycloalkyl.

In some embodiments of the Formulae provided herein, $R^2$ is —($C_{1-6}$ alkyl)-N($R^3$)$R^4$, —($C_{1-6}$ alkyl)-heterocyclyl or heterocycloalkyl;

In some embodiments of the Formulae provided herein, $R^2$ is phenyl, pyridinyl, —($C_{1-6}$ alkyl)-pyridinyl.

In some embodiments of the Formulae provided herein, $R^2$ is pyridinyl.

In some embodiments of the Formulae provided herein, $R^1$ and $R^2$, together with the nitrogen to which they are attached, form a heterocyclyl containing six ring atoms.

In some embodiments of the Formulae provided herein, $R^1$ and $R^2$, together with the nitrogen to which they are attached, form a heterocyclyl containing six ring atoms, wherein one or two of the ring atoms are, independently, O, S or N.

In some embodiments of the Formulae provided herein, $R^1$ and $R^2$, together with the nitrogen to which they are attached, form a heterocyclyl containing six ring atoms, wherein one or two of the ring atoms are N.

In some embodiments of the Formulae provided herein, $R^3$ and $R^4$ are H.

In some embodiments of the Formulae provided herein, $R^3$ and $R^4$ are, independently, $C_{1-6}$ alkyl.

In some embodiments of the Formulae provided herein, $R^3$ is H, and $R^4$ is $C_{1-6}$ alkyl.

In some embodiments of the Formulae provided herein, X, Y and Z are H.

In some embodiments of the Formulae provided herein, X is $C_{1-6}$ alkyl, halogen or hydroxyl; and Y and Z are H.

In some embodiments of the Formulae provided herein, X is halogen; and Y and Z are H.

In some embodiments of the Formulae provided herein, X is $C_{1-6}$ alkyl, halogen or hydroxyl.

In some embodiments of the Formulae provided herein, X is methyl, ethyl, $CF_3$, $CHF_2$ or $CH_2F$.

In some embodiments of the Formulae provided herein, Y is methyl, ethyl, $CF_3$, $CHF_2$ or $CH_2F$.

In some embodiments of the Formulae provided herein, Z is methyl, ethyl, $CF_3$, $CHF_2$ or $CH_2F$.

In some embodiments of the Formulae provided herein, X is halogen.

In some embodiments of the Formulae provided herein, X is F or Cl.

In some embodiments of the Formulae provided herein, X is Cl.

In some embodiments of the Formulae provided herein, X is methyl or halogen; Y is methyl or halogen; and Z is methyl or halogen.

In some embodiments of the Formulae provided herein, X is methyl, F or Cl; Y is methyl, F or Cl; and Z is methyl, F or Cl.

In some embodiments of the Formulae provided herein, X is halogen; and Y is hydroxyl.

In some embodiments of the Formulae provided herein, Y is hydroxyl.

In some embodiments of the Formulae provided herein, Z is H or F.

In some aspects, provided herein is a compound of Formula (1):

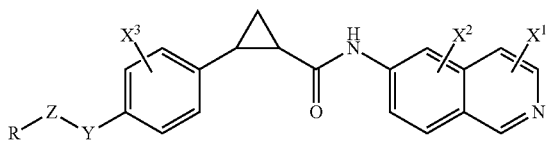

(1)

or a pharmaceutically acceptable salt thereof;
wherein
Y is —$C_{1-6}$-alkyl, —O—, —$(CH_2)_{1-2}OC(O)N(H)$—, —$(CH_2)_{1-2}N(H)$—, —C(O)N(H)— (i.e. an amide) or —C(O)O— (i.e. an ester);
$X^1$ is H, —OH, —$C_{1-3}$-alkyl (e.g., methyl), or halogen (e.g., F, Br or Cl);
$X^2$ is H or halogen (e.g., F, Cl or Br);
$X^3$ is H or halogen (e.g., F, Cl or Br);
Z is a bond, —$S(O)_2$—, ethenyl, ethynyl, methylene, ethylene, or propylene, or Z, together with the nitrogen to which Z is attached forms a —$C_{2-6}$-heterocyloalkyl; and R is —OH, —$NH_2$, —$NH(C_{1-3}$-alkyl), —$N(C_{1-3}$-alkyl)$(C_{1-3}$-alkyl), —C(O)O—$(C_{1-6}$-alkyl), —$N(H)C(O)$—$(C_{1-6}$-alkyl), —$C_{1-3}$-alkyl, pyridinyl, phenyl, halophenyl, methoxyphenyl, monohalomethoxyphenyl, diihalomethoxyphenyl, trihalomethoxyphenyl, monohalomethyl, dihalomethyl, trihalomethyl, thienyl, halothienyl, thiazolyl, benzothiophenyl, isoquinolinyl, —$C_{2-6}$-heterocyloalkyl, oxydiaryl (e.g., oxydiphenyl, oxydinaphthalenyl, or phenoxynaphthalenyl), or R is —$C_{2-6}$-heterocyloalkyl unsubstituted or substituted with one or more of —$C_{1-6}$-alkyl, halo, benzyl, halobenzyl, pyridinyl, carbonyl, monohalomethyl, dihalomethyl, trihalomethyl, or —C(O)O—$(C_{1-6}$-alkyl);

or Y and Z together are a bond, and R is —OH, —$NH_2$, —$NH(C_{1-3}$-alkyl), —$N(C_{1-3}$-alkyl)$(C_{1-3}$-alkyl), —$N(H)C(O)$—$(C_{1-6}$-alkyl), —$C(O)NH_2$, —$C_{1-3}$-alkyl, pyridinyl, phenyl, halophenyl, methoxyphenyl, monohalomethoxyphenyl, diihalomethoxyphenyl, trihalomethoxyphenyl, monohalomethyl, dihalomethyl, trihalomethyl, thienyl, halothienyl, thiazolyl, benzothiophenyl, isoquinolinyl, —$C_{2-6}$-heterocyloalkyl, oxydiaryl (e.g., oxydiphenyl, oxydinaphthalenyl, or phenoxynaphthalenyl), or R is —$C_{2-6}$-heterocyloalkyl unsubstituted or substituted with one or more of —$C_{1-6}$-alkyl, halo, benzyl, halobenzyl, pyridinyl, carbonyl, monohalomethyl, dihalomethyl, trihalomethyl, or —C(O)O—$(C_{1-6}$-alkyl).

In some embodiments, Y is —C(O)N(H)— (i.e. an amide). In some embodiments, Y is —C(O)O— (i.e. an ester). In some embodiments, Y is —$C_{1-6}$-alkyl. In some embodiments, Y is —$(CH_2)_{1-2}OC(O)N(H)$— or —$(CH_2)_{1-2}N(H)$—. In some embodiments, Y is —O—.

In some embodiments, Y and Z together are a bond.

In some embodiment, $X^1$ is —OH, methyl, F, Br or Cl.

In some embodiments, $X^2$ is F, Cl or Br.

In some embodiments, $X^3$ is F, Cl or Br.

In some embodiments, Z is —$S(O)_2$—. In some embodiments, Z is a bond. In some embodiments, Z is ethenyl, ethynyl, methylene, ethylene, or propylene. In some embodiments, Z, together with the nitrogen to which Z is attached forms a —$C_{2-6}$-heterocyloalkyl.

In some embodiments, R is —OH, —$NH_2$, —$NH(C_{1-3}$-alkyl), —$N(C_{1-3}$-alkyl)$(C_{1-3}$-alkyl), —C(O)O—$(C_{1-6}$-alkyl), —$N(H)C(O)$—$(C_{1-6}$-alkyl), or —$C_{1-3}$-alkyl. In some embodiments, R is —OH, —$NH_2$, —$NH(C_{1-3}$-alkyl), —$N(C_{1-3}$-alkyl)$(C_{1-3}$-alkyl), —$N(H)C(O)$—$(C_{1-6}$-alkyl), or —$C_{1-3}$-alkyl. In some embodiments, R is pyridinyl, phenyl, halophenyl, methoxyphenyl, monohalomethoxyphenyl, diihalomethoxyphenyl, trihalomethoxyphenyl, monohalomethyl, dihalomethyl, trihalomethyl, thienyl, halothienyl, thiazolyl, benzothiophenyl, isoquinolinyl, —$C_{2-6}$-heterocyloalkyl, oxydiaryl (e.g., oxydiphenyl, oxydinaphthalenyl, or phenoxynaphthalenyl). In some embodiments, R is —$C_{2-6}$-heterocyloalkyl unsubstituted or substituted with one or more of —$C_{1-6}$-alkyl, halo, benzyl, halobenzyl, pyridinyl, carbonyl, monohalomethyl, dihalomethyl, trihalomethyl, or —C(O)O—$(C_{1-6}$-alkyl).

In some embodiments, provided the compound of Formula (1) is a compound of Formula (2):

(2)

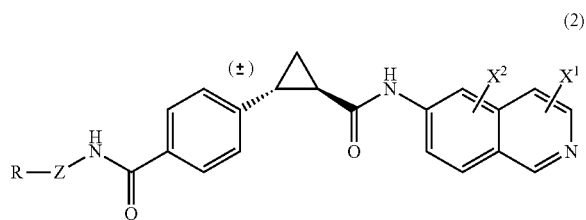

or a pharmaceutically acceptable salt thereof.

In some embodiments, provided the compound of Formula (1) is a compound of Formula (3):

(3)

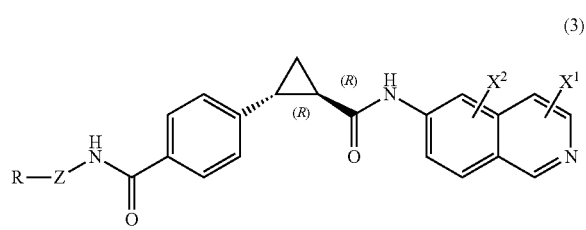

or a pharmaceutically acceptable salt thereof.

In some embodiments, provided the compound of Formula (1) is a compound of Formula (4):

(4)

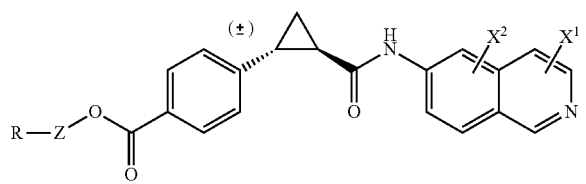

or a pharmaceutically acceptable salt thereof;
wherein
R—Z—N(R$^{N1}$) is —C$_{2-6}$-heterocyloalkyl unsubstituted or substituted with one or more of —C$_{1-6}$-alkyl, halo, phenyl, halophenyl, benzyl, halobenzyl, pyridinyl, carbonyl, monohalomethyl, dihalomethyl, trihalomethyl, or —C(O)O—(C$_{1-6}$-alkyl).

In some embodiments, provided the compound of Formula (1) is a compound of Formula (5):

(5)

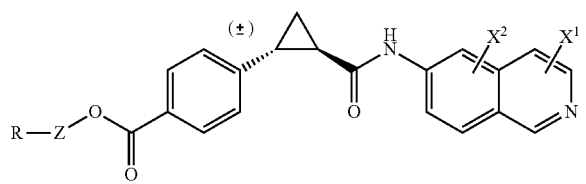

or a pharmaceutically acceptable salt thereof.

In some embodiments, provided the compound of Formula (1) is a compound of Formula (6):

(6)

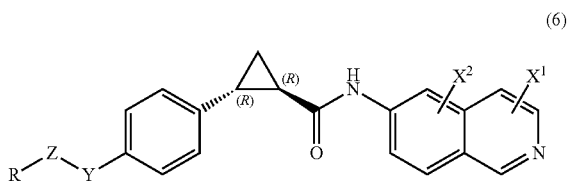

or a pharmaceutically acceptable salt thereof.

In some embodiments, provided the compound of Formula (1) is a compound of Formula (7):

(7)

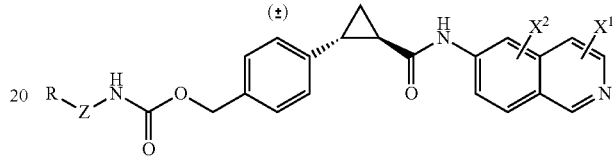

or a pharmaceutically acceptable salt thereof.

In some embodiments, provided the compound of Formula (1) is a compound of Formula (8):

(8)

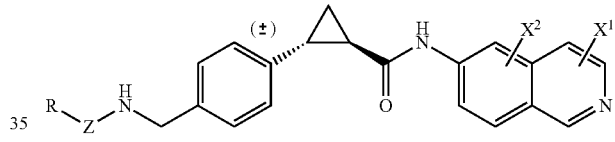

or a pharmaceutically acceptable salt thereof.

In some embodiments, provided the compound of Formula (1) is a compound of Formula (9):

(9)

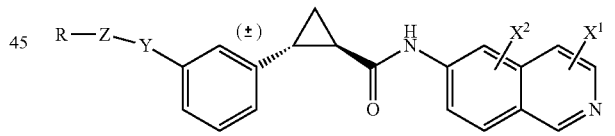

or a pharmaceutically acceptable salt thereof.

In some embodiments, provided the compound of Formula (1) is a compound of Formula (10):

(10)

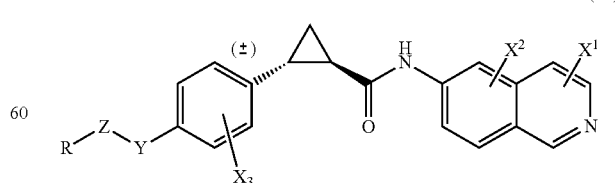

or a pharmaceutically acceptable salt thereof.

In some embodiments, provided the compound of Formula (1) is a compound of Formula (11):

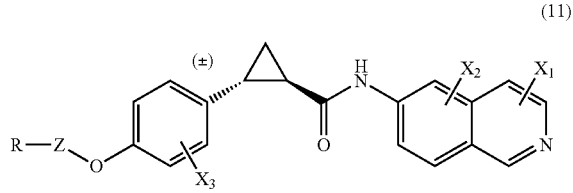

(11)

or a pharmaceutically acceptable salt thereof.

In another aspect, provided herein are compounds of Formula (1'):

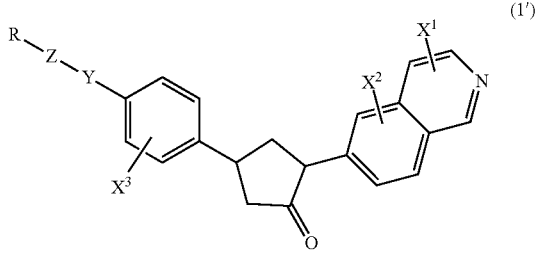

(1')

or a pharmaceutically acceptable salt thereof;
wherein
Y is —(CH$_2$)$_{1-2}$N(H)— or —C(O)N(H)— (i.e. an amide);
X$^1$ is H, —OH, —C$_{1-3}$-alkyl (e.g., methyl), or halogen (e.g., F, Br or Cl);
X$^2$ is H or halogen (e.g., F, Cl or Br);
X$^3$ is H, —C$_{1-3}$-alkyl (e.g., methyl), or halogen (e.g., F, Cl or Br);
Z is a bond, ethenyl, ethynyl, methylene, ethylene, or propylene, or Z, together with the nitrogen to which Z is attached forms a —C$_{2-6}$-heterocyloalkyl; and
R is —OH, —NH$_2$, —NH(C$_{1-3}$-alkyl), —N(C$_{1-3}$-alkyl)(C$_{1-3}$-alkyl), —C(O)O—(C$_{1-6}$-alkyl), —N(H)C(O)—(C$_{1-6}$-alkyl), —C$_{1-3}$-alkyl, pyridinyl, phenyl, halophenyl, methoxyphenyl, monohalomethoxyphenyl, diihalomethoxyphenyl, trihalomethoxyphenyl, monohalomethyl, dihalomethyl, trihalomethyl, thienyl, halothienyl, thiazolyl, benzothiophenyl, isoquinolinyl, —C$_{2-6}$-heterocyloalkyl, oxydiaryl (e.g., oxydiphenyl, oxydinaphthalenyl, or phenoxynaphthalenyl), or R is —C$_{2-6}$-heterocyloalkyl unsubstituted or substituted with one or more of —C$_{1-6}$-alkyl, halo, benzyl, halobenzyl, pyridinyl, carbonyl, monohalomethyl, dihalomethyl, trihalomethyl, or —C(O)O—(C$_{1-6}$-alkyl);
or Y and Z together are a bond, and R is —OH, —NH$_2$, —NH(C$_{1-3}$-alkyl), —N(C$_{1-3}$-alkyl)(C$_{1-3}$-alkyl), —N(H)C(O)—(C$_{1-6}$-alkyl), —C(O)NH$_2$, —C$_{1-3}$-alkyl, pyridinyl, phenyl, halophenyl, methoxyphenyl, monohalomethoxyphenyl, diihalomethoxyphenyl, trihalomethoxyphenyl, monohalomethyl, dihalomethyl, trihalomethyl, thienyl, halothienyl, thiazolyl, benzothiophenyl, isoquinolinyl, —C$_{2-6}$-heterocyloalkyl, oxydiaryl (e.g., oxydiphenyl, oxydinaphthalenyl, or phenoxynaphthalenyl), or R is —C$_{2-6}$-heterocyloalkyl unsubstituted or substituted with one or more of —C$_{1-6}$-alkyl, halo, benzyl, halobenzyl, pyridinyl, carbonyl, monohalomethyl, dihalomethyl, trihalomethyl, or —C(O)O—(C$_{1-6}$-alkyl).

In some embodiments, Y is —C(O)N(H)— (i.e. an amide). In some embodiments, Y is —C(O)O— (i.e. an ester). In some embodiments, Y is —C$_{1-6}$-alkyl. In some embodiments, Y is —(CH$_2$)$_{1-2}$OC(O)N(H)— or —(CH$_2$)$_{1-2}$N(H)—. In some embodiments, Y is —O—.
In some embodiments, Y and Z together are a bond.
In some embodiment, X$^1$ is —OH, methyl, F, Br or Cl.
In some embodiments, X$^2$ is F, Cl or Br.
In some embodiments, X$^3$ is F, Cl or Br.
In some embodiments, Z is —S(O)$_2$—. In some embodiments, Z is a bond. In some embodiments, Z is ethenyl, ethynyl, methylene, ethylene, or propylene. In some embodiments, Z, together with the nitrogen to which Z is attached forms a —C$_{2-6}$-heterocyloalkyl.
In some embodiments, R is —OH, —NH$_2$, —NH(C$_{1-3}$-alkyl), —N(C$_{1-3}$-alkyl)(C$_{1-3}$-alkyl), —C(O)O—(C$_{1-6}$-alkyl), —N(H)C(O)—(C$_{1-6}$-alkyl), or —C$_{1-3}$-alkyl. In some embodiments, R is —OH, —NH$_2$, —NH(C$_{1-3}$-alkyl), —N(C$_{1-3}$-alkyl)(C$_{1-3}$-alkyl), —N(H)C(O)—(C$_{1-6}$-alkyl), or —C$_{1-3}$-alkyl. In some embodiments, R is pyridinyl, phenyl, halophenyl, methoxyphenyl, monohalomethoxyphenyl, diihalomethoxyphenyl, trihalomethoxyphenyl, monohalomethyl, dihalomethyl, trihalomethyl, thienyl, halothienyl, thiazolyl, benzothiophenyl, isoquinolinyl, —C$_{2-6}$-heterocyloalkyl, oxydiaryl (e.g., oxydiphenyl, oxydinaphthalenyl, or phenoxynaphthalenyl). In some embodiments, R is —C$_{2-6}$-heterocyloalkyl unsubstituted or substituted with one or more of —C$_{1-6}$-alkyl, halo, benzyl, halobenzyl, pyridinyl, carbonyl, monohalomethyl, dihalomethyl, trihalomethyl, or —C(O)O—(C$_{1-6}$-alkyl).

In some embodiments, provided the compound of Formula (1') is a compound of Formula (12):

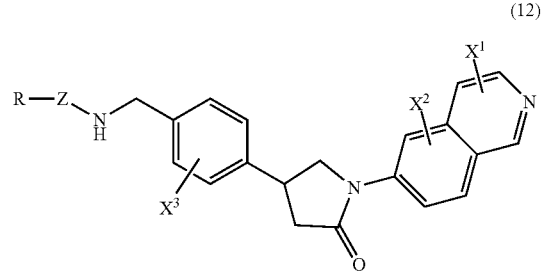

(12)

or a pharmaceutically acceptable salt thereof.

In some embodiments, provided the compound of Formula (1') is a compound of Formula (13):

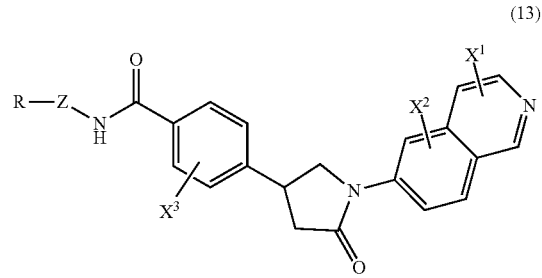

(13)

or a pharmaceutically acceptable salt thereof.

In some embodiments of the Formulae provided herein, the compound is a compound provided in Table 1, Table 2, Table 3, Table 4, Table 5, Table 6, Table 7, Table 8, Table 9, Table 10, Table 11, Table 12, Table 13, Table 14, Table 15, Table 16, Table 17 or Table 18, or a pharmaceutically acceptable salt thereof.

Isomers

Compounds described herein may exist in one or more particular geometric, optical, enantiomeric, diastereomeric, epimeric, atropic, stereoisomer, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and half chair-forms; and combinations thereof, hereinafter collectively referred to as "isomers" (or "isomeric forms").

In one embodiment, a compound described herein may be an enantiomerically enriched isomer of a stereoisomer described herein. For example, the compound may have an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%. Enantiomer, when used herein, refers to either of a pair of chemical compounds whose molecular structures have a mirror-image relationship to each other.

In one embodiment, a preparation of a compound disclosed herein is enriched for an isomer of the compound having a selected stereochemistry, e.g., R or S, corresponding to a selected stereocenter. For example, the compound has a purity corresponding to a compound having a selected stereochemistry of a selected stereocenter of at least about 60%, 65%, 70%, 75%, 80%, 85%, 90%, 95%, 96%, 97%, 98%, or 99%.

In one embodiment, a composition described herein includes a preparation of a compound disclosed herein that is enriched for a structure or structures having a selected stereochemistry, e.g., R or S, at a selected stereocenter. Exemplary R/S configurations can be those provided in an example described herein.

An "enriched preparation," as used herein, is enriched for a selected stereoconfiguration of one, two, three or more selected stereocenters within the subject compound. Exemplary selected stereocenters and exemplary stereoconfigurations thereof can be selected from those provided herein, e.g., in an example described herein. By enriched is meant at least 60%, e.g., of the molecules of compound in the preparation have a selected stereochemistry of a selected stereocenter. In an embodiment it is at least 65%, 70%, 75%, 80%, 85%, 90%, 95%, 96%, 97%, 98%, or 99%. Enriched refers to the level of a subject molecule(s) and does not connote a process limitation unless specified.

Compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral chromatography column. The enantiomers also may be obtained from kinetic resolution of the racemate of corresponding esters using lipase enzymes.

Except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_3$-alkyl or propyl includes n-propyl and iso-propyl; C$_4$-alkyl or butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hydroxyazo, and nitro/aci-nitro.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Salts

A compound described herein can be in the form of a salt, e.g., a pharmaceutically acceptable salt. The term "pharmaceutically acceptable salt" includes salts of the active compounds that are prepared with relatively nontoxic acids or bases, depending on the particular substituents found on the compounds described herein. Neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure. Examples of pharmaceutically acceptable salts are discussed in Berge et al, 1977, "Pharmaceutically Acceptable Salts." *J. Pharm. Sci.* Vol. 66, pp. 1-19. In an embodiment, the compound is present in mono-salt form. In embodiments, the compound is present in di-salt form.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations. Examples of suitable organic cations include, but are not limited to, ammonium ion (i.e., NH$_4^+$) and substituted ammonium ions (e.g., NH$_3$R$_1^+$, NH$_2$R$_2^+$, NHR$_3^+$, NR$_4^+$). Examples of some suitable substituted ammonium ions are those derived from: ethylamine, diethylamine, triethylamine, butylamine, ethylenediamine, ethanolamine, diethanolamine, piperazine, benzylamine, phenylbenzylamine, choline, meglumine, and tromethamine, as well as dibasic amino acids, such as lysine and arginine.

If the compound is cationic, or has a functional group that may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, p-toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Chemically Protected Forms

It may be convenient or desirable to prepare, purify, and/or handle an active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999). Unless otherwise specified, a reference to a particular compound also includes chemically protected forms thereof.

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

A hydroxyl group may be protected as an ether (—OR) or an ester (—OC(O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(O)CH$_3$, —OAc).

An aldehyde or ketone group may be protected as an acetal (RCH(OR)$_2$) or ketal (R$_2$C(OR)$_2$), respectively, in which the carbonyl group (R$_2$C=O) is converted to a diether (R$_2$C(OR)$_2$), by reaction with, for example, a primary alcohol. The aldehyde or ketone group is readily regenerated by hydrolysis using a large excess of water in the presence of acid.

An amine group may be protected, for example, as an amide (—NRC(O)R) or a urethane (—NRC(O)OR), for example, as: a methyl amide (—NHC(O)CH$_3$); a benzyloxy amide (—NHC(O)OCH$_2$C$_6$H$_5$, —NH-Cbz); as a tert-butoxy amide (—NHC(O)OC(CH$_3$)$_3$, —NH-Boc); a 2-biphenyl-2-propoxy amide (—NHCO(O)C(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH—Psec); or, in suitable cases (e.g., cyclic amines), as a nitroxide radical (>N—O«).

A carboxylic acid group may be protected as an ester, for example, as: an alkyl ester (e.g., a methyl ester; a t-butyl ester); a haloalkyl ester (e.g., a haloalkyl ester); a trialkylsilylalkyl ester; or an arylalkyl ester (e.g., a benzyl ester; a nitrobenzyl ester); or as an amide, for example, as a methyl amide.

A thiol group may be protected as a thioether (—SR), for example, as: a benzyl thioether; an acetamidomethyl ether (—S—CH$_2$NHC(O)CH$_3$)

Prodrugs and Other Modifications

In addition to salt forms, the present disclosure may also provide compounds that are in a prodrug form. Prodrugs of the compounds described herein are those compounds that readily undergo chemical changes under physiological conditions to provide the compounds described herein. Prodrugs can be converted to the compounds of the present disclosure by chemical or biochemical methods in an ex vivo environment. For example, prodrugs can be slowly converted to the compounds of the present disclosure when placed in a transdermal patch reservoir with or without a suitable enzyme or chemical reagent.

A compound described herein can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom substitution in aromatic rings.

Synthesis

The compounds may be synthesized according to the exemplary syntheses shown in the Examples.

Other methods of synthesizing the compounds of the formulae herein will be evident to those of ordinary skill in the art. Synthetic chemistry transformations and protecting group methodologies (protection and deprotection) useful in synthesizing the compounds are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Methods of Use and Activity

The compounds as disclosed herein and compositions including them have kinase inhibitory activity and are thus useful in modulating the action of kinases, and in treatment and/or prevention of diseases or conditions influenced by kinases. The above compounds and compositions may be used to modulate (e.g., influence or inhibit) the action of kinases either in a cell in vitro or in a cell in a living body in vivo. Specifically, in one embodiment, a method is provided of inhibiting the action of a kinase comprising applying to a medium such as an assay medium or contacting with a cell either in a cell in vitro or in a cell in a living body in vivo an effective inhibitory amount of a compound as disclosed herein. In one embodiment, the kinase inhibited is a rho kinase. In another embodiment, the kinase inhibited is a JAK (e.g., JAK2) kinase.

JAK inhibitors are useful in treating various JAK-associated diseases or disorders. Examples of JAK-associated diseases include diseases involving the immune system including, for example, organ transplant rejection (e.g., allograft rejection and graft versus host disease). Further examples of JAK-associated diseases include autoimmune diseases such as multiple sclerosis, rheumatoid arthritis, juvenile arthritis, psoriatic arthritis, type I diabetes, lupus, psoriasis, inflammatory bowel disease, ulcerative colitis, Crohn's disease, myasthenia gravis, immunoglobulin nephropathies, myocarditis, autoimmune thyroid disorders, chronic obstructive pulmonary disease (COPD), and the like. In some embodiments, the autoimmune disease is arthritis.

Further examples of JAK-associated diseases include allergic conditions such as asthma, food allergies, eczematous dermatitis, contact dermatitis, atopic dermatitis (atropic eczema), and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated diseases or conditions include those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, uterine leiomyosarcoma, melanoma etc.), hematological cancers (e.g., lymphoma, leukemia such as acute lymphoblastic leukemia (ALL), acute myelogenous leukemia (AML) or multiple myeloma), and skin cancer such as cutaneous T-cell lymphoma (CTCL) and cutaneous B-cell lymphoma. Example CTCLs include Sezary syndrome and mycosis fungoides. Other examples of JAK-associated diseases or conditions include pulmonary arterial hypertension.

Other examples of JAK-associated diseases or conditions include inflammation-associated cancers. In some embodiments, the cancer is associated with inflammatory bowel disease. In some embodiments, the inflammatory bowel disease is ulcerative colitis. In some embodiments, the inflammatory bowel disease is Crohn's disease. In some embodiments, the inflammation-associated cancer is colitis-associated cancer. In some embodiments, the inflammation-associated cancer is colon cancer or colorectal cancer. In some embodiments, the cancer is gastric cancer, gastrointestinal carcinoid tumor, gastrointestinal stromal tumor (GIST), adenocarcinoma, small intestine cancer, or rectal cancer.

The compounds of the present disclosure are used in methods of inhibiting kinases in a cell, a tissue or a subject such as a human comprising contacting the cell with an amount of one or more of the compounds of the present disclosure effective to inhibit the kinase. In one embodiment, the compounds are administered in a pharmaceutically acceptable composition, such as in or with a pharmaceutically acceptable carrier.

In another embodiment, the compounds of the present disclosure are used in methods for modulating the action of a kinase in a cell comprising contacting the cell with amount of one or more compounds of the present disclosure effective to modulate the action of a kinase in a cell. In one embodiment, the compounds of the present disclosure are administered in a pharmaceutically acceptable composition, such as in or with a pharmaceutically acceptable carrier.

Treatment or prevention of diseases or conditions for which the compounds of the present disclosure may be useful includes any of the diseases or conditions associated with kinase activity or diseases or conditions affected by kinases. Examples of these types of diseases include neurodegenerative diseases, such as Alzheimer's; ocular diseases, such as diabetic eye diseases, wet age-related macular degeneration, or dry age-related macular degeneration, inflammatory eye diseases, retinal degradation and glaucoma; cardiovascular diseases; and cancer. Additional examples include bone disorder, obesity, hepatic disease, renal disease, pancreatitis, gastric disturbance, hypertension, fertility control, disorders of hair growth, nasal congestion, neurogenic bladder disorder, gastrointestinal disorder, dermatological disorder, and respiratory indications.

In some embodiments, the compounds of the present disclosure will be administered in conjunction with one or more additional therapeutic agents. Suitable classes of additional therapeutic agents include, but are not limited to, beta blockers, alpha-agonists, carbonic anhydrase inhibitors, prostaglandin-like compounds, miotic or cholinergic agents, epinephrine compounds, or neuroprotective or anti-inflammatory compounds.

Beta blockers. These compounds are thought to lower intraocular pressure (IOP) by reducing the production of aqueous humor. Examples include levobunolol (BETAGAN™), timolol (BETIMOL™, TIMOPTIC™), betaxolol (BETOPTIC™) and metipranolol (OPTIPRANOLOL™).

Alpha-agonists. These compounds are thought to lower IOP by reducing the production of aqueous humor and increasing drainage. Examples include apraclonidine (IOPIDINE™) and brimonidine (ALPHAGAN™).

Carbonic anhydrase inhibitors. These compounds are thought to lower IOP by also reducing the production of aqueous humor. Examples include dorzolamide (TRUSOPT™) and brinzolamide (AZOPT™).

Prostaglandin-like compounds. These compounds are thought to lower IOP by increasing the outflow of aqueous humor by the uveoscleral pathway. Examples include AR-102, latanoprost (XALATAN™), bimatoprost (LUMIGAN™), tafluprost (ZIOPTAN™), and travoprost (TRAVATAN™).

Miotic or cholinergic agents. These agents are thought to function by causing the pupil to constrict, which opens drainage channels in the eye. Examples include pilocarpine (ISOPTO CARPINE™, PILOPINE™) and carbachol (ISOPTO CARBACHOL™).

Epinephrine compounds. These compounds, such as dipivefrin (PROPINE™), are thought to function by both decreasing the outflow of aqueous humor, as well as increasing fluid drainage.

Neuroprotective or anti-inflammatory compounds. These compounds, such as Aflibercept (EYLEA™) are treatments for conditions of the retina such as Macular Degeneration, and are designed as anti-VEGF treatments or have similar types of anti-growth or anti-inflammatory activity.

Thus, provided herein are methods of treating an ocular disorder in a subject in need thereof, comprising administering to the subject a compound, a composition, or a pharmaceutical composition provided herein.

Also provided herein are methods of reducing intraocular pressure in a subject in need thereof, comprising administering to the subject a compound, a composition, or a pharmaceutical composition provided herein.

In one aspect, provided herein are methods of treating an ocular disorder in a subject in need thereof, comprising administering to the subject a compound, or a pharmaceutically acceptable salt thereof, provided herein.

In some embodiments, the ocular disorder is glaucoma.

In another aspect, provided herein are methods of reducing intraocular pressure in a subject in need thereof, comprising administering to the subject a compound, or a pharmaceutically acceptable salt thereof, provided herein.

In some embodiments of these aspects, the compound is administered topically to an eye of the subject.

In some embodiments, provided herein are methods of treating an ocular disorder in a subject in need thereof, comprising administering to the subject a compound of any of the Formulae provided herein, or a pharmaceutically acceptable salt thereof.

In some embodiments, provided herein are methods of treating an ocular disorder in a subject in need thereof, comprising administering to the subject a compound provided in Table 1, Table 2, Table 3, Table 4, Table 5, Table 6, Table 7, Table 8, Table 9, Table 10, Table 11, Table 12, Table 13, Table 14, Table 15, Table 16, Table 17 or Table 18, or a pharmaceutically acceptable salt thereof.

In some embodiments, provided herein are methods of reducing intraocular pressure in a subject in need thereof, comprising administering to the subject a compound of any of the Formulae provided herein, or a pharmaceutically acceptable salt thereof.

In some embodiments, provided herein are methods of reducing intraocular pressure in a subject in need thereof, comprising administering to the subject a compound provided in Table 1, Table 2, Table 3, Table 4, Table 5, Table 6, Table 7, Table 8, Table 9, Table 10, Table 11, Table 12, Table 13, Table 14, Table 15, Table 16, Table 17 or Table 18, or a pharmaceutically acceptable salt thereof.

In some embodiments of these methods, the method further comprises administering one or more additional therapeutic agents. In some embodiments, the one or more additional therapeutic agents is a beta blocker, an alpha-agonist, a carbonic anhydrase inhibitor, a prostaglandin or a prostaglandin-like compound, a miotic or cholinergic agent, an epinephrine compound, or a neuroprotective or anti-inflammatory compound. In some embodiments, the one or more additional therapeutic agents is a prostaglandin or a prostaglandin-like compound. In some embodiment, the prostaglandin-like compound is AR-102, latanoprost, bimatoprost, tafluprost, or travoprost.

Also provided herein are methods of treating an autoimmune disease in a subject in need thereof, comprising administering to the subject a compound, a composition, or a pharmaceutical composition provided herein.

In some embodiments, provided herein are methods of treating an autoimmune disease in a subject in need thereof, comprising administering to the subject a compound of any of the Formulae provided herein, or a pharmaceutically acceptable salt thereof.

In some embodiments, provided herein are methods of treating an autoimmune disease in a subject in need thereof, comprising administering to the subject a compound provided in Table 1, Table 2, Table 3, Table 4, Table 5, Table 6, Table 7, Table 8, Table 9, Table 10, Table 11, Table 12, Table 13, Table 14, Table 15, Table 16, Table 17 or Table 18, or a pharmaceutically acceptable salt thereof.

In some embodiments, the autoimmune disease is multiple sclerosis, rheumatoid arthritis, juvenile arthritis, psoriatic arthritis, type I diabetes, lupus, psoriasis, inflammatory bowel disease, ulcerative colitis, Crohn's disease, myasthenia gravis, immunoglobulin nephropathies, myocarditis, autoimmune thyroid disorders, or chronic obstructive pulmonary disease.

Compositions and Administration

The additional therapeutic agent or agents can be administered simultaneously or sequentially with the compounds of the present disclosure. Sequential administration includes administration before or after the compounds of the present disclosure. In some embodiments, the additional therapeutic agent or agents can be administered in the same composition as the compounds of the present disclosure. In other embodiments, there can be an interval of time between administration of the additional therapeutic agent and the compounds of the present disclosure.

In some embodiments, the administration of an additional therapeutic agent with a compound of the present disclosure will enable lower doses of the other therapeutic agents to be administered for a longer period of time.

Also provided herein are compositions comprising a compound provided herein, or a pharmaceutically acceptable salt thereof. In one embodiment, the compositions provided herein are pharmaceutical compositions comprising a pharmaceutically acceptable carrier.

Pharmaceutical compositions for use in accordance with the present disclosure may be formulated in a conventional manner using one or more physiologically acceptable carriers or excipients. Thus, the compounds and their physiologically acceptable salts and solvates may be formulated for administration by, for example, solid dosing, eyedrop, in a topical oil-based formulation, injection (including injection of a drug-eluting device either into the body as a whole, or into specific tissues of the eye), inhalation (either through the mouth or the nose), implants, or oral, buccal, parenteral or rectal administration. Techniques and formulations may generally be found in "Remington's Pharmaceutical Sciences," (Meade Publishing Co., Easton, Pa.).

The route by which the compounds of the present disclosure (component A) will be administered and the form of the composition will dictate the type of carrier (component B) to be used. The composition may be in a variety of forms, suitable, for example, for systemic administration (e.g., oral, rectal, nasal, sublingual, buccal, implants, or parenteral, or by ocular injection into one of the chambers of the eye, such as intravitreal injection, intracameral injection, or injection into the aqueous humour.) or topical administration (e.g., local application on the skin, ocular, liposome delivery systems, or iontophoresis).

Carriers for systemic administration typically comprise at least one of a) diluents, b) lubricants, c) binders, d) disintegrants, e) colorants, f) flavors, g) sweeteners, h) antioxidants, j) preservatives, k) glidants, m) solvents, n) suspending agents, o) wetting agents, p) surfactants, combinations thereof, and others. All carriers are optional in the systemic compositions.

Ingredient a) is a diluent. Suitable diluents for solid dosage forms include sugars such as glucose, lactose, dextrose, and sucrose; diols such as propylene glycol; calcium carbonate; sodium carbonate; sugar alcohols, such as glycerin; mannitol; and sorbitol. The amount of ingredient a) in the systemic or topical composition is typically about 50 to about 90%.

Ingredient b) is a lubricant. Suitable lubricants for solid dosage forms are exemplified by solid lubricants including silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of *Theobroma*. The amount of ingredient b) in the systemic or topical composition is typically about 5 to about 10%.

Ingredient c) is a binder. Suitable binders for solid dosage forms include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of ingredient c) in the systemic composition is typically about 5 to about 50%, and in ocular solid dosing forms up to 99%.

Ingredient d) is a disintegrant. Suitable disintegrants for solid dosage forms include agar, alginic acid and the sodium salt thereof, effervescent mixtures, croscarmelose, crospovidone, sodium carboxymethyl starch, sodium starch glycolate, clays, and ion exchange resins. The amount of ingredient d) in the systemic or topical composition is typically about 0.1 to about 10%.

Ingredient e) for solid dosage forms is a colorant such as an FD&C dye. When used, the amount of ingredient e) in the systemic or topical composition is typically about 0.005 to about 0.1%.

Ingredient f) for solid dosage forms is a flavor such as menthol, peppermint, and fruit flavors. The amount of ingredient f), when used, in the systemic or topical composition is typically about 0.1 to about 1.0%.

Ingredient g) for solid dosage forms is a sweetener such as aspartame and saccharin. The amount of ingredient g) in the systemic or topical composition is typically about 0.001 to about 1%.

Ingredient h) is an antioxidant such as butylated hydroxyanisole ("BHA"), butylated hydroxytoluene ("BHT"), and vitamin E. The amount of ingredient h) in the systemic or topical composition is typically about 0.1 to about 5%.

Ingredient j) is a preservative such as benzalkonium chloride, methyl paraben and sodium benzoate. The amount of ingredient j) in the systemic or topical composition is typically about 0.01 to about 5%.

Ingredient k) for solid dosage forms is a glidant such as silicon dioxide. The amount of ingredient k) in the systemic or topical composition is typically about 1 to about 5%.

Ingredient m) is a solvent, such as water, isotonic saline, ethyl oleate, glycerine, hydroxylated castor oils, alcohols such as ethanol, and phosphate buffer solutions. The amount of ingredient m) in the systemic or topical composition is typically from about 0 to about 100%.

Ingredient n) is a suspending agent. Suitable suspending agents include AVICEL® RC-591 (from FMC Corporation of Philadelphia, Pa.) and sodium alginate. The amount of ingredient n) in the systemic or topical composition is typically about 1 to about 8%.

Ingredient o) is a surfactant such as lecithin, Polysorbate 80, and sodium lauryl sulfate, and the TWEENS® from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of ingredient o) in the systemic or topical composition is typically about 0.1% to about 5%.

Although the amounts of components A and B in the systemic compositions will vary depending on the type of systemic composition prepared, the specific derivative selected for component A and the ingredients of component B, in general, system compositions comprise 0.01% to 50% of component A and 50 to 99.99% of component B.

Compositions for parenteral administration typically comprise A) 0.1 to 10% of the compounds of the present disclosure and B) 90 to 99.9% of a carrier comprising a) a diluent and m) a solvent. In one embodiment, component a) comprises propylene glycol and m) comprises ethanol or ethyl oleate.

Compositions for oral administration can have various dosage forms. For example, solid forms include tablets, capsules, granules, and bulk powders. These oral dosage forms comprise a safe and effective amount, usually at least about 5%, and more particularly from about 25% to about 50% of component A). The oral dosage compositions further comprise about 50 to about 95% of component B), and more particularly, from about 50 to about 75%.

Tablets can be compressed, tablet triturates, enteric-coated, sugar-coated, film-coated, or multiple-compressed. Tablets typically comprise component A, and component B a carrier comprising ingredients selected from the group consisting of a) diluents, b) lubricants, c) binders, d) disintegrants, e) colorants, f) flavors, g) sweeteners, k) glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain g) sweeteners such as aspartame and saccharin, or f) flavors such as menthol, peppermint, fruit flavors, or a combination thereof.

Capsules (including implants, time release and sustained release formulations) typically comprise component A, and a carrier comprising one or more a) diluents disclosed above in a capsule comprising gelatin. Granules typically comprise component A, and preferably further comprise k) glidants such as silicon dioxide to improve flow characteristics. Implants can be of the biodegradable or the non-biodegradable type. Implants may be prepared using any known biocompatible formulation.

The selection of ingredients in the carrier for oral compositions depends on secondary considerations like taste, cost, and shelf stability, which are not critical for the purposes of this disclosure. One skilled in the art would know how to select appropriate ingredients without undue experimentation.

The solid compositions may also be coated by conventional methods, typically with pH or time-dependent coatings, such that component A is released in the gastrointestinal tract in the vicinity of the desired application, or at various points and times to extend the desired action.

The coatings typically comprise one or more components selected from the group consisting of cellulose acetate phthalate, polyvinyl acetate phthalate, hydroxypropyl methyl cellulose phthalate, ethyl cellulose, EUDRAGIT® coatings (available from Rohm & Haas G.M.B.H. of Darmstadt, Germany), waxes and shellac.

Compositions for oral administration can also have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically comprise component A and component B, namely, a carrier comprising ingredients selected from the group consisting of a) diluents, e) colorants, f) flavors, g) sweeteners, j) preservatives, m) solvents, n) suspending agents, and o) surfactants. Peroral liquid compositions preferably comprise one or more ingredients selected from the group consisting of e) colorants, f) flavors, and g) sweeteners.

Other compositions useful for attaining systemic delivery of the subject compounds include injection, sublingual, buccal and nasal dosage forms. Such compositions typically comprise one or more of soluble filler substances such as a) diluents including sucrose, sorbitol and mannitol; and c) binders such as acacia, microcrystalline cellulose, carboxymethyl cellulose, and hydroxypropyl methylcellulose. Such compositions may further comprise b) lubricants, e) colorants, f) flavors, g) sweeteners, h) antioxidants, and k) glidants.

In one embodiment of the disclosure, the compounds of the present disclosure are topically administered. Topical compositions that can be applied locally to the eye may be in any form known in the art, non-limiting Examples of which include solids, gelable drops, sprays, ointments, or a sustained or non-sustained release unit placed in the conjunctival cul-du-sac of the eye or another appropriate location.

Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions comprise: component A, the compounds described above, and component B, a carrier. The carrier of the topical composition preferably aids penetration of the compounds into the eye. Component B may further comprise one or more optional components.

An effective amount of a compound according to the present disclosure will vary with the particular condition being treated, the age and physical condition of the patient being treated, the severity of the condition, the duration of treatment, the nature of concurrent therapy, the route of administration, the particular pharmaceutically-acceptable carrier utilized, and like factors within the knowledge and expertise of the attending physician. For example, an effective amount of the compounds of the present disclosure for systemic administration is from about 0.01 to about 1000 µg/kg body weight, preferably from about 0.1 to about 100 µg/kg per body weight, most preferably form about 1 to about 50 µg/kg body weight per day. The transdermal dosages will be designed to attain similar serum or plasma levels, based upon techniques known to those skilled in the art of pharmacokinetics and transdermal formulations. Plasma levels for systemic administration are expected to be in the range of 0.01 to 100 ng/mL, more preferably from 0.05 to 50 ng/mL and most preferably from 0.1 to 10 ng/mL. While these dosages are based upon a daily administration rate, the compounds of the present disclosure may also be administered at other intervals, such as twice per day, twice weekly, once weekly, or once a month. One of ordinary skill in the art would be able to calculate suitable effective amounts for other intervals of administration.

The compounds of the present disclosure are useful in a method of reducing or decreasing intraocular pressure. The compounds of the present disclosure may be administered to a subject in need of treatment in an amount effective to reduce intraocular pressure. Thus, these compounds are useful in the treatment of glaucoma. The preferred route of administration for treating glaucoma is topically.

The exact amounts of each component in the topical composition depend on various factors. The amount of component A added to the topical composition is dependent on the $IC_{50}$ of component A, typically expressed in nanomolar (nM) units. For example, if the $IC_{50}$ of the medicament is 1 nM, the amount of component A will be from about 0.001 to about 0.3%. If the $IC_{50}$ of the medicament is 10 nM, the amount of component A) will be from about 0.01 to about 1%. If the $IC_{50}$ of the medicament is 100 nM, the amount of component A will be from about 0.1 to about 10%. If the amount of component A is outside the ranges specified above (i.e., lower), efficacy of the treatment may be reduced. One skilled in the art understands how to calculate and understand an $IC_{50}$. The remainder of the composition, up to 100%, is component B.

The amount of the carrier employed in conjunction with component A is sufficient to provide a practical quantity of composition for administration per unit dose of the medicament. Techniques and compositions for making dosage forms useful in the methods of this disclosure are described in the following references: *Modern Pharmaceutics*, Chapters 9 and 10, Banker & Rhodes, eds. (1979); Lieberman et al., *Pharmaceutical Dosage Forms: Tablets* (1981); and Ansel, *Introduction to Pharmaceutical Dosage Forms*, $2^{nd}$ Ed., (1976).

Component B may comprise a single ingredient or a combination of two or more ingredients. In the topical compositions, component B comprises a topical carrier. Suitable topical carriers comprise one or more ingredients selected from the group consisting of phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols and symmetrical alcohols.

The carrier of the topical composition may further comprise one or more ingredients selected from the group consisting of q) emollients, r) propellants, s) solvents, t) humectants, u) thickeners, v) powders, w) fragrances, x) pigments, and y) preservatives.

Ingredient q) is an emollient. The amount of ingredient q) in a skin-based topical composition is typically about 5 to about 95%. Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, *arachis* oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane.

Ingredient r) is a propellant. The amount of ingredient r) in the topical composition is typically about 0 to about 95%.

Suitable propellants include propane, butane, isobutane, dimethyl ether, carbon dioxide, nitrous oxide, and combinations thereof.

Ingredient s) is a solvent. The amount of ingredient s) in the topical composition is typically about 0 to about 95%. Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols.

Ingredient t) is a humectant. The amount of ingredient t) in the topical composition is typically 0 to 95%. Suitable humectants include glycerin, sorbitol, sodium 2-pyrrolidone-5-carboxylate, soluble collagen, dibutyl phthalate, gelatin, and combinations thereof. Specific humectants include glycerin.

Ingredient u) is a thickener. The amount of ingredient u) in the topical composition is typically about 0 to about 95%.

Ingredient v) is a powder. The amount of ingredient v) in the topical composition is typically 0 to 95%. Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. For ocular applications, specific powders include beta-cyclodextrin, hydroxypropyl cyclodextrin, and sodium polyacrylate. For gel dosing ocular formulations, sodium polyacrylate may be used.

Ingredient w) is a fragrance. The amount of ingredient w) in the topical composition is typically about 0 to about 0.5%, particularly, about 0.001 to about 0.1%. For ocular applications a fragrance is not typically used.

Ingredient x) is a pigment. Suitable pigments for skin applications include inorganic pigments, organic lake pigments, pearlescent pigments, and mixtures thereof. Inorganic pigments useful in this disclosure include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

The organic pigments and lakes useful in this disclosure include those selected from the group consisting of D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430), the dye or lakes based on Cochineal Carmine (CI 75,570) and mixtures thereof.

The pearlescent pigments useful in this disclosure include those selected from the group consisting of the white pearlescent pigments such as mica coated with titanium oxide, bismuth oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof. The amount of pigment in the topical composition is typically about 0 to about 10%. For ocular applications a pigment is generally not used.

In a particularly preferred embodiment of the disclosure, topical pharmaceutical compositions for ocular administration are prepared typically comprising component A and B (a carrier), such as purified water, and one or more ingredients selected from the group consisting of y) sugars or sugar alcohols such as dextrans, particularly mannitol and dextran 70, z) cellulose or a derivative thereof, aa) a salt, bb) disodium EDTA (Edetate disodium), and cc) a pH adjusting additive.

Examples of z) cellulose derivatives suitable for use in the topical pharmaceutical composition for ocular administration include sodium carboxymethylcellulose, ethylcellulose, methylcellulose, and hydroxypropyl-methylcellulose, particularly, hydroxypropyl-methylcellulose.

Examples of aa) salts suitable for use in the topical pharmaceutical composition for ocular administration include mono-, di- and trisodium phosphate, sodium chloride, potassium chloride, and combinations thereof.

Examples of cc) pH adjusting additives include HCl or NaOH in amounts sufficient to adjust the pH of the topical pharmaceutical composition for ocular administration to the range of 4.5-7.5 pH units.

Component A may be included in kits comprising a compound of Formulas (I)-(IX), a systemic or topical composition described above, or both; and information, instructions, or both that use of the kit will provide treatment for cosmetic and medical conditions in mammals (particularly humans). The information and instructions may be in the form of words, pictures, or both, and the like. In addition or in the alternative, the kit may comprise the medicament, a composition, or both; and information, instructions, or both, regarding methods of application of medicament, or of composition, preferably with the benefit of treating or preventing cosmetic and medical conditions in mammals (e.g., humans).

The disclosure will be further explained by the following illustrative Examples that are to be considered to be non-limiting.

EXAMPLES

All temperatures are given in degrees Centigrade. Reagents and starting materials were purchased from commercial sources or prepared following published literature procedures.

Unless otherwise noted, HPLC purification, when appropriate, was performed by redissolving the compound in a small volume of DMSO and filtering through a 0.45 micron (nylon disc) syringe filter. The solution was then purified using, for example, a 50 mm Varian Dynamax HPLC 21.4 mm Microsorb Guard-8 $C_8$ column. A typical initial eluting mixture of 40-80% MeOH:$H_2O$ was selected as appropriate for the target compound. This initial gradient was maintained for 0.5 minutes then increased to 100% MeOH:0% $H_2O$ over 5 minutes. 100% MeOH was maintained for 2 more minutes before re-equilibration back to the initial starting gradient. A typical total run time was 8 minutes. The resulting fractions were analyzed, combined as appropriate, and then evaporated to provide purified material.

Proton magnetic resonance ($^1$H NMR) spectra were recorded on either a Bruker 600 MHz spectrometer equipped with a sample changer and a cryoprobe, a Varian INOVA 600 MHz ($^1$H) NMR spectrometer, Varian INOVA 500 MHz (¹H) NMR spectrometer, Varian Mercury 300 MHz (¹H) NMR spectrometer, or a Varian Mercury 200 MHz (¹H) NMR spectrometer. All spectra were determined in the solvents indicated. Although chemical shifts are reported in ppm downfield of tetramethylsilane, they are referenced to the residual proton peak of the respective solvent peak for ¹H NMR. Interproton coupling constants are reported in Hertz (Hz).

Analytical LCMS spectra were obtained using a Waters Acquity QDA MS ESI instrument with an Alliance 2695 HPLC and a 2998 Photodiode Array Detector. Spectra were analyzed at 254 and 230 nm. Samples were passed through a Waters Atlantis T3 4.6×75 mm 3.5 µm column with a guard column (Atlantis T3 4.6×20 mm 5 µm. Gradients were typically run with mobile phase A: 0.1% formic acid in H₂O and mobile phase B: ACN with a flow rate of 0.8 mL/min. Two gradients will illustrate:

| Gradient A | | | Gradient B | | |
| --- | --- | --- | --- | --- | --- |
| Time | A % | B % | Time | A % | B % |
| 0.00 | 95 | 5.0 | 0.00 | 80.0 | 20.0 |
| 1.00 | 95 | 5.0 | 1.00 | 80.0 | 20.0 |
| 6.00 | 40 | 60 | 6.00 | 25.0 | 75.0 |
| 7.00 | 5.0 | 95.0 | 7.00 | 5.0 | 95.0 |
| 8.00 | 5.0 | 95.0 | 8.00 | 5.0 | 95.0 |
| 9.00 | 95 | 5.0 | 9.00 | 80.0 | 20.0 |
| 12.00 | 95 | 5.0 | 12.00 | 80.0 | 20.0 |

The settings for the MS probe are typically a cone voltage at 15 V, capillary voltage at 0.8 KV for Positive mode and 0.4 kV for negative mode. The probe temperature is 600° C. and the source temperature is 120° C. The following preparations illustrate procedures for the preparation of intermediates and methods for the preparation of an arylcyclopropyl amino isoquinolinyl amide derivative.

When used in the present application, the following abbreviations have the meaning set out below:

AcOH is acetic acid;
Bn is benzyl;
1,2, DCE is 1,2 dichloroethane
DCM is dichloromethane;
DCC is N,N'-dicyclohexylcarbodiimide;
DME is 1,2-dimethoxyethane;
DMF is N,N-dimethylformamide;
DMSO is dimethyl sulfoxide;
DBU is 1,8-diazabicyclo[5.4.0]undec-7-ene;
DMAP is 4-dimethylaminopyridine;
EDC/EDAC is N-(3-dimethylaminopropyl)-N'-ethylcarbodiimide hydrochloride;
EtOAc is ethyl acetate;
EtOH is ethanol;
HOBt is 1-hydroxybenzotriazole;
IOP is intraocular pressure;
MeOH is methanol;
rt is room temperature;
tBu or t-Bu is tert-butyl;
TFA is trifluoroacetic acid;
THF is tetrahydrofuran;

TLC is thin-layer chromatography and
TMSOI is trimethylsulfoxonium iodide

Example 1

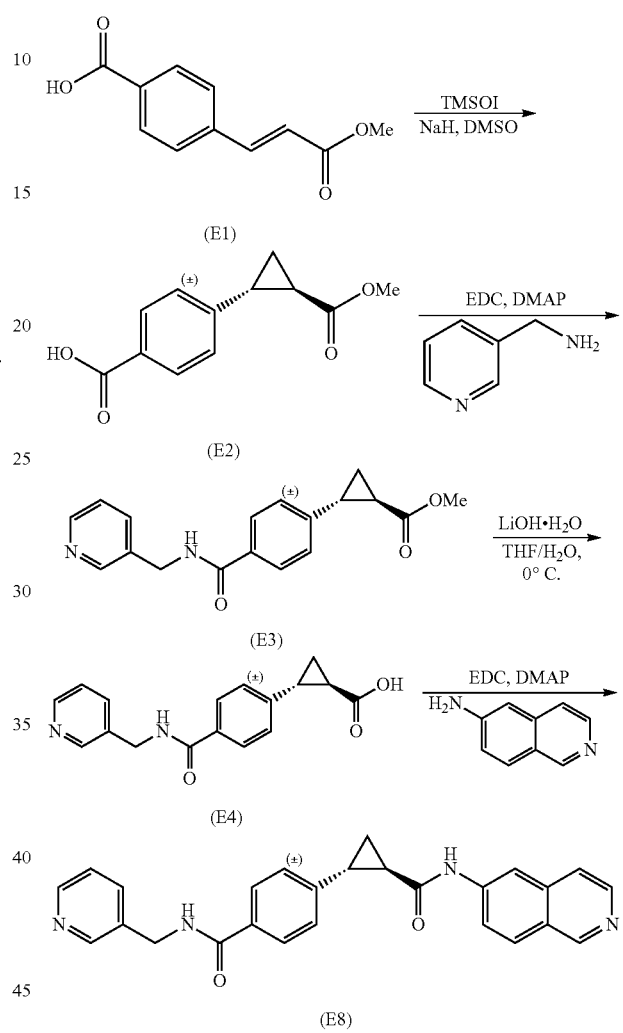

Preparation of
4-(2-(methoxycarbonyl)cyclopropyl)benzoic acid
(E2)

To trimethylsulfoxonium iodide (TMSOI) in DMSO was added NaH and the solution was stirred for one hour under N₂. (E)-4-(3-methoxy-3-oxoprop-1-en-1-yl)benzoic acid (E1) dissolved in DMSO was added and the solution was stirred for 3 hours at room temperature. The mixture was poured into cold EtOAc and HCl (1N) and extracted with EtOAc. The organics were dried (Na₂SO₄), filtered and evaporated. Column chromatography over silica gel eluting with 0-4% MeOH/CH₂Cl₂ gave pure 4-(2-(methoxycarbonyl)cyclopropyl)benzoic acid (E2).

Preparation of trans-methyl 2-(4-((pyridin-3-ylmethyl) carbamoyl) phenyl)cyclopropane-1-carboxylate (E3)

To 4-(2-(methoxycarbonyl)cyclopropyl)benzoic acid (E2), in CH₂Cl₂ were added EDC, DMAP and pyridin-3- ylmethanamine and the solution was stirred under N₂ at room temperature for 7 hours. The reaction was poured into EtOAc/NaHCO₃ (sat) and extracted with EtOAc, dried (Na₂SO₄), filtered and evaporated. Column chromatography over silica gel eluting with 0-5% MeOH/CH₂Cl₂ gave pure trans-methyl 2-(4-((pyridin-3-ylmethyl)carbamoyl)phenyl) cyclopropane-1-carboxylate (E3).

Preparation of trans-2-(4-((pyridin-3-ylmethyl) carbamoyl)phenyl) cyclopropane-1-carboxylic acid (E4)

To trans-methyl 2-(4-((pyridin-3-ylmethyl)carbamoyl) phenyl)cyclopropane-1-carboxylate (E3) in THF/H₂O at 0° C. was added LiOH—H₂O and the solution was warmed to room temperature and stirred for 3 hours. The pH was adjusted to 5 with HCl (1N). The aqueous layer was extracted with EtOAc, dried (Na₂SO₄), filtered and evaporated to give trans-2-(4-((pyridin-3-ylmethyl)carbamoyl) phenyl)cyclopropane-1-carboxylic acid (E4).

Preparation of trans-4-(2-(isoquinolin-6-ylcarbamoyl) cyclopropyl)-N-(pyridin-3-ylmethyl) benzamide (E8)

To trans-2-(4-((pyridin-3-ylmethyl) carbamoyl) phenyl) cyclo-propane-1-carboxylic acid (E4) in pyridine were added EDC, DMAP and 6-aminoisoquinoline and the solution was stirred under N₂ overnight. The mixture was poured into NaHCO₃ and extracted with EtOAc, dried (Na₂SO₄), filtered and evaporated. Column chromatography over silica gel eluting with 0-3% MeOH/CH₂Cl₂ gave pure trans-4-(2-(isoquinolin-6-ylcarbamoyl)cyclopropyl)-N-(pyridin-3-ylmethyl)benzamide (E8).

Using procedures analogous to those set forth above for Scheme 1 and substituting the appropriate starting materials, the compounds E8-E39.1, and E39.2-E39.38 were made and E40-E48 (see Table 2) could be synthesized.

TABLE 2

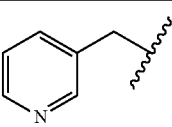

| Example | R—Z— | X₁ | X₂ |
|---|---|---|---|
| E8 | 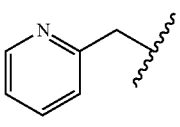 [SMILES: *Cc1ccccn1] | H | H |
| E9 | 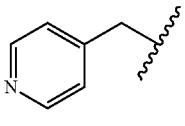 [SMILES: *Cc1ccncc1] | H | H |
| E10 | 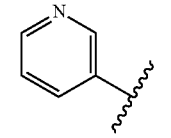 [SMILES: *c1cccnc1] | H | H |
| E11 | 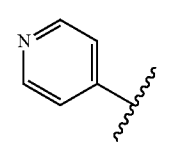 [SMILES: *c1ccncc1] | H | H |
| E12 | 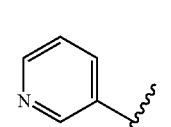 | H | H |
| E13 |  | H | H |

TABLE 2-continued
| | | | |
|---|---|---|---|
| E14 | 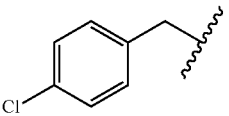 [SMILES: *Cc1ccc(Cl)cc1] | H | H |
| E15 | 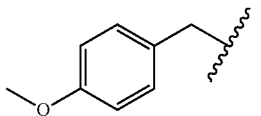 [SMILES: *Cc1ccc(OC)cc1] | H | H |
| E15.1 | 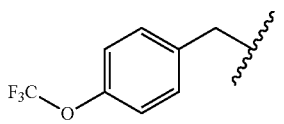 [SMILES: *Cc1ccc(OC(F)(F)F)cc1] | H | H |
| E16 | 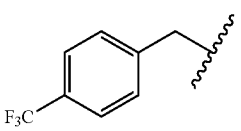 | H | H |
| E17 | 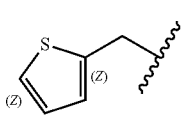 | H | H |
| E18 | 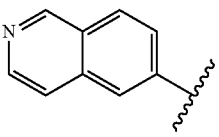 [SMILES: *c1ccc2cnccc2c1] | H | H |
| E19.1 | 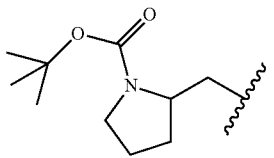 [SMILES: *CC1CCCN1C(=O)OC(C)(C)C] | H | H |
| E19.2 | 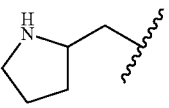 [SMILES: *CC1CCCN1] | H | H |
| E20.1 | 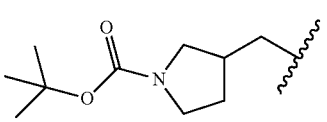 [SMILES: *CC1CCN(C(=O)OC(C)(C)C)C1] | H | H |
| E20.2 | 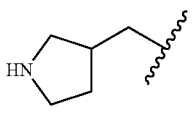 | H | H |
| E29.1 | 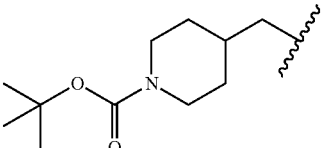 | H | H |
| E29..2 | 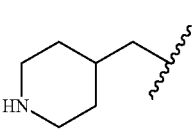 [SMILES: *CC1CCNCC1] | H | H |

TABLE 2-continued
| | | | |
|---|---|---|---|
| E30.1 | 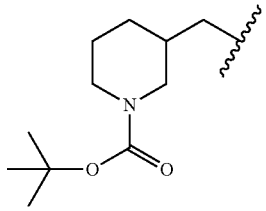 [SMILES: *CC1CCCN(C(=O)OC(C)(C)C)C1] | H | H |
| E30.2 | 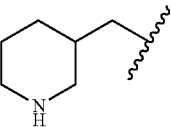 [SMILES: *CC1CCCNC1] | H | H |
| E31 | 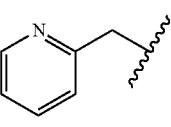 | 1-OH | H |
| E32 | 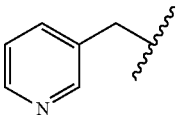 [SMILES: *Cc1cccnc1] | H | 7-Br |
| E33 | 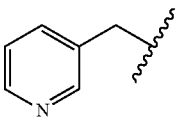 [SMILES: *Cc1cccnc1] | 4-F | H |
| E34 | 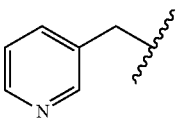 [SMILES: *Cc1cccnc1] | 4-CH$_3$ | H |
| E35 | 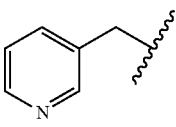 [SMILES: *Cc1cccnc1] | H | 5-F |
| E36 | 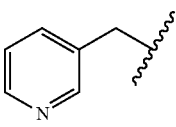 [SMILES: *Cc1cccnc1] | 1-CH$_3$ | H |
| E37 | 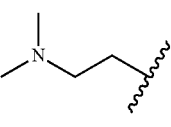 [SMILES: *CCN(C)C] | H | H |
| E38 | 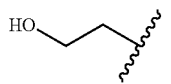 | H | H |
| E39 | 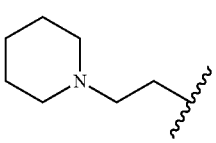 [SMILES: *CCN1CCCCC1] | H | H |

TABLE 2-continued
| E39.1 | 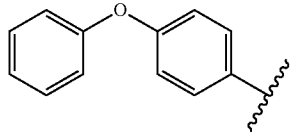 [SMILES: *c1ccc(Oc2ccccc2)cc1] | H | H |
| Example | Structure: -4-Substutituted Cyclopropyl Analogs (para) |
| --- | --- |
| E39.2 | 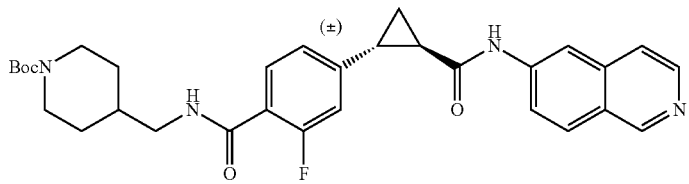 |
| E39.3 | 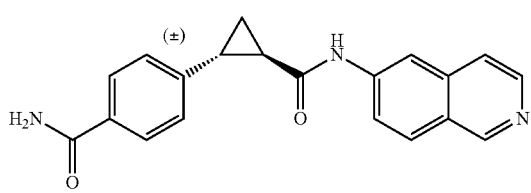 |
| E39.4 | 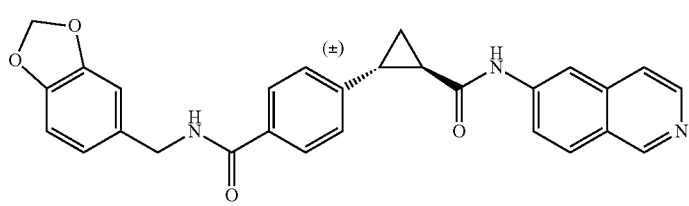 |
| E39..5 | 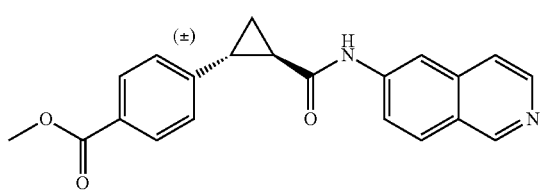 |
| E39.6 | 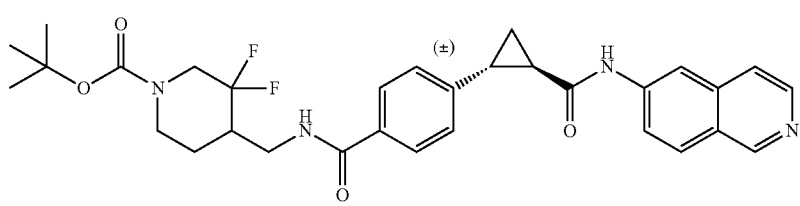 |
| E39.7 | 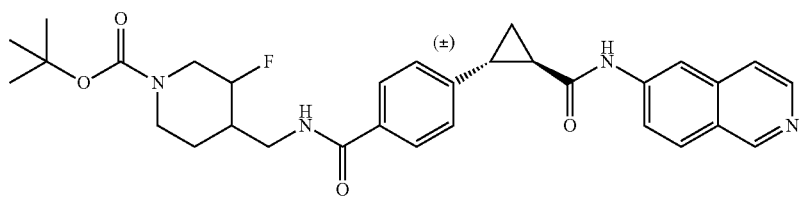 |
| E39.8 | *2HCl 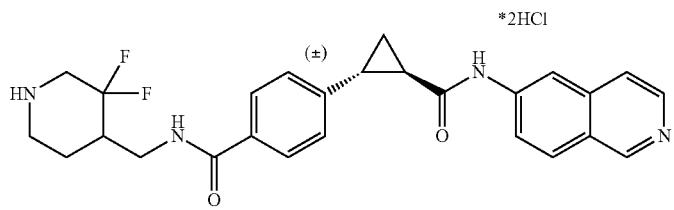 |

TABLE 2-continued
E39.9 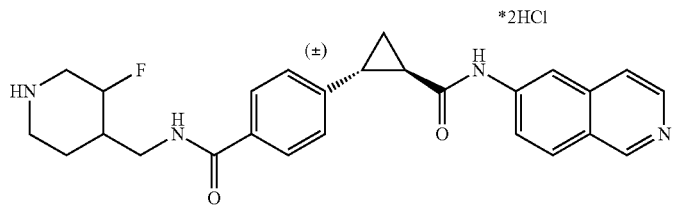
E39.10 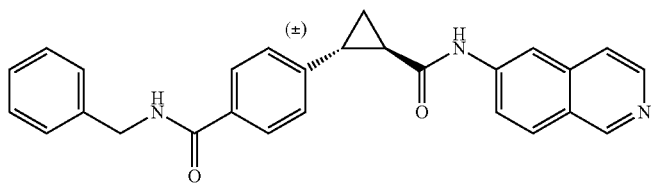
E39.11 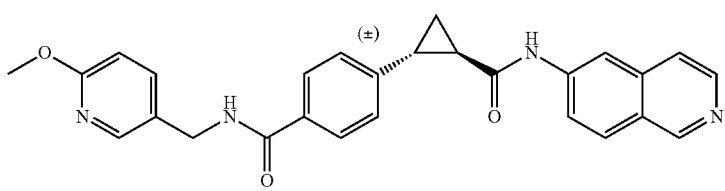
E39.12 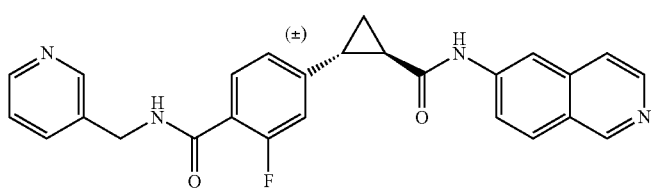
E39.13 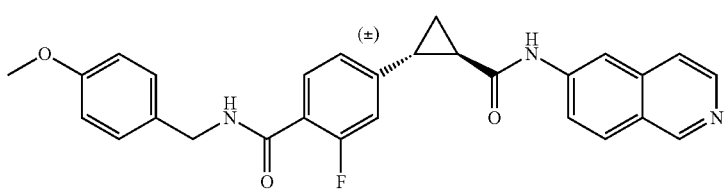
E39.14 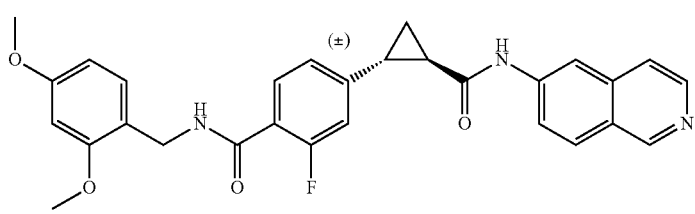
E39.15 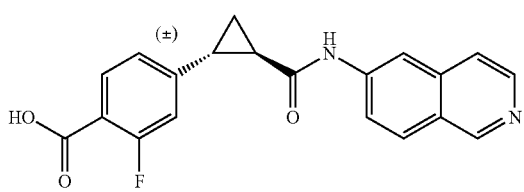
E39.16 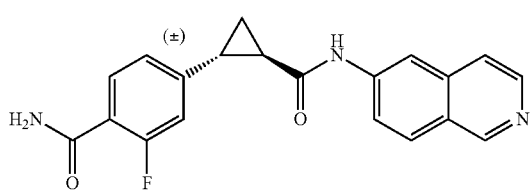

TABLE 2-continued
E39.17 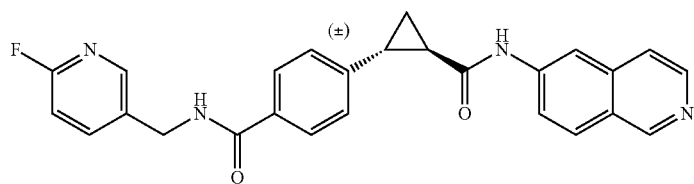
E39.18 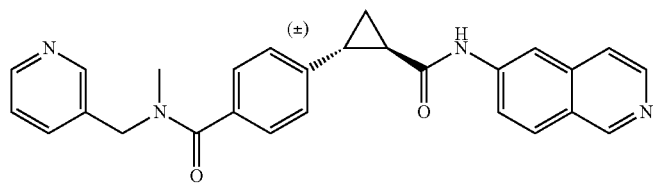
E39.19 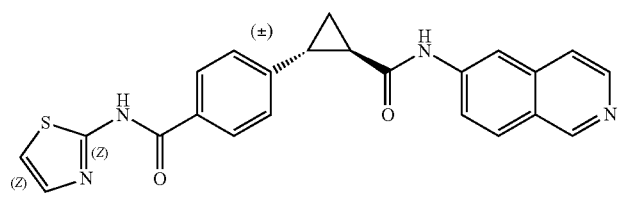
E39.20 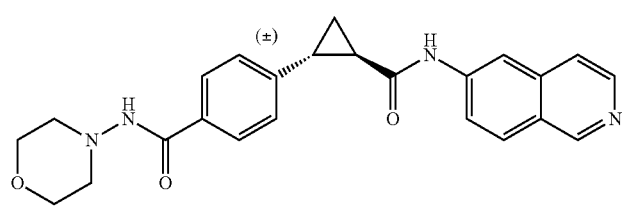
E39.21 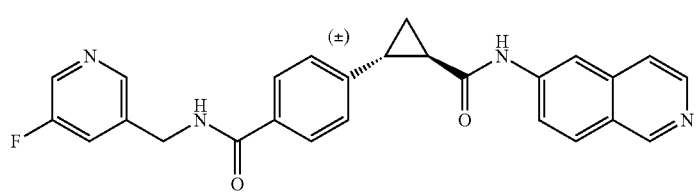
E39.22 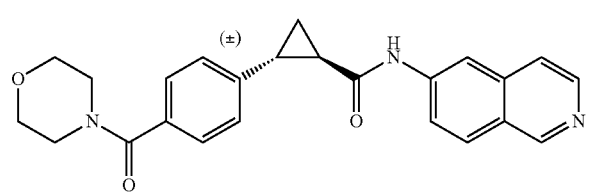
E39.23 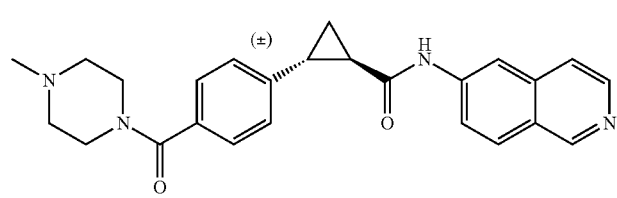
E39.24 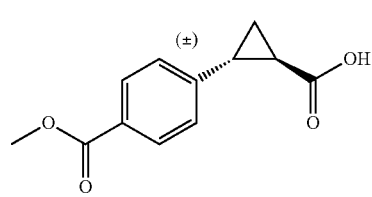

TABLE 2-continued
E39.25 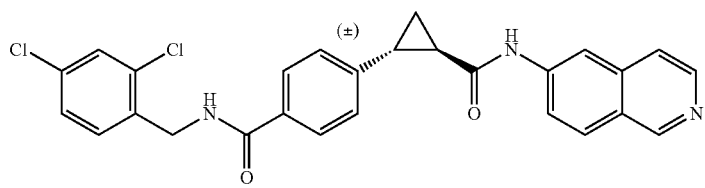
E39.26 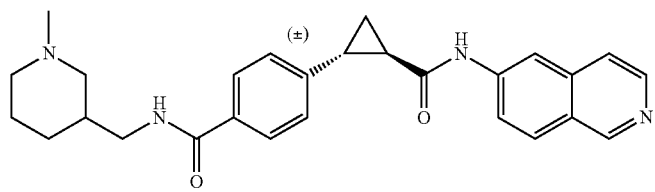
E39.27 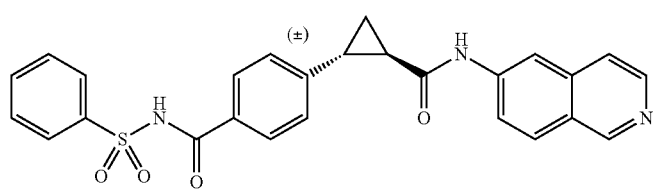
E39.28 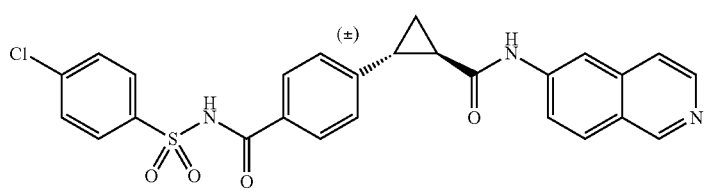
E39.29 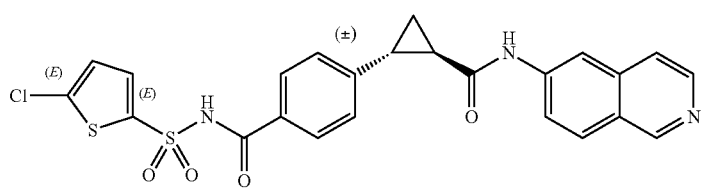
E39.30 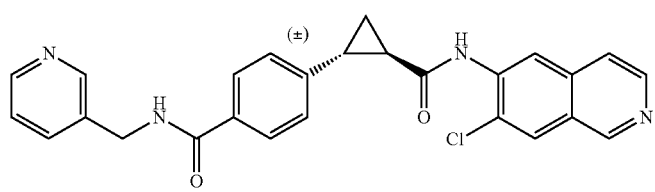
E39.31 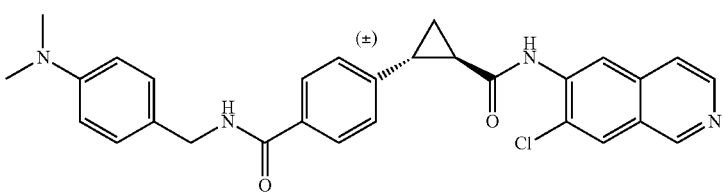
E39.32 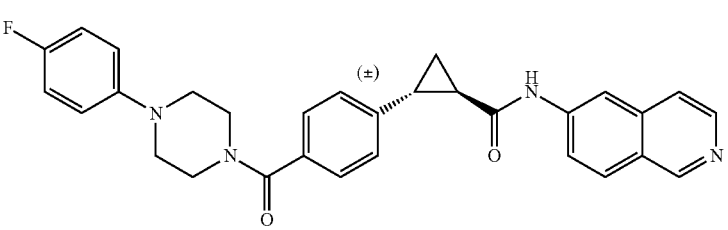

TABLE 2-continued
E39.33 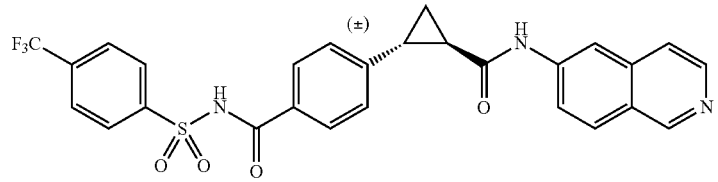
E39.34 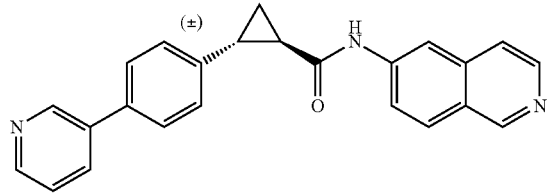
E39.35 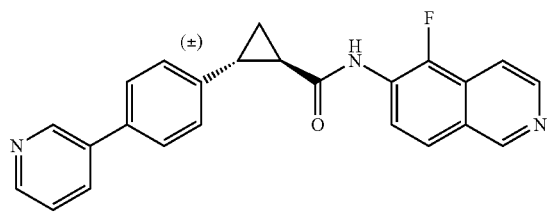
E39.36 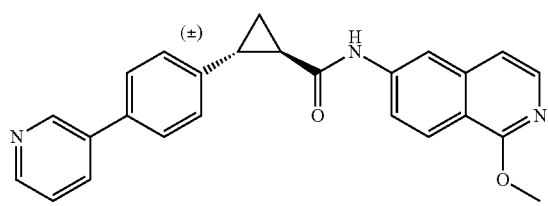
E39.37 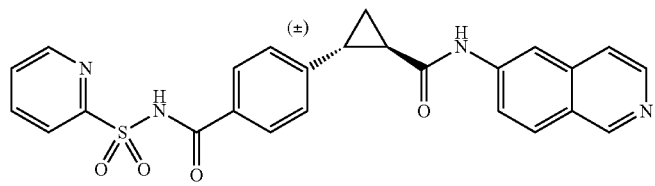
E39.38 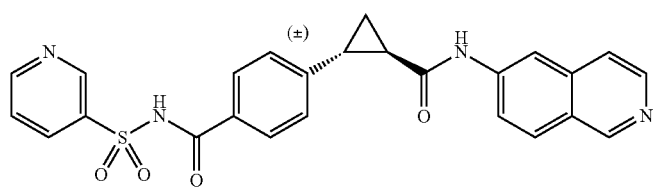

TABLE 2-continued
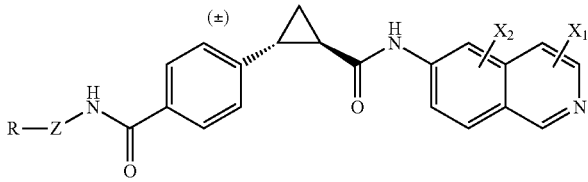
| Example | R—Z— | X$_1$ | X$_2$ |
|---|---|---|---|
| E40 | 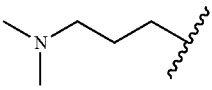 [SMILES: *CCCN(C)C] | 3-Cl | H |
| E41 | 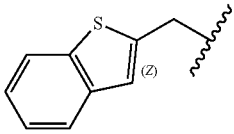 (Z) | H | 5-Cl |
| E42 | 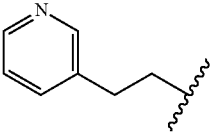 [SMILES: *CCc1cccnc1] | H | H |
| E43 | 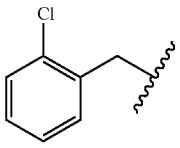 [SMILES: *Cc1ccccc1Cl] | H | 7-Br |
| E44 | 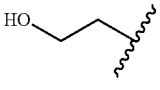 [SMILES: *CCO] | 1-OH | 7-Cl |
| E45 | 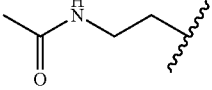 | H | H |
| E46 | 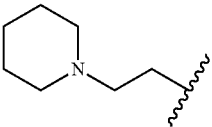 [SMILES: *CCN1CCCCC1] | 4-F | H |
| E47 | 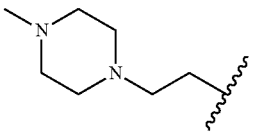 [SMILES: *CCN1CCN(C)CC1] | 4-Cl | H |
| E48 | 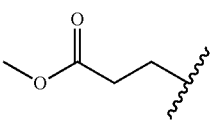 [SMILES: *CCC(=O)OC] | H | H |

Example 2
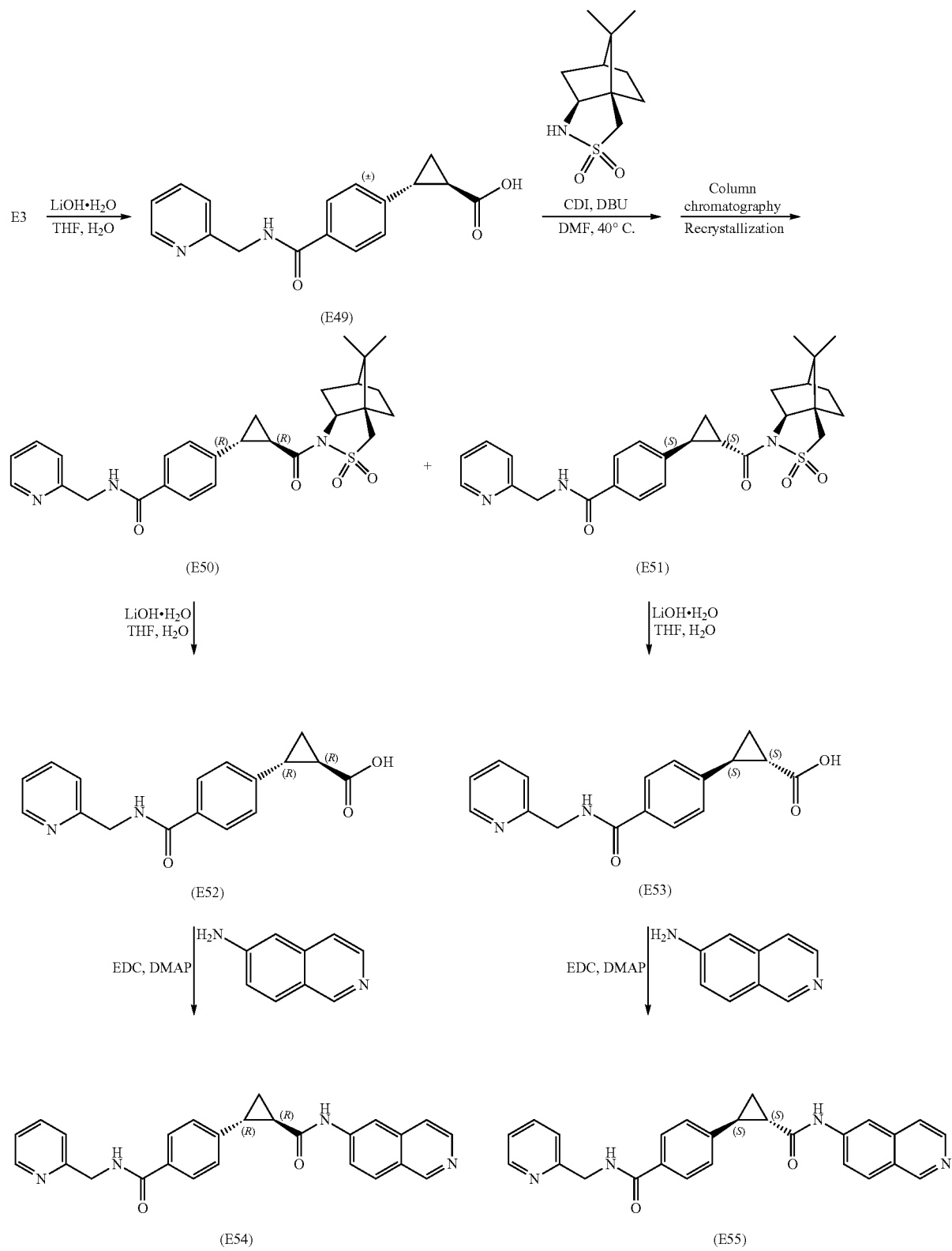

Preparation of trans-methyl 2-(4-((pyridin-2-ylmethyl) carbamoyl)phenyl) cyclopropane-1-carboxylic acid (E49)

To trans-2-(4-((pyridin-2-ylmethyl)carbamoyl) phenyl) cyclopropane-1-carboxylate (E3) in THF-H₂O was added LiOH—H₂O and the solution was stirred at room temperature for 4 hours. The solution was acidified with HCl (1N) to pH 5 and extracted with EtOAc, dried (Na₂SO₄), filtered and evaporated to give trans-2-(4-((pyridin-2-ylmethyl)carbamoyl)phenyl)cyclopropane-1-carboxylic acid (E49).

Preparation of 4-((1R,2R)-2-((3aR,6S,7aS)-8,8-dimethyl-2,2-dioxidohexahydro-3H-3a,6-methanobenzo[c]isothiazole-1-carbonyl) cyclopropyl)-N-(pyridin-2-ylmethyl)benzamide (E50) and 4-((1S,2S)-2-((3aR,6S,7aS)-8,8-dimethyl-2,2-dioxidohexahydro-3H-3a, 6-methanobenzo[c]isothiazole-1-carbonyl) cyclopropyl)-N-(pyridin-2-ylmethyl)benzamide (E51)

To trans-2-(4-((pyridin-2-ylmethyl)carbamoyl)phenyl) cyclopropane-1-carboxylic acid (E49) in DMF was added carbonyldiimidazole and the solution was heated to 40° C. for 2 hours under N₂.

Then (1R)-(+)-2,10-camphorsultam chiral auxiliary and DBU were added and the solution was stirred 5-6 hours at 40° C. After cooling the mixture was poured into NaHCO₃ (saturated) and extracted with EtOAc, dried (Na₂SO₄), filtered and evaporated. Automated column chromatography over silica gel eluting with 0-20% EtOAc-Hexanes gave a mixture of E50 and E51.

Column Chromatography over silica gel eluting with 40% EtOAc-Hexanes with 1-2% NEt₃ gave pure 4-((1R,2R)-2-((3aR,6S,7aS)-8,8-dimethyl-2,2-dioxidohexahydro-3H-3a, 6-methanobenzo[c]isothiazole-1-carbonyl)cyclopropyl)-N-(pyridin-2-ylmethyl)benzamide (E50) as the faster eluting isomer. 4-((1S,2S)-2-((3aR,6S,7aS)-8,8-Dimethyl-2,2-dioxidohexahydro-3H-3a,6-methanobenzo[c]isothiazole-1-carbonyl)cyclopropyl)-N-(pyridin-2-ylmethyl)benzamide (E51) was obtained from the chromatography as the slower eluting isomer and was further purified by recrystallization from MeOH to give pure 4-((1S,2S)-2-((3aR,6S,7aS)-8,8-dimethyl-2,2-dioxidohexahydro-3H-3a,6-methanobenzo[c]isothiazole-1-carbonyl)cyclopropyl)-N-(pyridin-2-ylmethyl)benzamide (E51).

Preparation of (1R,2R)-2-(4-((pyridin-2-ylmethyl) carbamoyl)phenyl) cyclopropane-1-carboxylic acid (E52)

To 4-((1R,2R)-2-((3aR,6S,7aS)-8,8-dimethyl-2,2-dioxidohexahydro-3H-3a,6-methanobenzo[c]isothiazole-1-carbonyl)cyclopropyl)-N-(pyridin-2-ylmethyl)benzamide (E50) in THF-H₂O was added LiOH—H₂O and the solution was stirred for 6 hours at room temperature. The solution was acidified (HCl, 1N, pH approximately 2) and extracted with EtOAc to remove (1R)-(+)-2,10-camphorsultam chiral auxiliary. Then, NaHCO₃ (saturated) was added to the aqueous layer until the pH=5. The aqueous layer was extracted with EtOAc, dried (Na₂SO₄), filtered and evaporated to give pure (1R,2R)-2-(4-((pyridin-2-ylmethyl)carbamoyl)phenyl) cyclopropane-1-carboxylic acid (E52).

Preparation of (1S,2S)-2-(4-((pyridin-2-ylmethyl) carbamoyl)phenyl) cyclopropane-1-carboxylic acid (E53)

To 4-((1S,2S)-2-((3aR,6S,7aS)-8,8-dimethyl-2,2-dioxidohexahydro-3H-3a,6-methanobenzo[c]isothiazole-1-carbonyl)cyclopropyl)-N-(pyridin-2-ylmethyl)benzamide (E51) in THF-H₂O was added LiOH—H₂O and the solution was stirred for 6 hours at room temperature. The solution was acidified (HCl, 1N, pH approximately 2) and extracted with EtOAc to remove (1R)-(+)-2,10-camphorsultam chiral auxiliary. Then NaHCO₃ (saturated) was added to the aqueous layer until the pH=5. The aqueous layer was extracted with EtOAc, dried (Na₂SO₄), filtered and evaporated to give pure (1S,2S)-2-(4-((pyridin-2-ylmethyl)carbamoyl)phenyl) cyclopropane-1-carboxylic acid (E53).

Preparation of (4-((1R,2R)-2-(isoquinolin-6-ylcarbamoyl)cyclopropyl)-N-(pyridin-2-ylmethyl)benzamide (E54)

To (1R,2R)-2-(4-((pyridin-2-ylmethyl)carbamoyl)phenyl)cyclopropane-1-carboxylic acid (E52) in pyridine was added EDC, DMAP and 6-aminoisoquinoline and the solution was stirred under N₂ overnight. The mixture was poured into NaHCO₃ and extracted with EtOAc, dried (Na₂SO₄), filtered and evaporated. Column chromatography over silica gel eluting with 5-8% MeOH—CH₂Cl₂ gave pure (4-((1R,2R)-2-(isoquinolin-6-ylcarbamoyl)cyclopropyl)-N-(pyridin-2-ylmethyl)benzamide (E54, 96% R,R)

Preparation of (4-((1S,2S)-2-(isoquinolin-6-ylcarbamoyl)cyclopropyl)-N-(pyridin-2-ylmethyl)benzamide (E55)

To (1S,2S)-2-(4-((pyridin-2-ylmethyl)carbamoyl)phenyl) cyclopropane-1-carboxylic acid (E53) in pyridine was added EDC, DMAP and 6-aminoisoquinoline and the solution was stirred under N₂ overnight. The mixture was poured into NaHCO₃ and extracted with EtOAc, dried (Na₂SO₄), filtered and evaporated. Column chromatography over silica gel eluting with 5-8% MeOH—CH₂Cl₂ gave pure (4-((1S,2S)-2-(isoquinolin-6-ylcarbamoyl)cyclopropyl)-N-(pyridin-2-ylmethyl)benzamide (E55, 97% S,S)

Using procedures analogous to those set forth above for Scheme 2 and substituting the appropriate starting materials, the compounds E56-E57.2 were made and E58-E91 (see Table 3 and Table 4) could be synthesized

TABLE 3

| Example | R—Z— | X₁ | X₂ |
|---|---|---|---|
| E54 | (2-pyridylmethyl) | H | H |
| E56 | (3-pyridylmethyl) | H | H |

TABLE 3-continued
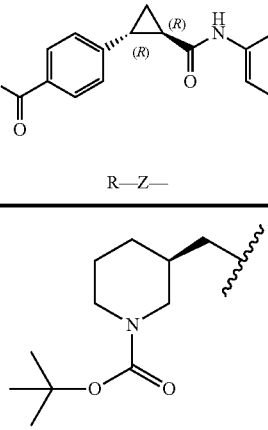
| Example | R—Z— | X₁ | X₂ |
|---|---|---|---|
| E57.1 | 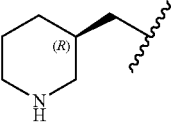 | H | H |
| E57.2 | 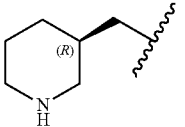 | H | H |
| E58 | 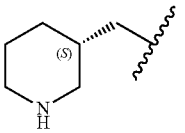 | 1-OH | H |
| E59 | 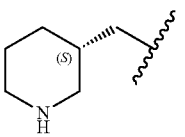 | H | H |
| E60 | 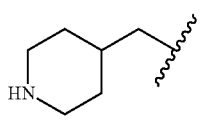 | 1-Cl | H |
| E61 | 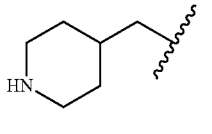 [SMILES: *CC1CCNCC1] | H | H |
| E62 | 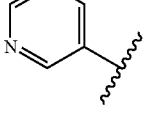 | H | 5-F |
| E63 | 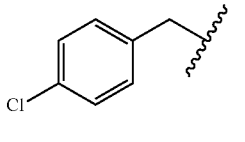 [SMILES: *Cc1ccc(Cl)cc1] | H | H |
| E64 | 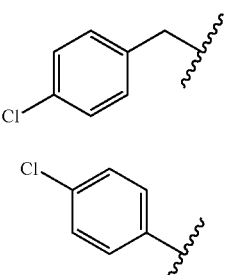 | H | H |
| E65 | 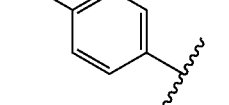 | 4-F | H |
| E66 | 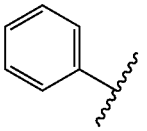 [SMILES: *c1ccccc1] | 1-OH | 4-Cl |
| E67 | 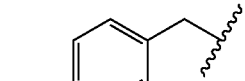 | H | H |
| E68 | 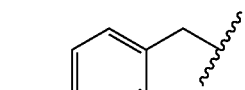 | 1-OH | 7-Cl |
| E69 | 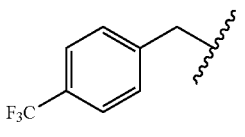 | H | H |
| E70 | 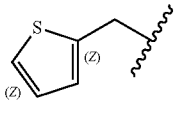 | H | H |
| E71 | 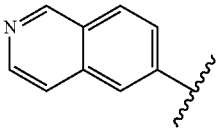 | H | H |
| E72 | 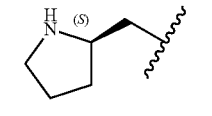 | H | H |
| E73 | 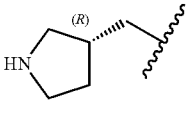 | H | H |
| E74 |  | H | H |

TABLE 3-continued
| Example | R—Z— | X₁ | X₂ |
|---|---|---|---|
| E75 | 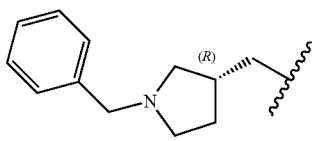 | 3-Cl | H |
| E76 | 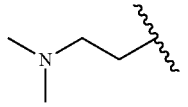 [SMILES: *CCN(C)C] | H | 7-Cl |
| E77 | 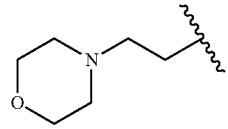 [SMILES: *CCN1CCOCC1] | H | 8-F |
| E78 | 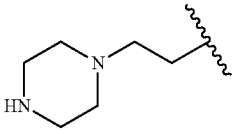 [SMILES: *CCN1CCNCC1] | 1-OH | 7-Br |
| E79 | 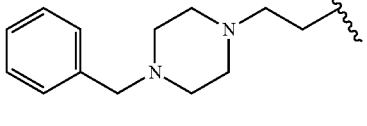 | H | H |
| E80 | 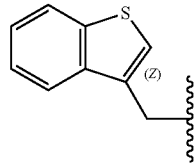 | H | 7-Br |
| E81 | 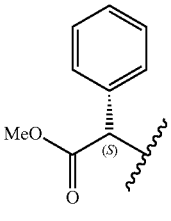 | H | H |
| E82 | 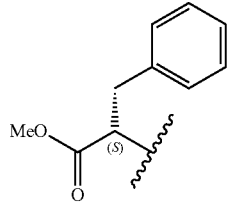 | 1-OH | H |
TABLE 4
| Example | R—Z—N(R^{N1}) | X₁ | X₂ |
|---|---|---|---|
| E83 | 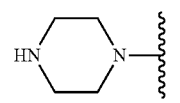 | H | H |
| E84 | 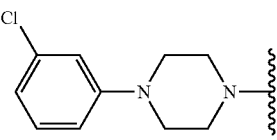 [SMILES: *N1CCN(c2cccc(Cl)c2)CC1] | 1-OH | H |
| E85 | 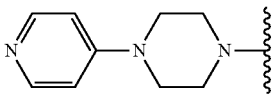 | H | H |
| E86 | 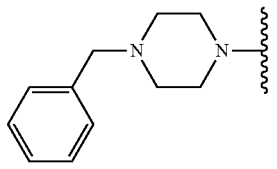 [SMILES: *N1CCN(Cc2ccccc2)CC1] | 4-Cl | H |
| E87 | 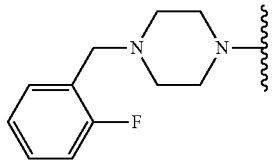 [SMILES: *N1CCN(Cc2ccccc2F)CC1] | H | H |
| E88 | 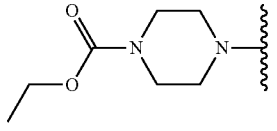 | 4-Cl | H |
| E89 | 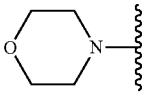 | H | 5-F |
| E90 | 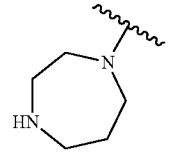 [SMILES: *N1CCCNCC1] | H | H |
| E91 | 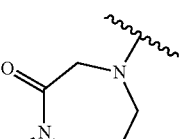 | H | H |

Example 3

Scheme 3.

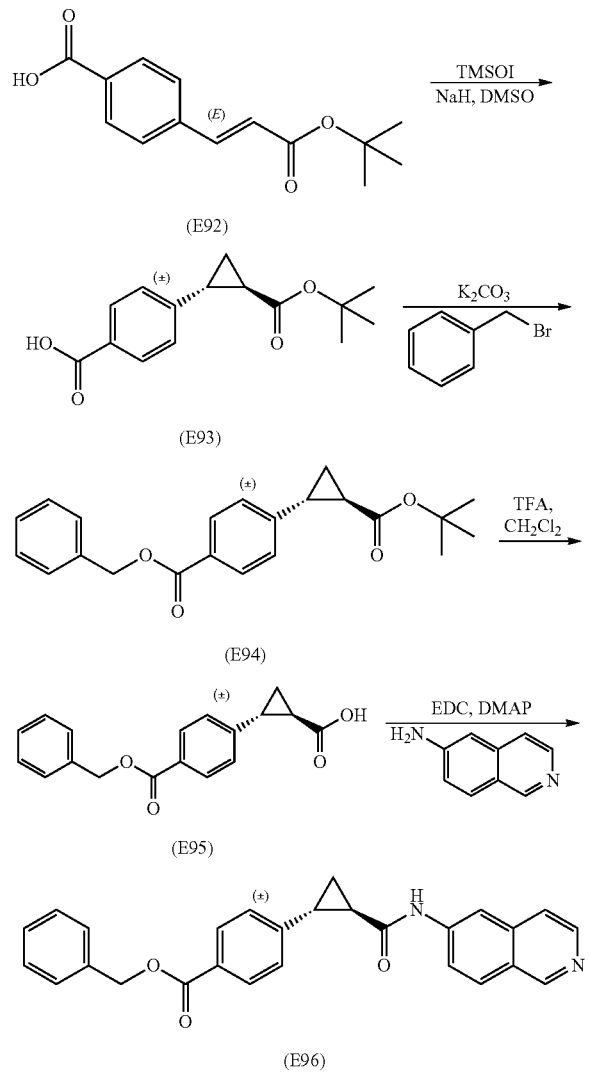

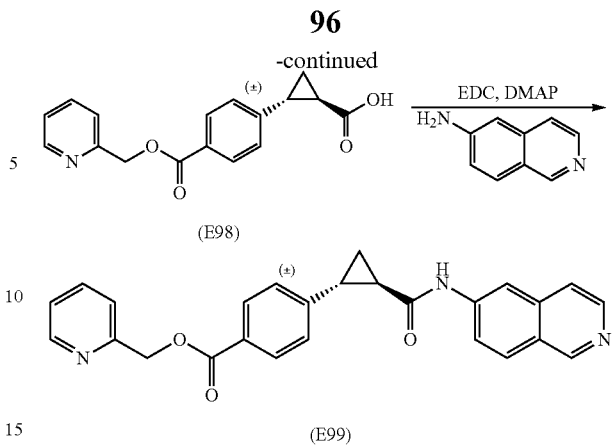

Preparation of trans-4-(2-(tert-butoxycarbonyl)cyclopropyl)benzoic acid (E93)

To TMSOI in DMSO was added NaH and the solution was stirred for one hour under $N_2$. (E)-4-(3-(tert-butoxy)-3-oxoprop-1-en-1-yl)benzoic acid (E92) dissolved in DMSO was added and the solution was stirred for 3 hours at room temperature. The mixture was poured into cold EtOAc and was HCl (1 N) and extracted with EtOAc. The organics were dried ($Na_2SO_4$), filtered and evaporated. Column chromatography over silica gel eluting with 5% MeOH—$CH_2Cl_2$ gave pure trans-4-(2-(tert-butoxycarbonyl)cyclopropyl)benzoic acid (E93).

Preparation of trans-benzyl 4-(2-(tert-butoxycarbonyl)cyclopropyl)benzoate (E94)

To trans-4-(2-(tert-butoxycarbonyl)cyclopropyl)benzoic acid (E93) in DMF cooled to 0° C. was added $K_2CO_3$ and the solution was stirred for 30 minutes at 0° C. under $N_2$. Then, benzyl bromide was added and the solution was warmed and stirred at room temperature for 2-3 hours. The reaction was poured into EtOAc/HCl (1N) and extracted with EtOAc, dried ($Na_2SO_4$), filtered and evaporated. Column chromatography over silica gel eluting with 0-5% EtOAc-Hexanes gave pure trans-benzyl 4-(2-(tert-butoxycarbonyl)cyclopropyl)benzoate (E94).

Preparation of trans-2-(4-((benzyloxy) carbonyl)phenyl) cyclopropane-1-carboxylic acid (E95)

To trans-benzyl 4-(2-(tert-butoxycarbonyl)cyclopropyl)benzoate (E94) in $CH_2Cl_2$ was added TFA and the solution was stirred 3-6 hours at room temperature. The solvents were evaporated and column chromatography 0-5% MeOH—$CH_2Cl_2$ gave pure trans-2-(4-((benzyloxy)carbonyl)phenyl)cyclopropane-1-carboxylic acid (E95).

Preparation of trans-benzyl 4-(2-(isoquinolin-6-ylcarbamoyl)cyclopropyl)benzoate (E96)

To trans-2-(4-((benzyloxy)carbonyl)phenyl)cyclopropane-1-carboxylic acid (E95) in pyridine was added EDC, DMAP and 6-aminoisoquinoline and the solution was stirred under $N_2$ overnight. The mixture was poured into $NaHCO_3$ and extracted with EtOAc, dried ($Na_2SO_4$), filtered and evaporated. Column chromatography over silica gel eluting

Scheme 4.

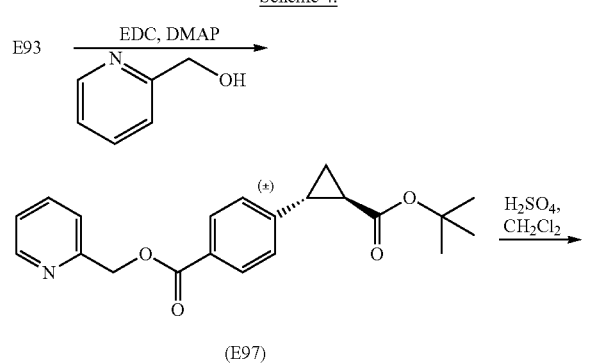

with 5-8% MeOH—CH₂Cl₂ gave pure trans-benzyl 4-(2-(isoquinolin-6-ylcarbamoyl)cyclopropyl)benzoate (E96).

Preparation of trans-pyridin-2-ylmethyl 4-(2-(tert-butoxycarbonyl)cyclopropyl)benzoate (E97)

To trans-4-(2-(tert-butoxycarbonyl)cyclopropyl)benzoic acid (E93) in CH₂Cl₂ was added EDC, DMAP and pyridin-2-ylmethanol and the solution was stirred under N₂ at room temperature for 7 hours. The reaction was poured into EtOAc/NaHCO₃ (sat) and extracted with EtOAc, dried (Na₂SO₄), filtered and evaporated. Column chromatography over silica gel eluting with 0-60%-70% EtOAc-Hexanes gave pure trans-benzyl pyridin-2-ylmethyl 4-(2-(tert-butoxycarbonyl)cyclopropyl)benzoate (E97).

Preparation of trans-2-(4-((pyridin-2-ylmethoxy)carbonyl)phenyl) cyclopropane-1-carboxylic acid (E98)

To trans-benzyl pyridin-2-ylmethyl 4-(2-(tert-butoxycarbonyl)cyclopropyl)benzoate (E97) in CH₂Cl₂ at 0° C. was added H₂SO₄ and the solution was warmed to room temperature at stirred for 12 hours. The solvents were evaporated and mixture was taken up in NaHCO₃ (saturated) and the pH was adjusted to 5 with HCl (1 N). The aqueous layer was extracted with EtOAc, dried (Na₂SO₄), filtered and evaporated to give trans-pyridin-2-ylmethyl 4-(2-(tert-butoxycarbonyl)cyclopropyl)benzoate (E98).

Preparation of trans-pyridin-2-ylmethyl 4-(2-(isoquinolin-6-ylcarbamoyl)cyclopropyl) benzoate (E99)

To trans-2-(4-((pyridin-2-ylmethoxy)carbonyl)phenyl) cyclopropane-1-carboxylic acid (E98) in pyridine was added EDC, DMAP and 6-aminoisoquinoline and the solution was stirred under N₂ overnight. The mixture was poured into NaHCO₃ and extracted with EtOAc, dried (Na₂SO₄), filtered and evaporated. Column chromatography over silica gel eluting with 5-8% MeOH—CH₂Cl₂ gave pure pyridin-2-ylmethyl 4-(2-(isoquinolin-6-ylcarbamoyl)cyclopropyl) benzoate (E99).

Using procedures analogous to those set forth above for Schemes 3 and 4 and substituting the appropriate starting materials, the compounds E100-E111 (see Table 5) could be synthesized.

TABLE 5

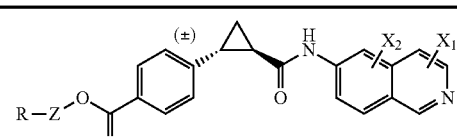

| Example | R—Z— | X₁ | X₂ |
|---|---|---|---|
| E96 | benzyl | H | H |
| E99 | pyridin-2-ylmethyl | H | H |
| E100 | pyridin-2-ylmethyl | 1-OH | H |
| E100.1 | benzyl | 1-OH | H |
| E101 | (dimethylamino)propyl | 1-Cl | H |
| E102 | (dimethylamino)propyl | H | 5-F |
| E103 | piperidin-2-ylmethyl | 4-Cl | H |
| E104 | piperidin-4-ylmethyl | H | 7-Cl |
| E104.1 | benzyl | H | 7-Cl |
| E105 | piperidin-3-ylethyl | H | H |
| E106 | pyrrolidin-3-ylmethyl | 3-F | H |
| E107 | 3-chlorobenzyl | 1-OH | 4-Cl |
| E108 | 4-fluorobenzyl | H | H |

TABLE 5-continued

Example 4

| Example | R—Z— | X₁ | X₂ |
|---|---|---|---|
| E109 | 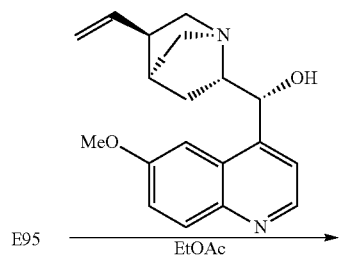 | 1-OH | H |
| E110 | | H | H |
| E111 | | H | 5-Cl |

Preparation of (1S,2S)-2-(4-((benzyloxy) carbonyl) phenyl) cyclopropane-1-carboxylic acid quinine salt (E112) and (1R,2R)-2-(4-((benzyloxy)carbonyl) phenyl) cyclopropane-1-carboxylic acid quinine salt (E113)

To trans-2-(4-((benzyloxy)carbonyl) phenyl)cyclopropane-1-carboxylic acid (E95) in EtOAc was added (R)-(6-methoxyquinolin-4-yl)((1S,2S,4S,5R)-5-vinylquinuclidin-2-yl)methanol (quinine) and the solution was heated to 80-85° C. The round bottom flask containing the solution was moved to a cork ring and cooled to room temperature. Crystals were formed over 2 days. The filtrate was removed to give (1R,2R)-2-(4-((benzyloxy)carbonyl)phenyl)cyclopropane-1-carboxylic acid quinine salt (E113, 44%, 92% RR, 8% SS). The crystals gave (1S,2S)-2-(4-((benzyloxy)carbonyl)phenyl) cyclopropane-1-carboxylic acid quinine salt (E112 59% SS, 41% RR).

Preparation of (1S,2S)-2-(4-((benzyloxy) carbonyl) phenyl) cyclopropane-1-carboxylic acid quinine salt (E103)

To trans-2-(4-((benzyloxy)carbonyl)phenyl) cyclopropane-1-carboxylic acid in EtOAc was added (R)-(6-methoxyquinolin-4-yl)((1S,2S,4S,5R)-5-vinylquinuclidin-2-yl)methanol (quinine) and the solution was heated to 80-85° C. The round bottom flask containing the solution was moved to a cork ring and cooled to room temperature. Crystals were formed over 1 day. The filtrate was removed to give (1R,2R)-2-(4-((benzyloxy)carbonyl)phenyl)cyclopropane-1-carboxylic acid quinine salt (E113, 60%, 64% RR, 35% SS) and the crystals left behind were (1S,2S)-2-(4-((benzyloxy)carbonyl)phenyl)cyclopropane-1-carboxylic Scheme 5.

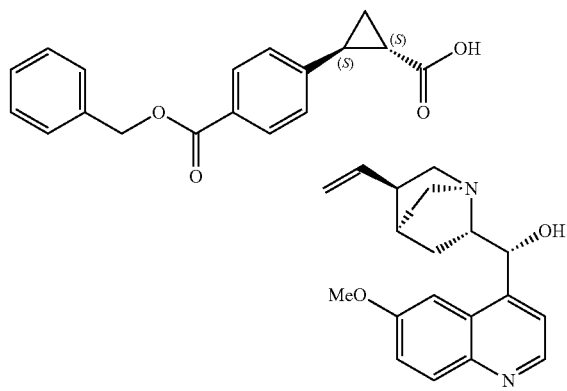

(E112, crystals)

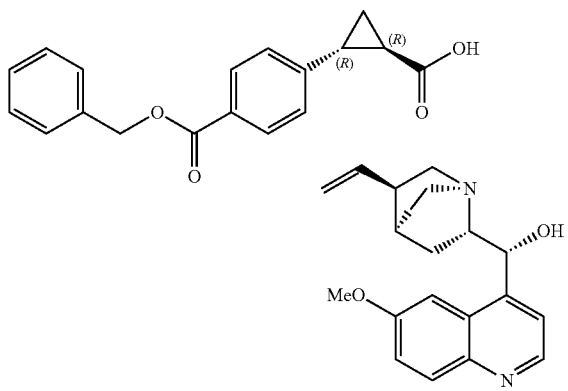

(E113, mother liquor, filtrate)

acid quinine salt (E112, 84% SS, 16% RR). E112 was recrystallized from EtOAc two additional times to give (1S,2S)-2-(4-((benzyloxy)carbonyl)phenyl)cyclopropane-1-carboxylic acid quinine salt (E112, 98% SS, 2% RR).

evaporated. Column chromatography over silica gel eluting with 5-8% MeOH—CH$_2$Cl$_2$ gave pure benzyl 4-((1R,2R)-2-(isoquinolin-6-ylcarbamoyl)cyclopropyl)benzoate (E115).

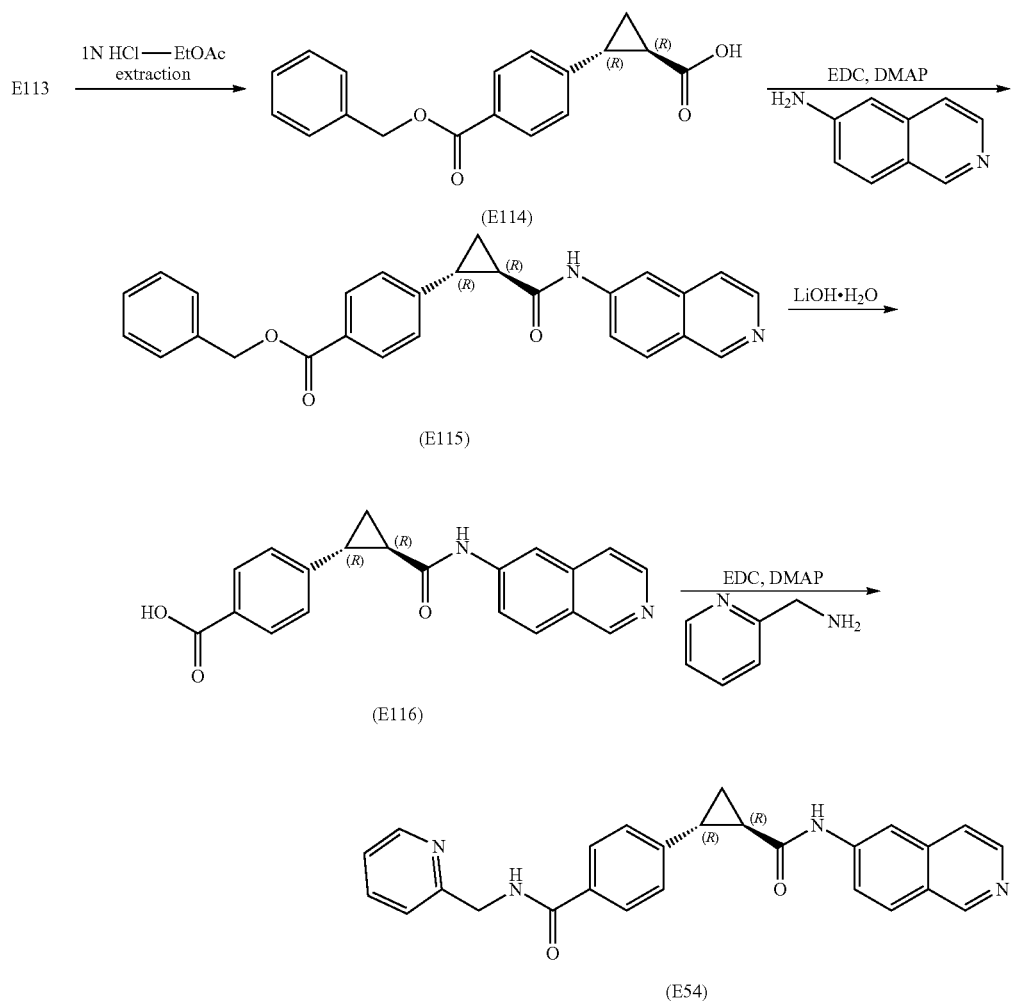

Preparation of (1R,2R)-2-(4-((benzyloxy)carbonyl) phenyl) cyclopropane-1-carboxylic acid (E114)

(1R,2R)-2-(4-((benzyloxy)carbonyl)phenyl)cyclopropane-1-carboxylic acid quinine salt (E113) was dissolved in EtOAc and extracted with HCl (1N). The organics were dried (Na$_2$SO$_4$), filtered and evaporated to give (1R,2R)-2-(4-((benzyloxy)carbonyl)phenyl)cyclopropane-1-carboxylic acid (E114).

Preparation of benzyl 4-((1R,2R)-2-(isoquinolin-6-ylcarbamoyl)cyclopropyl)benzoate (E115)

To (1R,2R)-2-(4-((benzyloxy)carbonyl)phenyl)cyclopropane-1-carboxylic acid (E114) in pyridine was added EDC, DMAP and 6-aminoisoquinoline and the solution was stirred under N$_2$ overnight. The mixture was poured into NaHCO$_3$ and extracted with EtOAc, dried (Na$_2$SO$_4$), filtered and

Preparation of 4-((1R,2R)-2-(isoquinolin-6-ylcarbamoyl)cyclopropyl)benzoic acid (E116)

To 4-((1R,2R)-2-(isoquinolin-6-ylcarbamoyl)cyclopropyl)benzoate (E115) in THF-H$_2$O at 0° C. was added LiOH—H$_2$O and the solution was stirred at room temperature for 24 hours. The reaction was acidified to pH 5 with HCl (1 N) and the solids were filtered to give 4-((1R,2R)-2-(isoquinolin-6-ylcarbamoyl)cyclopropyl)benzoic acid (E116).

Preparation of 4-((1R,2R)-2-(isoquinolin-6-ylcarbamoyl) cyclopropyl)-N-(pyridin-2-ylmethyl)benzamide (E54)

To 4-((1R,2R)-2-(isoquinolin-6-ylcarbamoyl)cyclopropyl) benzoic acid (E116) in CH$_2$Cl$_2$ was added EDC, DMAP and 2-picolylamine and the solution was stirred under N$_2$ at room temperature overnight. The reaction was poured into EtOAc/NaHCO$_3$ (saturated) and extracted with EtOAc, dried ($Na_2SO_4$), filtered and evaporated. Column chromatography over silica gel eluting with 5-8% MeOH—$CH_2Cl_2$ gave pure 4-((1R,2R)-2-(isoquinolin-6-ylcarbamoyl)cyclopropyl)-N-(pyridin-2-ylmethyl)benzamide (E54).
Scheme 6.1. Synthesis of R,R and S,S enantiomers through Supercritical Fluid Column Chromatography. (SFC)
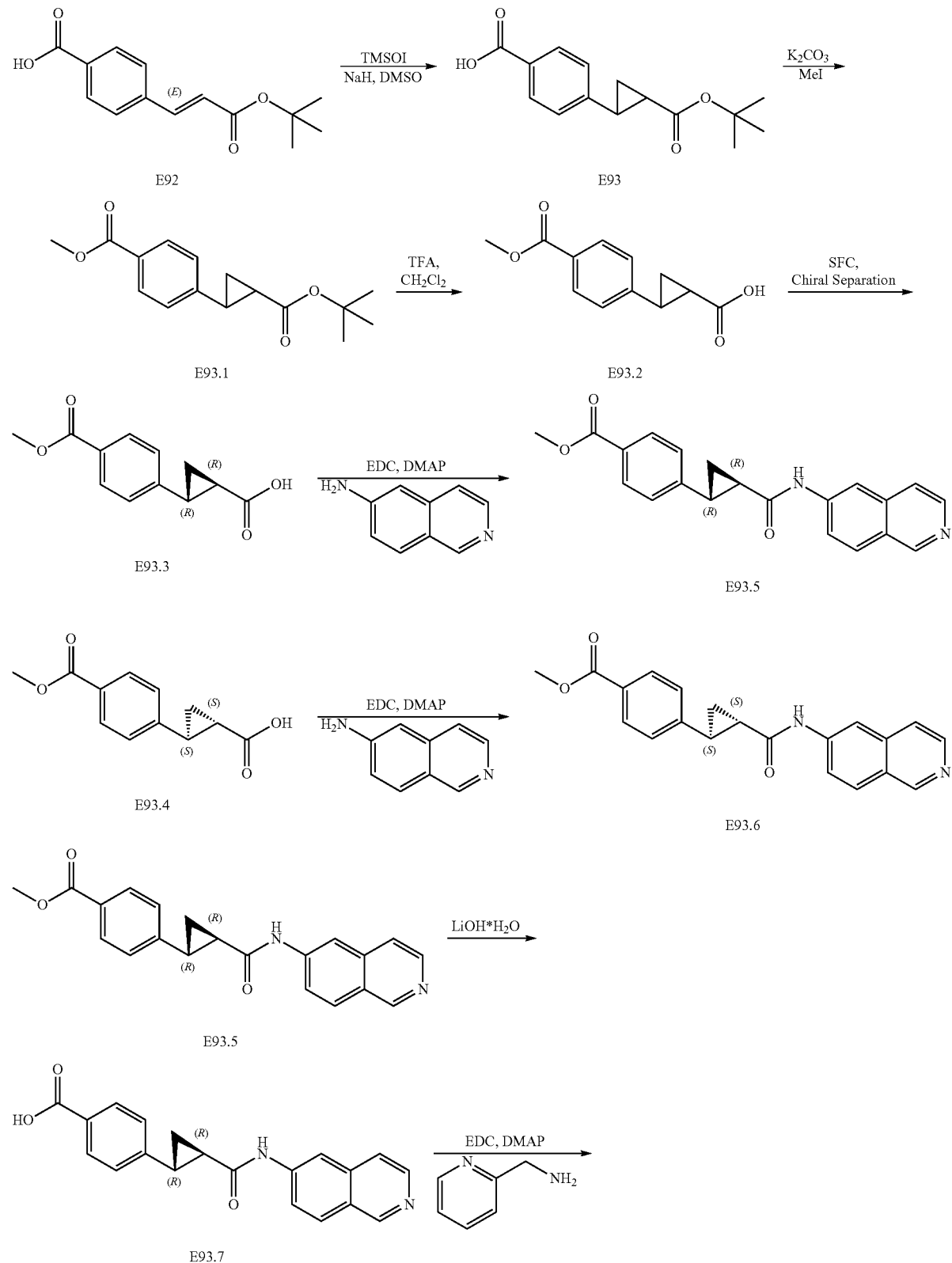

-continued
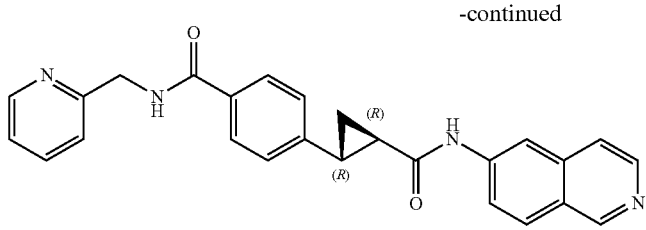
E93.9
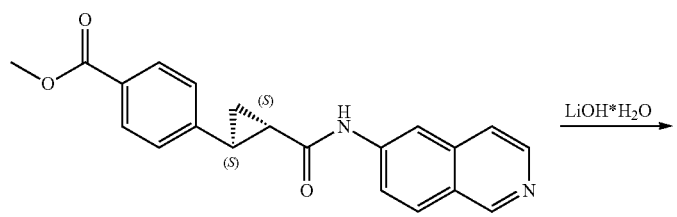
E93.6
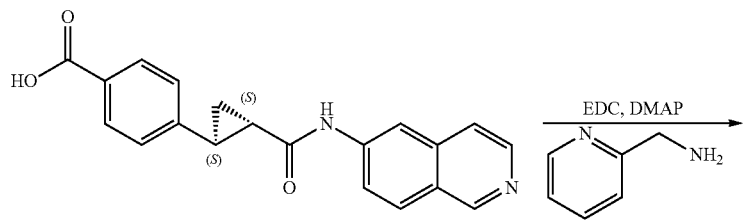
E93.8
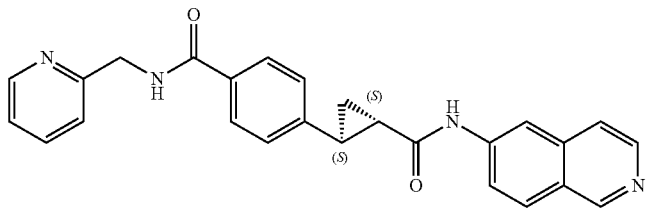
E93.10
Using procedures analogous to those set forth above for Scheme 6 substituting the appropriate starting materials, the compound E69 was made and E56, E56.1, E90, and E115.1, and E117-E138 (see Table 6) could be synthesized.
TABLE 6
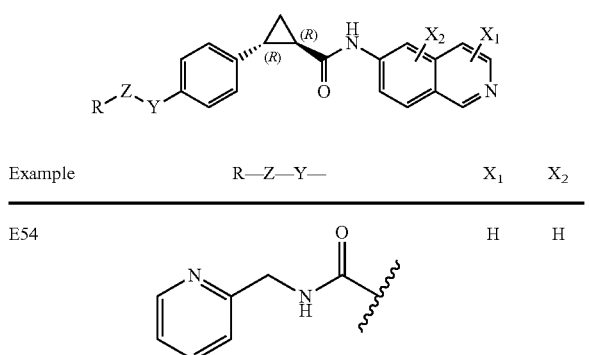
| Example | R—Z—Y— | $X_1$ | $X_2$ |
|---|---|---|---|
| E54 | <br> | H | H |
TABLE 6-continued
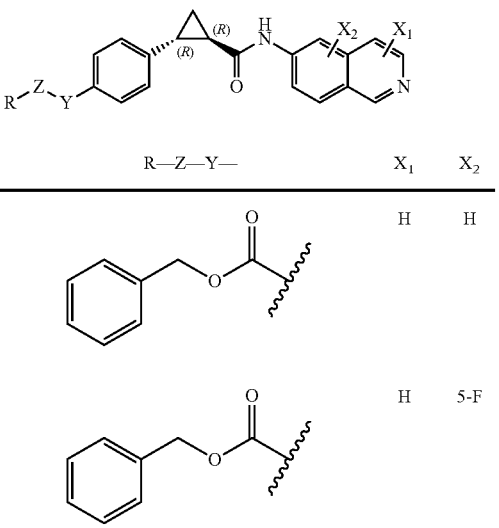
| Example | R—Z—Y— | $X_1$ | $X_2$ |
|---|---|---|---|
| E115 | <br> | H | H |
| E115.1 | <br> | H | 5-F |

TABLE 6-continued

| Example | R—Z—Y— | X₁ | X₂ |
|---|---|---|---|
| E116 | HOOC-CH(~)- (carboxylic acid substituent) | H | H |
| E69 | 4-methoxybenzyl-NH-C(O)- | H | H |
| E117 | 3-fluorophenethyl-NH-C(O)- | H | H |
| E56 | pyridin-3-ylmethyl-NH-C(O)- | H | H |
| E56.1 | pyridin-3-ylmethyl-NH-C(O)- | H | 5-F |
| E118 | pyridin-4-ylmethyl-NH-C(O)- | 1-OH | H |
| E119 | piperidin-3-ylmethyl-NH-C(O)- | 5-Cl | H |
| E120 | piperidin-3-ylmethyl-NH-C(O)- | H | 7-F |
| E121 | piperidin-2-ylmethyl-NH-C(O)- | H | H |
| E122 | piperidin-2-ylmethyl-NH-C(O)- | H | H |
| E123 | piperidin-4-ylmethyl-NH-C(O)- | 1-OH | 7-Cl |
| E124 | pyrrolidin-3-ylmethyl-NH-C(O)- | H | 7-Br |
| E125 | pyrrolidin-3-ylmethyl-NH-C(O)- | H | H |
| E126 | (dimethylamino)ethyl-NH-C(O)- | H | H |
| E127 | morpholin-4-yl-C(O)- | 1-OH | 4-Cl |
| E128 | 4-phenylpiperazin-1-yl-C(O)- | H | H |
| E90 | 1,4-diazepan-1-yl-C(O)- | H | H |
| E129 | 2-morpholinoethyl-NH-C(O)- | H | H |
| E130 | butyl-NH-C(O)- | 1-OH | H |

TABLE 6-continued

| Example | R—Z—Y— | X₁ | X₂ |
|---|---|---|---|
| E131 | (pyridin-3-yl)methyl ester | 3-Cl | H |
| E132 | (2-methylphenyl)methyl ester | 1-F | H |
| E133 | ((R)-piperidin-3-yl)methyl ester | H | H |
| E134 | (piperidin-4-yl)methyl ester | H | H |
| E135 | 2-(4-trifluoromethylphenyl)ethyl ester | 5-Cl | H |
| E136 | 2-(dimethylamino)ethyl ester | 4-F | H |
| E137 | cinnamyl ester | H | H |
| E138 | isopentyl ester | H | H |

Using procedures analogous to those set forth above for Scheme 6.1 substituting the appropriate starting materials, E138.1-E138.41 were (see Table 6.1) synthesized.

TABLE 6.1

| Example | Structure: -R,R and S,S- 4-Substutituted Analogs (para) |
|---|---|
| E138.1 | 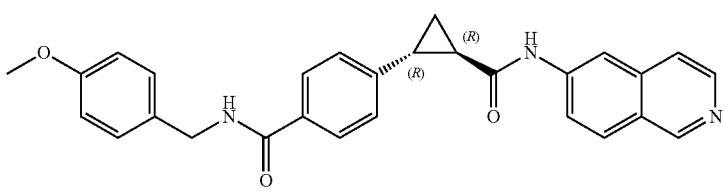 |
| E138.2 | 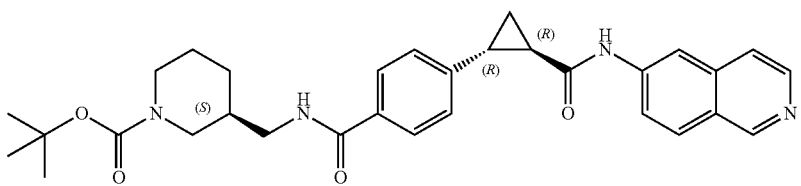 |
| E138.3 | * 2 HCl 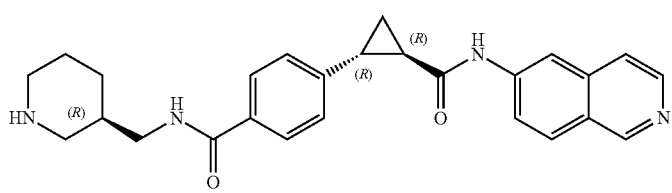 |

TABLE 6.1-continued
| Example | Structure: -R,R and S,S- 4-Substitututed Analogs (para) |
|---|---|
| E138.4 | 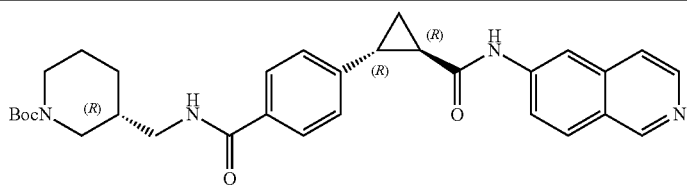 |
| E138.5 | 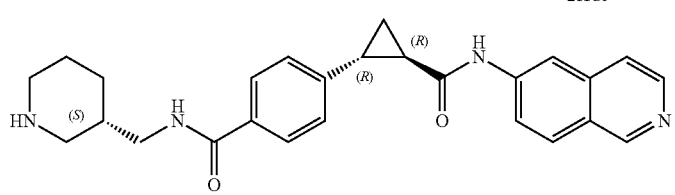 *2HCl |
| E138.6 | 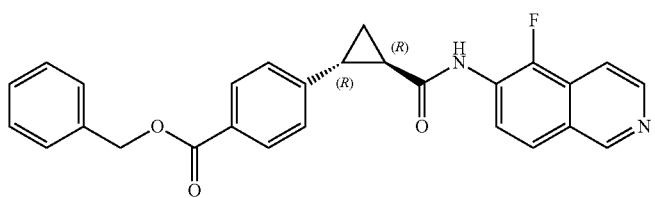 |
| E138.7 | 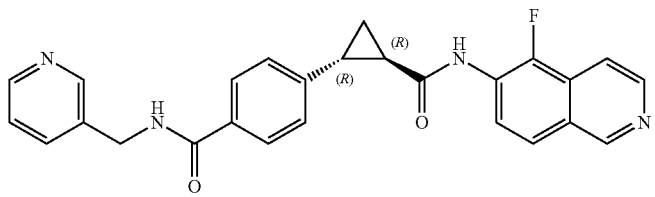 |
| E138.8 | 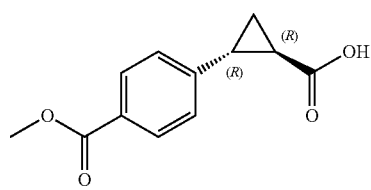 |
| E138.9 | 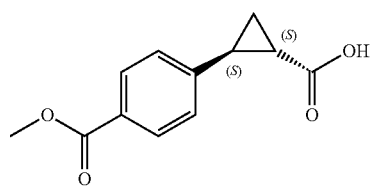 |
| E138.10 | 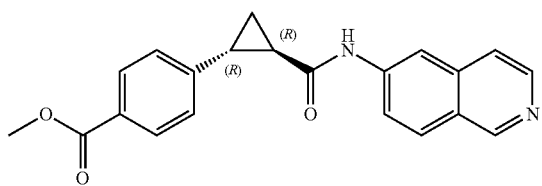 |
| E138.11 | 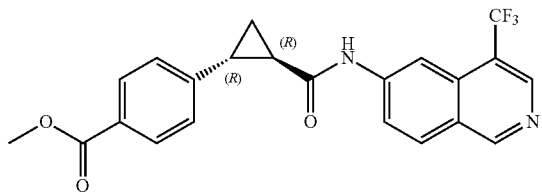 |

TABLE 6.1-continued
| Example | Structure: -R,R and S,S- 4-Substutituted Analogs (para) |
|---|---|
| E138.12 | 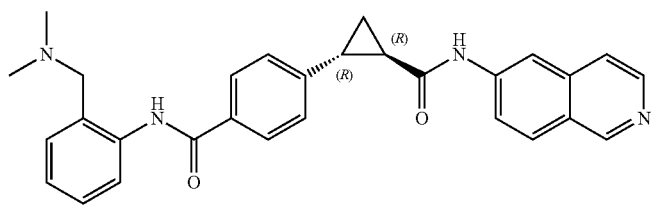 |
| E138.13 | 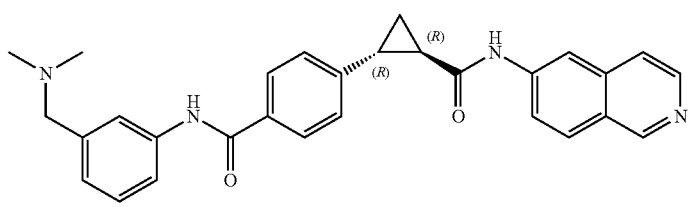 |
| E138.14 | 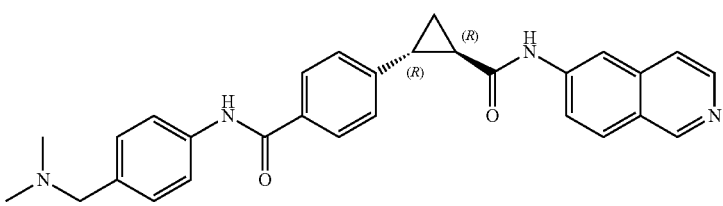 |
| E138.15 | 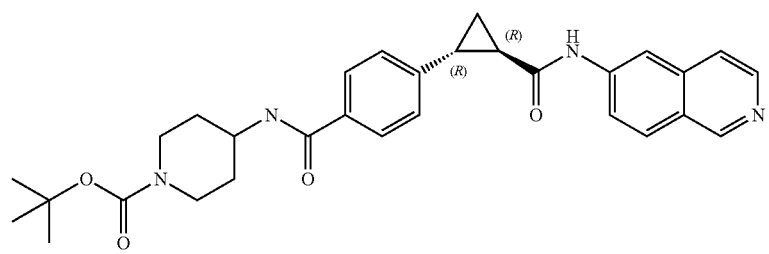 |
| E138.16 | *2HCl 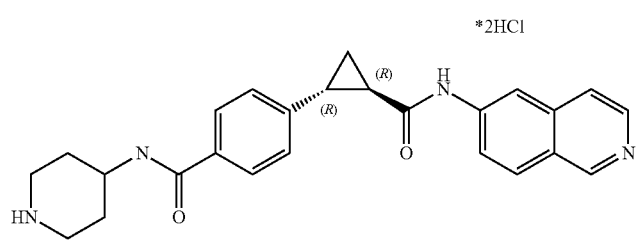 |
| E138.17 | 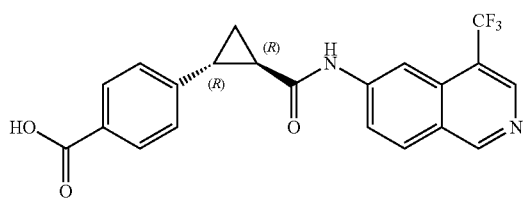 |
| E138.18 | 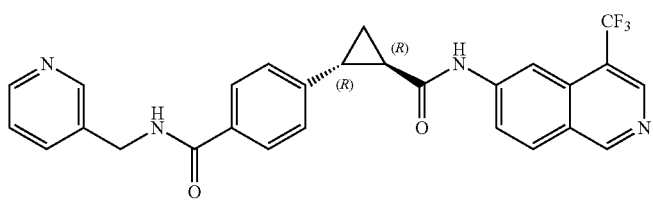 |

TABLE 6.1-continued

| Example | Structure: -R,R and S,S- 4-Substutituted Analogs (para) |
|---|---|
| E138.19 | |
| E138.20 | |
| E138.21 | |
| E138.22 | |
| E138.23 | |
| E138.24 | |
| E138.25 | *2HCl |

TABLE 6.1-continued
| Example | Structure: -R,R and S,S- 4-Substutituted Analogs (para) |
|---|---|
| E138.26 | 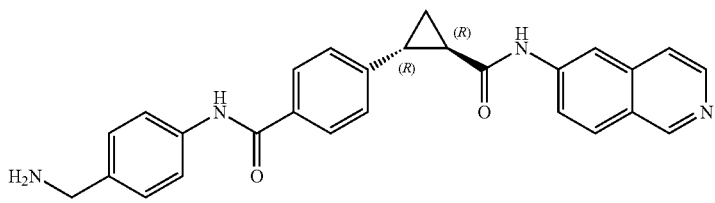 *2HCl |
| E138.27 | 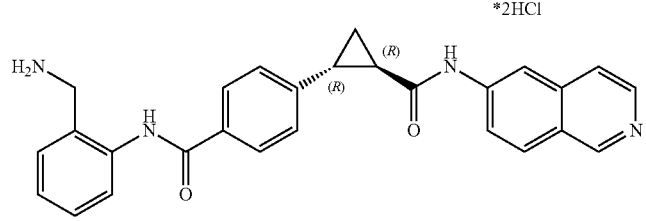 *2HCl |
| E138.28 | 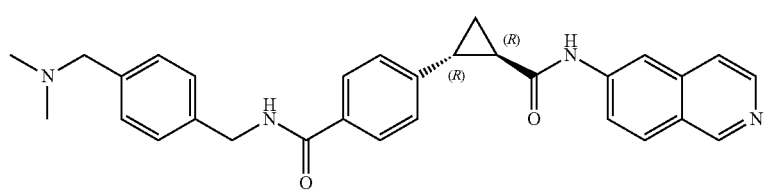 |
| E138.29 | 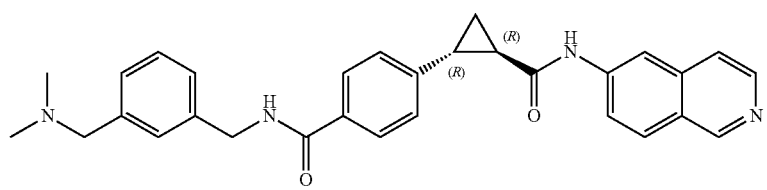 |
| E138.30 | 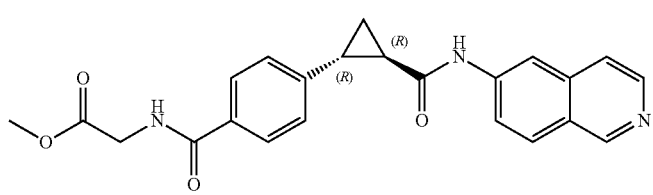 |
| E138.31 | 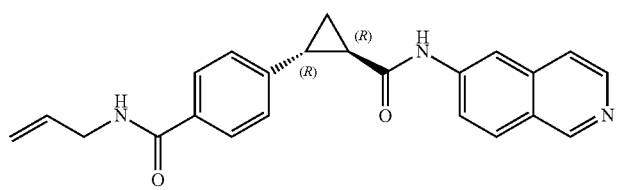 |
| E138.32 | 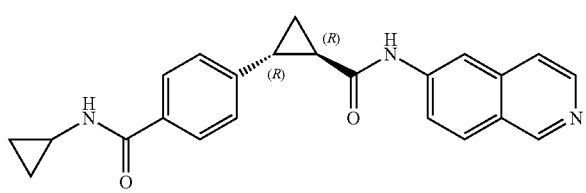 |

TABLE 6.1-continued
| Example | Structure: -R,R and S,S- 4-Substutituted Analogs (para) |
|---|---|
| E138.33 | 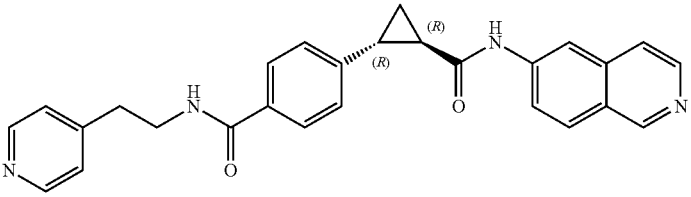 |
| E138.34 | 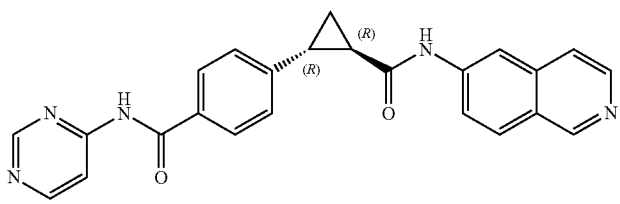 |
| E138.35 | 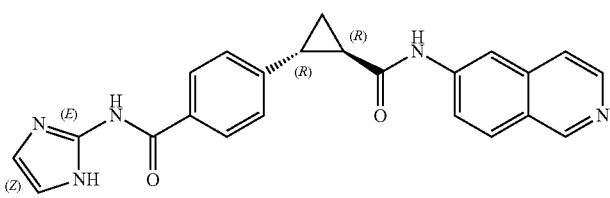 |
| E138.36 | 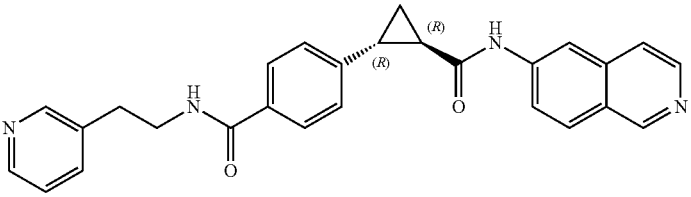 |
| E138.37 | 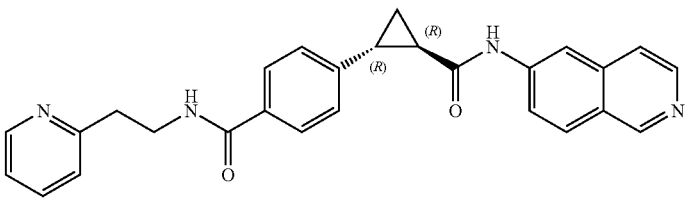 |
| E138.38 | 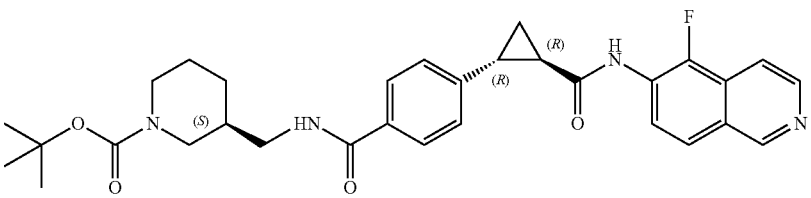 |
| E138.39 | 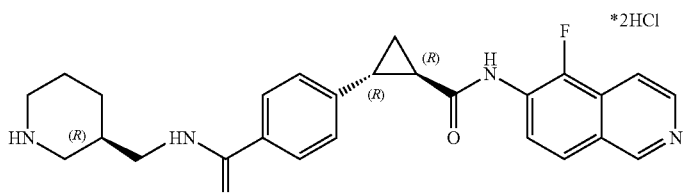 |

TABLE 6.1-continued

| Example | Structure: -R,R and S,S- 4-Substutituted Analogs (para) |
|---|---|
| E138.40 | 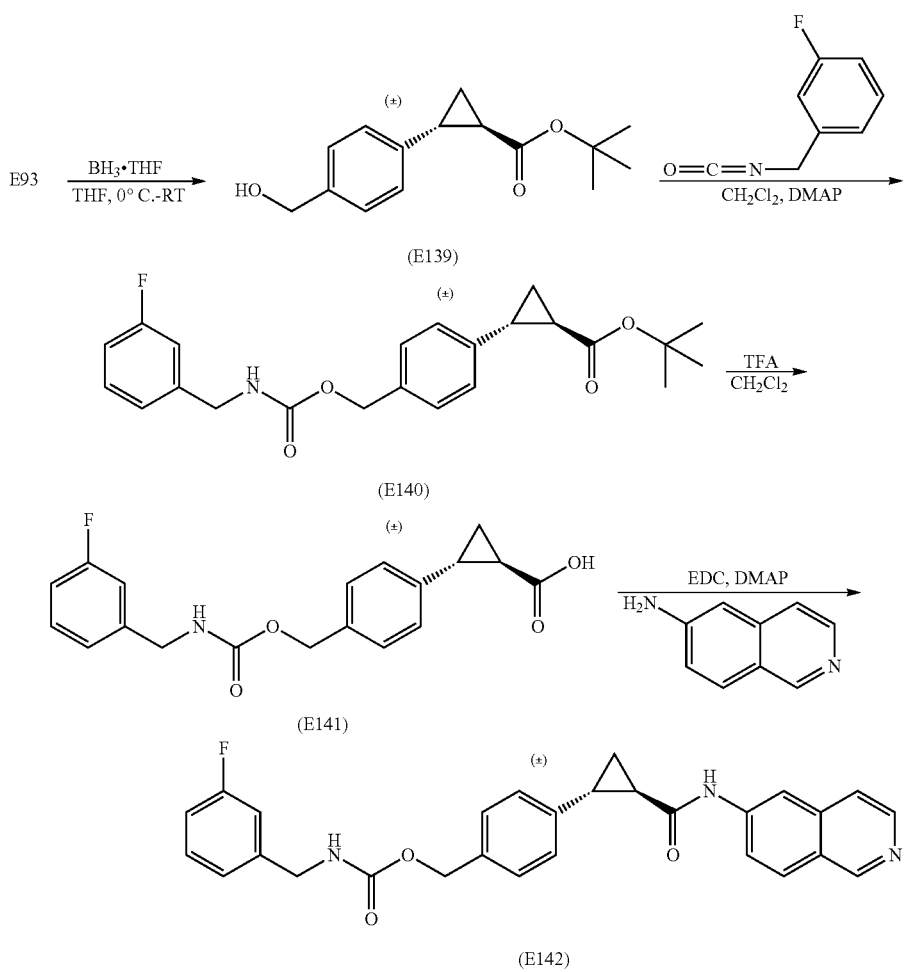 |

Example 5

Scheme 7.

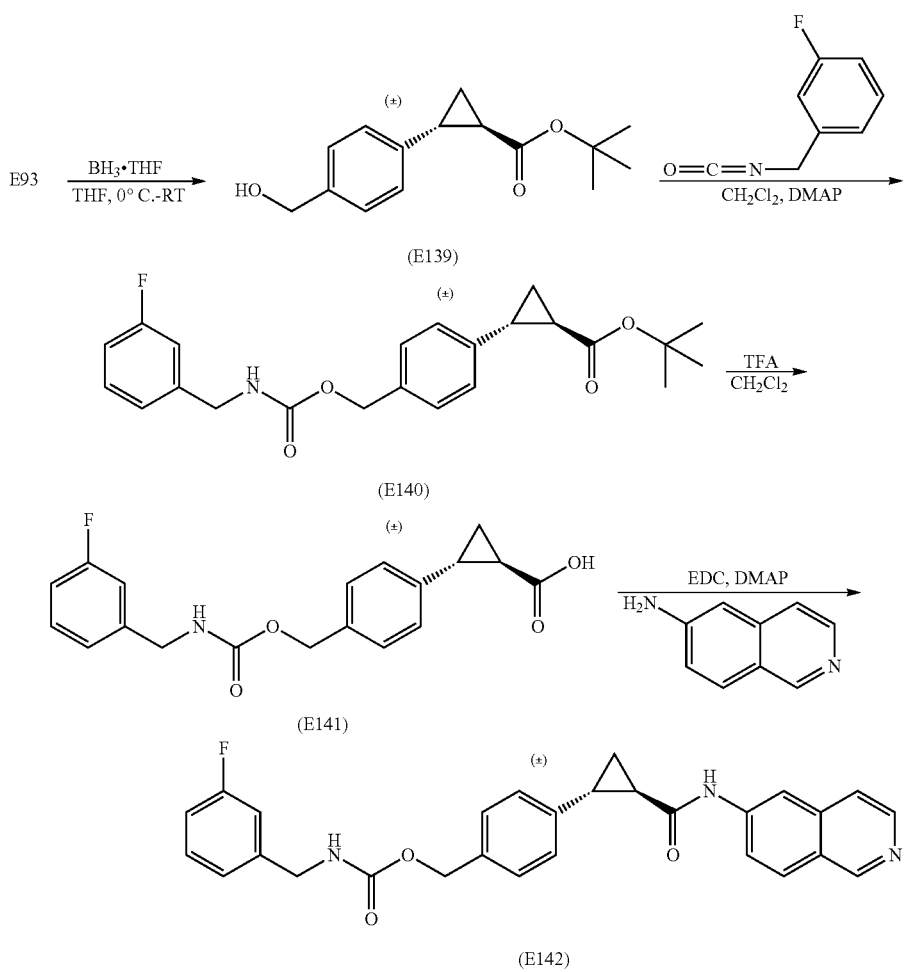

Preparation of trans-tert-butyl 2-(4-(hydroxymethyl)phenyl)cyclopropane-1-carboxylate (E139)

To trans-4-(2-(tert-butoxycarbonyl)cyclopropyl)benzoic acid (E93) in THF cooled to 0° C. under $N_2$ was added $BH_3$-THF and the solution was warmed to room temperature. After 5 hours the mixture was poured into $NaHCO_3$ (saturated) and extracted with EtOAc, dried ($Na_2SO_4$), filtered and evaporated. Column chromatography over silica gel eluting with 0-30% EtOAc-Hexanes gave pure of trans-tert-butyl 2-((hydroxymethyl)phenyl)cyclopropane-1-carboxylate (E139).

Preparation of trans-tert-butyl 2-(4-((((3-fluorobenzyl) carbamoyl) oxy)methyl)phenyl)cyclopropane-1-carboxylate (E140)

To trans-tert-butyl 2-((hydroxymethyl)phenyl)cyclopropane-1-carboxylate (E139) in $CH_2Cl_2$ was added DMAP and 1-fluoro-3-(isocyanatomethyl)benzene and the solution was stirred for 24 hours at room temperature under N$_2$. The mixture was poured into EtOAc—NH$_4$Cl, extracted, dried (Na$_2$SO$_4$), filtered and evaporated. Column chromatography over silica gel eluting with 0-30% EtOAc gave trans-tert-butyl 2-(4-((((3-fluorobenzyl) carbamoyl)oxy)methyl)phenyl)cyclopropane-1-carboxylate (E140).

Preparation of trans-2-(4-((((3-fluorobenzyl) carbamoyl) oxy)methyl)phenyl)cyclopropane-1-carboxylic acid (E141)

To trans-tert-butyl 2-(4-((((3-fluorobenzyl)carbamoyl) oxy)methyl)phenyl)cyclopropane-1-carboxylate (E140) in CH$_2$Cl$_2$ was added TFA and the solution was stirred at room temperature overnight. The solvents were evaporated and column chromatography over silica gel eluting with 20% EtOAc-Hexanes, 2% AcOH gave pure trans-2-(4-((((3-fluorobenzyl)carbamoyl)oxy)methyl)phenyl)cyclopropane-1-carboxylic acid (E141).

Preparation of trans-4-(2-(isoquinolin-6-ylcarbamoyl)cyclopropyl)benzyl (3-fluorobenzyl)carbamate (E142)

To trans-2-(4-((((3-fluorobenzyl)carbamoyl)oxy) methyl) phenyl)cyclopropane-1-carboxylic acid (E141) in pyridine were added EDC, DMAP and 6-aminoisoquinoline and the solution was stirred under N$_2$, overnight at room temperature. The reaction mixture was poured into NaHCO$_3$ (saturated) and extracted with EtOAc, dried (Na$_2$SO$_4$), filtered and evaporated. Column chromatography over silica gel eluting with 4% MeOH—CH$_2$Cl$_2$ gave pure trans-4-(2-(isoquinolin-6-ylcarbamoyl) cyclopropyl)benzyl (3-fluorobenzyl)carbamate (E142).

Using procedures analogous to those set forth for Scheme 7 and substituting the appropriate starting materials, the compound E143 was made and E144-E153 (see Table 7) could be synthesized.

TABLE 7

| Example | R—Z— | X$_1$ | X$_2$ |
|---|---|---|---|
| E142 | 3-fluorobenzyl | H | H |
| E143 | 2-chlorobenzyl | H | H |
| E144 | pyridin-3-yl methyl | H | H |
| E145 | 4-chlorophenyl | H | H |
| E146 | 4-fluoro-2-methylphenyl | 1-OH | H |
| E147 | 3-(trifluoromethyl)benzyl | H | 5-Cl |

TABLE 7-continued
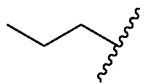 [SMILES: *CCC]
| Example | R—Z— | $X_1$ | $X_2$ |
|---|---|---|---|
| E148 | 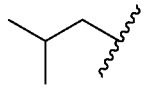 | H | 7-F |
| E149 | 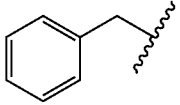 [SMILES: *Cc1ccccc1] | H | H |
| E150 | 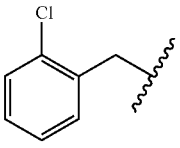 [SMILES: *Cc1ccccc1Cl] | 1-OH | H |
| E151 | 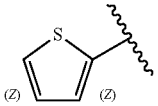 | 1-OH | 7-Cl |
| E152 | 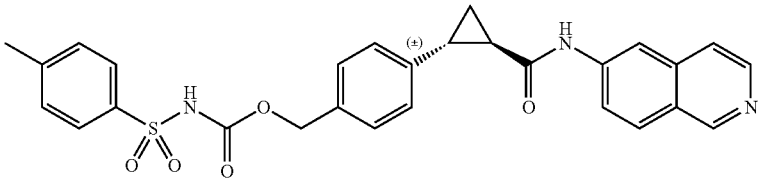 | H | 7-Br |
Using procedures analogous to those set forth for Scheme 7 and substituting the appropriate starting materials, the compound E153.1-E153.4 were made (Table 7.1)
TABLE 7.1
Structure: -4-Substutituted Cyclopropyl Analogs
Example (para)
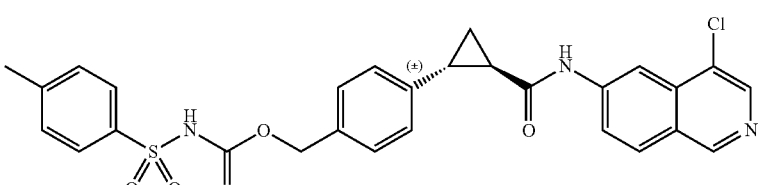
E153.1
E153.2

TABLE 7.1-continued

Structure: -4-Substitututed Cyclopropyl Analogs (para)

| Example | |
|---|---|
| E153.3 | 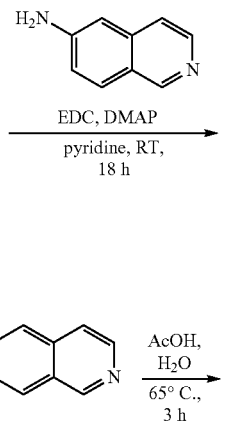 |
| E153.4 | |

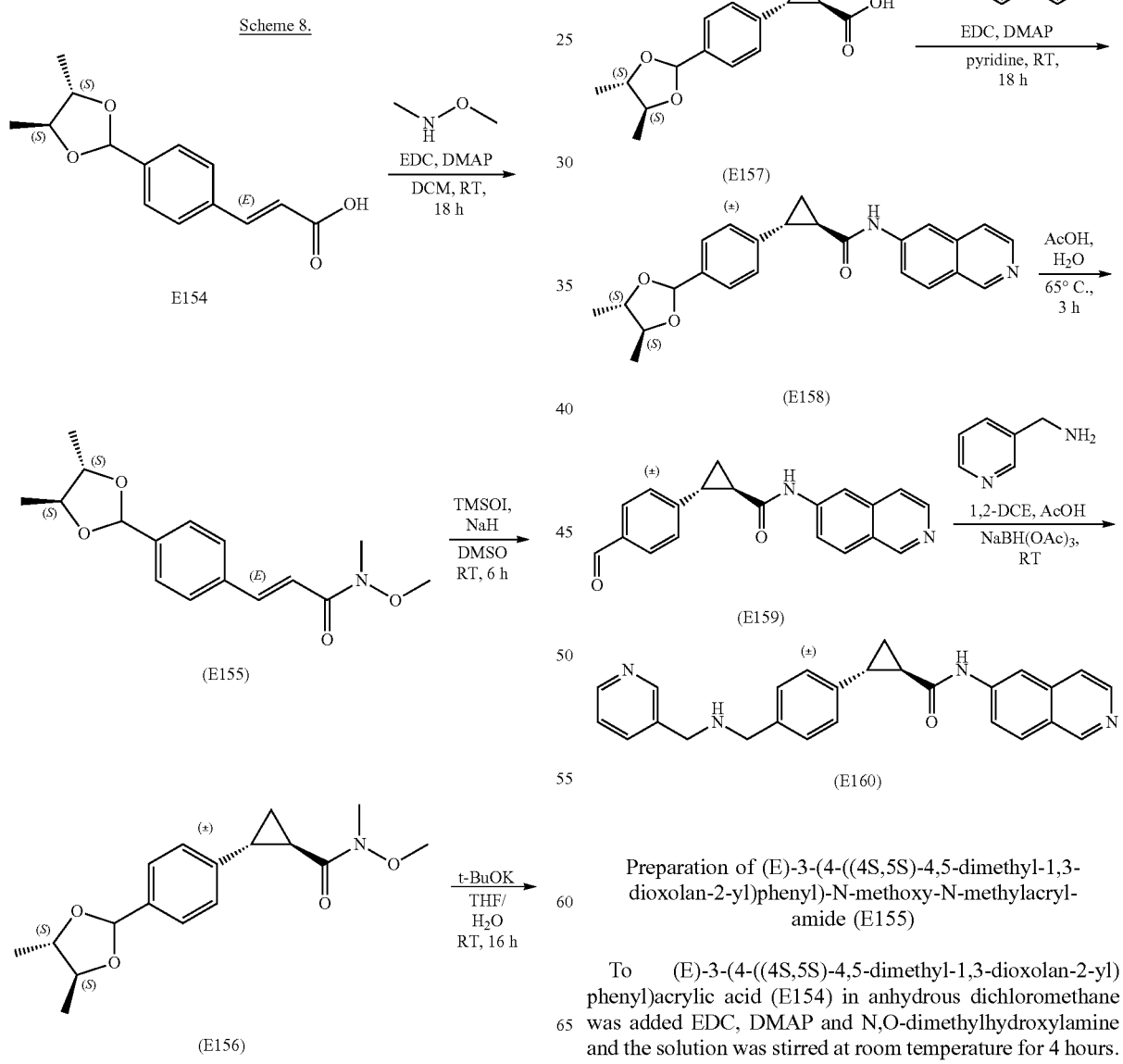

Example 6

Scheme 8.

Preparation of (E)-3-(4-((4S,5S)-4,5-dimethyl-1,3-dioxolan-2-yl)phenyl)-N-methoxy-N-methylacrylamide (E155)

To (E)-3-(4-((4S,5S)-4,5-dimethyl-1,3-dioxolan-2-yl)phenyl)acrylic acid (E154) in anhydrous dichloromethane was added EDC, DMAP and N,O-dimethylhydroxylamine and the solution was stirred at room temperature for 4 hours. The reaction was diluted with dichloromethane and washed with deionized H₂O, dried over Na₂SO₄, filtered and concentrated. Column chromatography over silica gel eluting with 0 to 2% MeOH/CH₂Cl₂ gave pure (E)-3-(4-((4S,5S)-4,5-dimethyl-1,3-dioxolan-2-yl)phenyl)-N-methoxy-N-methylacrylamide (E155).

Preparation of trans2-(4-((4S,5S)-4,5-dimethyl-1,3-dioxolan-2-yl)phenyl)-N-methoxy-N-methylcyclopropane-1-carboxamide (E156)

To TMSOI in DMSO was added NaH and the solution was stirred for one hour under N₂. (E)-3-(4-((4S,5S)-4,5-dimethyl-1,3-dioxolan-2-yl)phenyl)-N-methoxy-N-methylacrylamide (E155) dissolved in DMSO was added dropwise and the solution was stirred for 3 hours at room temperature. The mixture was poured over deionized H₂O and extracted with EtOAc. The organics were dried (Na₂SO₄), filtered and concentrated. Column chromatography over silica gel eluting with 0-5% MeOH/CH₂Cl₂ gave pure trans-2-(4-((4S,5S)-4,5-dimethyl-1,3-dioxolan-2-yl)phenyl)-N-methoxy-N-methylcyclopropane-1-carboxamide (E156).

Preparation of trans-2-(4-((4S,5S)-4,5-dimethyl-1,3-dioxolan-2-yl)phenyl) cyclopropane-1-carboxylic acid (E157)

To a suspension of trans-2-(4-((4S,5S)-4,5-dimethyl-1,3-dioxolan-2-yl)phenyl)-N-methoxy-N-methylcyclopropane-1-carboxamide (E156) in diethyl ether and deionized water was added potassium t-butoxide and stirred at room temperature 16 hours. The pH was adjusted to 5 with HCl (1N) and the aqueous layer was extracted with EtOAc, dried (Na₂SO₄), filtered and concentrated to give trans-2-(4-((4S,5S)-4,5-dimethyl-1,3-dioxolan-2-yl)phenyl)cyclopropane-1-carboxylic acid (E157).

Preparation of trans-2-(4-((4S,5S)-4,5-dimethyl-1,3-dioxolan-2-yl)phenyl)-N-(isoquinolin-6-yl)cyclopropane-1-carboxamide (E158)

To trans-2-(4-((4S,5S)-4,5-dimethyl-1,3-dioxolan-2-yl)phenyl)cyclopropane-1-carboxylic acid (E157) in anhydrous pyridine were added EDC, DMAP and 6-aminoisoquinoline and the solution was stirred under N₂ overnight. The reaction mixture was concentrated. Column chromatography over silica gel eluting with 0-5% MeOH/CH₂Cl₂ gave pure trans-2-(4-((4S,5S)-4,5-dimethyl-1,3-dioxolan-2-yl) phenyl)-N-(isoquinolin-6-yl)cyclopropane-1-carboxamide (E158).

Preparation of trans-2-(4-formylphenyl)-N-(isoquinolin-6-yl)cyclopropane-1-carboxamide (E159)

To a suspension of trans-2-(4-((4S,5S)-4,5-dimethyl-1,3-dioxolan-2-yl)phenyl)-N-(isoquinolin-6-yl)cyclopropane-1-carboxamide (E158) in deionized H₂O was added AcOH and the solution was heated to 65° C. for 3 hours. The reaction was quenched with NaHCO₃ (saturated) and extracted with EtOAc, dried (Na₂SO₄), filtered and concentrated. Column chromatography over silica gel eluting with 0-5% MeOH—CH₂Cl₂ gave pure trans-2-(4-formylphenyl)-N-(isoquinolin-6-yl)cyclopropane-1-carboxamide (E159).

Preparation of trans-N-(isoquinolin-6-yl)-2-(4-(((pyridin-3-ylmethyl)amino)methyl)phenyl)cyclopropane-1-carboxamide (E160)

To trans-2-(4-formylphenyl)-N-(isoquinolin-6-yl)cyclopropane-1-carboxamide (E159) in anhydrous 1,2-dichloroethane was added pyridin-3-ylmethanamine and the solution was stirred at room temperature under N₂ for 30 minutes before adding sodium triacetoxyborohydride and stirring overnight. The reaction was poured into EtOAc/NaHCO₃ (saturated) and extracted with EtOAc, dried (Na₂SO₄), filtered and evaporated. Column chromatography over silica gel eluting with 0-5% MeOH/CH₂Cl₂ gave pure trans-N-(isoquinolin-6-yl)-2-(4-(((pyridin-3-ylmethyl)amino) methyl)phenyl)cyclopropane-1-carboxamide (E160).

Using the procedures analogous to those set forth for Scheme 8 and substituting the appropriate starting materials, the compounds E161-E162.2 were made and E163-E165 (see Table 8) could be synthesized.

TABLE 8

| Example | R—Z— | X₁ | X₂ |
|---|---|---|---|
| E160 | 3-pyridylmethyl | H | H |
| E161 | 2-pyridylmethyl | H | H |
| E-162.1 | (1-Boc-piperidin-4-yl)methyl | H | H |
| E162.2 | (piperidin-4-yl)methyl | H | H |
| E163 | (3-pyridyl)methylene | H | H |
| E164 | (4-chlorophenyl)methylene | H | H |
| E165 | (4-methoxyphenyl)methylene | H | H |

Example 7

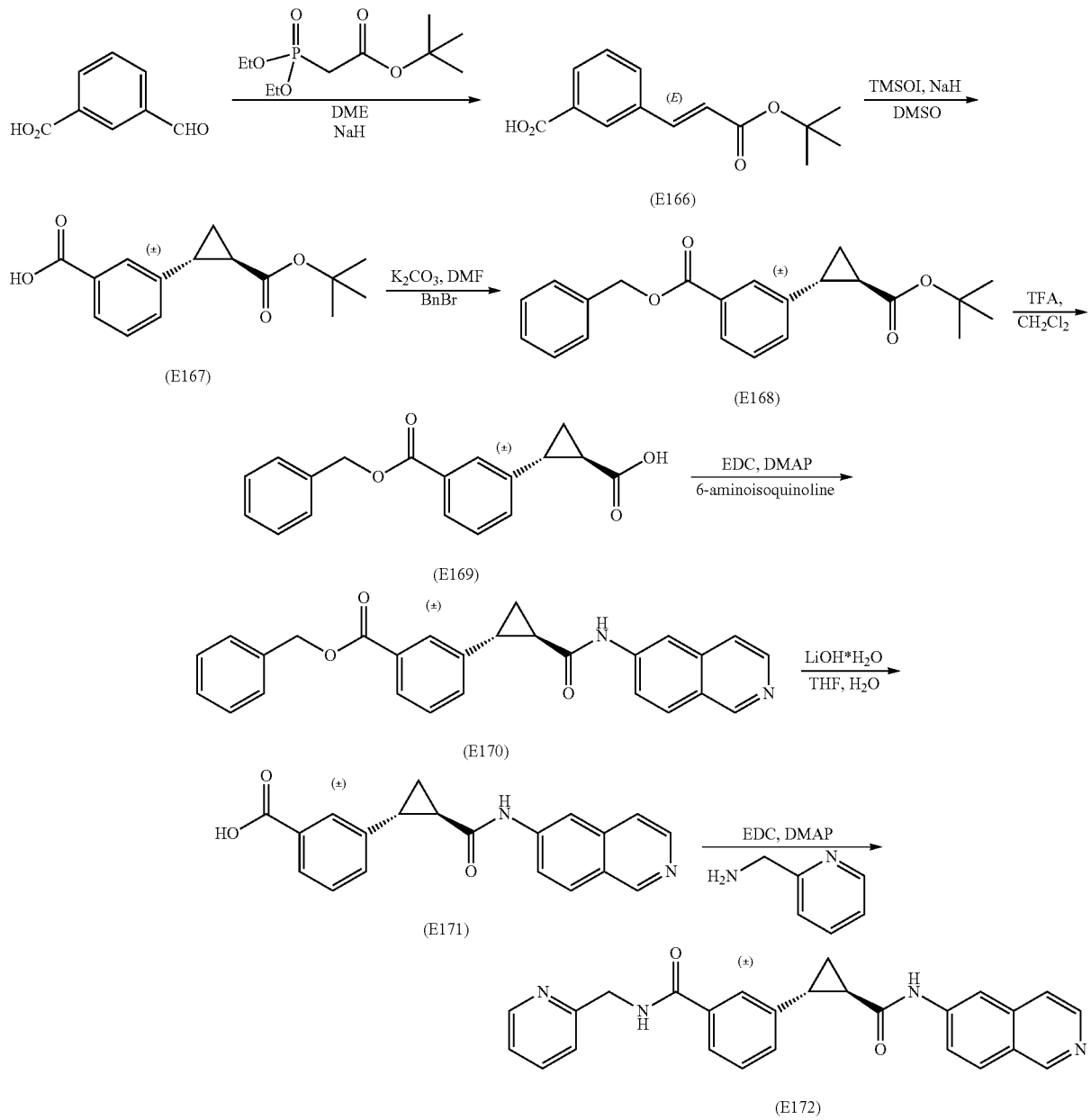

Scheme 9

Preparation of (E)-3-(3-(tert-butoxy)-3-oxoprop-1-en-1-yl)benzoic acid (E166)

To 3-formyl benzoic acid and tert-butyldiethyl phosphonoacetate in 1,2-dimethoxyethane cooled to 0° C. was added NaH and the solution was stirred for 1 hour at 0° C. and 2.5 hours at room temperature under $N_2$. The solution was quenched with HCl (1 N) and extracted with EtOAc, dried ($Na_2SO_4$), filtered and evaporated. Column chromatography over silica gel eluting with 15% EtOAc-Hexanes gave pure (E)-3-(3-(tert-butoxy)-3-oxoprop-1-en-1-yl)benzoic acid (E166).

Preparation of trans-3-(2-(tert-butoxycarbonyl)cyclopropyl)benzoic acid (E167)

To TMSOI in DMSO was added NaH and the mixture was stirred at room temperature under $N_2$ for one hour. Then, (E)-3-(3-(tert-butoxy)-3-oxoprop-1-en-1-yl)benzoic acid (E166) in DMSO was added and the solution stirred for 3 hours at room temperature. The solution was poured into HCl (1N) and EtOAc and extracted with EtOAc, dried ($Na_2SO_4$), filtered and evaporated. Column chromatography over silica gel eluting with 0-5% MeOH—CH$_2$Cl$_2$ gave pure trans-3-(2-(tert-butoxycarbonyl)cyclopropyl)benzoic acid (E167).

Preparation of trans-benzyl 3-(2-(tert-butoxycarbonyl)cyclopropyl)benzoate (E168)

To trans-3-(2-(tert-butoxycarbonyl)cyclopropyl)benzoic acid (E167) in DMF at 0° C. was added K$_2$CO$_3$ and the solution stirred for 40 minutes under N$_2$. Then, benzyl bromide was added and the mixture was warmed to room temperature and stirred for 1 hour. The mixture was poured into HCl (1N)-EtOAc and extracted with EtOAc, dried (Na$_2$SO$_4$), filtered and evaporated. Column chromatography over silica gel eluting with 0-5% EtOAc-Hexanes gave pure trans-benzyl 3-(2-(tert-butoxycarbonyl)cyclopropyl)benzoate (E168).

Preparation of trans-benzyl 2-(3-((benzyloxy) carbonyl)phenyl) cyclopropane-1-carboxylic acid (E169)

To trans-benzyl 3-(2-(tert-butoxycarbonyl)cyclopropyl) benzoate (E168) in CH$_2$Cl$_2$ at 0° C. was added TFA and the solution was warmed to room temperature and stirred for 1.5 hours. The solvents were evaporated and column chromatography over silica gel eluting with 5%-MeOH—CH$_2$Cl$_2$ gave pure trans-benzyl 2-(3-((benzyloxy)carbonyl)phenyl) cyclopropane-1-carboxylic acid (E169).

Preparation of trans-benzyl 3-(2-(isoquinolin-6-ylcarbamoyl)cyclopropyl) benzoate (E170)

To trans-benzyl 2-(3-((benzyloxy)carbonyl)phenyl)cyclopropane-1-carboxylic acid (E169) in pyridine were added EDC, DMAP and 6-aminoisoquinoline and the solution was stirred overnight at room temperature under N$_2$. The solution was poured into NaHCO$_3$ and extracted with EtOAc, dried (Na$_2$SO$_4$), filtered and evaporated. Column chromatography over silica gel eluting with 0-4% MeOH—CH$_2$Cl$_2$ gave pure trans-benzyl 3-(2-(isoquinolin-6-ylcarbamoyl)cyclopropyl) benzoate (E170).

Preparation of trans-benzyl 3-(2-(isoquinolin-6-ylcarbamoyl)cyclopropyl)benzoic acid (E171)

To trans-benzyl 3-(2-(isoquinolin-6-ylcarbamoyl)cyclopropyl)benzoate (E170) in THF and H$_2$O was added LiOH—H$_2$O and the solution was stirred at room temperature for 2.5 hours. HCl (1N) was added until the pH=5 and then EtOAc was added to precipitate. The solids were filtered, washed with water and Et$_2$O and dried to give trans-benzyl 3-(2-(isoquinolin-6-ylcarbamoyl)cyclopropyl) benzoic acid (E171).

Preparation of trans-3-(2-(isoquinolin-6-ylcarbamoyl)cyclopropyl)-N-(pyridin-2-ylmethyl)benzamide (E172)

To trans-benzyl 3-(2-(isoquinolin-6-ylcarbamoyl)cyclopropyl) benzoic acid (E171) in pyridine were added EDC, DMAP and 2-picolylamine and the solution was stirred at room temperature overnight under N$_2$. Then the solution was poured into NaHCO$_3$ (saturated) and extracted with EtOAc, dried (Na$_2$SO$_4$), filtered and evaporated. Column chromatography over silica gel eluting with 5-9% MeOH—CH$_2$Cl$_2$ gave pure trans-3-(2-(isoquinolin-6-ylcarbamoyl)cyclopropyl)-N-(pyridin-2-ylmethyl)benzamide (E172).

Using procedures analogous to those set forth for Scheme 9 and substituting the appropriate starting materials, the compounds E173-E175 were made and E176-E186 (see Table 9) could be synthesized.

TABLE 9

| Example | R—Z— | Y | X$_1$ | X$_2$ |
|---|---|---|---|---|
| E170 | benzyl | —OC(O)— | H | H |
| E172 | pyridin-2-ylmethyl | —NHC(O)— | H | H |
| E173 | pyridin-3-ylmethyl | —NHC(O)— | H | H |
| E174 | pyridin-4-ylmethyl | —NHC(O)— | H | H |
| E175 | 4-methoxybenzyl | —NHC(O)— | H | H |
| E176 | 4-chlorobenzyl | —OC(O)— | 5-F | H |
| E177 | 3-fluorobenzyl | —OC(O)— | H | H |
| E178 | 4-methylbenzyl | —OC(O)— | 4-Cl | H |
| E179 | 2-(dimethylamino)ethyl | —NHC(O)— | H | H |

TABLE 9-continued

| Example | R—Z— | Y | X₁ | X₂ |
|---|---|---|---|---|
| E180 | (3-pyridyl-propyl) | —NHC(O)— | H | H |
| E181 | (4-methylpiperazin-1-yl-ethyl) | —NHC(O)— | 1-OH | 5-Cl |
| E182 | (but-3-enyl) | —NHC(O)— | H | H |
| E183 | (piperidin-3-yl-methyl) | —NHC(O)— | 4-Cl | H |
| E184 | (piperidin-4-yl-methyl) | —NHC(O)— | 4-F | H |
| E185 | (pyrrolidin-3-yl-methyl) | —NHC(O)— | 3-Me | H |
| E186 | (4-dimethylaminophenyl-methyl) | —NHC(O)— | H | H |

Using procedures analogous to those set forth for Scheme 9 and substituting the appropriate starting materials, the compounds E186.1-E186.36 were also made. (see Table 9.1)

TABLE 9.1

Structure: -3-Substututed Cyclopropyl Analogs
(meta)

| Example | |
|---|---|
| E186.1 | benzoate-O-CH₂-(3-phenyl)-(E)-CH=CH-C(O)NH-isoquinolin-6-yl |
| E186.2 | HOOC-(3-phenyl)-cyclopropyl-C(O)NH-isoquinolin-6-yl |
| E186.3 | (CH₃)₂N-CH₂CH₂-NH-C(O)-(3-phenyl)-cyclopropyl-C(O)NH-isoquinolin-6-yl |
| E186.4 | (pyridin-3-yl)-NH-C(O)-(3-phenyl)-cyclopropyl-C(O)NH-isoquinolin-6-yl |

TABLE 9.1-continued

| Example | Structure: -3-Substututed Cyclopropyl Analogs (meta) |
|---|---|
| E186.5 | [structure: Boc-piperidine with gem-difluoro, NH-C(O)-phenyl-cyclopropyl-C(O)-NH-isoquinolin-6-yl] |
| E186.6 | [structure: Boc-pyrrolidine with gem-difluoro, NH-C(O)-phenyl-cyclopropyl-C(O)-NH-isoquinolin-6-yl] |
| E186.7 | [structure: piperidine with gem-difluoro, NH-C(O)-phenyl-cyclopropyl-C(O)-NH-isoquinolin-6-yl] *2HCl |
| E186.8 | [structure: pyrrolidine with gem-difluoro, NH-C(O)-phenyl-cyclopropyl-C(O)-NH-isoquinolin-6-yl] *2HCl |
| E186.9 | [structure: benzyl ester of phenyl-cyclopropyl-C(O)-NH-(5-fluoroisoquinolin-6-yl)] |
| E186.10 | [structure: HOOC-phenyl-cyclopropyl-C(O)-NH-(4-chloroisoquinolin-6-yl)] |
| E186.11 | [structure: N-Boc-piperidin-3-yl-CH2-NH-C(O)-phenyl-cyclopropyl-C(O)-NH-isoquinolin-6-yl] |
| E186.12 | [structure: 2,4-dimethoxybenzyl-NH-C(O)-phenyl-cyclopropyl-C(O)-NH-isoquinolin-6-yl] |
| E186.13 | [structure: piperidin-3-yl-CH2-NH-C(O)-phenyl-cyclopropyl-C(O)-NH-isoquinolin-6-yl] *2HCl |

TABLE 9.1-continued
| Example | Structure: -3-Substutituted Cyclopropyl Analogs (meta) |
|---|---|
| E186.14 | 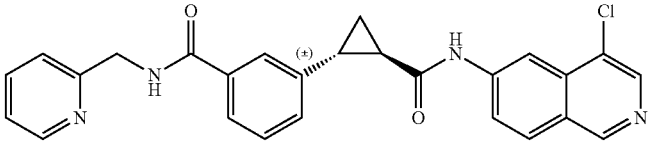 [SMILES: O=C(NCc1ccccn1)c1cccc([C@@H]2C[C@H]2C(=O)Nc2ccc3cncc(Cl)c3c2)c1] |
| E186.15 | 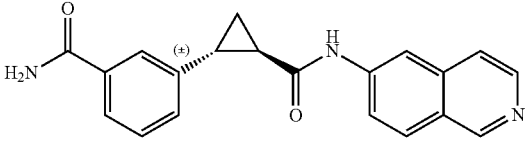 [SMILES: NC(=O)c1cccc([C@@H]2C[C@H]2C(=O)Nc2ccc3cnccc3c2)c1] |
| E186.16 | 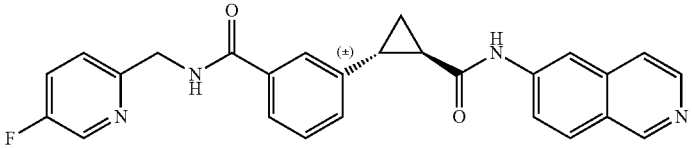 [SMILES: O=C(NCc1ccc(F)cn1)c1cccc([C@@H]2C[C@H]2C(=O)Nc2ccc3cnccc3c2)c1] |
| E186.17 | 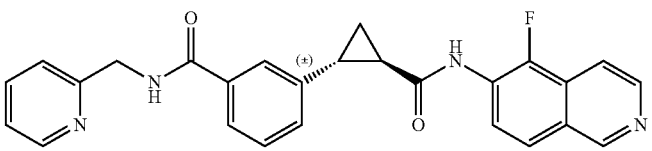 [SMILES: O=C(NCc1ccccn1)c1cccc([C@@H]2C[C@H]2C(=O)Nc2ccc3cnccc3c2F)c1] |
| E186.18 | 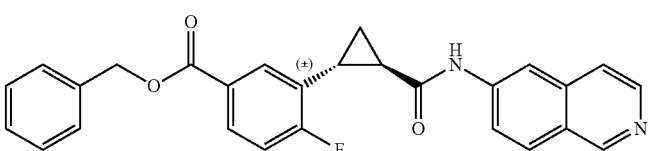 |
| E186.19 | 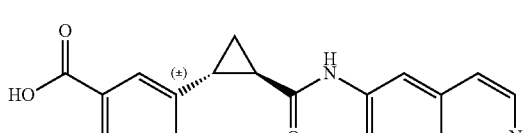 |
| E186.20 | 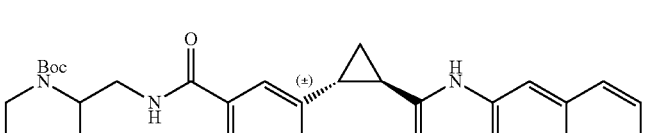 |
| E186.21 | 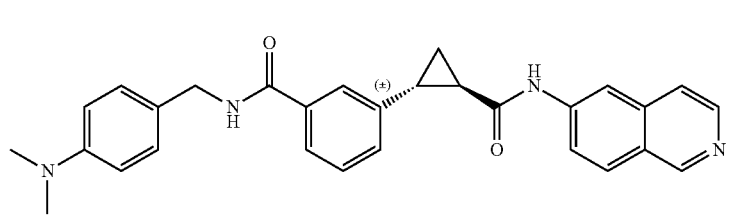 [SMILES: CN(C)c1ccc(CNC(=O)c2cccc([C@@H]3C[C@H]3C(=O)Nc3ccc4cnccc4c3)c2)cc1] |
| E186.22 | 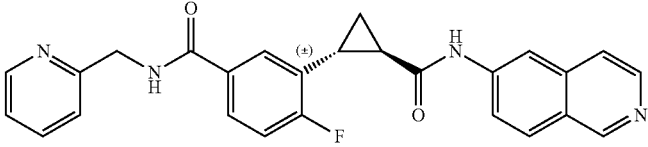 [SMILES: O=C(NCc1ccccn1)c1ccc(F)c([C@@H]2C[C@H]2C(=O)Nc2ccc3cnccc3c2)c1] |

TABLE 9.1-continued

| Example | Structure: -3-Substutituted Cyclopropyl Analogs (meta) |
|---|---|
| E186.23 | benzyl 2-fluoro-5-[(±)-trans-2-(isoquinolin-6-ylcarbamoyl)cyclopropyl]benzoate |
| E186.24 | (±)-trans-2-[3-(methoxycarbonyl)phenyl]cyclopropanecarboxylic acid |
| E186.25 | methyl 3-[(±)-trans-2-(isoquinolin-6-ylcarbamoyl)cyclopropyl]benzoate |
| E186.26 | 3-[(±)-trans-2-(isoquinolin-6-ylcarbamoyl)cyclopropyl]-N-(piperidin-2-ylmethyl)benzamide *2HCl |
| E186.27 | tert-butyl 4-[[3-[(±)-trans-2-(isoquinolin-6-ylcarbamoyl)cyclopropyl]benzoyl]amino]piperidine-1-carboxylate |
| E186.28 | 3-[(±)-trans-2-(isoquinolin-6-ylcarbamoyl)cyclopropyl]-N-(piperidin-4-yl)benzamide *2HCl |
| E186.29 | N-[2-[(dimethylamino)methyl]phenyl]-3-[(±)-trans-2-(isoquinolin-6-ylcarbamoyl)cyclopropyl]benzamide |
| E186.30 | N-[3-[(dimethylamino)methyl]phenyl]-3-[(±)-trans-2-(isoquinolin-6-ylcarbamoyl)cyclopropyl]benzamide |
| E186.31 | N-[4-[(dimethylamino)methyl]phenyl]-3-[(±)-trans-2-(isoquinolin-6-ylcarbamoyl)cyclopropyl]benzamide |

TABLE 9.1-continued

| Example | Structure: -3-Substutituted Cyclopropyl Analogs (meta) |
|---|---|
| E186.32 | |
| E186.33 | |
| E186.34 | |
| E186.35 | |
| E186.36 | |

Using procedures analogous to those set forth for Scheme 6.1 and substituting the appropriate starting materials (E-166), the compounds E186.37-E186.44 were made. (See Table 9.2)

TABLE 9.2

| Example | Structure: -R,R and S,S-3-Substutituted Cyclopropyl Analogs (meta) |
|---|---|
| E186.37 | |
| E186.38 | |

TABLE 9.2-continued
| Example | Structure: -R,R and S,S-3-Substutituted Cyclopropyl Analogs (meta) |
|---|---|
| E186.39 | |
| E186.40 | |
| E186.41 | |
| E186.42 | |
| E186.43 | |
| E186.44 | |
Example 8
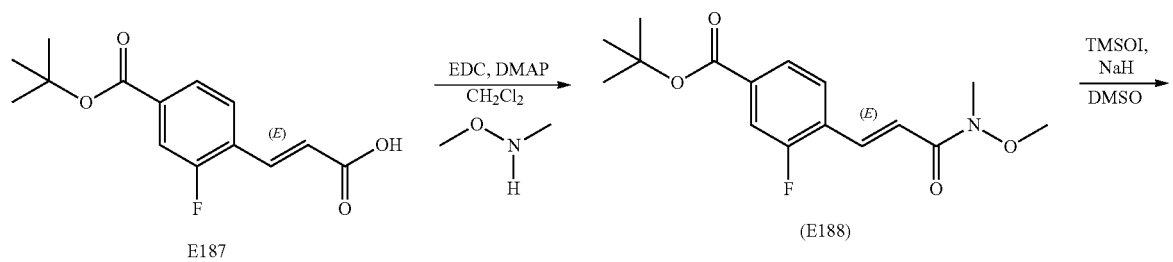
Scheme 10

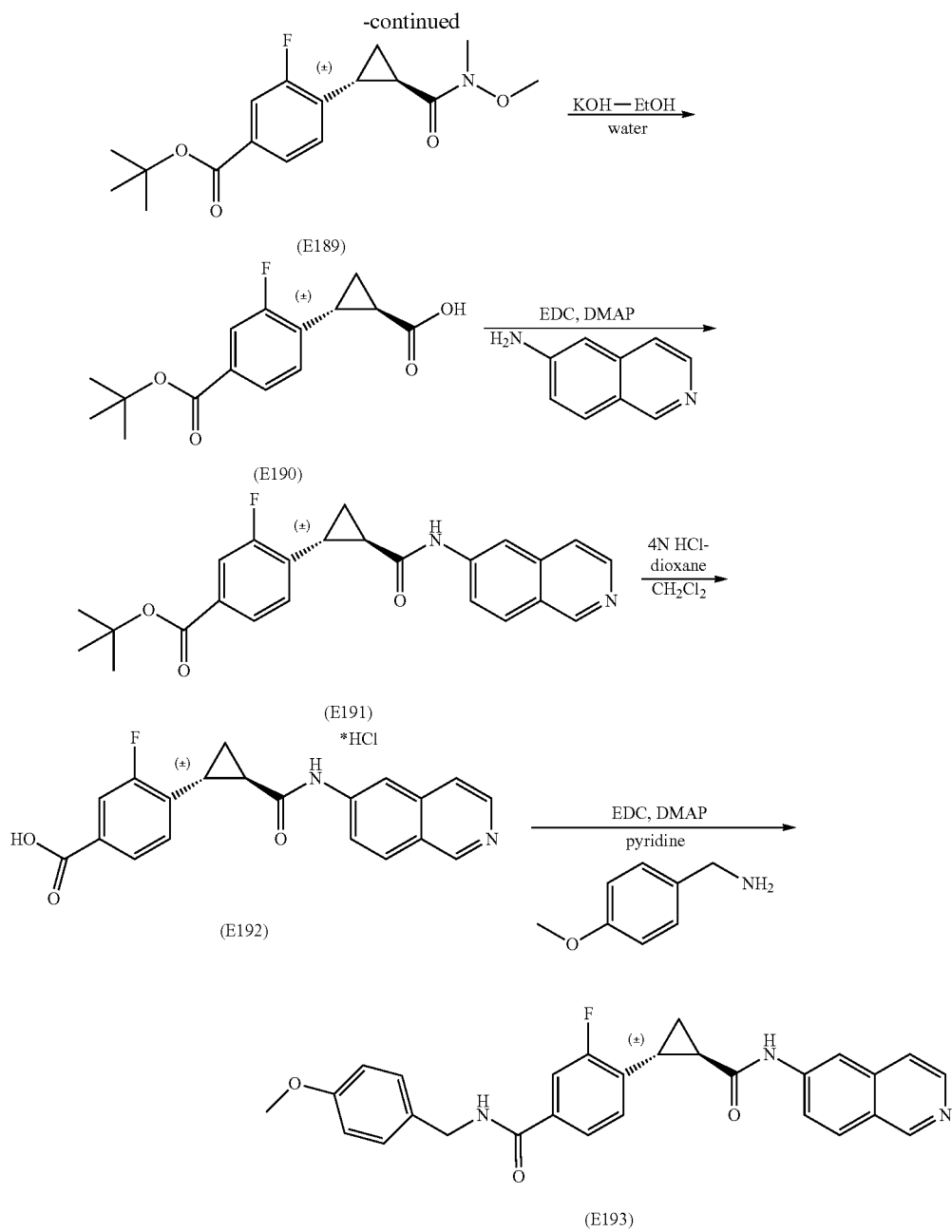

Preparation of tert-butyl (E)-3-fluoro-4-(3-(methoxy (methyl)amino)-3-oxoprop-1-en-1-yl)benzoate (E188)

To (E)-3-(4-(tert-butoxycarbonyl)-2-fluorophenyl)acrylic acid (E187) in CH₂Cl₂ were added EDC, DMAP and N,O-dimethylhydroxylamine and the solution was stirred at room temperature for 6.5 hours. Then the mixture was poured into a cold (0° C.) solution of HCl (1N) and EtOAc and further extracted with EtOAc. The organics were extracted with NaCl (saturated), dried (Na₂SO₄) filtered and evaporated. Column chromatography over silica gel eluting with 0-50% EtOAc-Hexanes gave tert-butyl (E)-3-fluoro-4-(3-(methoxy (methyl)amino)-3-oxoprop-1-en-1-yl)benzoate (E188).

Preparation of trans-tert-butyl 3-fluoro-4-(2-(methoxy(methyl) carbamoyl)cyclopropyl)benzoate (E189)

To TMSOI in DMSO was added NaH and the mixture was stirred at room temperature for one hour. Then, tert-butyl (E)-3-fluoro-4-(3-(methoxy(methyl)amino)-3-oxoprop-1-en-1-yl)benzoate (E188) in DMSO was added and the solution stirred for 3.5 hours at room temperature. The solution was poured into HCl (1N) and EtOAc (cooled to 0° C.) and extracted with EtOAc, dried (Na₂SO₄), filtered and evaporated. Column chromatography over silica gel eluting with 0-50% EtOAc-Hexanes gave pure trans-tert-butyl 3-fluoro-4-(2-(methoxy(methyl)carbamoyl)cyclopropyl) benzoate (E189).

Preparation of trans-2-(4-(tert-butoxycarbonyl)-2-fluorophenyl)cyclopropane-1-carboxylic acid (E190)

To tert-butyl 3-fluoro-4-(2-(methoxy(methyl)carbamoyl)cyclopropyl)benzoate (E189) in EtOH was added a solution of KOH in water and the solution was stirred for 24 hours. The solution was poured into HCl (1 N) and EtOAc and further extracted with EtOAc, dried (Na$_2$SO$_4$), filtered and evaporated. Column chromatography over silica gel eluting with 5% MeOH—CH$_2$Cl$_2$ gave pure trans-2-(4-(tert-butoxycarbonyl)-2-fluorophenyl)cyclopropane-1-carboxylic acid (E190).

Preparation of trans-tert-butyl 3-fluoro-4-(2-(isoquinolin-6-ylcarbamoyl) cyclopropyl)benzoate (E191)

To trans-2-(4-(tert-butoxycarbonyl)-2-fluorophenyl)cyclopropane-1-carboxylic acid (E190) in pyridine were added EDC, DMAP and 6-aminoisoquinoline and the solution was stirred at room temperature overnight. The solution was poured into NaHCO$_3$ (saturated) and extracted with EtOAc, dried (Na$_2$SO$_4$), filtered and evaporated. Column chromatography over silica gel eluting with 4% MeOH—CH$_2$Cl$_2$ gave trans-tert-butyl 3-fluoro-4-(2-(isoquinolin-6-ylcarbamoyl)cyclopropyl)benzoate (E191).

Preparation of trans-3-fluoro-4-(2-(isoquinolin-6-ylcarbamoyl)cyclopropyl)benzoic acid hydrochloride (E192)

To trans-tert-butyl 3-fluoro-4-(2-(isoquinolin-6-ylcarbamoyl)cyclopropyl)benzoate (E191) in CH$_2$Cl$_2$ was added HCl (4 N in dioxane) and the reaction was allowed to stir overnight. The solvents were evaporated and the compound was dried on the high vacuum to give trans-3-fluoro-4-(2-(isoquinolin-6-ylcarbamoyl)cyclopropyl)benzoic acid hydrochloride (E192).

Preparation of trans-3-fluoro-4-(2-(isoquinolin-6-ylcarbamoyl) cyclopropyl)-N-(4-methoxybenzyl) benzamide (E193)

To trans-3-fluoro-4-(2-(isoquinolin-6-ylcarbamoyl)cyclopropyl)benzoic acid hydrochloride (E192) in pyridine were added EDC, DMAP and 4-methoxybenzylamine and the solution was stirred overnight at room temperature. The reaction was poured into NaHCO$_3$ (saturated) and extracted with EtOAc, dried (Na$_2$SO$_4$), filtered and evaporated. Column chromatography over silica gel eluting with 5% MeOH—CH$_2$Cl$_2$ gave pure trans-3-fluoro-4-(2-(isoquinolin-6-ylcarbamoyl)cyclopropyl)-N-(4-methoxybenzyl)benzamide (E193).

Using procedures analogous to those set forth for Scheme 10 and substituting the appropriate starting materials, the compounds E194-E195.2 were made and E191.1 and E196-E206 (see Table 10) could be synthesized.

TABLE 10

| Example | R—Z— | Y | X$_1$ | X$_2$ | X$_3$ |
|---|---|---|---|---|---|
| E193 | 4-methoxybenzyl | —NHC(O)— | H | H | 3-F |
| E194 | 2-pyridylmethyl | —NHC(O)— | H | H | 3-F |
| E195 | 3-chlorophenyl | —NHC(O)— | H | H | 3-F |
| E195.1 | isoquinolin-6-yl | —NHC(O)— | H | H | 2-F |

TABLE 10-continued
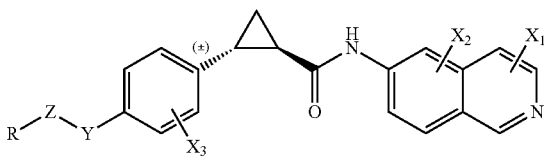
| Example | R—Z— | Y | X₁ | X₂ | X₃ |
|---|---|---|---|---|---|
| E195.2 | tert-butyl 4-methyl-piperidine-1-carboxylate | —NHC(O)— | H | H | 2-F |
| E196 | 3-pyridyl-methyl | —OC(O)— | H | H | 3-F |
| E197 | (R)-3-piperidinyl-methyl | —OC(O)— | 1-OH | 4-Cl | 2-Cl |
| E198 | 3-fluorobenzyl | —OC(O)— | 4-Cl | H | 2-F |
| E199 | 2-(dimethylamino)ethyl | —NHC(O)— | H | 5-F | 3-Cl |
| E200 | 2-(3-pyridyl)ethyl | —NHC(O)— | H | H | 2-F |
| E201 | 2-thienyl | —NHC(O)— | H | H | 3-F |
| E202 | benzothiophen-3-ylmethyl | —NHC(O)— | 1-OH | 5-Cl | 2-OMe |
| E203 | 2-morpholinoethylamino | —NHC(O)— | H | H | 2-F |
| E204 | 3-pyridyl | —NHC(O)— | H | H | 2-F |

TABLE 10-continued

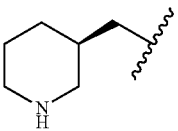 [SMILES: *C[C@@H]1CCCNC1]

| Example | R—Z— | Y | X₁ | X₂ | X₃ |
|---|---|---|---|---|---|
| E205 | 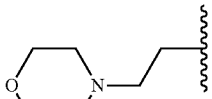 | —NHC(O)— | H | 5-Cl | 2-CF3 |
| E206 | 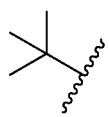 | —NHC(O)— | H | H | 3-OMe |
| E191.1 | | —OC(O)— | H | H | H |

Example 9

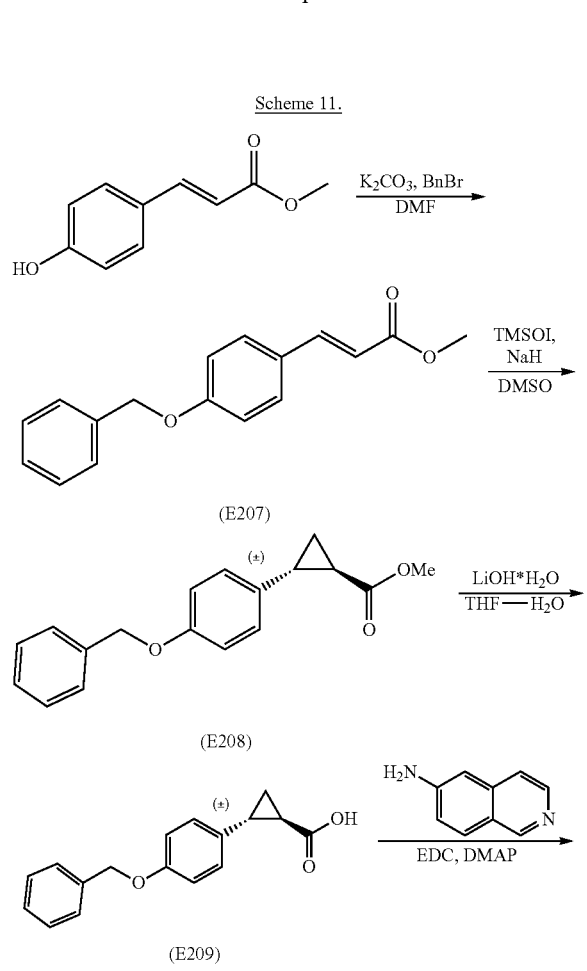

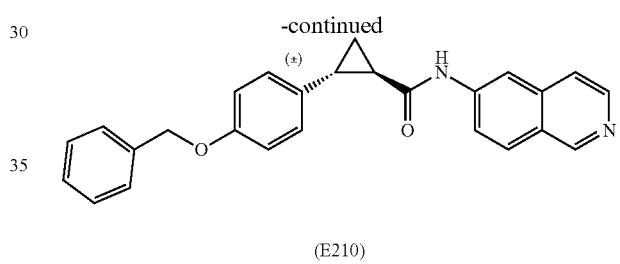

(E210)

Preparation of methyl (E)-3-(4-(benzyloxy)phenyl) acrylate (E207)

To methyl (E)-3-(4-hydroxyphenyl)acrylate in DMF at 0° C. was added $K_2CO_3$ and the solution stirred at 0° C. for 30 minutes. Then benzyl bromide was added and the reaction was warmed to room temperature and stirred overnight under $N_2$. The mixture was poured into HCl (1N) and EtOAc and extracted with EtOAc, dried ($Na_2SO_4$), filtered and evaporated. Column chromatography over silica gel eluting with 0-70% EtOAc-Hexanes gave pure (E)-3-(4-(benzyloxy)phenyl)acrylate (E207).

Preparation of trans-methyl-2-(4-(benzyloxy)phenyl)cyclopropane-1-carboxylate (E208)

To TMSOI in DMSO was added NaH and the solution was stirred for 1 hour. Then a solution of (E)-3-(4-(benzyloxy)phenyl)acrylate (E207) in DMSO was added and the reaction stirred for an additional 3 hours, poured into HCl (1N) and EtOAc and extracted with EtOAc, dried ($Na_2SO_4$), filtered and evaporated. Column chromatography over silica gel eluting with 0-10% EtOAc-Hexanes gave pure trans-methyl-2-(4-(benzyloxy)phenyl) cyclopropane-1-carboxylate (E208).

Preparation of trans-2-(4-(benzyloxy)phenyl)cyclopropane-1-carboxylic acid (E209)

To trans-methyl-2-(4-(benzyloxy)phenyl)cyclopropane-1-carboxylate (E208) in THF and water was added LiOH.H$_2$O and the reaction was stirred at room temperature for 4 days. The mixture was poured into HCl (1 N) and EtOAc and extracted with EtOAc, dried (Na$_2$SO$_4$), filtered and evaporated. Column chromatography over silica gel eluting with 20% EtOAc-Hexanes 0.2% AcOH gave pure trans-2-(4-(benzyloxy)phenyl)cyclopropane-1-carboxylic acid (E209).

Preparation of trans-2-(4-(benzyloxy)phenyl)-N-(isoquinolin-6-yl)cyclopropane-1-carboxamide (E210)

To 2-(4-(benzyloxy)phenyl)cyclopropane-1-carboxylic acid (E209) in pyridine were added EDC, DMAP and 6-aminoisoquinoline and the solution was stirred at room temperature under N$_2$ overnight. The reaction mixture was poured into NaHCO$_3$ (saturated) and extracted with EtOAc, dried (Na$_2$SO$_4$), filtered and evaporated to give trans-2-(4-(benzyloxy)phenyl)-N-(isoquinolin-6-yl)cyclopropane-1-carboxamide (E210).

Using procedures analogous to those set forth for Scheme 11 and substituting the appropriate starting materials, the compounds E211-E221 (see Table 11) could be synthesized.

TABLE 11

| Example | R—Z | X$_1$ | X$_2$ | X$_3$ |
|---|---|---|---|---|
| E210 | benzyl | H | H | H |
| E211 | 4-fluorobenzyl | H | H | H |
| E212 | 4-methylbenzyl | H | 5-F | H |
| E213 | 2-methylbenzyl | 4-Cl | H | 3-F |
| E214 | 3-methoxybenzyl | H | H | 2-F |
| E215 | 2-chlorobenzyl | 1-OH | H | H |
| E216 | (E)-2-bromostyryl | H | 5-Cl | 3-F |
| E217 | pyridin-3-ylmethyl | 3-Cl | H | H |
| E218 | pyridin-2-ylmethyl | H | 7-Cl | H |
| E219 | piperidin-4-ylmethyl | H | H | H |
| E220 | piperidin-2-ylmethyl | H | H | H |
| E221 | 2-(dimethylamino)ethyl | H | 5-F | 3-F |

Using procedures analogous to those set forth for Scheme 11 and substituting the appropriate starting materials, the compounds E221.1-E221.3 (see Table 11.1) were made.

TABLE 11.1

| Example | |
|---|---|
| E221.1 | 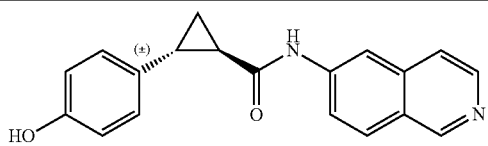 |
| E221.2 | 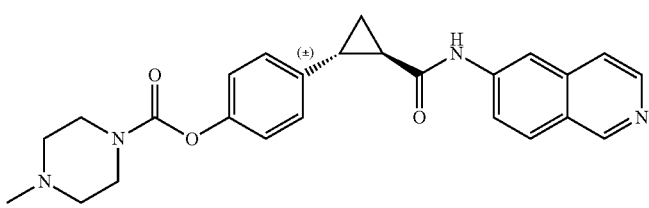 [SMILES: CN1CCN(C(=O)Oc2ccc([C@@H]3C[C@H]3C(=O)Nc3ccc4cnccc4c3)cc2)CC1] |
| E221.3 | 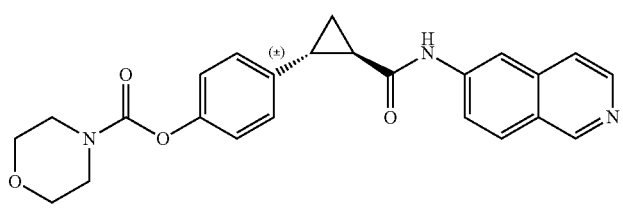 [SMILES: O=C(Nc1ccc2cnccc2c1)[C@@H]1C[C@H]1c1ccc(OC(=O)N2CCOCC2)cc1] |

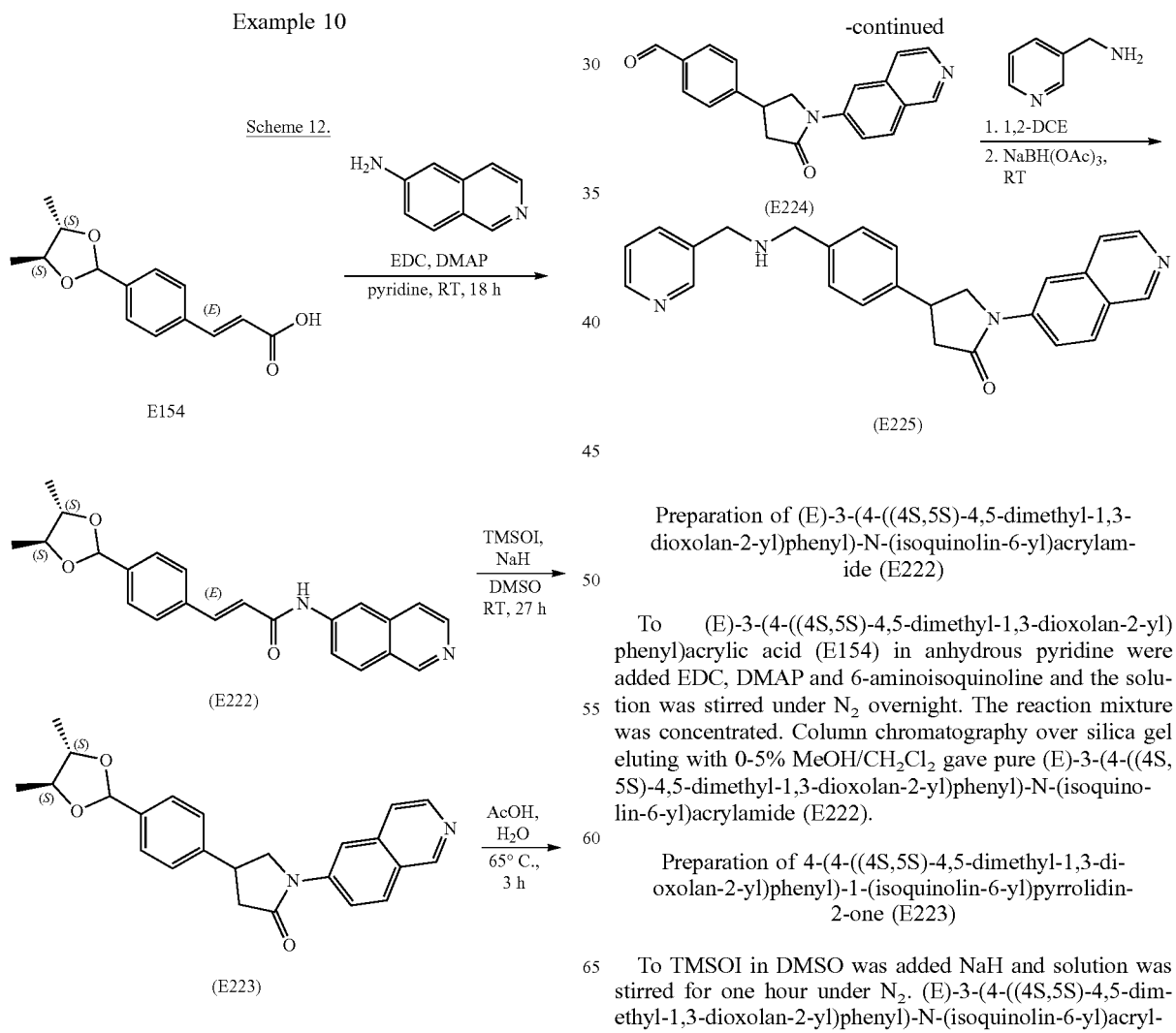

Example 10

Preparation of (E)-3-(4-((4S,5S)-4,5-dimethyl-1,3-dioxolan-2-yl)phenyl)-N-(isoquinolin-6-yl)acrylamide (E222)

To (E)-3-(4-((4S,5S)-4,5-dimethyl-1,3-dioxolan-2-yl)phenyl)acrylic acid (E154) in anhydrous pyridine were added EDC, DMAP and 6-aminoisoquinoline and the solution was stirred under $N_2$ overnight. The reaction mixture was concentrated. Column chromatography over silica gel eluting with 0-5% MeOH/$CH_2Cl_2$ gave pure (E)-3-(4-((4S,5S)-4,5-dimethyl-1,3-dioxolan-2-yl)phenyl)-N-(isoquinolin-6-yl)acrylamide (E222).

Preparation of 4-(4-((4S,5S)-4,5-dimethyl-1,3-dioxolan-2-yl)phenyl)-1-(isoquinolin-6-yl)pyrrolidin-2-one (E223)

To TMSOI in DMSO was added NaH and solution was stirred for one hour under $N_2$. (E)-3-(4-((4S,5S)-4,5-dimethyl-1,3-dioxolan-2-yl)phenyl)-N-(isoquinolin-6-yl)acrylamide (E222) dissolved in DMSO was added dropwise and the solution was stirred for 3 hours at room temperature. The mixture was poured over deionized H₂O and extracted with EtOAc. The organics were dried (Na₂SO₄), filtered and concentrated. Column chromatography over silica gel eluting with 0-5% MeOH/CH₂Cl₂ gave pure 4-(4-((4S,5S)-4,5-dimethyl-1,3-dioxolan-2-yl)phenyl)-1-(isoquinolin-6-yl)pyrrolidin-2-one (E223).

Preparation of 4-(1-(isoquinolin-6-yl)-5-oxopyrrolidin-3-yl)benzaldehyde (E224)

To a suspension of 4-(4-((4S,5S)-4,5-dimethyl-1,3-dioxolan-2-yl)phenyl)-1-(isoquinolin-6-yl)pyrrolidin-2-one (E223) in deionized water was added AcOH and stirred at 65° C. for 3 hours. The reaction was poured into EtOAc/NaHCO₃ (saturated) and extracted with EtOAc, dried (Na₂SO₄), filtered and evaporated. Column chromatography over silica gel eluting with 0-5% MeOH/CH₂Cl₂ gave pure 4-(1-(isoquinolin-6-yl)-5-oxopyrrolidin-3-yl)benzaldehyde (E224).

Preparation of 1-(isoquinolin-6-yl)-4-(4-(((pyridin-3-ylmethyl)amino)methyl) phenyl)pyrrolidin-2-one (E225)

To 4-(1-(isoquinolin-6-yl)-5-oxopyrrolidin-3-yl)benzaldehyde (E224) in anhydrous 1,2-dichloroethane was added pyridin-3-ylmethanamine and the solution was stirred at room temperature under N₂ for 30 minutes before adding sodium triacetoxyborohydride and stirring overnight. The reaction was poured into EtOAc/NaHCO₃ (saturated) and extracted with EtOAc, dried (Na₂SO₄), filtered and evaporated. Column chromatography over silica gel eluting with 0-5% MeOH/CH₂Cl₂ gave pure 1-(isoquinolin-6-yl)-4-(4-(((pyridin-3-ylmethyl)amino)methyl)phenyl)pyrrolidin-2-one (E225).

Using procedures analogous to those set forth for Scheme 12 and substituting the appropriate starting materials, the compounds E226-E228 (see Table 12) were made.

TABLE 12

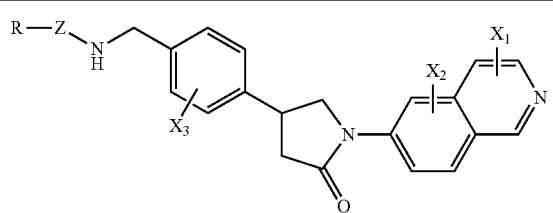

| Example | R—Z— | X₁ | X₂ | X₃ |
|---|---|---|---|---|
| E225 | (pyridin-3-ylmethyl) | H | H | H |
| E226 | (pyridin-2-ylmethyl) | H | H | H |
| E227 | (piperidin-4-ylmethyl) | H | H | H |

TABLE 12-continued

| Example | R—Z— | X₁ | X₂ | X₃ |
|---|---|---|---|---|
| E228 | (1-Boc-piperidin-4-ylmethyl) | H | H | H |

Example 11

Scheme 13.

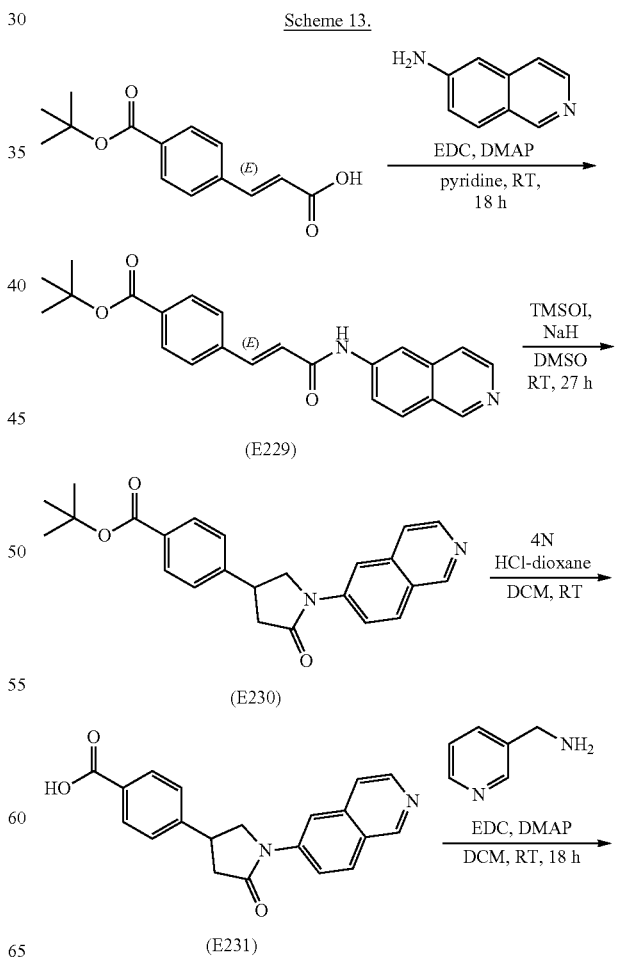

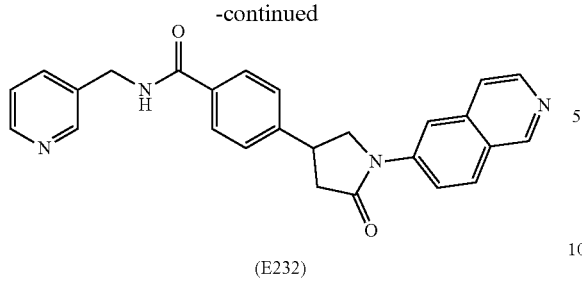

(E232)

Preparation of tert-butyl (E)-4-(3-(isoquinolin-6-ylamino)-3-oxoprop-1-en-1-yl)benzoate (E229)

To (E)-3-(4-(tert-butoxycarbonyl)phenyl)acrylic acid in anhydrous pyridine were added EDC, DMAP and 6-aminoisoquinoline and the solution was stirred under $N_2$ overnight. The reaction mixture was concentrated. Column chromatography over silica gel eluting with 0-4% MeOH/$CH_2Cl_2$ gave pure tert-butyl (E)-4-(3-(isoquinolin-6-ylamino)-3-oxoprop-1-en-1-yl)benzoate (E229).

Preparation of tert-butyl 4-(1-(isoquinolin-6-yl)-5-oxopyrrolidin-3-yl)benzoate (E230)

To TMSOI in DMSO was added NaH and solution was stirred for one hour under $N_2$. tert-Butyl (E)-4-(3-(isoquinolin-6-ylamino)-3-oxoprop-1-en-1-yl)benzoate (E229) dissolved in DMSO was added dropwise and the solution was stirred for 3 hours at room temperature. The mixture was poured over deionized $H_2O$ and extracted with EtOAc. The organics were dried ($Na_2SO_4$), filtered and concentrated. Column chromatography over silica gel eluting with 0-5% MeOH/$CH_2Cl_2$ gave pure tert-butyl 4-(1-(isoquinolin-6-yl)-5-oxopyrrolidin-3-yl)benzoate (E230).

Preparation of 4-(1-(isoquinolin-6-yl)-5-oxopyrrolidin-3-yl)benzoic acid (E231)

To tert-butyl 4-(1-(isoquinolin-6-yl)-5-oxopyrrolidin-3-yl)benzoate (E230) in dichloromethane was added 4M HCl in dioxane and stirred at room temperature for 3 hours. The reaction mixture was concentrated to give pure 4-(1-(isoquinolin-6-yl)-5-oxopyrrolidin-3-yl)benzoic acid (E231).

Preparation of 4-(1-(isoquinolin-6-yl)-5-oxopyrrolidin-3-yl)-N-(pyridin-3-ylmethyl) benzamide (E232)

To 4-(1-(isoquinolin-6-yl)-5-oxopyrrolidin-3-yl)benzoic acid (E231) in anhydrous $CH_2Cl_2$ were added EDC, DMAP and pyridin-3-ylmethanamine and the solution was stirred under $N_2$ at room temperature for 7 hours. The reaction was poured into EtOAc/$NaHCO_3$ (saturated) and extracted with EtOAc, dried ($Na_2SO_4$), filtered and evaporated. Column chromatography over silica gel eluting with 0-5% MeOH/$CH_2Cl_2$ gave pure 4-(1-(isoquinolin-6-yl)-5-oxopyrrolidin-3-yl)-N-(pyridin-3-ylmethyl)benzamide (E232).

Using procedures analogous to those set forth for Scheme 13 and substituting the appropriate starting materials, the compounds E233-E234.2 were made and E235-E243 (see Table 13) could be synthesized.

TABLE 13

| Example | R—Z— | $X_1$ | $X_2$ | $X_3$ |
|---|---|---|---|---|
| E232 | 3-pyridylmethyl | H | H | H |
| E233 | 2-pyridylmethyl | H | H | H |
| E234.1 | N-Boc-piperidin-4-ylmethyl | H | H | H |
| E234.2 | piperidin-4-ylmethyl | H | H | H |
| E235 | (R)-pyrrolidin-3-ylmethyl | H | H | H |
| E236 | 3-fluorophenethyl | H | H | 3-F |
| E237 | 2-chlorobenzyl | 1-OH | 5-F | H |
| E238 | benzyl | H | H | 3-Me |
| E239 | 2-morpholinoethyl | 4-Cl | H | H |

TABLE 13-continued
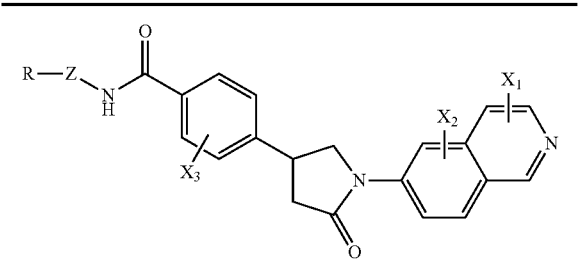
| Example | R—Z— | $X_1$ | $X_2$ | $X_3$ |
|---|---|---|---|---|
| E240 | | 5-F | H | 2-Cl |
| E241 | | H | H | H |
TABLE 13-continued
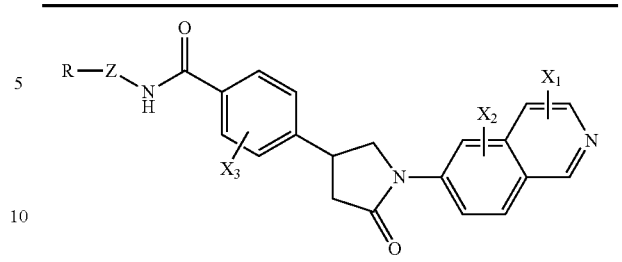
| Example | R—Z— | $X_1$ | $X_2$ | $X_3$ |
|---|---|---|---|---|
| E242 | | 5-F | H | 2-F |
| E243 | | H | H | 3-F |
Using procedures analogous to those set forth for Scheme 13 and substituting the appropriate starting materials, the compounds E243.1-E243.3 were made (see Table 13.1)
TABLE 13.1
| Example | Pyrrolidinone Analogs |
|---|---|
| E243.1 | |
| E243.2 | |
| E243.3 | *2HCl |

Example 12

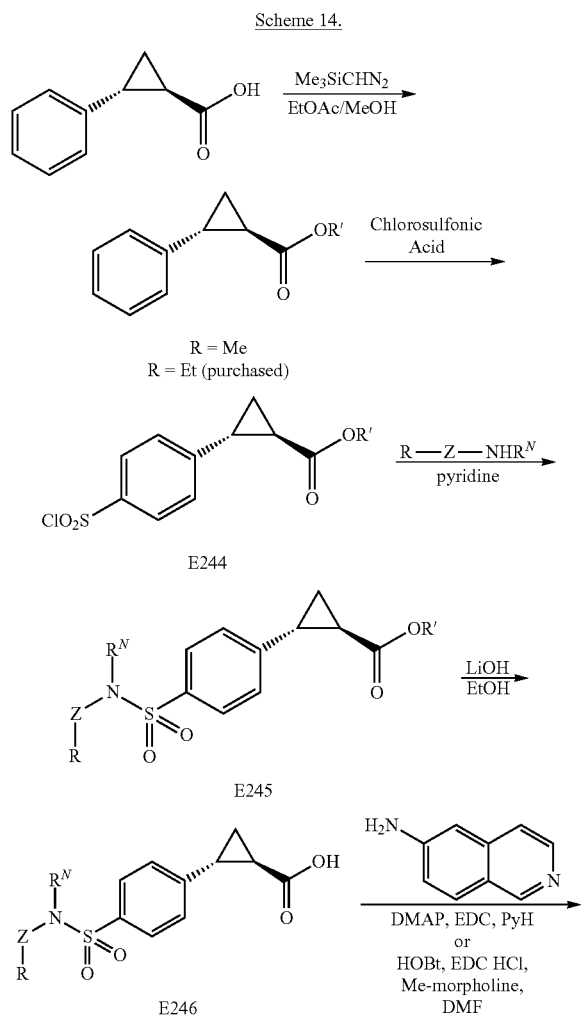

Below are the typical procedures used for the synthesis of the products from the above scheme 14.

Methyl (trans)-2-phenylcyclopropane-1-carboxylate

A solution of commercially-available trans-2-phenylcyclopropane-1-carboxylic acid (204 mg, 1.26 mmol) in 3 mL ethyl acetate (EtOAc) and 0.2 mL MeOH was treated with Me$_3$SiCHN$_2$ (0.69 mL of 2.0 M solution in heptane, 1.38 mmol) over about 1 minute dropwise and the resulting yellow solution was stirred 1 hour at room temperature. TLC (Hexanes-EtOAc-HOAc, 80:20:1) showed the completion of the reaction. The reaction mixture was concentrated on a rotovap (220 mg of the crude material) and purified using column chromatography on silica gel (Hexane-EtOAc, 95:5-80-20). Methyl trans)-2-phenylcyclopropane-1-carboxylate (178 mg) was isolated as an oil. ES-API calc'd for C$_{11}$H$_{12}$O$_2$ 176.08, [M+H]$^+$ found 177.1.

Ethyl-(trans)-2-(4-(chlorosulfonyl)phenyl) cyclopropane-1-carboxylate (E244.1)

Chlorosulfonic acid (15 mL) in dry 50 mL round-bottomed flask was cooled with an ice bath and treated portionwise with ethyl rel-(1R,2R)-2-phenylcyclopropane-1-carboxylate (3.15 g, 15.56 mmol) during 30 minutes under N$_2$ and stirring. Then the cooling bath was removed and the reaction mixture (pale brown solution) was stirred 3 hours at room temperature. TLC (Hexane-EtOAc 60:40) showed the completion of the reaction. The reaction mixture was slowly and carefully poured into a 500 mL Erlenmeyer flask with 100 g of ice, stirred 5 minutes and then extracted with EtOAc (200 mL, 2×100 mL). The combined organic layers were washed with water-brine (1:1, 2×50 mL), dried over $Na_2SO_4$ and concentrated. The crude product (5.2 g) was purified using column chromatography on silica gel (Hexane-EtOAc, 99:1-90-10). Chlorosulfonate E244.1 (3 g) was isolated as an oil. ES-API calcd for $C_{12}H_{13}ClO_4S$ 288.02 $[M+H]^+$; found 289.0.

trans-Methyl 2-(4-(chlorosulfonyl)phenyl)cyclopropane-1-carboxylate (E244.2)

The title compound was prepared from methyl trans-2-phenylcyclopropane-1-carboxylate using the procedure of E244.1. E244.2: ES-API calc'd for $C_{11}H_{11}ClO_4S$ 274.01, $[M+NH_4]^+$ found 293.0.

trans-methyl 2-(4-(N-benzylsulfamoyl)phenyl)cyclopropane-1-carboxylate (E245A)

Sulfonyl chloride E244.2 (110 mg, 0.4 mmol) in dry pyridine (2 mL) in a dried 10 mL round-bottomed flask was cooled with an ice bath and treated with aniline (0.04 mL, 0.44 mmol) in one portion under $N_2$ and stirring. Then the cooling bath was removed and the reaction mixture (deep orange slurry) was stirred for 1 hour at room temperature. TLC (Hexane-EtOAc 60:40) showed the completion of the reaction; no starting material remained and a more polar product was formed. The reaction mixture was concentrated, diluted with EtOAc (50 mL), washed with water-brine (1:1, 2×5 mL), brine (5 mL), dried over $Na_2SO_4$ and concentrated. The crude product (104 mg) was purified using column chromatography on silica gel (Hexane-EtOAc, 90:10-75:25). E245A (90 mg) was isolated as an oil. ES-API calc'd for $C_{17}H_{17}NO_4S$ 331.09, $[M+H]^+$ found 332.0.

Using similar procedures, the following compounds were synthesized:

trans-ethyl 2-(4-(N-(pyridin-3-ylmethyl)sulfamoyl) phenyl) cyclopropane-1-carboxylate (E245B)

ES-API calc'd for $C_{18}H_{20}N_2O_4S$ 360.11, $[M+H]^+$ found 361.0.

trans-Ethyl 2-(4-(N-(3-(dimethylamino)propyl)sulfamoyl)phenyl) cyclopropane-1-carboxylate (E245C)

ES-API calc'd for $C_{17}H_{26}N_2O_4S$ 354.16, $[M+H]^+$ found 355.1.

trans-tert-butyl 4-(((4-(2-(ethoxycarbonyl)cyclopropyl)phenyl)sulfonamido)methyl)piperidine-1-carboxylate (E245D)

ES-API calc'd for $C_{23}H_{34}N_2O_6S$ 466.21, $[M+Na]^+$ found 489.1.

trans-tert-butyl (3S)-3-(((4-(2-(ethoxycarbonyl) cyclopropyl)phenyl)sulfonamido)methyl)piperidine-1-carboxylate E245E)

ES-API calc'd for $C_{23}H_{34}N_2O_6S$ 466.21, $[M-H]^+$ found 465.2.

trans-tert-butyl (3R)-3-(((4-(2-(ethoxycarbonyl) cyclopropyl)phenyl)sulfonamido)methyl)piperidine-1-carboxylate E245F)

ES-API calc'd for $C_{23}H_{34}N_2O_6S$ 466.21, $[M-H]^+$ found 465.2.

trans-tert-butyl 4-((4-(2-(ethoxycarbonyl) cyclopropyl) phenyl) sulfonamido) piperidine-1-carboxylate (E245G)

ES-API calc'd for $C_{22}H_{32}N_2O_6S$ 452.20, $[M+Na]^+$ found 475.1.

trans-tert-butyl 4-((4-(2-(ethoxycarbonyl) cyclopropyl)phenyl)sulfonyl)piperazine-1-carboxylate (E245H)

ES-API calc'd for $C_{21}H_{30}N_2O_6S$ 438.18, $[M+Na]^+$ found 461.1—Preparation of the Isoquinolyl amides from their respective esters:

(trans)-2-(4-(N-phenylsulfamoyl)phenyl)cyclopropane-1-carboxylic acid (E246A)

A solution of ester E245A in ethanol was treated with 1N LiOH and left to stir overnight at room temperature. The next day TLC (Hexane-EtOAc-HOAc, 60:40:1) showed the completion of the reaction. The reaction mixture was acidified till pH 3 using $KHSO_4$, extracted with EtOAc (50 mL, 2×20 mL), the organic layers were washed with brine (5 mL), dried over $Na_2SO_4$ and concentrated. The crude product (77 mg) was purified using column chromatography on silica gel (Hexane-EtOAc-HOAc, 90:10:0.1-70:30:0.1). E246A (67 mg) was isolated as an oil. ES-API calc'd for $C_{16}H_{15}NO_4S$ 317.07, $[M+H]^+$ found 318.0.

Using similar procedures, the following compounds were synthesized:

trans-2-(4-(N-(pyridin-3-ylmethyl)sulfamoyl)phenyl) cyclopropane-1-carboxylic acid (E246B)

Crude material carried on to next step. No $^1$H NMR because used in next reaction without purification; ES-API calc'd for $C_{16}H_{16}N_2O_4S$ 332.08, $[M+H]^+$ found 333.0.

trans-2-(4-(N-(3-(dimethylamino) propyl)sulfamoyl) phenyl) cyclopropane-1-carboxylic acid (E246C)

Crude material carried on to next step without purification; ES-API calc'd for $C_{15}H_{22}N_2O_4S$ 326.13, $[M+H]^+$ found 327.1.

trans-2-(4-(N-((1-(tert-butoxycarbonyl)piperidin-4-yl)methyl)sulfamoyl) phenyl) cyclopropane-1-carboxylic acid (E246D)

Crude material carried on to next step. No $^1$H NMR because used in next reaction without purification; ES-API calc'd for $C_{21}H_{30}N_2O_6S$ 438.18, $[M+Na]^+$ found 461.1.

trans-2-(4-(N-(((S)-1-(tert-butoxycarbonyl) piperidin-3-yl)methyl) sulfamoyl) phenyl) cyclopropane-1-carboxylic acid (E246E)

Crude material carried on to next step. No $^1$H NMR was taken because it was used in next reaction without purification; ES-API calc'd for $C_{21}H_{30}N_2O_6S$ 438.18, $[M+Na]^+$ found 461.1.

trans-2-(4-(N—(((R)-1-(tert-butoxycarbonyl)piperidin-3-yl)methyl)sulfamoyl) phenyl)cyclopropane-1-carboxylic acid (E246F)

ES-API calcd for $C_{21}H_{30}N_2O_6S$ 438.18, [M+Na]$^+$ found 461.1.

trans-2-(4-(N-(1-(tert-butoxycarbonyl)piperidin-4-yl)sulfamoyl)phenyl) cyclopropane-1-carboxylic acid (E246G)

ES-API calc'd for $C_{20}H_{28}N_2O_6S$ 424.17, [M+Na]$^+$ found 447.1.

trans-2-(4-((4-(tert-butoxycarbonyl)piperazin-1-yl)sulfonyl)phenyl) cyclopropane-1-carboxylic acid (E246H)

No $^1$H NMR; used in next reaction without purification; ES-API calc'd for $C_{19}H_{26}N_2O_6S$ 410.15, [M+Na]$^+$ found 433.1.

trans-N-(isoquinolin-6-yl)-2-(4-(N-phenylsulfamoyl)phenyl) cyclopropane-1-carboxamide (E247A)

A solution of acid E246A (65 mg, 0.2 mmol) in DMF (2 mL) in a dried 10 mL round-bottomed flask was treated with HOBt (36.5 mg, 0.27 mmol), 6-aminoisoquinoline (28.8 mg, 0.2 mmol), and N-methylmorpholine (0.029 mL, 0.27 mmol), cooled with an ice bath and then EDC HCl (42 mg, 0.22 mmol) was added in one portion under $N_2$ and stirring. Then the cooling bath was removed and the reaction mixture was left to stir 3 days at room temperature. After that TLC (DCM-MeOH-HOAc, 93:7:1) showed the completion of the reaction. The reaction mixture was diluted with water (5 mL), extracted with EtOAc (50 mL, 2×20 mL), the organic layers were washed with brine (5 mL), dried over $Na_2SO_4$ and concentrated. The crude product (75 mg) was purified using column chromatography on silica gel (DCM-MeOH, 99:1-95:5). E247A (25 mg) was isolated as an oil. ES-API calc'd for $C_{25}H_{21}N_3O_3S$ 443.13, [M+H]$^+$ found 444.1.

Using similar procedures, the following compounds were synthesized:

trans-N-(isoquinolin-6-yl)-2-(4-(N-(pyridin-3-ylmethyl)sulfamoyl)phenyl)cyclo-propane-1-carboxamide (E247B)

ES-API calc'd for $C_{25}H_{22}N_4O_3S$ 458.14, [M+H]$^+$ found 459.1.

trans-2-(4-(N-(3-(dimethylamino)propyl)sulfamoyl)phenyl)-N-(isoquinolin-6-yl) cyclopropane-1-carboxamide (E247C)

tert-butyl 4-(((4-((trans)-2-(isoquinolin-6-ylcarbamoyl)cyclopropyl)phenyl)sulfonamido)methyl)piperidine-1-carboxylate (E247D)

ES-API calc'd for $C_{30}H_{36}N_4O_5S$ 564.24, [M+H]$^+$ found 565.2.

tert-butyl (S)-3-(((4-((trans)-2-(isoquinolin-6-ylcarbamoyl)cyclopropyl)phenyl)sulfonamido)methyl) piperidine-1-carboxylate (E247E)

ES-API calc'd for $C_{30}H_{36}N_4O_5S$ 564.24, [M+H]$^+$ found 565.2.

tert-butyl (R)-3-(((4-((trans)-2-(isoquinolin-6-ylcarbamoyl)cyclopropyl)phenyl)sulfonamido)methyl) piperidine-1-carboxylate (E247F)

ES-API calc'd for $C_{30}H_{36}N_4O_5S$: 564.24, [M+H]$^+$, found 565.24.

tert-butyl 4-((4-((trans)-2-(isoquinolin-6-ylcarbamoyl) cyclopropyl)phenyl)sulfonamido)piperidine-1-carboxylate (E247G)

ES-API calc'd for $C_{29}H_{34}N_4O_5S$ 550.22, [M+H]$^+$ found 551.2.

tert-butyl 4-((4-((trans)-2-(isoquinolin-6-ylcarbamoyl) cyclopropyl) phenyl)sulfonyl)piperazine-1-carboxylate (E247H)

ES-API calc'd for $C_{28}H_{32}N_4O_5S$ 536.21, [M+H]$^+$ found 537.2.

Example 13

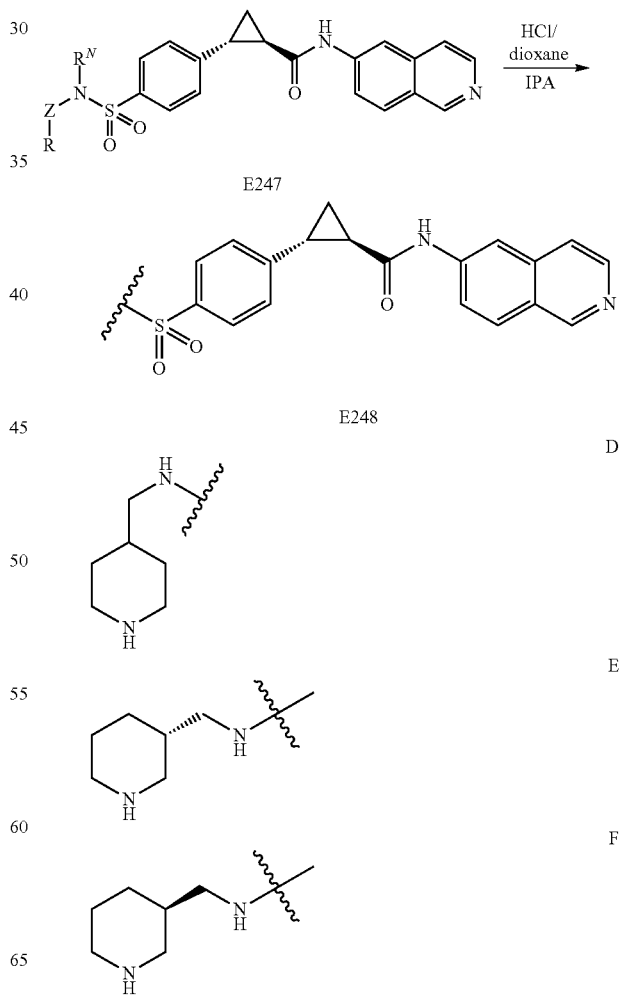

Scheme 15. Preparation of amino sulfonamides as HCl salts

-continued

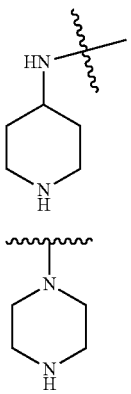

G trans-N-(isoquinolin-6-yl)-2-(4-(N—(((R)-piperidin-3-yl)methyl)sulfamoyl)phenyl)-cyclopropane-1-carboxamide dihydrochloride (E248F HCl)

A solution of Boc-protected amine E247F (17 mg, 0.03 mmol) in 2 mL isopropyl alcohol (IPA) was treated with 4N HCl in dioxane (0.075 mL, 0.3 mmol) under $N_2$ and left to stir overnight at room temperature. TLC ($CH_2Cl_2$-MeOH-HOAc, 90:10:1) showed disappearance of the starting material and the formation of the product. Reaction mixture was concentrated with ether (3×5 mL) and dried in high vacuum providing pure product E248F.HCl (17 mg).

trans-N-(isoquinolin-6-yl)-2-(4-(N-(piperidin-4-ylmethyl)sulfamoyl)phenyl) cyclopropane-1-carboxamide dihydrochloride (E248D HCl)

ES-API calc'd for $C_{25}H_{28}N_4O_3S$ (free base) 464.19, $[M+H]^+$ found 465.1.

trans-N-(isoquinolin-6-yl)-2-(4-(N-(((S)-piperidin-3-yl)methyl)sulfamoyl) phenyl)cyclopropane-1-carboxamide dihydrochloride (E248E HCl)

ES-API calc'd for $C_{25}H_{28}N_4O_3S$ (free base) 464.19, $[M+H]^+$ found 465.1.

trans-N-(isoquinolin-6-yl)-2-(4-(N-(piperidin-4-yl)sulfamoyl)phenyl)cyclo-propane-1-carboxamide dihydrochloride (E248G HCl)

trans)-N-(isoquinolin-6-yl)-2-(4-(piperazin-1-ylsulfonyl)phenyl) cyclopropane-1-carboxamide dihydrochloride (E248H HCl)

ES-API calc'd for $C_{23}H_{24}N_4O_3S$ (free base) 436.16, $[M+H]^+$ found 437.1.

Using analogous or modified procedure to those set forth for Scheme 14-15 or and substituting the appropriate starting materials, the compounds E247A, E247B, E248D-H and E249.1-249.10 were made (see Table 13.1)

TABLE 13.1

| Examples | |
|---|---|
| E247A | 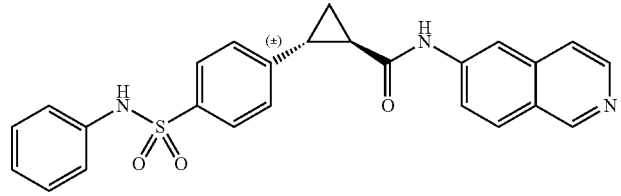 [SMILES: O=C(Nc1ccc2cnccc2c1)[C@@H]1C[C@H]1c1ccc(S(=O)(=O)Nc2ccccc2)cc1] |
| E247B | 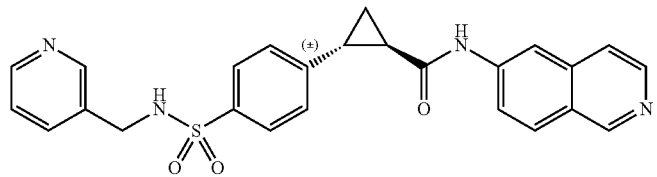 [SMILES: O=C(Nc1ccc2cnccc2c1)[C@@H]1C[C@H]1c1ccc(S(=O)(=O)NCc2cccnc2)cc1] |
| E248D | 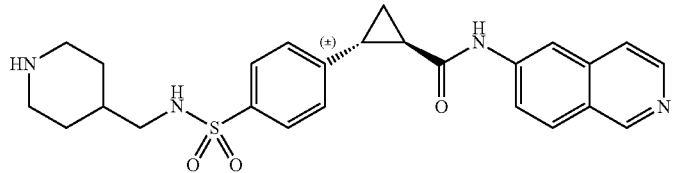 [SMILES: O=C(Nc1ccc2cnccc2c1)[C@@H]1C[C@H]1c1ccc(S(=O)(=O)NCC2CCNCC2)cc1] |
| E248E | 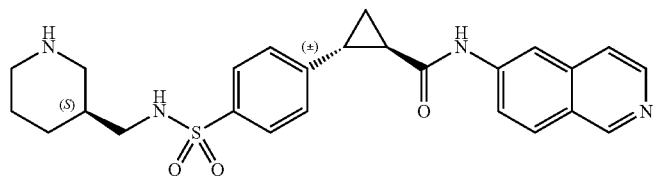 |

US 10,858,339 B2
TABLE 13.1-continued
Examples
E248H
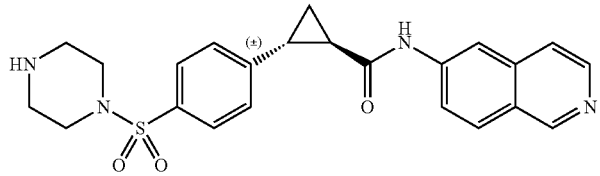 [SMILES: O=C(Nc1ccc2cnccc2c1)[C@@H]1C[C@H]1c1ccc(S(=O)(=O)N2CCNCC2)cc1]
E248F
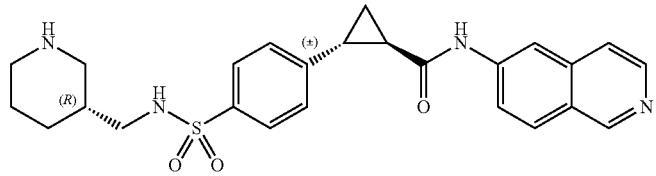
E248G
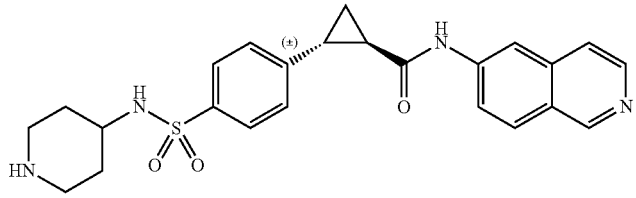 [SMILES: O=C(Nc1ccc2cnccc2c1)[C@@H]1C[C@H]1c1ccc(S(=O)(=O)NC2CCNCC2)cc1]
E249.1
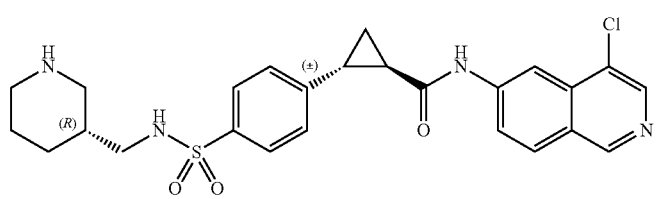
E249.2
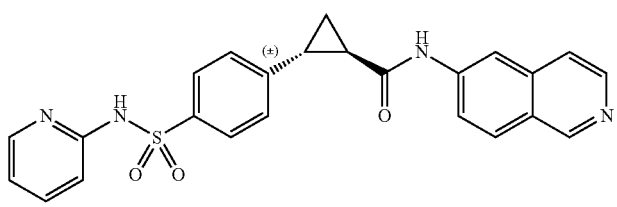
E249.4
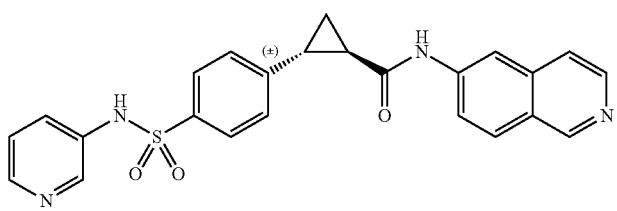 [SMILES: O=C(Nc1ccc2cnccc2c1)[C@@H]1C[C@H]1c1ccc(S(=O)(=O)Nc2cccnc2)cc1]
E249.5
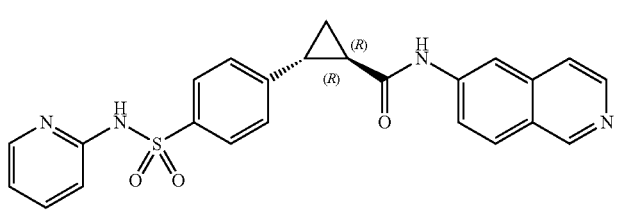
E249.6
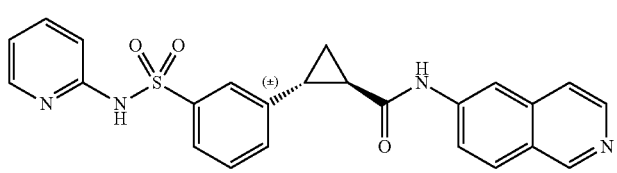 [SMILES: O=C(Nc1ccc2cnccc2c1)[C@@H]1C[C@H]1c1cccc(S(=O)(=O)Nc2ccccn2)c1]

175 176
TABLE 13.1-continued
Examples
E249.7
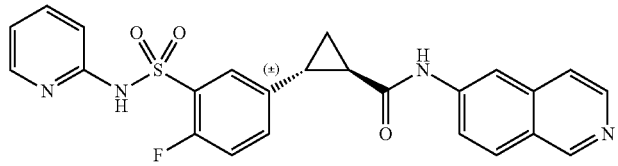 [SMILES: O=C(Nc1ccc2cnccc2c1)[C@@H]1C[C@H]1c1ccc(F)c(S(=O)(=O)Nc2ccccn2)c1]
E249.8
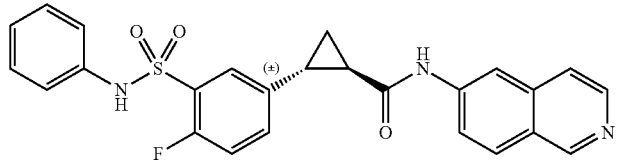
E249.9
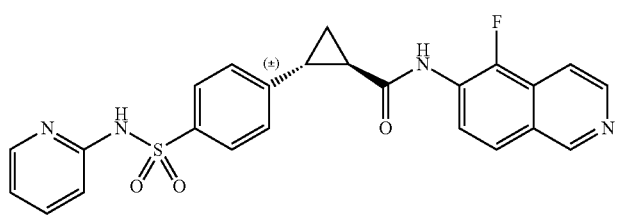 [SMILES: O=C(Nc1ccc2cnccc2c1F)[C@@H]1C[C@H]1c1ccc(S(=O)(=O)Nc2ccccn2)cc1]
E249.10
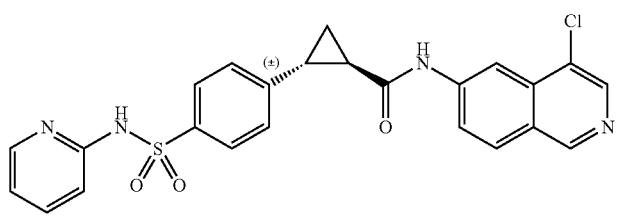 [SMILES: O=C(Nc1ccc2cncc(Cl)c2c1)[C@@H]1C[C@H]1c1ccc(S(=O)(=O)Nc2ccccn2)cc1]
Example 14
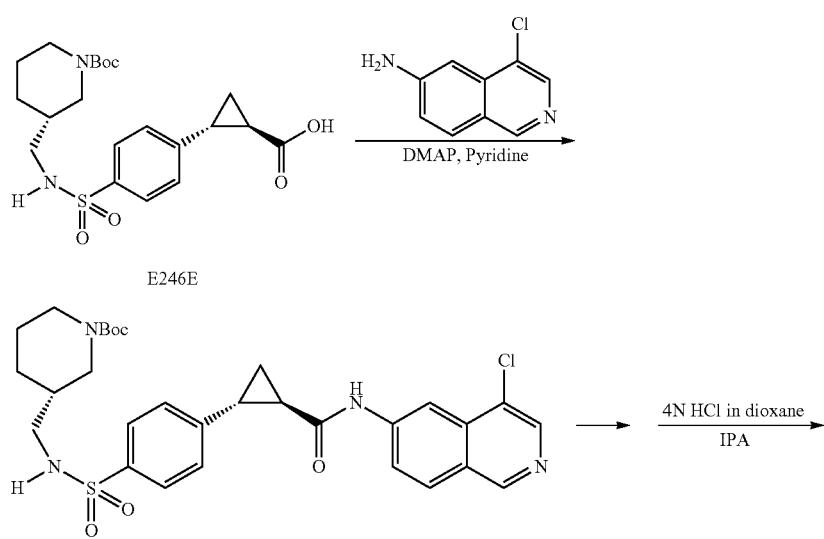

-continued

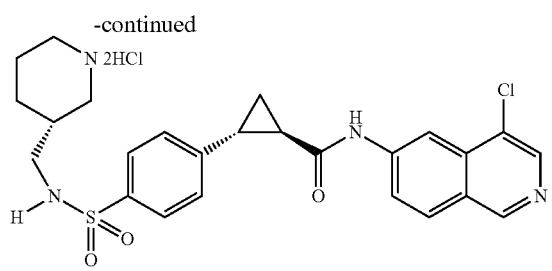

E250E HCl

E250E HCl was prepared using the procedures described above.

Using procedures analogous to those set forth for Schemes 15 and 16 and substituting appropriate starting materials, Examples E252-E254 (see Table 14) could be synthesized.

TABLE 14

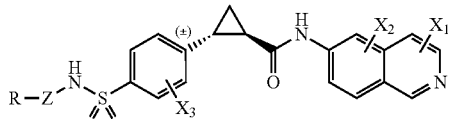

| Example | R—Z— | X₁ | X₂ | X₃ |
|---|---|---|---|---|
| E252 | 3-pyridyl | 3-Cl | 5-F | 3-F |
| E253 | 4-pyridyl | 4-Cl | H | 3-F |
| E253.1 | 3-pyridyl | H | H | H |
| E253.2 | 3-ethylpiperidinyl-HN | 4-Me | 5-F | 2-F |
| E254 | 2-pyridyl | H | 4-Cl | 3-F |
| E254.1 | 3-ethylpiperidinyl-HN | 4-Me | 5-F | 2-F |
| E254.2 | 3-ethylpiperidinyl-HN | 4-Cl | H | 3-F |

TABLE 14-continued

| Example | R—Z— | X₁ | X₂ | X₃ |
|---|---|---|---|---|
| E254.3 | 3-ethylpiperidinyl-HN | H | 5-F | 3-F |
| E254.4 | 4-pyridyl | 4-Me | H | H |
| E254.5 | 2-pyridyl | H | H | H |

Example 15

Scheme 17.

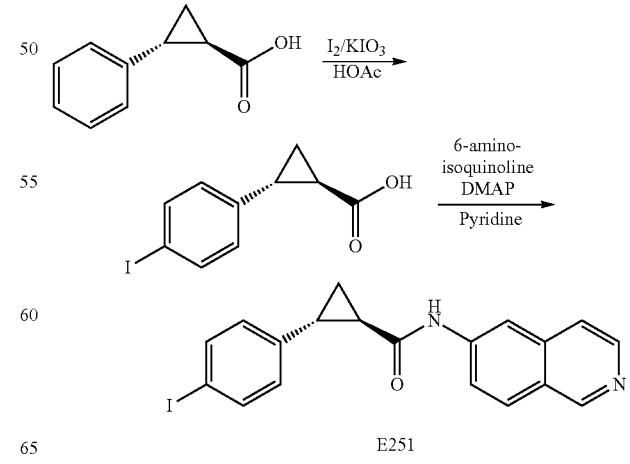

E251

A solution of rel-trans-2-phenylcyclopropane-1-carboxylic acid (2.0 g, 12.33 mmol) in acetic acid (40 mL) was heated to 110° C. and treated with iodine (1.72 g, 6.78 mmol), KIO$_3$ (580 mg, 2.71 mmol) and 10% H$_2$SO$_4$ (11 mL) and stirred at this temperature for 1 hour. TLC (Hexane-EtOAc-HOAc, 80:20:1) showed some starting material and mostly the product. The reaction mixture was treated with iodine (200 mg), stirred 30 minutes at 110° C., cooled to the room temperature, treated with the mixture of saturated solutions of KHSO$_4$/Na$_2$S$_2$O$_3$ (50 mL/50 mL), extracted with EtOAc (300 mL, 2×100 mL), the organic layers were washed with brine (50 mL), dried over Na$_2$SO$_4$ and concentrated. The crude product (4.5 g) was purified using column chromatography on silica gel (Hexanes-EtOAc-HOAc, 99:1:0.1-90:10:0.1). rel-(1R,2R)-2-(4-iodophenyl)cyclopropane-1-carboxylic acid (3.2 g) was isolated as a tan colored crystalline material. ES-API calc'd for C$_{10}$H$_9$IO$_2$ 287.96, [M–H]$^+$ found 286.9.

rel-(1R,2R)-2-(4-iodophenyl)-N-(isoquinolin-6-yl)cyclopropane-1-carboxamide (E251) was prepared the same way as other amides (e.g., E247), ES-API calc'd for C$_{19}$H$_{15}$IN$_2$O 414.02, [M+H]$^+$ found 415.0.

Example 16

Scheme 18.

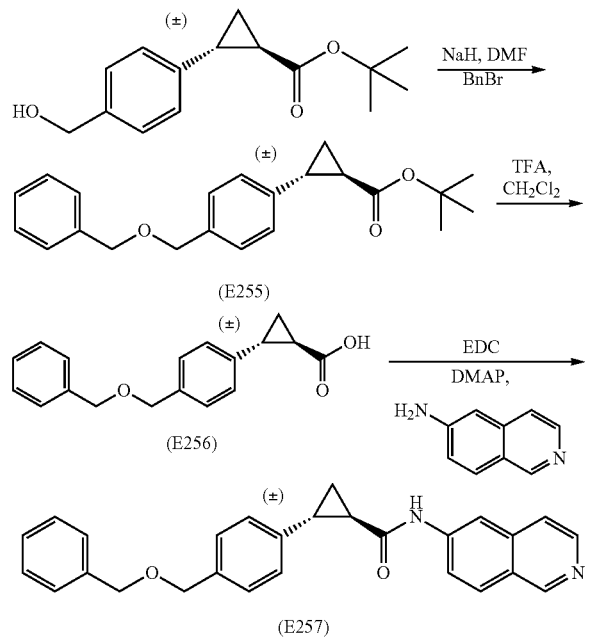

(E257)

Preparation of tert-butyl 2-(4-((benzyloxy)methyl)phenyl)cyclopropane-1-carboxylate (E255)

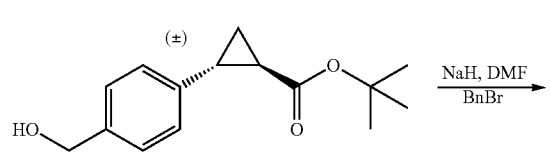

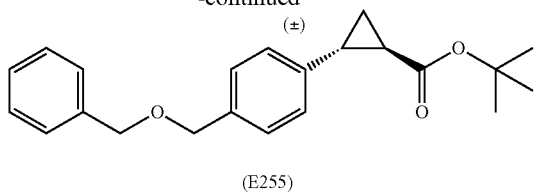

(E255)

To trans-tert-butyl 2-((hydroxymethyl)phenyl)cyclopropane-1-carboxylate in DMF cooled to −40° was added NaH and the solution was stirred at −35° C.--45° C. The reaction was warmed to −20° C. and benzyl bromide was added and the solution was warmed to 0° C. then to room temperature. After 2.5 hours the solution was poured into EtOAc and HCl (1 N) and further extracted with EtOAc, dried (Na$_2$SO4) filtered and evaporated. Column chromatography 0-10% EtOAc-Hexanes have pure trans tert-butyl 2-(4-((benzyloxy)methyl)phenyl)cyclopropane-1-carboxylate (E255).

Preparation of trans-2-(4-((benzyloxy)methyl)phenyl)cyclopropane-1-carboxylic acid (E256)

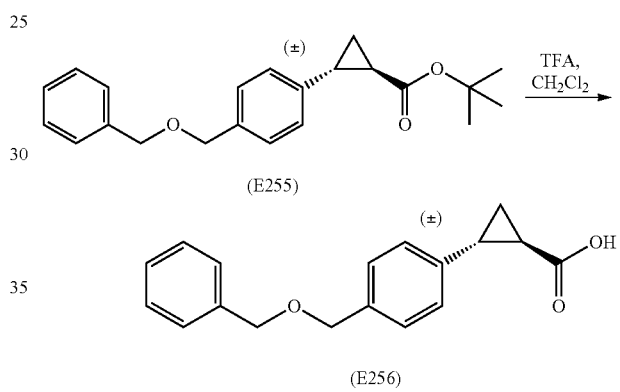

(E256)

To trans tert-butyl 2-(4-((benzyloxy)methyl)phenyl)cyclopropane-1-carboxylate (E255) in CH$_2$Cl$_2$ was added trifluoroacetic acid and the solution was stirred at room temperature for 7 hours. The solvents were evaporated to give trans-2-(4-((benzyloxy)methyl)phenyl)cyclopropane-1-carboxylic acid (E256).

Preparation of 2-(4-((benzyloxy)methyl)phenyl)-N-(isoquinolin-6-yl)cyclopropane-1-carboxamide (E257)

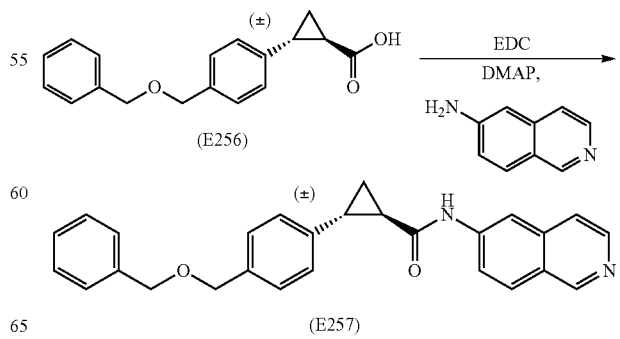

(E257)

To trans-2-(4-((benzyloxy)methyl)phenyl)cyclopropane-1-carboxylic acid (E256) in pyridine was added EDC, DMAP and 6-aminoisoquinoline and the solution was stirred at room temperature under N$_2$ overnight. The mixture was poured into NaHCO$_3$ (sat) and EtOAc and further extracted with EtOAc, dried (Na$_2$SO$_4$), filtered and evaporated. Column chromatography 4% MeOH—CH$_2$Cl$_2$ gave pure 2-(4-((benzyloxy)methyl)phenyl)-N-(isoquinolin-6-yl)cyclopropane-1-carboxamide (E257).

EtOAc and NaHCO$_3$ (sat) and extracted with NaHCO$_3$ (sat). The organics were dried (Na$_2$SO$_4$), filtered and evaporated. Column chromatography 50-70% EtOAc-Hexanes gave pure N-(isoquinolin-6-yl)-2-phenylcyclopropane-1-carboxamide (E259).

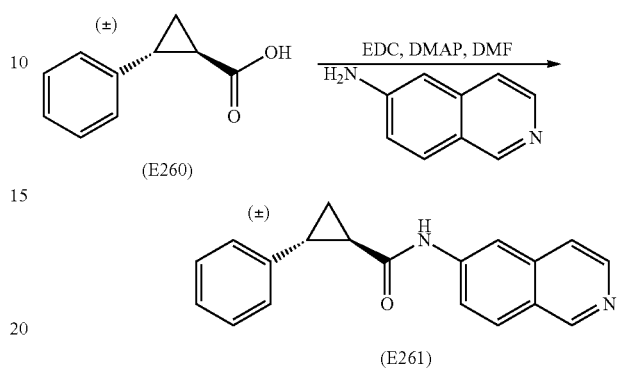

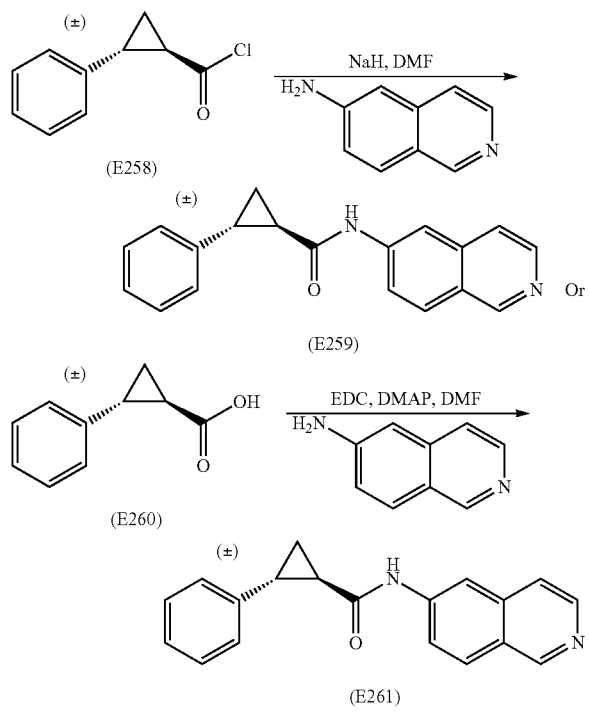

To 2-phenylcyclopropane-1-carboxylic acid in DMF was added EDC, DMAP and 6-aminoisoquinoline and the solution was stirred overnight at room temperature under N$_2$. The mixture was poured into water and EtOAc and extracted, dried (Na$_2$SO$_4$) filtered and evaporated. Column chromatography 0-10% MeOH—CH$_2$Cl$_2$ gave pure N-(isoquinolin-6-yl)-2-phenylcyclopropane-1-carboxamide (E261).

Preparation of N-(isoquinolin-6-yl)-2-phenylcyclopropane-1-carboxamide (E259)

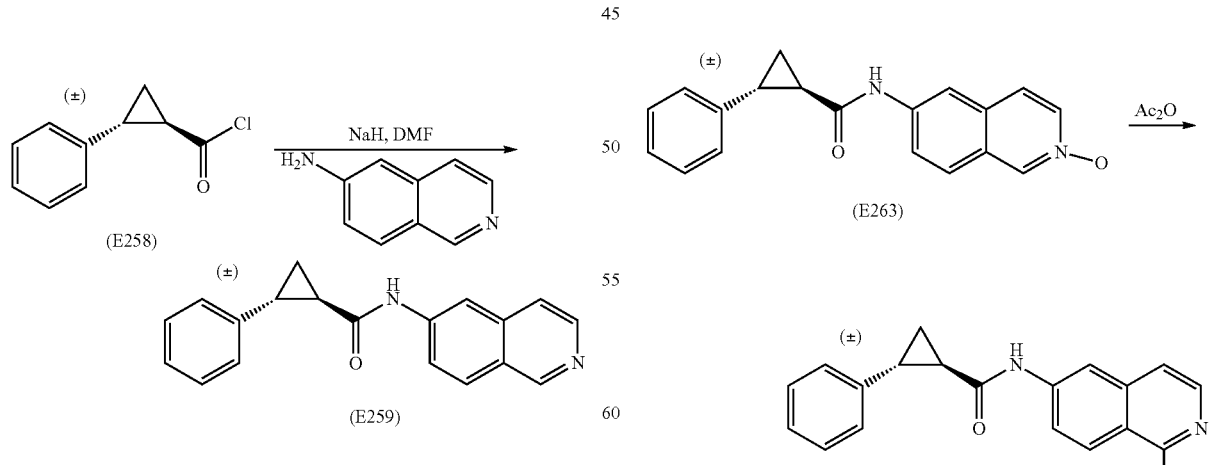

To 6-aminoisoquinoline in DMF cooled to 0° C. was added NaH and the solution was stirred for 30 minutes. Then, 2-phenylcyclopropane-1-carbonyl chloride was added and the solution was stirred at 0° C. and warmed to room temperature for 3 hours. The solution was poured into

Preparation of N-(2-(☐1-oxidanyl)-2l4-isoquinolin-6-yl)-2-phenylcyclopropane-1-carboxamide (E263)

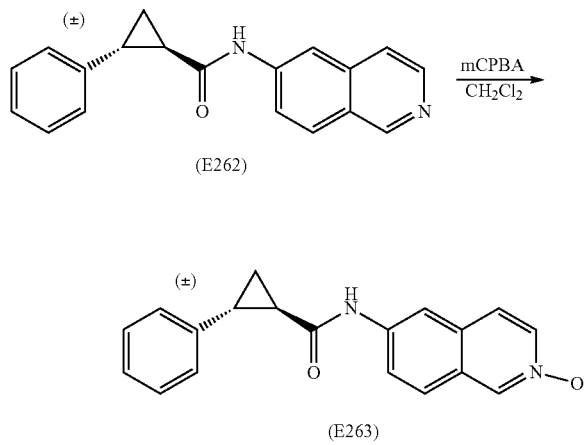

To N-(isoquinolin-6-yl)-2-phenylcyclopropane-1-carboxamide (E262) in $CH_2Cl_2$ was added mCPBA and the solution was stirred at room temperature overnight. The mixture was poured into dilute $NaHSO_3$ and extracted with EtOAc. The organics were dried ($Na_2SO_4$), filtered and evaporated. Column chromatography 0-10% MeOH—$CH_2Cl_2$ gave pure N-(2-(I1-oxidanyl)-2l4-isoquinolin-6-yl)-2-phenylcyclopropane-1-carboxamide (E263).

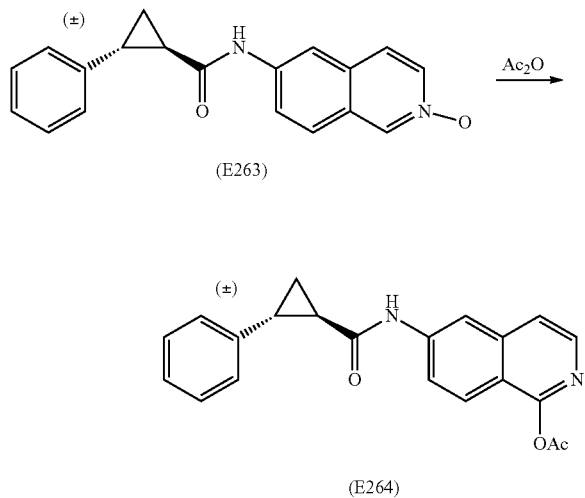

Preparation of 6-(2-phenylcyclopropane-1-carboxamido)isoquinolin-1-yl acetate (E264). N-(2-(I1-oxidanyl)-2☐4-isoquinolin-6-yl)-2-phenylcyclopropane-1-carboxamide (E263) was dissolved acetic anhydride and heated to reflux for 3.5 h. The acetic anhydride was evaporated and the mixture was taken up in $CH_2Cl_2$ and washed with $NaHCO_3$ (sat) and NaCl (sat), dried ($Na_2SO_4$), filtered and evaporated. Column chromatography 0-10% MeOH—$CH_2Cl_2$ gave 6-(2-phenylcyclopropane-1-carboxamido)isoquinolin-1-yl acetate (E264)

Example 17: ROCK and JAK Assays

ROCK Kinase Inhibition Assays.

All compounds were initially prepared as 10 mM stocks in anhydrous dimethylsulfoxide (DMSO). A 20 μl aliquot of the 10 mM solutions was transferred to individual wells in column 1 of a 96-well polypropylene microtiter plate (Corning #3363) and diluted with DMSO to give a final compound concentration of 4 mM. Test compounds were then serially diluted 1:5 in DMSO for an 11-point concentration response and further diluted in the assay buffer bringing all compound concentrations to a final range of 100 μM to 10 μM in 2.5% DMSO. The assay was performed in white 96-well, flat-bottom, half-area, non-binding assay plate (Corning #3642) in assay buffer consisting of 20 mM HEPES (pH 7.5), 10 mM $MgCl_2*6H_2O$, 100 μM sodium orthovanadate, 0.05% CHAPS and 0.1% bovine serum albumin. A 10 μL aliquot of compound from each well of the intermediate dilution plate and 20 μL of a 2× substrate/enzyme solution containing acceptor substrate (800 nM RSK2 peptide KRRRLSSLRA (SEQ ID NO: 1)), ROCK2 enzyme (10 nM), or ROCK1 enzyme, and 1,4-Dithiothreitol (DTT, 2 uM) were added to all wells. The reaction was initiated by the addition of 10 μL of 4× stock solution ATP (2 μM). Reactions were thoroughly mixed manually, covered and allowed to incubate at room temperature for 75 min. Protein kinase activity was quantitated using Promega's KINASE-GLO™ luminescent Kinase Assay Kit according to the manufacturer's directions. ATP concentrations remaining in Test wells following the termination of the enzymatic reaction were compared against control wells containing equivalent amounts of DMSO containing no inhibitor (CTRL). ATP concentrations in both Test wells and CTRL wells were normalized against background (BKG) ATP concentrations in wells containing concentrations of inhibitor that completely inhibited the protein kinase under investigation (i.e. a concentration that prevented any consumption of ATP over the course of the incubation). Percent of Control (POC) values were determined for each concentration of compound tested according to the equation:

POC=((Test well value−BKG)/(CTRL−BKG))*100

$IC_{50}$ values were calculated using the following 4-parameter logistic curve-fitting algorithm:

$f(x)=(A+((B-A)/(1+((x/C)\char`\^D))))$ $IC_{50}$ values were converted to $K_i$ values using the Cheng-Prusoff Equation: $K_i=IC_{50}/(1+([ATP]/Km\ ATP]))$.

JAK Kinase Assays.

Compounds were prepared in the exact same manner as described in the ROCK Kinase Assay with the exception to the substrate and enzyme. The JAK 2× substrate/enzyme solution consisted of acceptor substrate (800 nM Abl peptide EAIYAAPFAKKK (SEQ ID NO: 2)), JAK2 or JAK3 enzyme (10 nM) and DTT (2 μM). All other steps and solutions remain identical to the ROCK Kinase Assay above.

Results are shown below in Table 15, Table 16, and Table 17.

TABLE 15

| Example No. | Molecular Structure | Rho Kinase Activity (JAK 2/3 activity) |
|---|---|---|
| E39.1 | 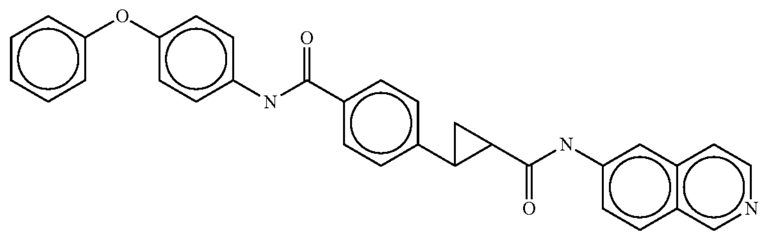 | 75-110 nM |
| E9 | 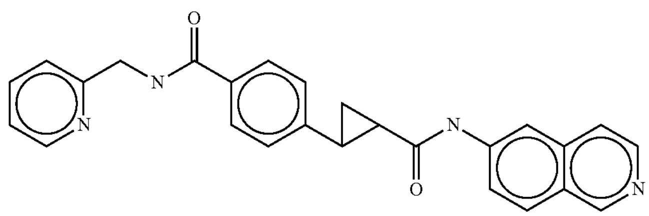 | 3-5 nM (JAK2 65-100 nM) |
| E12 | 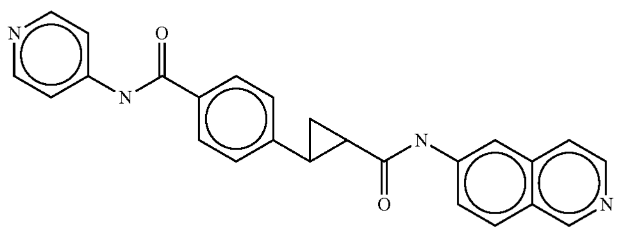 | 1-4 nM (JAK2 400 nM) |
| E11/E13 | 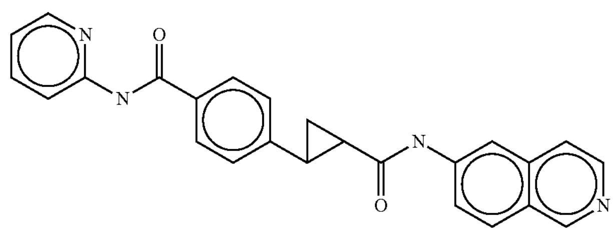 | 1-5 nM (JAK2 40-65 nM) |
| E10 | 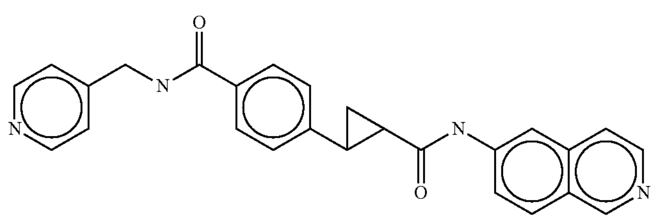 | 1-7 nM |
| | | 5-13 nM |
| E55 | 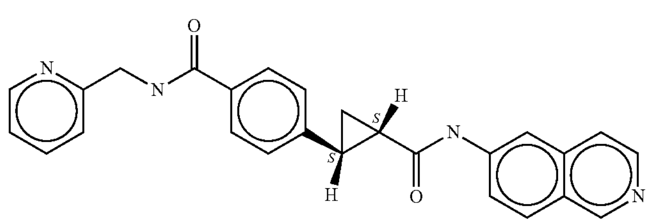 | 12,000-52,000 nM (JAK2-inactive) |

TABLE 15-continued

| Example No. | Molecular Structure | Rho Kinase Activity (JAK 2/3 activity) |
|---|---|---|
| E54 | 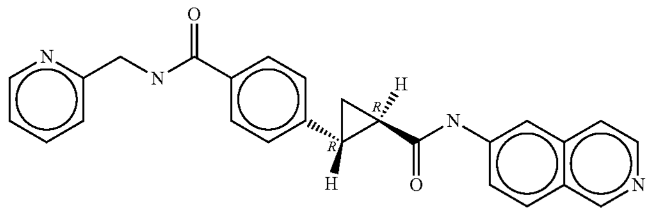 | 1-2 nM (JAK2 15-90 nM) |
| E8 | 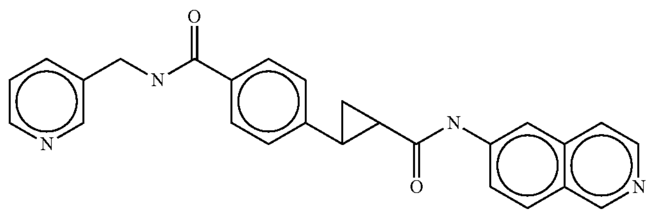 | 1-10 nM (JAK2 200 nM) |
| E11/E13 | 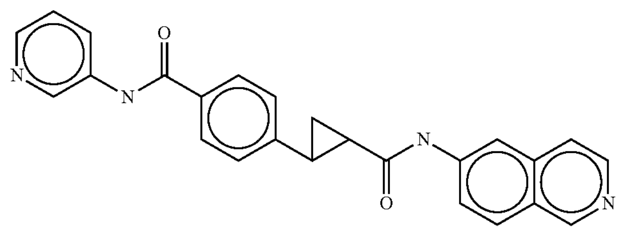 | 1.5-14 nM |
| E14 | 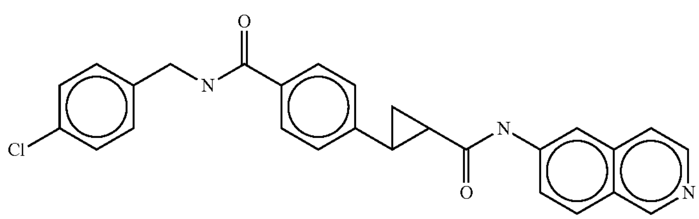 | 3.0-43 nM |
| E30.1 | 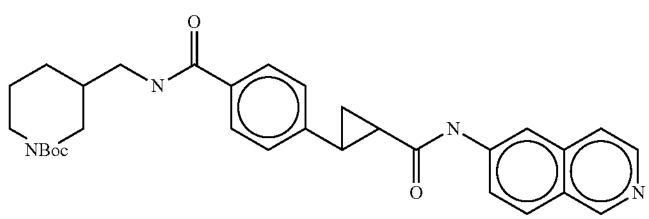 | 10-37 nM |
| E15 | 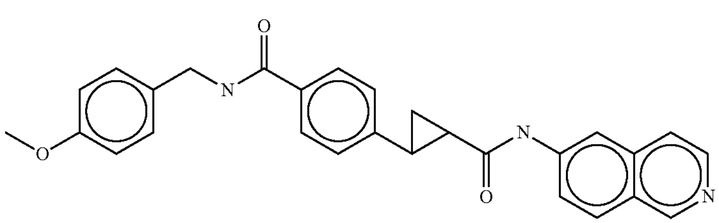 | 1-5 nM |
| E17 | 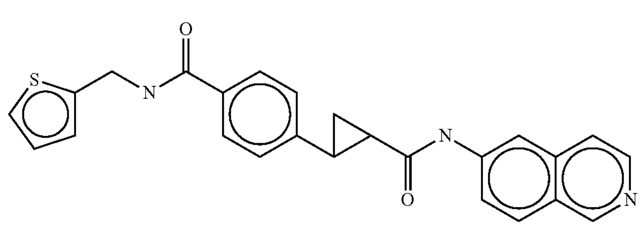 | 2-4 nM |

TABLE 15-continued

| Example No. | Molecular Structure | Rho Kinase Activity (JAK 2/3 activity) |
|---|---|---|
| E30.2 | 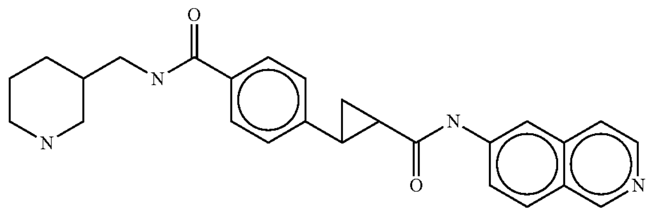 | 1-8 nM |
| E56 | 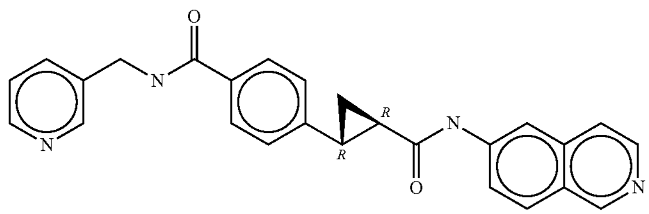 | 0.5-3.0 nM (40-120 nM JAK2) |
| E96 | 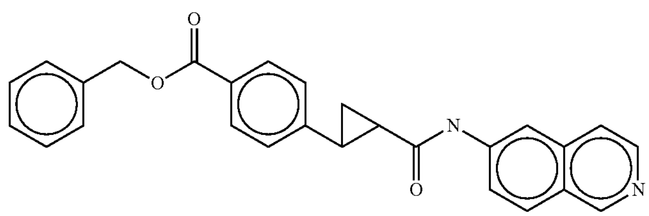 | 20-130 nM (1600-5000 nM JAK2) |
| E99 | 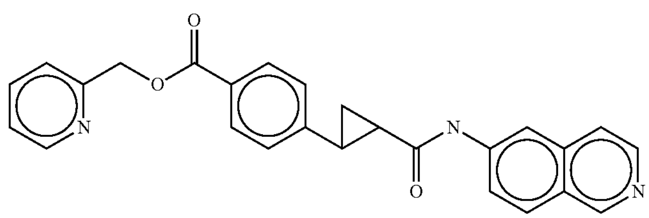 | 0.5-6.0 nM (250-600 nM JAK2) |
| E18 | 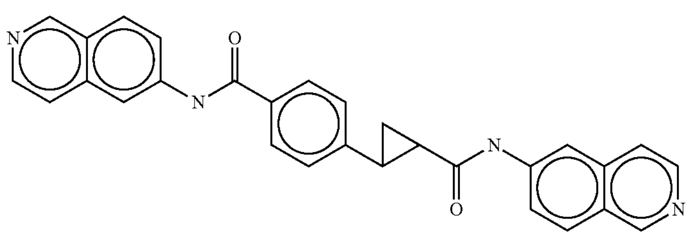 | 0.8-8.0 nM (1000-1200 nM JAK2) |
| E115 | 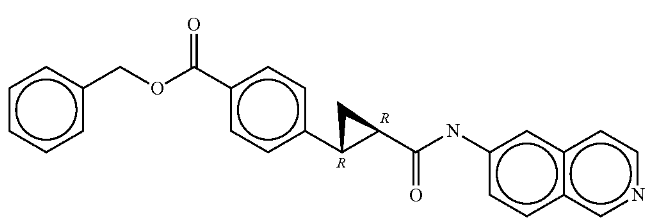 | 40-75 nM (3000-5000 nM JAK2) |
| E116 | 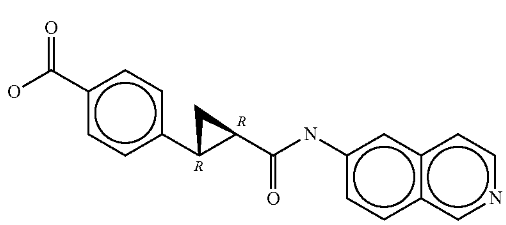 | 100-400 nM (400-700 nM JAK2) |

TABLE 15-continued

| Example No. | Molecular Structure | Rho Kinase Activity (JAK 2/3 activity) |
|---|---|---|
| E29.1 | 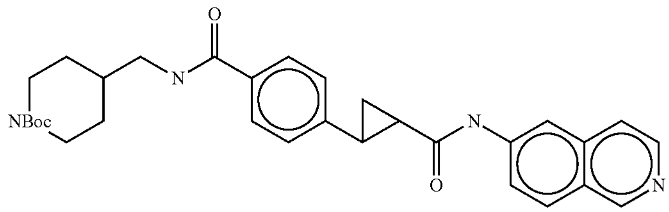 | 0.5-1.0 nM (1000-6000 nM JAK2) |
| 19.1 | 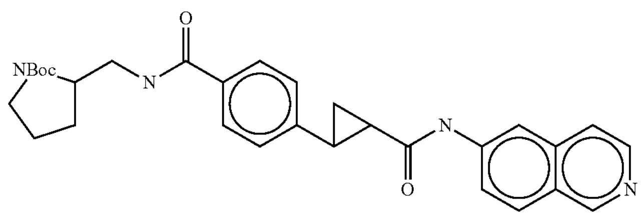 | 30-60 nM (1500-3500 nM JAK2) |
| E20.1 | 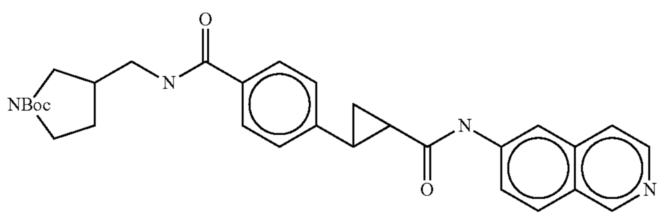 | 0.5-2.0 nM (700-2000 nM JAK2) |
| E16 | 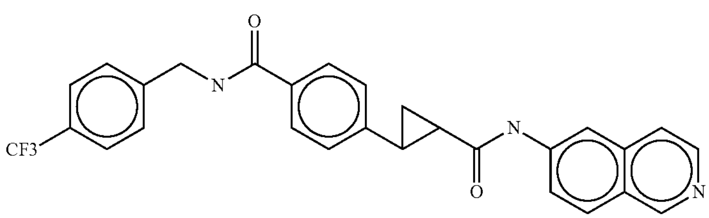 | 5.0-75 nM (2500-9000 nM JAK2) |
| E251 | 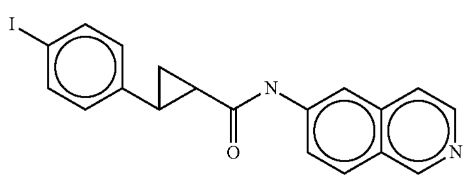 | 150-400 nM (500-800 nM JAK2) |
| E247A | 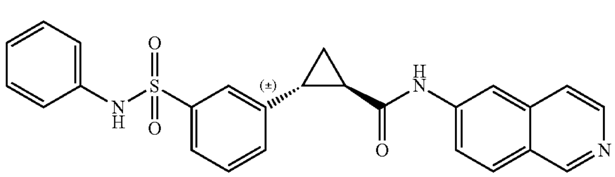 [SMILES: O=C(Nc1ccc2cnccc2c1)[C@@H]1C[C@H]1c1cccc(S(=O)(=O)Nc2ccccc2)c1] | 70-350 nM (5.0-25 nM JAK2) |
| E247B | 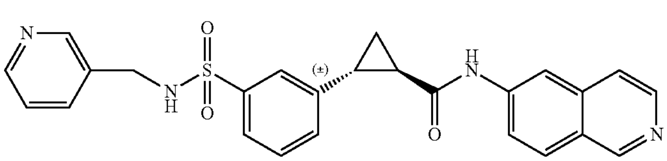 [SMILES: O=C(Nc1ccc2cnccc2c1)[C@@H]1C[C@H]1c1cccc(S(=O)(=O)NCc2cccnc2)c1] | 8.0-35 nM (450-1450 nM JAK2) |

TABLE 15-continued

| Example No. | Molecular Structure | Rho Kinase Activity (JAK 2/3 activity) |
|---|---|---|
| E142 | 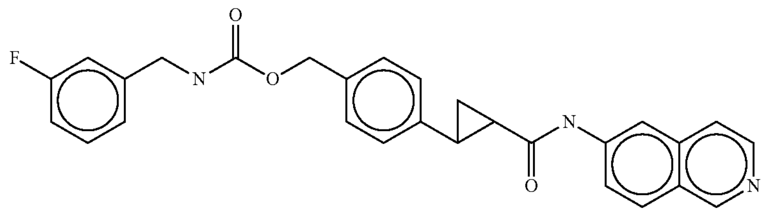 | 30-800 nM |
| E143 | 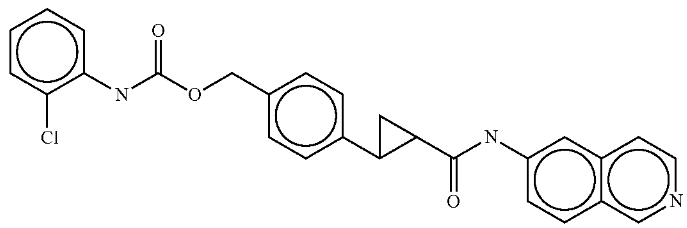 | 190-250 nM (JAK2, 1300-2700 nM) |
| E248D | 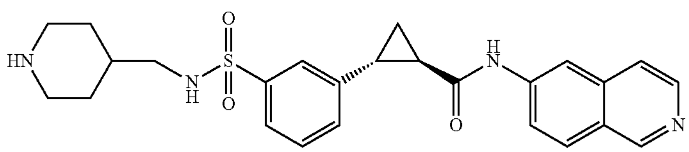 [SMILES: O=C(Nc1ccc2cnccc2c1)[C@@H]1C[C@H]1c1cccc(S(=O)(=O)NCC2CCNCC2)c1] | 5.0-9.0 nM (JAK2 70-115 nM) |
| E248E | 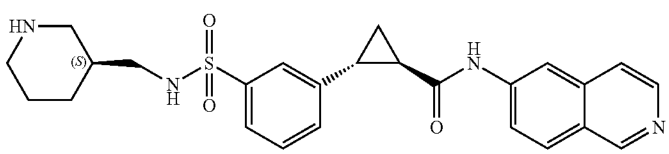 | 2.0-4.5 nM (JAK2 55-85 nM) |
| E248H | 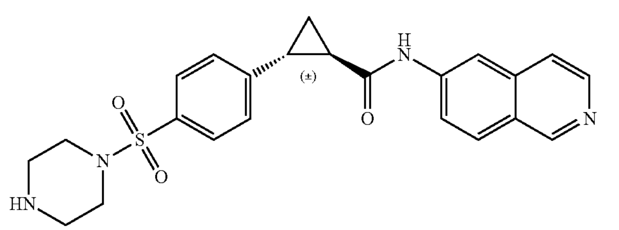 [SMILES: O=C(Nc1ccc2cnccc2c1)[C@@H]1C[C@H]1c1ccc(S(=O)(=O)N2CCNCC2)cc1] | 30-50 nM (JAK2 500-650 nM) |
| E100.1 | 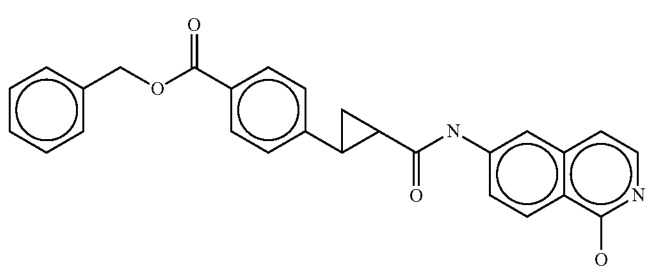 | 25 nM (JAK2 inactive) |
| E104.1 | 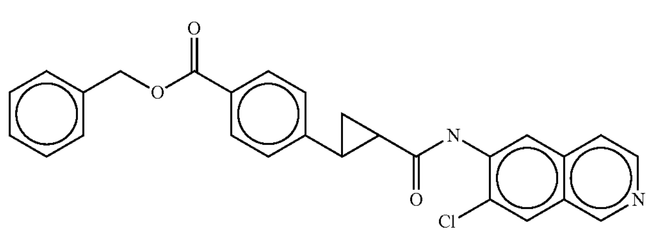 | 15-75 nM (JAK2, inactive) |

TABLE 15-continued

| Example No. | Molecular Structure | Rho Kinase Activity (JAK 2/3 activity) |
|---|---|---|
|  |  | 350-600 nM |
| E19.2 | 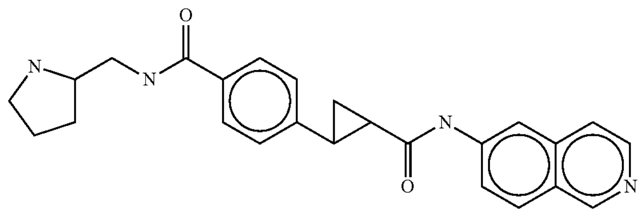 | 6.0-12 nM (JAK2, 300-350 nM) |
| E20.2 | 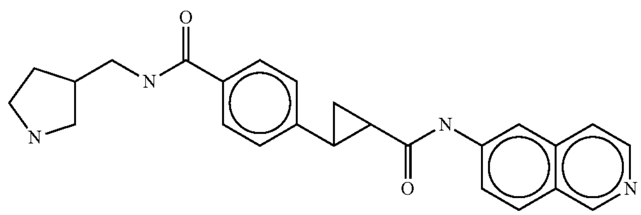 | 4.0-6.0 nM (JAK2, 27-150 nM) |
| E32 | 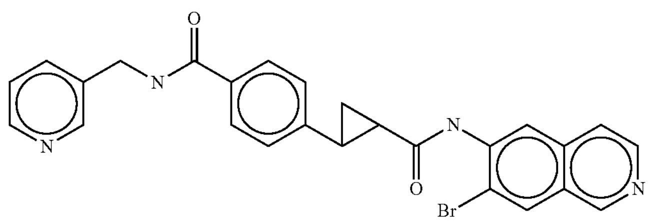 | 2.5-4.5 nM (JAK2 400-1300 nM) |
| E31 | 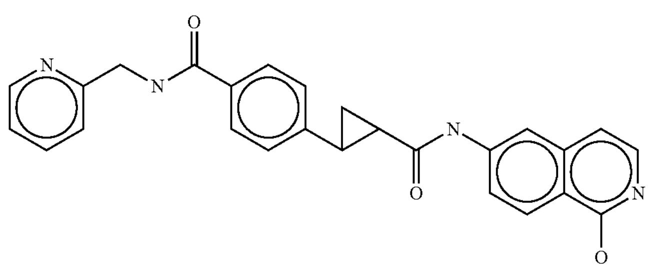 | 5.0-7.0 nM (JAK2, 375-570 nM) |
| E248F | 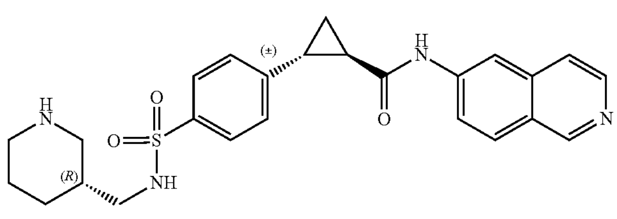 | 3.0-5.0 nM (JAK2, 45-95 nM) |
| E248G | 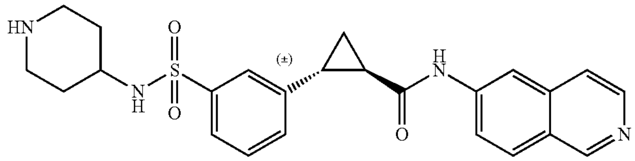 [SMILES: O=C(Nc1ccc2cnccc2c1)[C@@H]1C[C@H]1c1cccc(S(=O)(=O)NC2CCNCC2)c1] | 5.0-9.5 nM (JAK2, 50-65 nM) |

TABLE 15-continued

| Example No. | Molecular Structure | Rho Kinase Activity (JAK 2/3 activity) |
|---|---|---|
| E250E* | 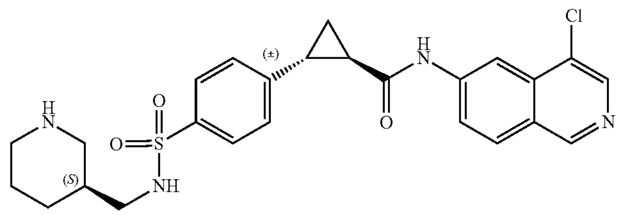 | 9.0-11 nM (JAK2, 13-17 nM) |
| E33 | 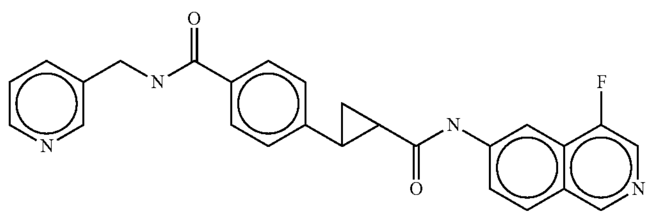 | 5.0-8.0 nM (JAK2, 75-110 nM) |
| E34 | 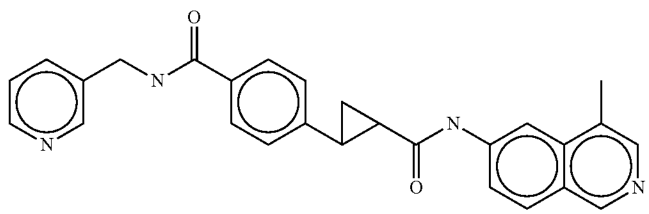 | 7.0-14 nM (JAK2, 30-45 nM) |
| E35 | 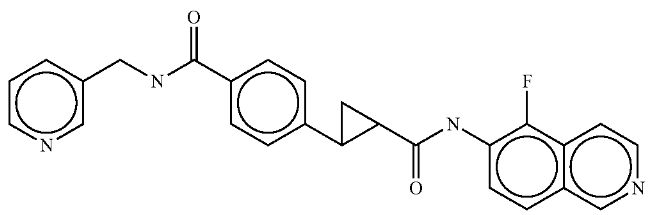 | 0.5-8.0 nM (JAK2, 300-950 nM) |
| E191.1 | 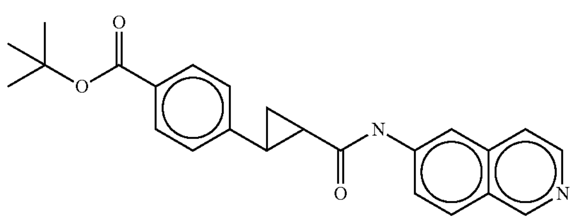 | 105-155 nM (JAK2, 5200 nM) |
| E37 | 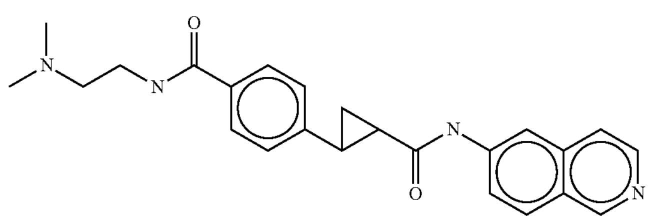 | 4.3-9.0 nM (JAK2, 800 nM) |
| E38 | 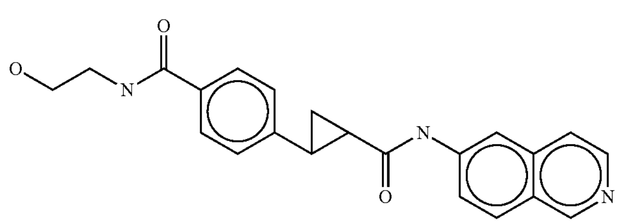 | 7.0-9.5 nM (JAK2 136 nM) |

TABLE 15-continued

| Example No. | Molecular Structure | Rho Kinase Activity (JAK 2/3 activity) |
|---|---|---|
| E191 | 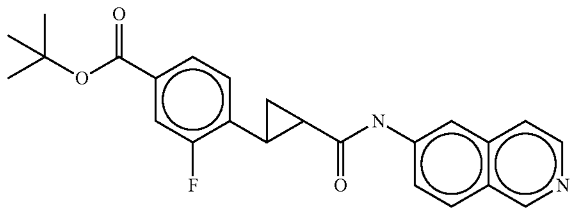 | 125-185 nM (JAK2 3000 nM) |
| E158 | 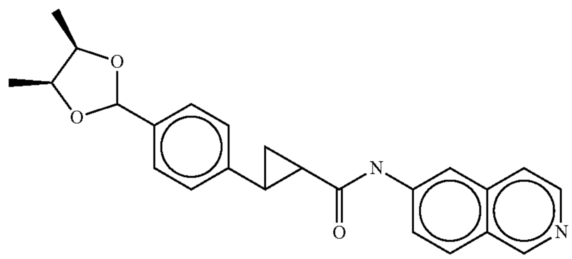 | 165-215 nM (JAK2 1000 nM) |
| E39 | 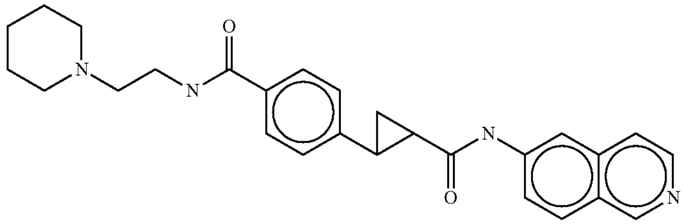 | 5.0-7.0 nM (JAK2 400 nM) |
| E193 | 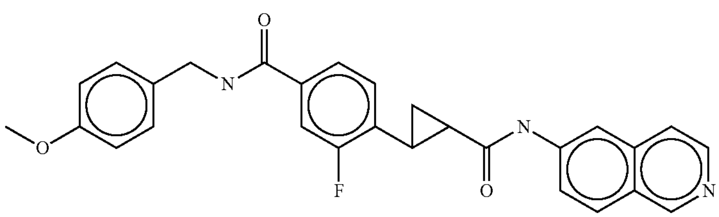 | 6.0-8.0 nM (JAK2 110 nM) |
| E194 | 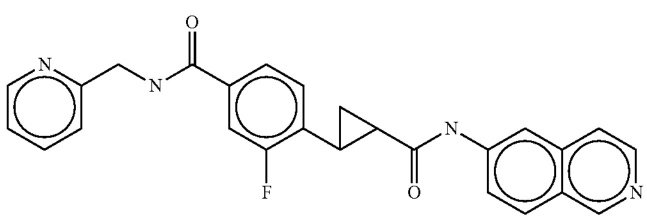 | 3.5-4.0 nM (JAK2 15 nM) |
| E195.1 | 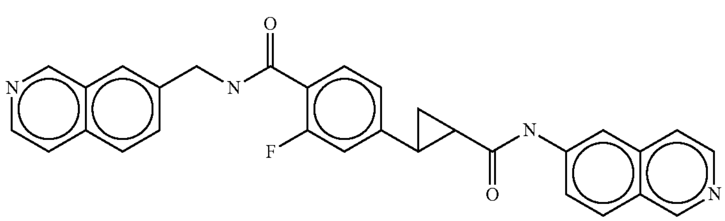 | 4.0-7.0 nM |
| E195 | 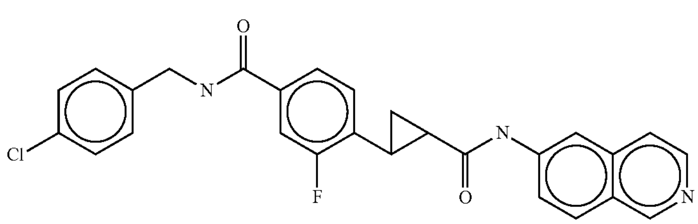 | 70-100 nM |

TABLE 15-continued

| Example No. | Molecular Structure | Rho Kinase Activity (JAK 2/3 activity) |
|---|---|---|
| E160 | 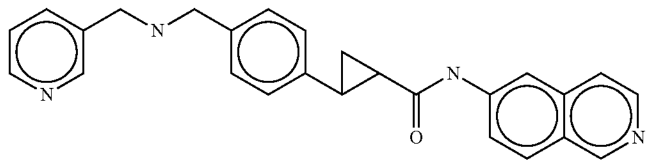 | 250-800 nM |
| E162.1 | 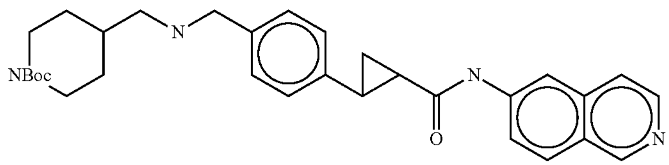 | 200-600 nM |
| E36 | 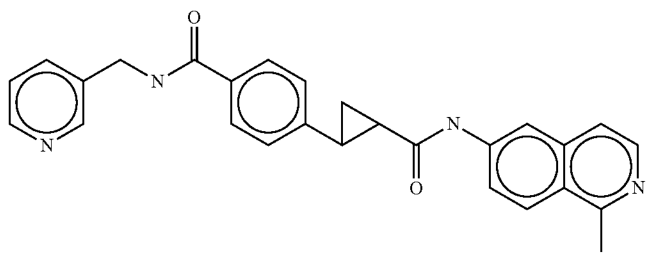 | 75-200 nM |
| E15.1 | 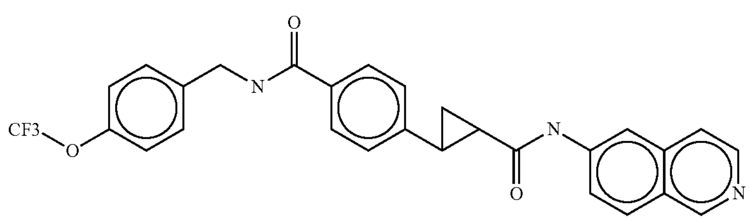 | 65-110 nM |
| E162.2 | 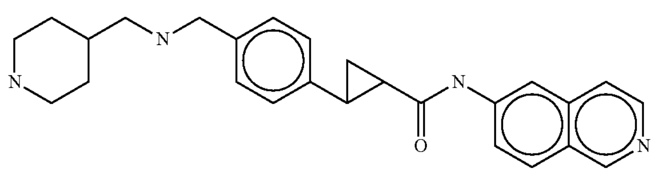 | 125-300 nM |
| E170 | 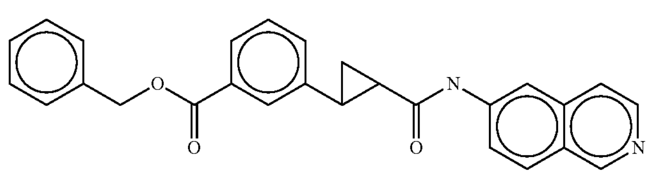 | 650-1250 nM |
| E159 | 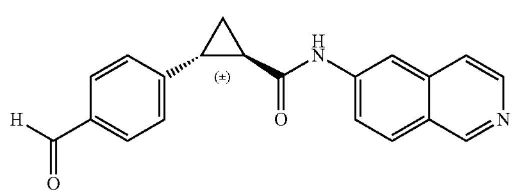 [SMILES: O=Cc1ccc([C@@H]2C[C@H]2C(=O)Nc2ccc3cnccc3c2)cc1] | 20-50 nM (JAK2 270 nM) |

TABLE 15-continued

| Example No. | Molecular Structure | Rho Kinase Activity (JAK 2/3 activity) |
|---|---|---|
| E195.2 | 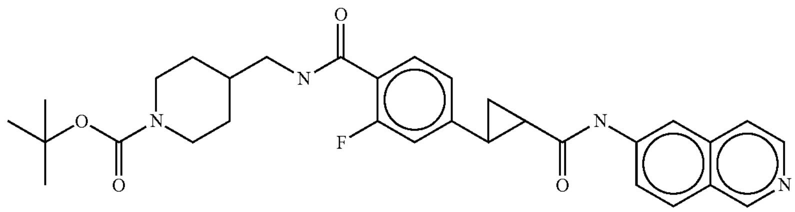 | 0.40-1.0 nM |
| E57.1 | 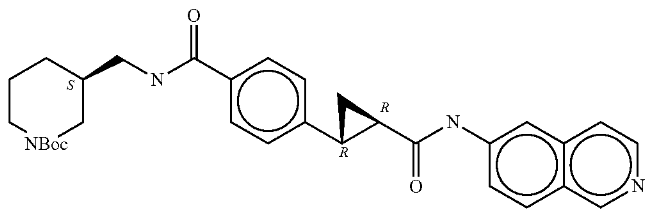 | 0.15-1.0 nM (JAK2 45-65 nM) |
| E174 | 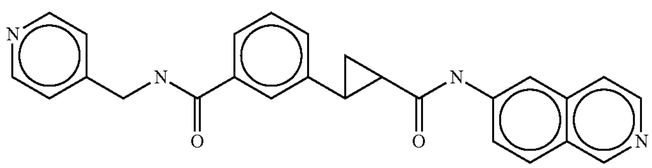 | 0.15-0.30 nM |
| E173 | 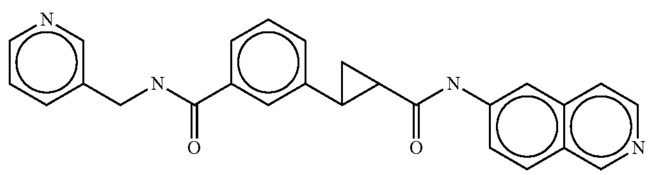 | 0.7-1.0 nM (JAK2 200 nM) |
| E57.2 | 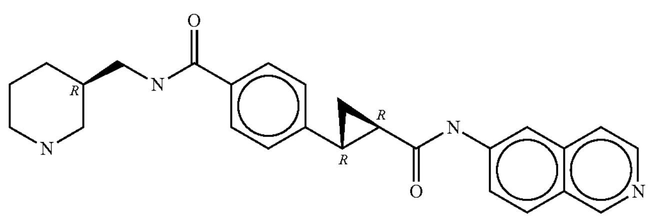 | <0.10-1.0 nM (JAK2 7.0 nM) |
| E115.1 | 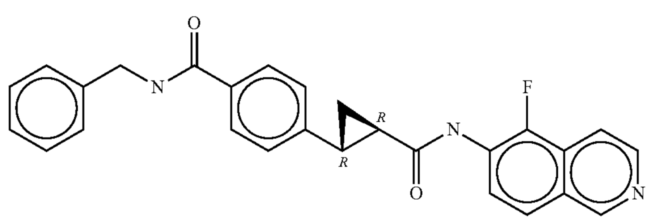 | <0.10-1.0 nM |
| E210 | 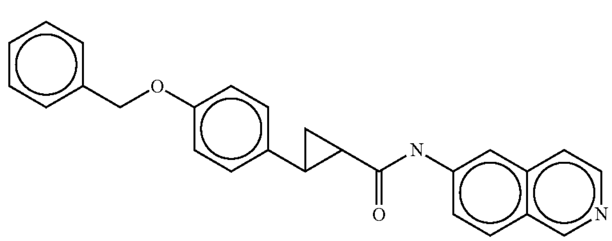 | 60-300 nM |

TABLE 15-continued
| Example No. | Molecular Structure | Rho Kinase Activity (JAK 2/3 activity) |
|---|---|---|
| E56.1 | 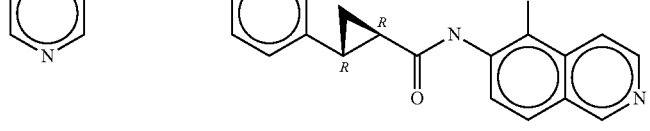 | <0.10-0.5 nM (JAK2 40-75 nM) |
| Pyrrolidones | | |
| | 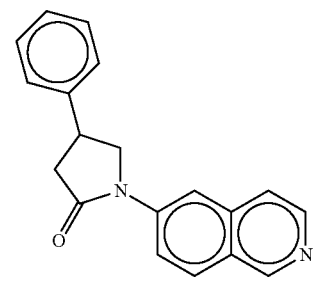 | 650-1350 nM |
| E223 | 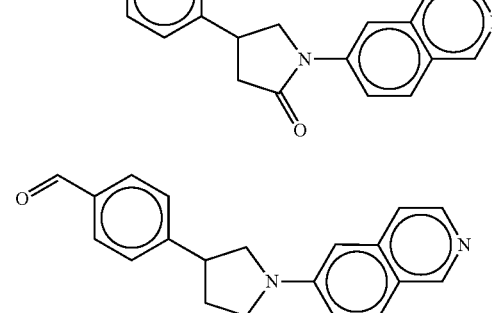 | 8000-15000 nM |
| E224 | 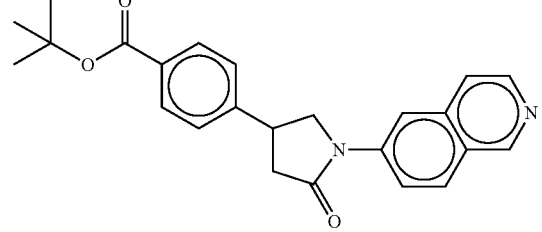 | 2600-6750 nM |
| E230 | 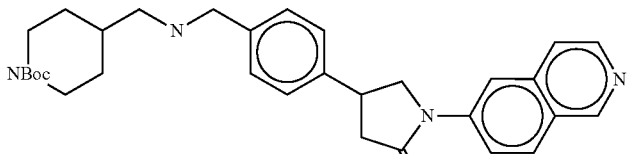 | 14000-25000 nM |
| E227.1 | 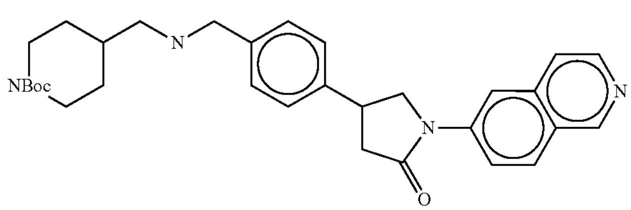 | 1300-4000 nM |

TABLE 15-continued

| Example No. | Molecular Structure | Rho Kinase Activity (JAK 2/3 activity) |
|---|---|---|
| E225 | 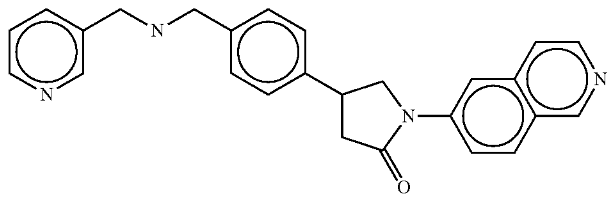 | 1350-2200 nM |
| E227.2 | 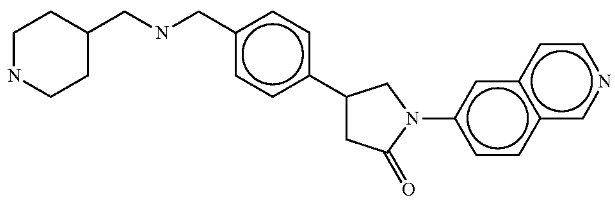 | 300-600 nM |
| E230.1 | 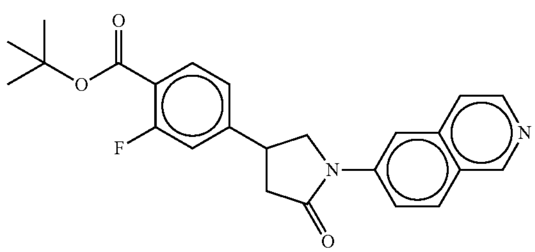 | 9300 nM |
| E231 | 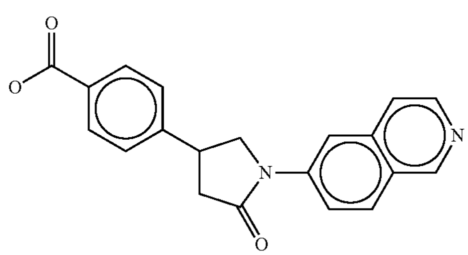 | 34000-68000 nM |
| E226 | 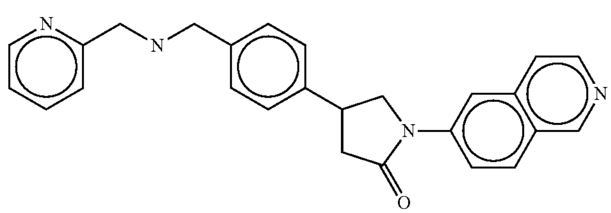 | 1900-9300 nM |
| E232 | 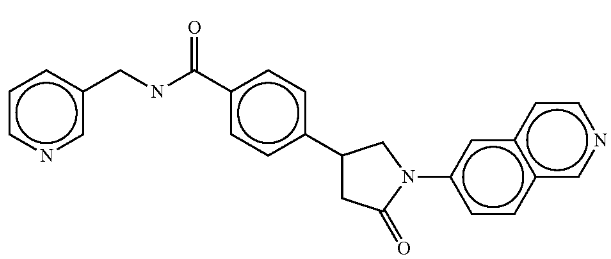 | 6500-16000 nM |

TABLE 15-continued

| Example No. | Molecular Structure | Rho Kinase Activity (JAK 2/3 activity) |
|---|---|---|
| E233 | 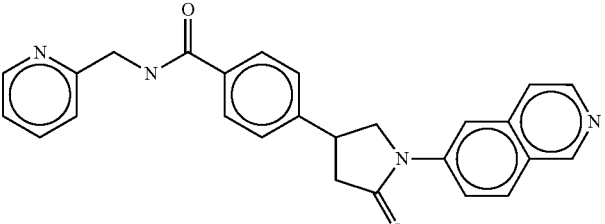 | 4350-8400 nM (JAK2 5800-13500 nM; JAK3 3400-3800 nM) |
| E234.2 | 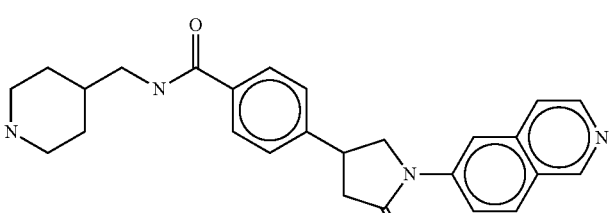 | 1000-1250 nM |

Compounds of Table 16, Table 17 and Table 18 can be prepared as described in the typical procedures provided herein.

TABLE 16

| Example No. | Structure | Amount Rho Kinase Activity (JAK 2/3 activity) |
|---|---|---|
| E265 | 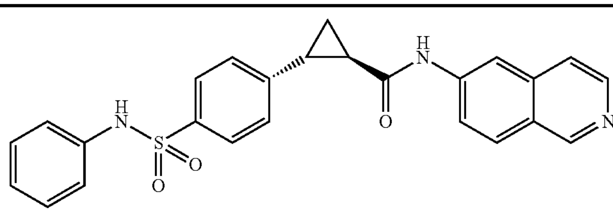 | 75 nM ROCK2<br>154 nM ROCK1<br>17 nM JAK2<br>36 nM JAK3 |
| E266 | 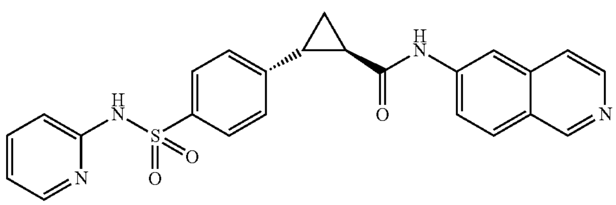 | 6 nM ROCK2<br>9 nM ROCK1<br>2.0 nM JAK2<br>12 nM JAK3<br>9 nM IKKb |
| E267 | R, R | 2.5 nM ROCK2<br>3.4 nM ROCK1<br>1.0 nM JAK2<br>5.8 nM JAK3<br>4.5 nM IKKb |
| E268 | 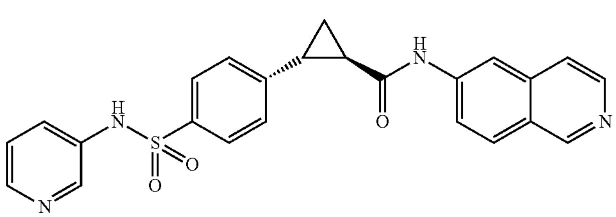 | 24 nM ROCK2<br>85 nM ROCK1<br>12 nM JAK2<br>125 nM JAK3<br>650 nM IKKb |

TABLE 16-continued

| Example No. | Structure | Amount Rho Kinase Activity (JAK 2/3 activity) |
|---|---|---|
| | (structure with pyridin-4-yl sulfonamide, phenyl cyclopropyl carboxamide, isoquinoline) | |
| E269 | (structure with pyridin-3-yl-methyl sulfonamide, phenyl cyclopropyl carboxamide, isoquinoline) | 9 nM ROCK2<br>25 nM ROCK1 |
| E270 | (structure with dimethylamino-propyl sulfonamide, phenyl cyclopropyl carboxamide, isoquinoline) | |
| E271 | (structure with piperidin-4-yl-methyl sulfonamide, phenyl cyclopropyl carboxamide, isoquinoline) 2HCl | 8 nM ROCK2<br>9 nM ROCK1<br>116 nM JAK2 |
| E272 | (structure with piperidin-3-yl-methyl sulfonamide, phenyl cyclopropyl carboxamide, isoquinoline) 2HCl | 5 nM ROCK2<br>5 nM ROCK1<br>87 nM JAK2 |
| E273 | (structure with (S)-piperidin-3-yl-methyl sulfonamide, phenyl cyclopropyl carboxamide, isoquinoline) 2HCl | 4.0 nM ROCK2<br>4.0 nM ROCK1<br>70 nM JAK2<br>1140 nM JAK3 |
| E274 | (structure with (S)-piperidin-3-yl-methyl sulfonamide, phenyl cyclopropyl carboxamide, 4-chloro-isoquinoline) 2HCl | 10 nM ROCK2<br>10 nM ROCK1<br>15 nM JAK2<br>160 nM JAK3 |

TABLE 16-continued

| Example No. | Structure | Amount Rho Kinase Activity (JAK 2/3 activity) |
| --- | --- | --- |
| E275 | 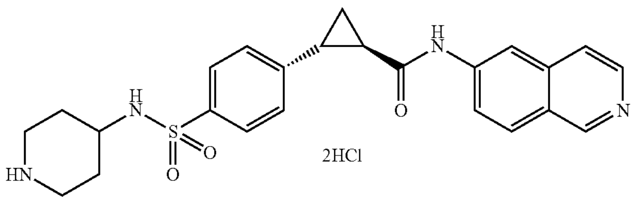 | 7.0 nM ROCK2<br>8.2 nM ROCK1<br>60 nM JAK2 |
| E276 | 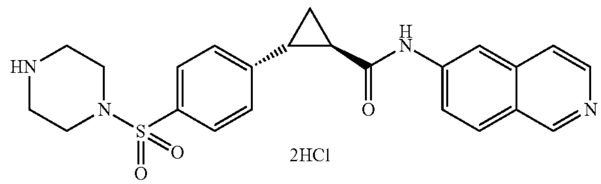 | 31 nM ROCK2<br>48 nM ROCK1<br>652 nM JAK2 |
| E277 | 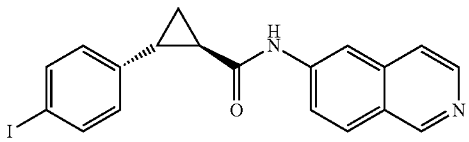 | 175 nM ROCK2<br>270 nM ROCK1<br>650 nM JAK2 |
| E278 | 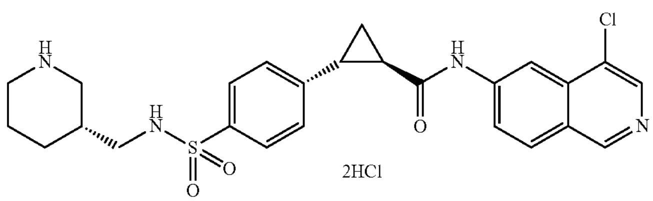 | 10 nM ROCK2<br>10 nM ROCK1<br>15 nM JAK2<br>160 nM JAK3 |
| E279 | 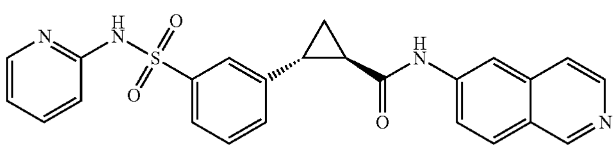 [SMILES: O=C(Nc1ccc2cnccc2c1)[C@@H]1C[C@H]1c1cccc(S(=O)(=O)Nc2ccccn2)c1] | 7.5 nM ROCK2<br>11 nM ROCK1<br>1150 nM JAK2<br>2500 nM JAK3 |
| E280 | 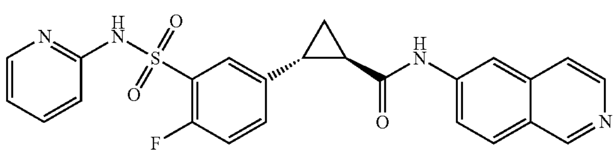 [SMILES: O=C(Nc1ccc2cnccc2c1)[C@@H]1C[C@H]1c1ccc(F)c(S(=O)(=O)Nc2ccccn2)c1] | 12.5 nM ROCK2<br>15 nM ROCK1<br>1400 nM JAK2<br>1060 nM JAK3 |
| E281 | 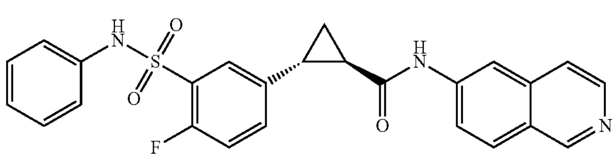 [SMILES: O=C(Nc1ccc2cnccc2c1)[C@@H]1C[C@H]1c1ccc(F)c(S(=O)(=O)Nc2ccccc2)c1] | 240 nM ROCK2<br>150 nM ROCK1<br>3000 nM JAK2<br>7500 nM JAK3 |
| E282 | 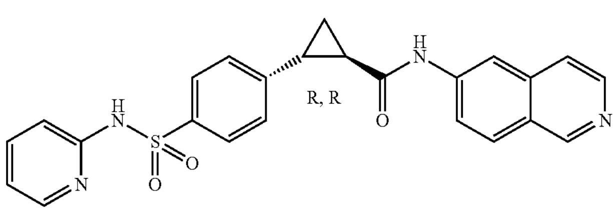 | |

TABLE 16-continued

| Example No. | Structure | Amount Rho Kinase Activity (JAK 2/3 activity) |
|---|---|---|
| E283 | 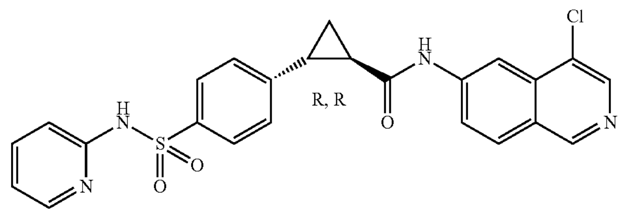 | |
| E284 | 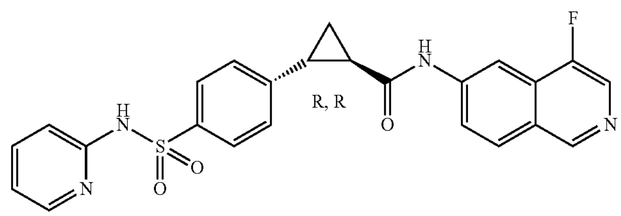 | |
| E285 | 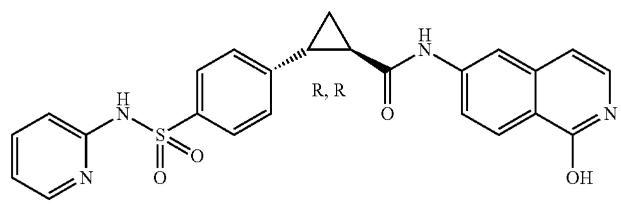 | |
| E286 | 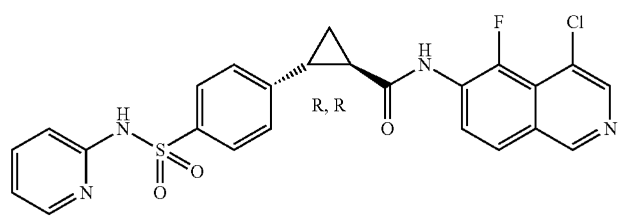 | |
| E287 | 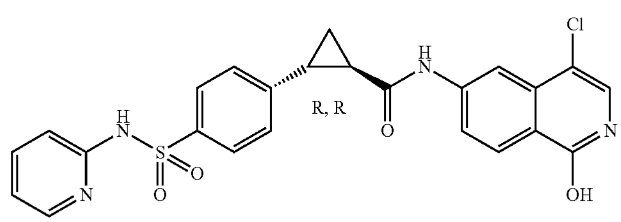 | |
| E288 | 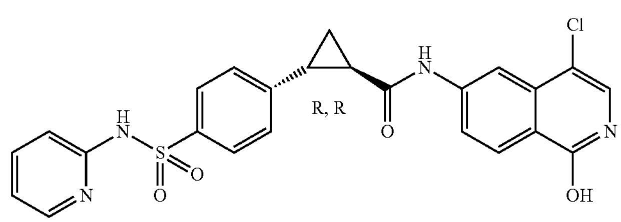 | |
| E289 | 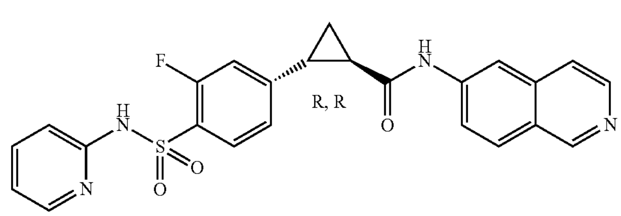 | |

TABLE 16-continued

| Example No. | Structure | Amount Rho Kinase Activity (JAK 2/3 activity) |
|---|---|---|
| E290 | 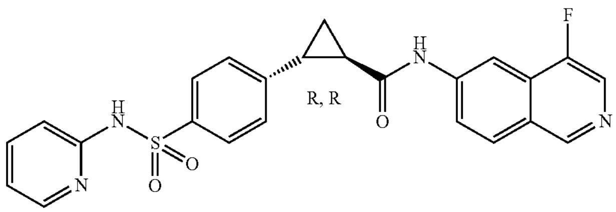 | |
| E291 | 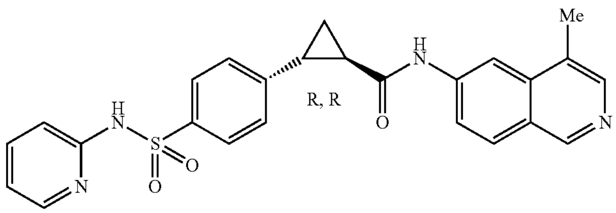 | |
| E292 | 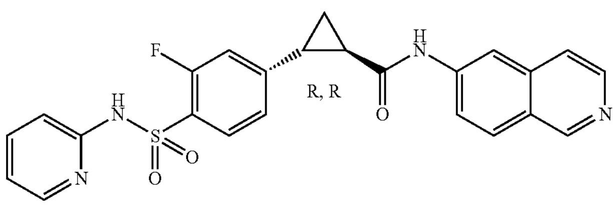 | |
| E293 | 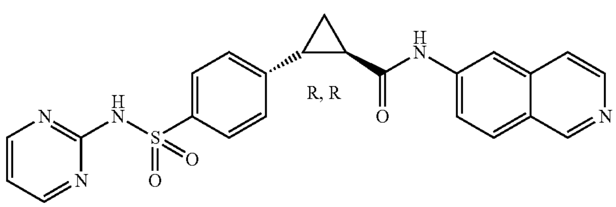 | |
| E294 | 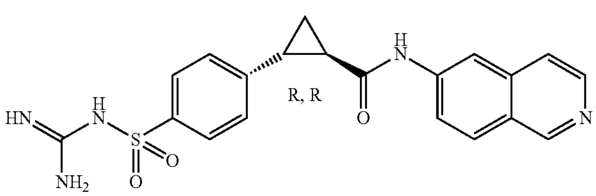 | |

TABLE 17

| | |
|---|---|
| | (rel)-(1R,2R)-N-(isoquinolin-6-yl)-2-(4-(N-phenylsulfamoyl)phenyl)cyclopropane-1-carboxamide<br>75 nM ROCK2; 154 nM ROCK1<br>17 nM JAK2; 36 nM JAK3<br>racemic |
| | 6 nM ROCK2; 9 nM ROCK1<br>2.0 nM JAK2; 12 nM JAK3<br>9 nM IKKb<br>racemic |

TABLE 17-continued

| Structure | Description |
|---|---|
| (structure) | (1R,2R)-N-(isoquinolin-6-yl)-2-(4-(N-(pyridin-2-yl)sulfamoyl) phenyl) cyclopropane-1-carboxamide<br>1.0 nM ROCK2; 3.0 nM ROCK1<br>0.6 nM JAK2; 4.3 nM JAK3<br>3.6 nM IKKb<br>PTM: 61 nM |
| (structure) | 24 nM ROCK2; 85 nM ROCK1<br>12 nM JAK2; 125 nM JAK3<br>650 nM IKKb<br>7-fold selective JAK2/ROCK1<br>3.5-fold selective Rock2/1 |
| (structure) | |
| (structure) | |
| (structure) | (rel)-(1R,2R)-N-(isoquinolin-6-yl)-2-(4-(N-(pyridin-3-ylmethyl)sulfamoyl)phenyl)cyclopropane-1-carboxamide<br>9 nM ROCK2; 25 nM ROCK1 |
| (structure) | (rel)-(1R,2R)-2-(4-(N-(3-(dimethylamino)propyl)sulfamoyl)phenyl)-N-(isoquinolin-6-yl)cyclopropane-1-carboxamide |
| (structure) 2HCl | (rel)-(1R,2R)-N-(isoquinolin-6-yl)-2-(4-(N-(piperidin-4-ylmethyl)sulfamoyl)phenyl)cyclopropane-1-carboxamide dihydrochloride<br>8 nM ROCK2; 9 nM ROCK1<br>JAK2 116 nM |
| (structure) 2HCl | (rel)-(1R,2R)-N-(isoquinolin-6-yl)-2-(4-(N-(((S)-piperidin-3-yl)methyl)sulfamoyl)phenyl)cyclopropane-1-carboxamide dihydrochloride<br>5 nM ROCK2; 5 nM ROCK1<br>JAK2 87 nM |

TABLE 17-continued

| Structure | Description |
|---|---|
| (piperidin-3-ylmethylamino sulfonyl phenyl cyclopropyl isoquinoline) · 2HCl | (rel)-(1R,2R)-N-(isoquinolin-6-yl)-2-(4-(N-(((R)-piperidin-3-yl)methyl)sulfamoyl)phenyl)cyclopropane-1-carboxamide dihydrochloride<br>4.0 nM ROCK2; 4.0 nM ROCK1<br>JAK2- 70 nM; JAK3- 1140 nM |
| (piperidin-3-ylmethylamino sulfonyl phenyl cyclopropyl 4-chloroisoquinoline) · 2HCl | 10 nM ROCK2; 10 nM ROCK1<br>15 nM JAK2 160 nM JAK3 |
| (piperidin-4-ylamino sulfonyl phenyl cyclopropyl isoquinoline) · 2HCl | (rel)-(1R,2R)-N-(isoquinolin-6-yl)-2-(4-(N-(piperidin-4-yl)sulfamoyl)phenyl)cyclopropane-1-carboxamide dihydrochloride<br>7.0 nM ROCK2; 8.2 nM ROCK1<br>JAK2 60 nM |
| (piperazin-1-ylsulfonyl phenyl cyclopropyl isoquinoline) · 2HCl | (rel)-(1R,2R)-N-(isoquinolin-6-yl)-2-(4-(piperazin-1-ylsulfonyl)phenyl)cyclopropane-1-carboxamide dihydrochloride<br>31 nM ROCK2; 48 nM ROCK1<br>JAK2 652 nM |
| (4-methylpiperazin-1-ylsulfonyl phenyl cyclopropyl isoquinoline) · 2HCl | (rel)-(1R,2R)-N-(isoquinolin-6-yl)-2-(4-(methylpiperazin-1-ylsulfonyl)phenyl)cyclopropane-1-carboxamide dihydrochloride |
| (4-iodophenyl cyclopropyl isoquinoline) | (rel)-(1R,2R)-2-(4-iodophenyl)-N-(isoquinolin-6-yl)cyclopropane-1-carboxamide<br>175 nM ROCK2; 270 nM ROCK1<br>JAK2 650 nM |
| (piperidin-3-ylmethylamino sulfonyl phenyl cyclopropyl 4-chloroisoquinoline) · 2HCl | (rel)-(1R,2R)-N-(4-chloroisoquinolin-6-yl)-2-(4-(N-(((R)-piperidin-3-yl)methyl)sulfamoyl)phenyl)cyclopropane-1-carboxamide dihydrochloride<br>10 nM ROCK2; 10 nM ROCK1<br>15 nM JAK2 160 nM JAK3 |
| (pyridin-2-ylamino sulfonyl phenyl cyclopropyl isoquinoline) | (rel)-(1R,2R)-N-(isoquinolin-6-yl)-2-(3-(N-phenylsulfamoyl)phenyl)cyclopropane-1-carboxamide<br>7.5 nM ROCK2; 11 nM ROCK1<br>1150 nM JAK2; 2500 nM JAK3 |

TABLE 17-continued

| | |
|---|---|
| 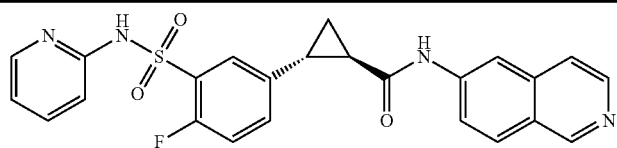 | 12.5 nM ROCK2; 15 nM ROCK1<br>1400 nM JAK2; 1060 nM JAK3 |
| 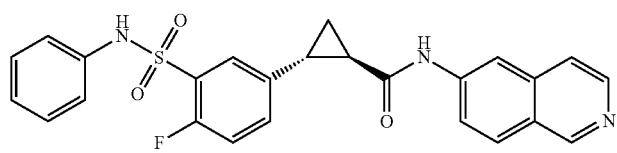 [SMILES: O=C(Nc1ccc2cnccc2c1)[C@@H]1C[C@H]1c1ccc(F)c(S(=O)(=O)Nc2ccccc2)c1] | 240 nM ROCK2; 150 nM ROCK1<br>3000 nM JAK2; 7500 nM JAK3 |
| 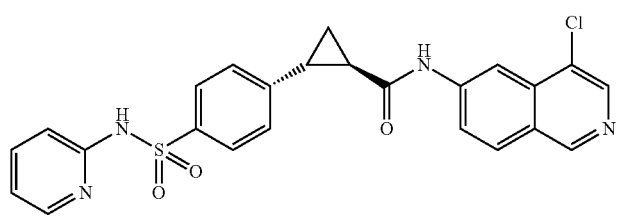 | rel-N-(4-chloroisoquinolin-6-yl)-2-(4-(N-(pyridin-2-yl)sulfamoyl)phenyl)cyclopropane-1-carboxamide<br>racemic<br>8.0 nM ROCK2; 13 nM ROCK1<br>0.55 nM JAK2; 0.70 nM JAK3<br>9.0 nM IKKb<br>PTM: 227 nM<br>(PKA = 285 nM,<br>Promiscuity Index = 475) |
| 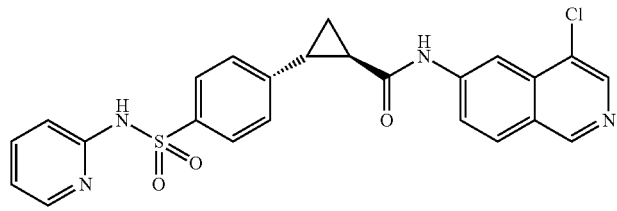 | N-(4-chloroisoquinolin-6-yl)-2-(4-(N-(pyridin-2-yl)sulfamoyl)phenyl)cyclopropane-1-carboxamide<br>chiral, nonracemic |
| 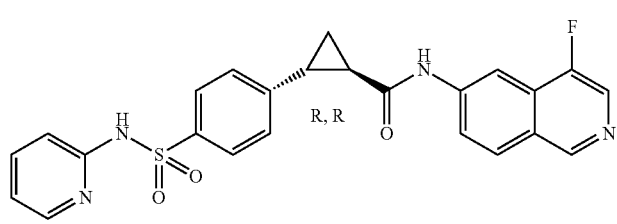 | |
| 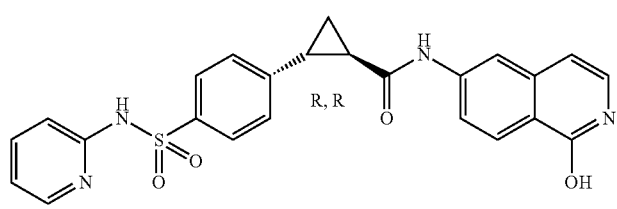 | |
| 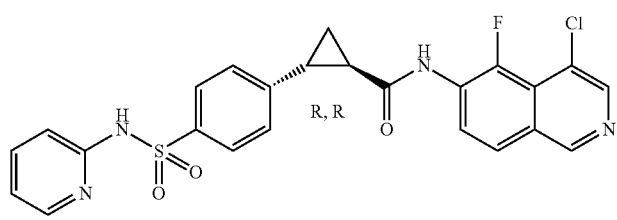 | |
| 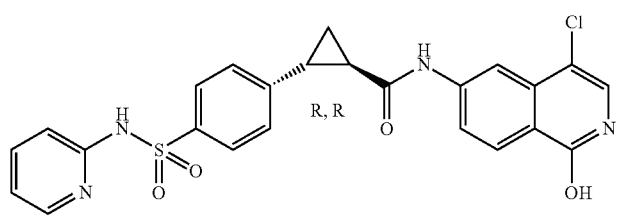 | |

TABLE 17-continued
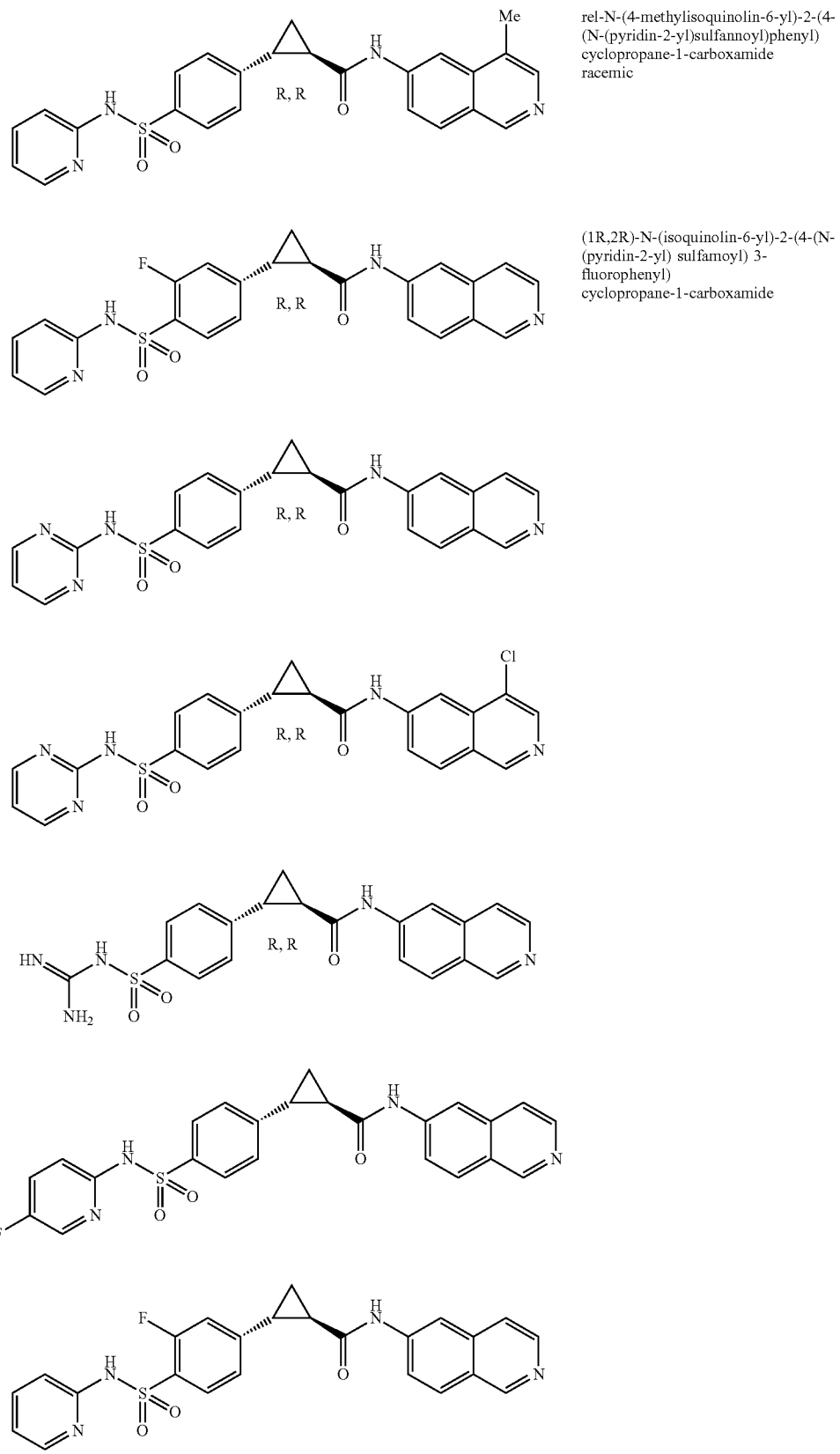
rel-N-(4-methylisoquinolin-6-yl)-2-(4-(N-(pyridin-2-yl)sulfannoyl)phenyl)cyclopropane-1-carboxamide racemic
(1R,2R)-N-(isoquinolin-6-yl)-2-(4-(N-(pyridin-2-yl) sulfamoyl) 3-fluorophenyl)cyclopropane-1-carboxamide TABLE 17-continued
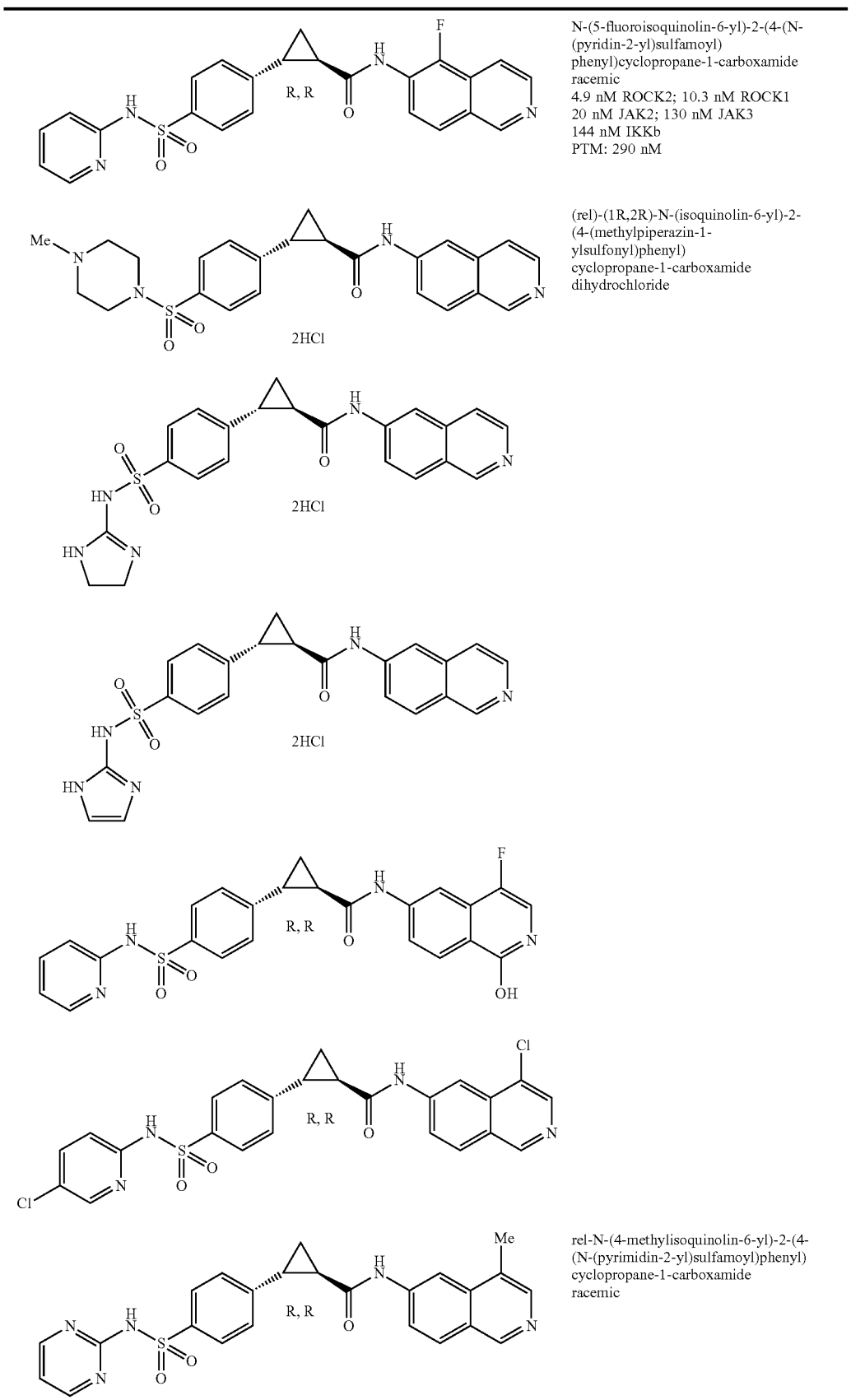
N-(5-fluoroisoquinolin-6-yl)-2-(4-(N-(pyridin-2-yl)sulfamoyl)phenyl)cyclopropane-1-carboxamide
racemic
4.9 nM ROCK2; 10.3 nM ROCK1
20 nM JAK2; 130 nM JAK3
144 nM IKKb
PTM: 290 nM
(rel)-(1R,2R)-N-(isoquinolin-6-yl)-2-(4-(methylpiperazin-1-ylsulfonyl)phenyl)cyclopropane-1-carboxamide
dihydrochloride
rel-N-(4-methylisoquinolin-6-yl)-2-(4-(N-(pyrimidin-2-yl)sulfamoyl)phenyl)cyclopropane-1-carboxamide
racemic TABLE 17-continued
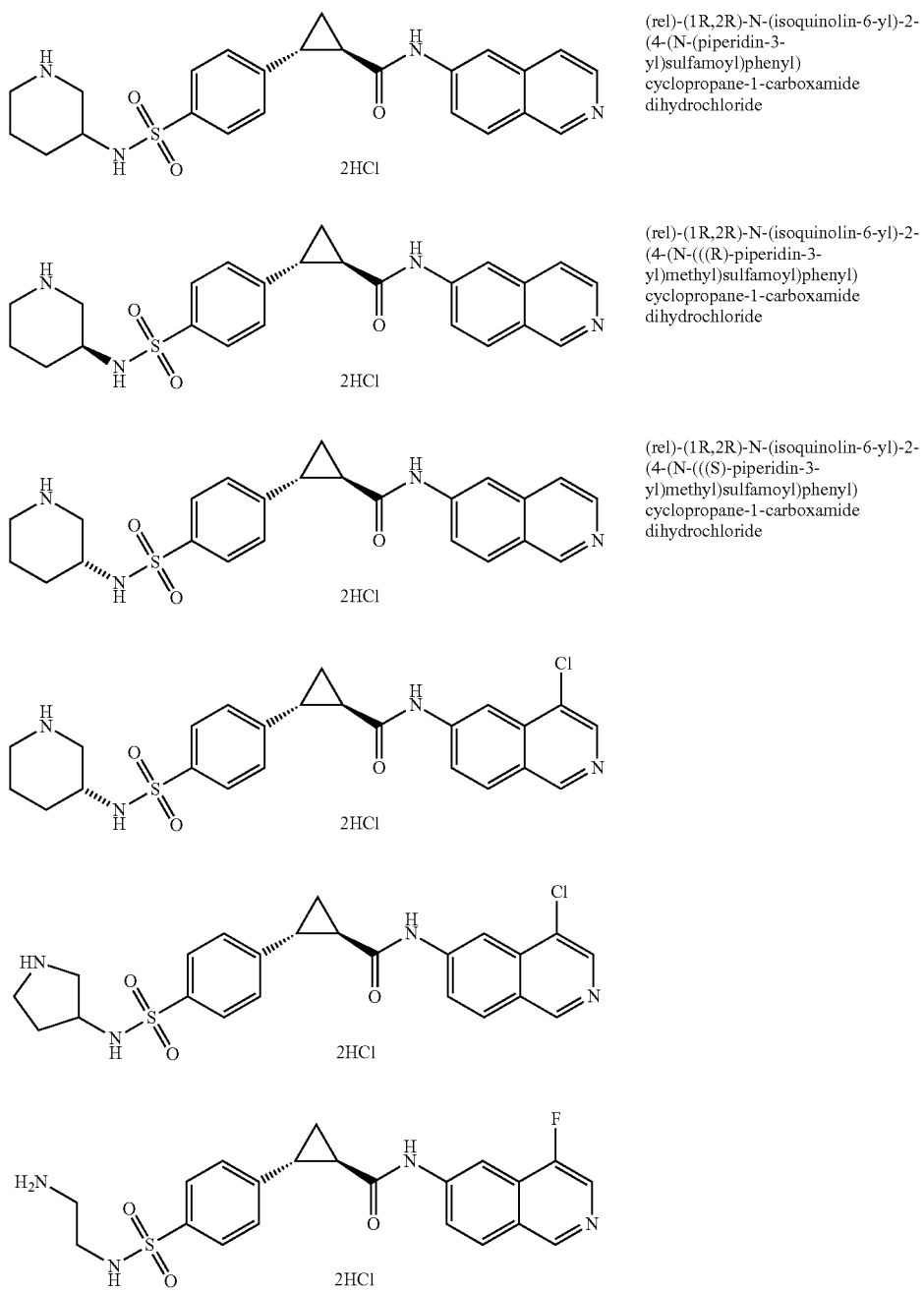
(rel)-(1R,2R)-N-(isoquinolin-6-yl)-2-(4-(N-(piperidin-3-yl)sulfamoyl)phenyl)cyclopropane-1-carboxamide dihydrochloride
(rel)-(1R,2R)-N-(isoquinolin-6-yl)-2-(4-(N-(((R)-piperidin-3-yl)methyl)sulfamoyl)phenyl)cyclopropane-1-carboxamide dihydrochloride
(rel)-(1R,2R)-N-(isoquinolin-6-yl)-2-(4-(N-(((S)-piperidin-3-yl)methyl)sulfamoyl)phenyl)cyclopropane-1-carboxamide dihydrochloride
TABLE 18
(±) trans
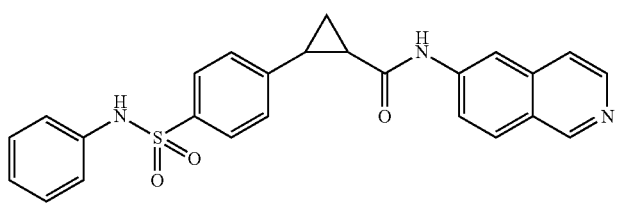 [SMILES: O=C(Nc1ccc2cnccc2c1)C1CC1c1ccc(S(=O)(=O)Nc2ccccc2)cc1]

TABLE 18-continued
(±) trans
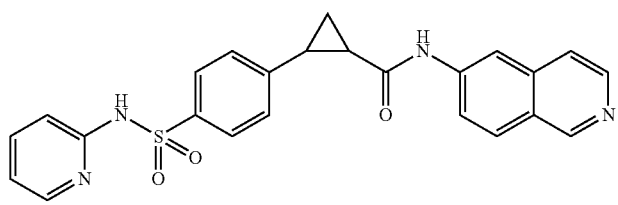 [SMILES: O=C(Nc1ccc2cnccc2c1)C1CC1c1ccc(S(=O)(=O)Nc2ccccn2)cc1]
(±) trans
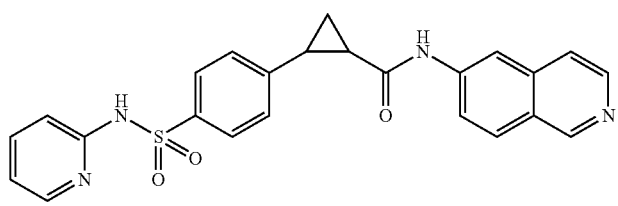 [SMILES: O=C(Nc1ccc2cnccc2c1)C1CC1c1ccc(S(=O)(=O)Nc2ccccn2)cc1]
(±) trans
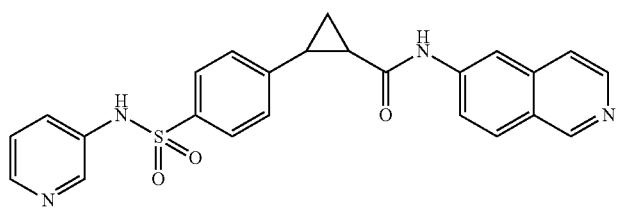 [SMILES: O=C(Nc1ccc2cnccc2c1)C1CC1c1ccc(S(=O)(=O)Nc2cccnc2)cc1]
(±) trans
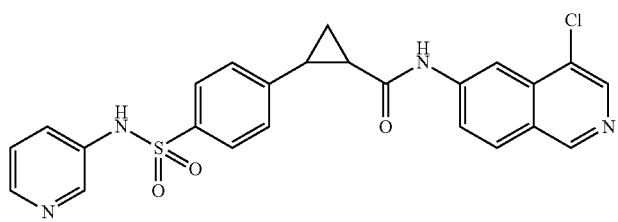 [SMILES: O=C(Nc1ccc2cncc(Cl)c2c1)C1CC1c1ccc(S(=O)(=O)Nc2cccnc2)cc1]
(±) trans
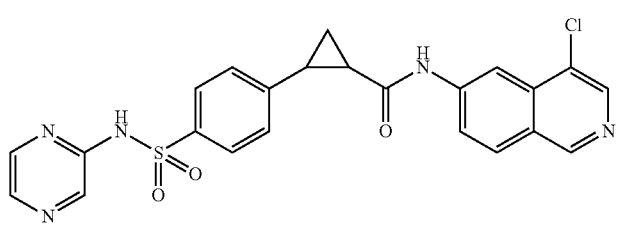 [SMILES: O=C(Nc1ccc2cncc(Cl)c2c1)C1CC1c1ccc(S(=O)(=O)Nc2cnccn2)cc1]
(±) trans
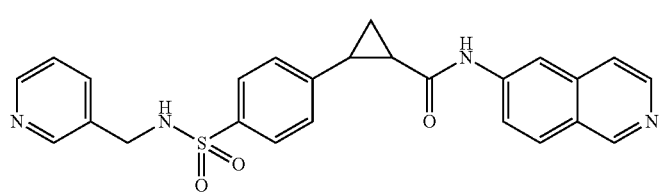 [SMILES: O=C(Nc1ccc2cnccc2c1)C1CC1c1ccc(S(=O)(=O)NCc2cccnc2)cc1]

TABLE 18-continued
(±) trans
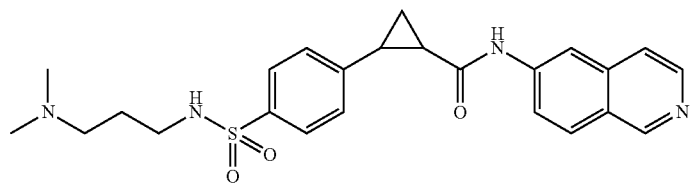 [SMILES: CN(C)CCCNS(=O)(=O)c1ccc(C2CC2C(=O)Nc2ccc3cnccc3c2)cc1]
(±) trans
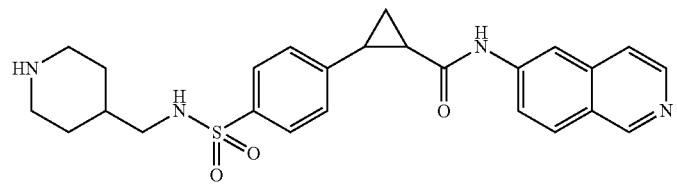 [SMILES: O=C(Nc1ccc2cnccc2c1)C1CC1c1ccc(S(=O)(=O)NCC2CCNCC2)cc1]
(±) trans
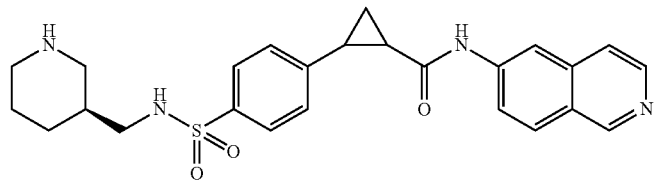 [SMILES: O=C(Nc1ccc2cnccc2c1)C1CC1c1ccc(S(=O)(=O)NC[C@H]2CCCNC2)cc1]
(±) trans
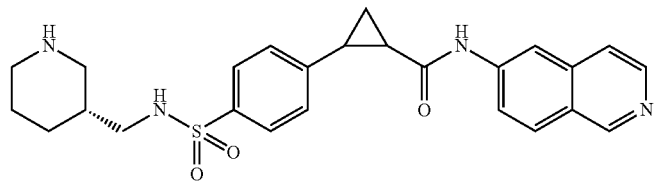 [SMILES: O=C(Nc1ccc2cnccc2c1)C1CC1c1ccc(S(=O)(=O)NC[C@@H]2CCCNC2)cc1]
(±) trans
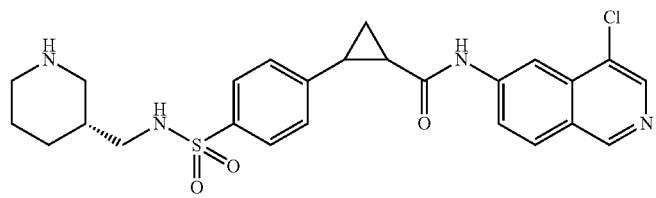 [SMILES: O=C(Nc1ccc2cncc(Cl)c2c1)C1CC1c1ccc(S(=O)(=O)NC[C@@H]2CCCNC2)cc1]
(±) trans
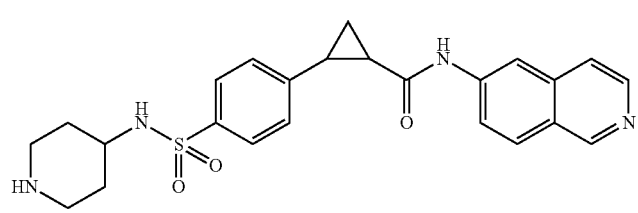 [SMILES: O=C(Nc1ccc2cnccc2c1)C1CC1c1ccc(S(=O)(=O)NC2CCNCC2)cc1]

TABLE 18-continued
(±) trans
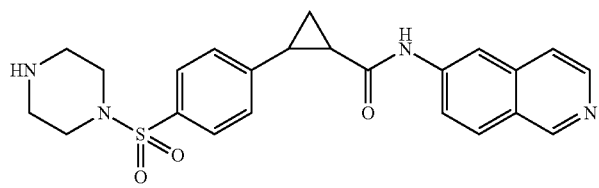 [SMILES: O=C(Nc1ccc2cnccc2c1)C1CC1c1ccc(S(=O)(=O)N2CCNCC2)cc1]
(±) trans
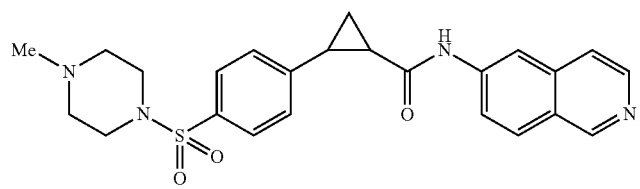 [SMILES: CN1CCN(S(=O)(=O)c2ccc(C3CC3C(=O)Nc3ccc4cnccc4c3)cc2)CC1]
(±) trans
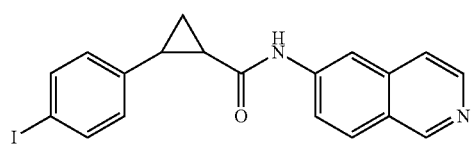 [SMILES: O=C(Nc1ccc2cnccc2c1)C1CC1c1ccc(I)cc1]
(±) trans
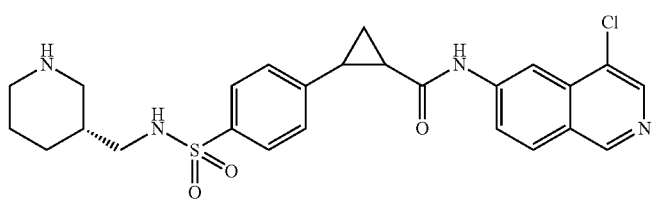 [SMILES: O=C(Nc1ccc2cncc(Cl)c2c1)C1CC1c1ccc(S(=O)(=O)NC[C@@H]2CCCNC2)cc1]
(±) trans
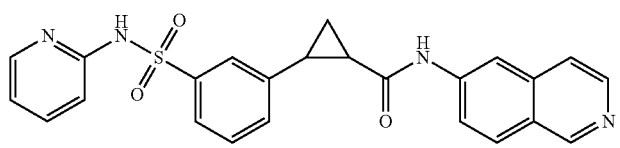 [SMILES: O=C(Nc1ccc2cnccc2c1)C1CC1c1cccc(S(=O)(=O)Nc2ccccn2)c1]
(±) trans
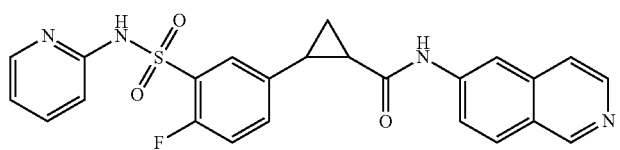
(±) trans
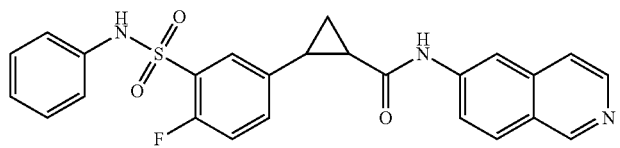 [SMILES: O=C(Nc1ccc2cnccc2c1)C1CC1c1ccc(F)c(S(=O)(=O)Nc2ccccn2)c1]

TABLE 18-continued
(±) trans
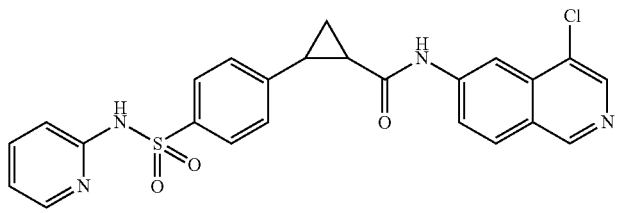 [SMILES: O=C(Nc1ccc2cncc(Cl)c2c1)C1CC1c1ccc(S(=O)(=O)Nc2ccccn2)cc1]
(±) trans
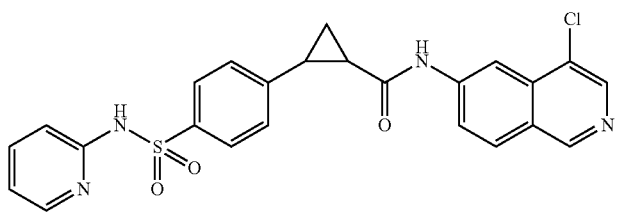
(±) trans
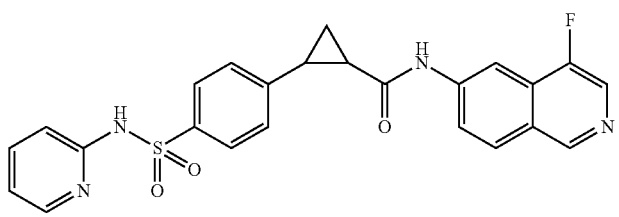 [SMILES: O=C(Nc1ccc2cncc(Cl)c2c1)C1CC1c1ccc(S(=O)(=O)Nc2ccccn2)cc1]
(±) trans
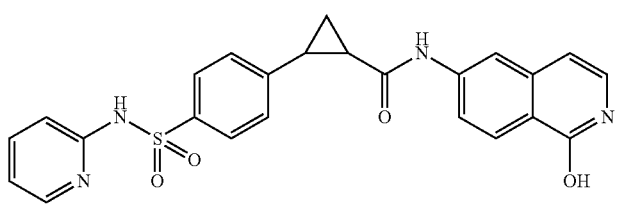 [SMILES: O=C(Nc1ccc2c(O)nccc2c1)C1CC1c1ccc(S(=O)(=O)Nc2ccccn2)cc1]
(±) trans
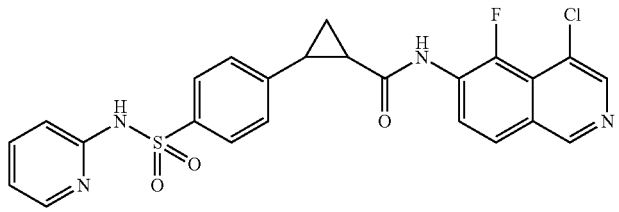 [SMILES: O=C(Nc1ccc2cncc(Cl)c2c1F)C1CC1c1ccc(S(=O)(=O)Nc2ccccn2)cc1]
(±) trans
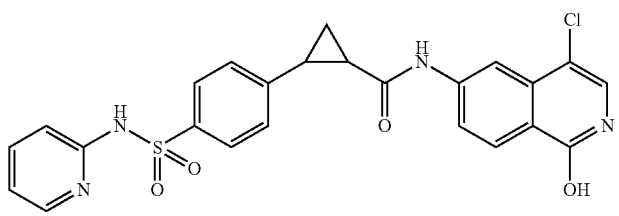

TABLE 18-continued
(±) trans
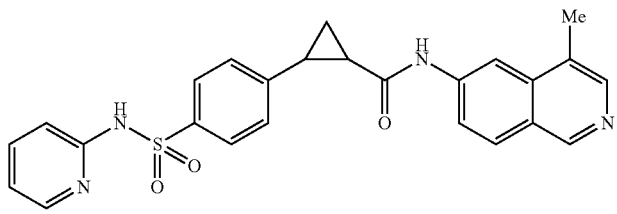 [SMILES: Cc1cncc2ccc(NC(=O)C3CC3c3ccc(S(=O)(=O)Nc4ccccn4)cc3)cc12]
(±) trans
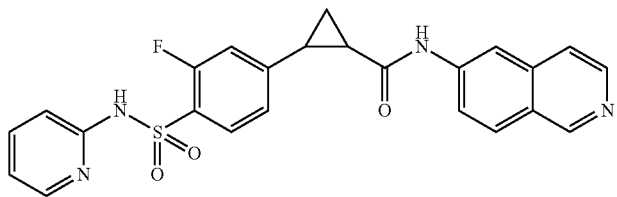 [SMILES: O=C(Nc1ccc2cnccc2c1)C1CC1c1ccc(S(=O)(=O)Nc2ccccn2)c(F)c1]
(±) trans
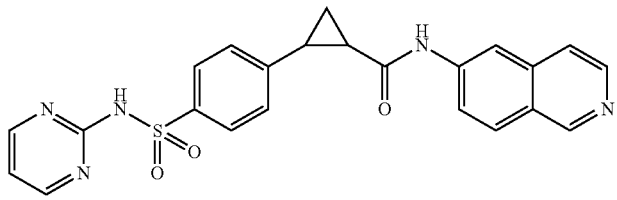
(±) trans
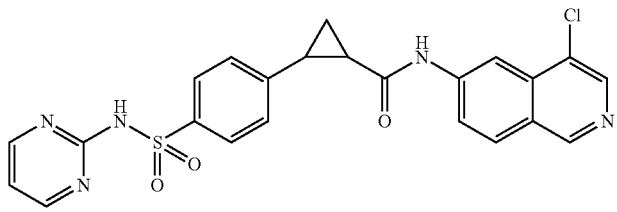 [SMILES: O=C(Nc1ccc2cncc(Cl)c2c1)C1CC1c1ccc(S(=O)(=O)Nc2ncccn2)cc1]
(±) trans
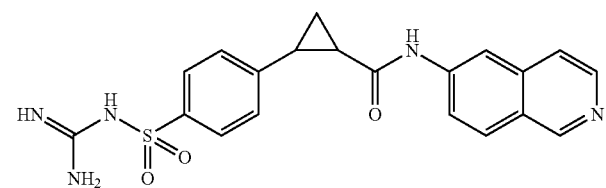 [SMILES: N=C(N)NS(=O)(=O)c1ccc(C2CC2C(=O)Nc2ccc3cnccc3c2)cc1]
(±) trans
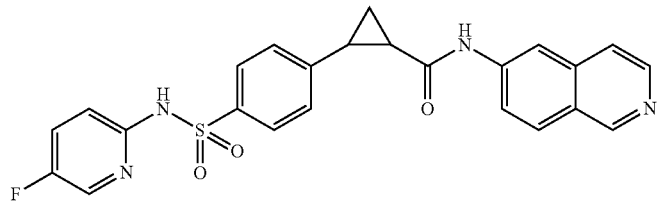 [SMILES: O=C(Nc1ccc2cnccc2c1)C1CC1c1ccc(S(=O)(=O)Nc2ccc(F)cn2)cc1]

TABLE 18-continued
(±) trans
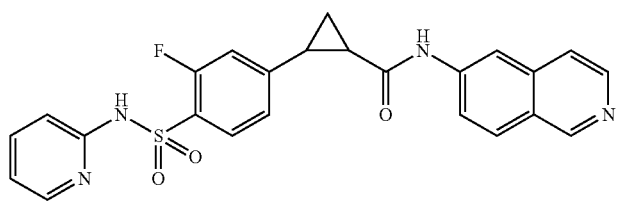 [SMILES: O=C(Nc1ccc2cnccc2c1)C1CC1c1ccc(S(=O)(=O)Nc2ccccn2)c(F)c1]
(±) trans
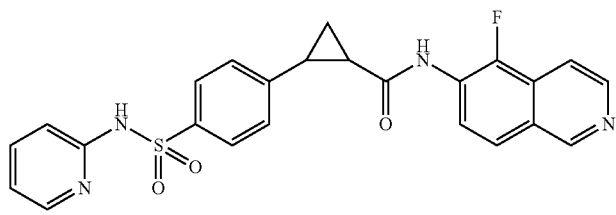 [SMILES: O=C(Nc1ccc2cnccc2c1F)C1CC1c1ccc(S(=O)(=O)Nc2ccccn2)cc1]
(±) trans
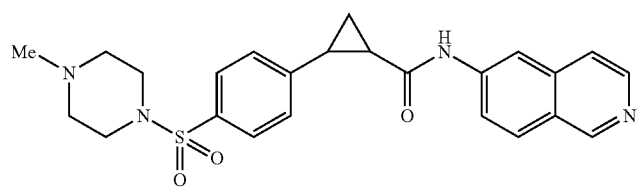 [SMILES: CN1CCN(S(=O)(=O)c2ccc(C3CC3C(=O)Nc3ccc4cnccc4c3)cc2)CC1]
(±) trans
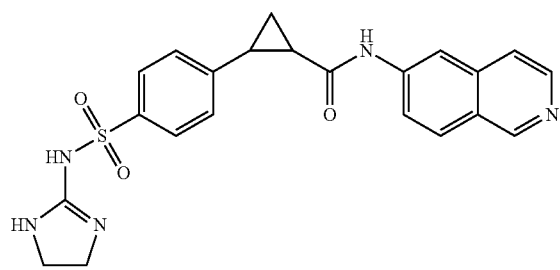 [SMILES: O=C(Nc1ccc2cnccc2c1)C1CC1c1ccc(S(=O)(=O)NC2=NCCN2)cc1]
(±) trans
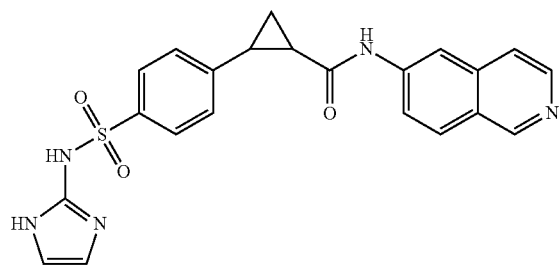 [SMILES: O=C(Nc1ccc2cnccc2c1)C1CC1c1ccc(S(=O)(=O)Nc2ncc[nH]2)cc1]
(±) trans
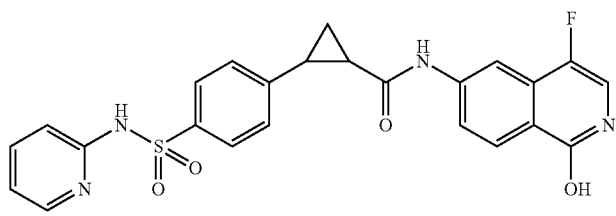 [SMILES: O=C(Nc1ccc2c(O)ncc(F)c2c1)C1CC1c1ccc(S(=O)(=O)Nc2ccccn2)cc1]

TABLE 18-continued
(±) trans
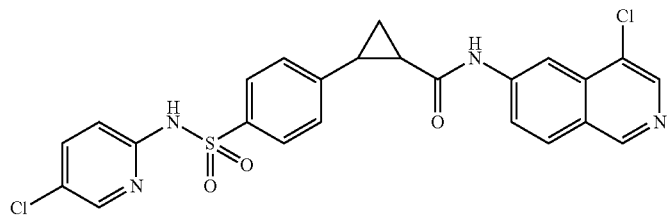 [SMILES: O=C(Nc1ccc2cncc(Cl)c2c1)C1CC1c1ccc(S(=O)(=O)Nc2ccc(Cl)cn2)cc1]
(±) trans
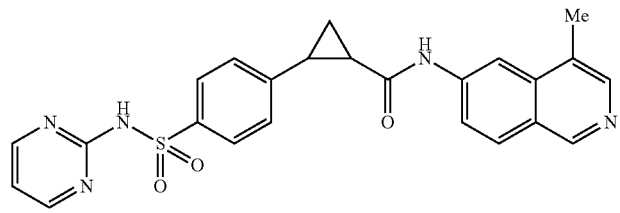 [SMILES: Cc1cncc2ccc(NC(=O)C3CC3c3ccc(S(=O)(=O)Nc4ncccn4)cc3)cc12]
(±) trans
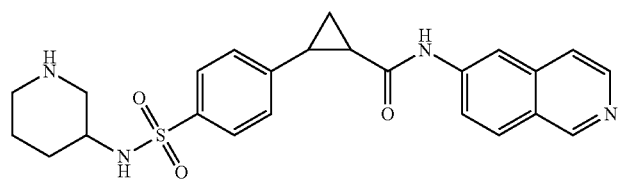 [SMILES: O=C(Nc1ccc2cnccc2c1)C1CC1c1ccc(S(=O)(=O)NC2CCCNC2)cc1]
(±) trans
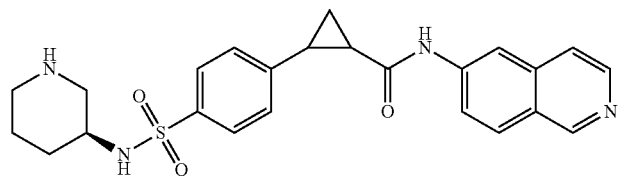 [SMILES: O=C(Nc1ccc2cnccc2c1)C1CC1c1ccc(S(=O)(=O)N[C@H]2CCCNC2)cc1]
(±) trans
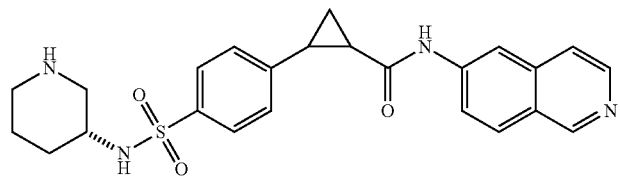
(±) trans
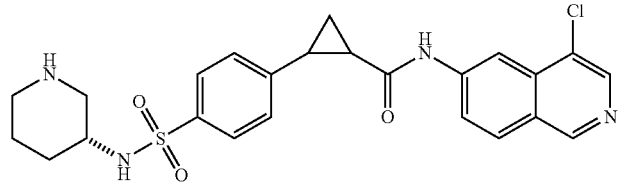

TABLE 18-continued

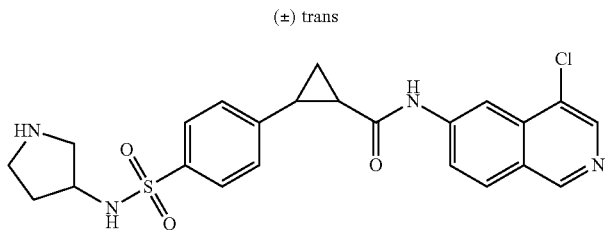

(±) trans

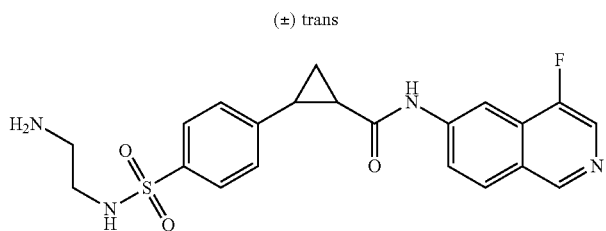

(±) trans

Example 18. PTM-HTM Assay

Porcine Trabecular Meshwork cells (PTM) were isolated from freshly obtained enucleated porcine eyes. Immortalized Human Trabecular Meshwork cells (TM-1) were obtained through a kind gift from Donna Peters in the Department of Ophthalmology and Visual Sciences at the University of Wisconsin. Cells were plated onto fibronectin coated glass-bottom 96-well plates and allowed to attach overnight. Media was removed and replaced with test compound in media with 1% fetal bovine serum and incubated for various times. After incubation, cells were formaldehyde fixed, triton solubilized, and stained. PTM cells were stained with Alexa Fluor®488 phalloidin (F-actin) and Hoechst 33342 (nuclei). TM-1 cells were stained with anti-paxillin followed by Alexa Fluor®488 goat-anti-mouse IgG (focal adhesions) and Hoechst 33342 (nuclei). All staining reagents were obtained through Invitrogen. Images were collected on an INCell 2200 imager with a 20× objective. The actin fiber length and total area of focal adhesions were analyzed using custom algorithms developed in the INCell Developer Toolbox, v1.9.3. Data collected were converted to percent of control (untreated cells). Curves were fit to data in GraphPad Prizm using sigmoidal dose-response and constraining top and bottom to 100% and 0%, respectively.

Example 19

Topical pharmaceutical compositions for lowering intraocular pressure are prepared by conventional methods and formulated as follows:

| Ingredient | Amount (wt %) |
|---|---|
| Arylcyclopropyl amino acid isoquinolyl amide | 0.50 |
| Dextran 70 | 0.1 |
| Hydroxpropyl methylcellulose | 0.3 |
| Sodium Chloride | 0.77 |
| Potassium chloride | 0.12 |

-continued

| Ingredient | Amount (wt %) |
|---|---|
| Disodium EDTA | 0.05 |
| Benzalkonium chloride | 0.01 |
| HCl and/or NaOH | pH 4.5-6.5 |
| Purified water | q.s. to 100% |

A compound according to this disclosure is used as the arylcyclopropyl amino acid isoquinolyl amide. When the composition is topically administered to the eyes once daily, the above composition decreases intraocular pressure in a subject suffering from glaucoma.

Example 20

Reference Example One. Pharmacological Activity for Glaucoma Assay

Pharmacological activity for glaucoma can also be demonstrated using assays designed to test the ability of the subject compounds to decrease intraocular pressure. Examples of such assays are described in the following reference, incorporated herein by reference: C. Liljebris, G. Selen, B. Resul, J. Sternschantz, and U. Hacksell, "Derivatives of 17-phenyl-18,19,20-trinorprostaglandin $F_{2\alpha}$ Isopropyl Ester: Potential Anti-glaucoma Agents", *Journal of Medicinal Chemistry* 1995, 38 (2): 289-304.

FIG. 1 shows changes (reductions) in rabbit IOP achieved with intracameral injection of a formulation of a (1R,2R)—N-(fluoroisoquinolin-6-yl)-2-(4-(pyridinylmethyl)phenyl)cyclopropane-1-carboxamide.

While the disclosure has been described in detail and with reference to specific embodiments thereof, it will be apparent to one skilled in the art that various changes and modifications can be made without departing from the spirit and scope of the disclosure.

What is claimed is:

1. A compound, wherein the compound is:

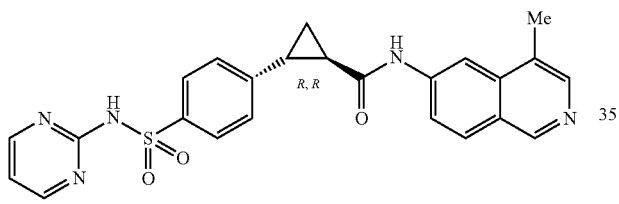

or a pharmaceutically acceptable salt thereof.

2. A composition, comprising the compound of claim 1.

3. A pharmaceutical composition, comprising the compound of claim 1 and a pharmaceutically acceptable carrier.

* * * * *

SEQUENCE LISTING

<160> NUMBER OF SEQ ID NOS: 2

<210> SEQ ID NO 1
<211> LENGTH: 10
<212> TYPE: PRT
<213> ORGANISM: Artificial Sequence
<220> FEATURE:
<223> OTHER INFORMATION: RSK2 peptide

<400> SEQUENCE: 1

Lys Arg Arg Arg Leu Ser Ser Leu Arg Ala
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Abl peptide

<400> SEQUENCE: 2

Glu Ala Ile Tyr Ala Ala Pro Phe Ala Lys Lys Lys
1               5                   10